US011690885B2

(12) United States Patent
Fevre et al.

(10) Patent No.: US 11,690,885 B2
(45) Date of Patent: Jul. 4, 2023

(54) ANTI-BACTERIAL COMPOSITIONS AND USES THEREOF

(71) Applicant: PHERECYDES PHARMA, Romainville (FR)

(72) Inventors: Cindy Fevre, Paris (FR); Hélène Blois, Paris (FR); Mathieu Medina, Saint Denis (FR)

(73) Assignee: PHERECYDES PHARMA, Romainville (FR)

( * ) Notice: Subject to any disclaimer, the term of this patent is extended or adjusted under 35 U.S.C. 154(b) by 768 days.

(21) Appl. No.: 16/491,176

(22) PCT Filed: Mar. 7, 2018

(86) PCT No.: PCT/EP2018/055629
§ 371 (c)(1),
(2) Date: Sep. 5, 2019

(87) PCT Pub. No.: WO2018/162566
PCT Pub. Date: Sep. 13, 2018

(65) Prior Publication Data

US 2020/0030392 A1 Jan. 30, 2020

(30) Foreign Application Priority Data

Mar. 8, 2017 (EP) .................................... 17305245

(51) Int. Cl.

| | |
|---|---|
| ***A61K 35/76*** | (2015.01) |
| ***A61P 31/04*** | (2006.01) |
| ***C12N 7/00*** | (2006.01) |
| ***A01N 63/40*** | (2020.01) |
| ***C12Q 1/18*** | (2006.01) |
| ***C07K 14/005*** | (2006.01) |
| *A61K 38/00* | (2006.01) |

(52) U.S. Cl.
CPC .............. *A61K 35/76* (2013.01); *A01N 63/40* (2020.01); *A61P 31/04* (2018.01); *C07K 14/005* (2013.01); *C12N 7/00* (2013.01); *C12Q 1/18* (2013.01); *A61K 38/00* (2013.01); *C12N 2795/10122* (2013.01); *C12N 2795/10131* (2013.01); *C12N 2795/10132* (2013.01); *C12N 2795/10171* (2013.01); *C12N 2795/10222* (2013.01); *C12N 2795/10231* (2013.01); *C12N 2795/10232* (2013.01); *C12N 2795/10271* (2013.01)

(58) Field of Classification Search
None
See application file for complete search history.

(56) References Cited

U.S. PATENT DOCUMENTS

| | | | |
|---|---|---|---|
| 10,077,431 | B2 | 9/2018 | Pouillot et al. |
| 10,260,051 | B2 | 4/2019 | Pouillot et al. |
| 10,898,530 | B2 | 1/2021 | Pouillot et al. |
| 10,918,680 | B2 | 2/2021 | Pouillot et al. |
| 2010/0203019 | A1 | 8/2010 | Yoon et al. |
| 2021/0060100 | A1 | 3/2021 | Pouillot et al. |
| 2021/0228659 | A1 | 7/2021 | Pouillot et al. |

FOREIGN PATENT DOCUMENTS

| | | |
|---|---|---|
| KR | 20130-142820 | 12/2013 |
| WO | WO 2009/087356 | 7/2009 |
| WO | WO 2010/033546 | 3/2010 |
| WO | WO 2017/015652 | 1/2017 |

OTHER PUBLICATIONS

El Haddad, L. et al. "Efficacy of two *Staphylococcus aureus* phage cocktails in cheese production" *International Journal of Food Microbiology*, 2016 (available online Oct. 5, 2015), pp. 7-13, vol. 217.
Deghorain, M. et al. "The Staphylococci Phages Family: An Overview" *Viruses*, 2012, pp. 3316-3335, vol. 4, No. 12.
Database EMBL [Online] Accession No. AB626963, "*Staphylococcus* phage S13' DNA, complete qenome" Dec. 22, 2011, pp. 1-10, XP-002770466.
Hsieh, S.-E. et al. "Genomic analysis of *Staphylococcus* phage Stau2 isolated from medical specimen" *Virus Genes*, 2016, pp. 107-116, vol. 52, No. 1.
Written Opinion in International Application No. PCT/EP2018/055629, dated Jun. 4, 2018, pp. 1-11.
Gibson, D. G. et al. "Creation of a Bacterial Cell Controlled by a Chemically Synthesized Genome" *Science*, pp. 1-7, supplemental pp. 1-5, May 20, 2010, vol. 329, No. 5987.
Smith, H. O. et al. "Generating a synthetic genome by whole genome assembly: ϕX174 bacteriophage from synthetic oligonucleotides" *PNAS*, Dec. 23, 2003, pp. 15440-15445, vol. 100, No. 26.

*Primary Examiner* — Nicole Kinsey White
(74) *Attorney, Agent, or Firm* — Saliwanchik, Lloyd & Eisenschenk

(57) ABSTRACT

The present invention relates to bacteriophage therapy. More particularly, the present invention relates to novel bacteriophages having a high specificity against *Staphylococcus aureus* strains, their manufacture, components thereof, compositions comprising the same and the uses thereof in phage therapy and as companion diagnostic.

17 Claims, No Drawings

Specification includes a Sequence Listing.

SEQUENCE LISTING

```
<160> NUMBER OF SEQ ID NOS: 4

<210> SEQ ID NO 1
<211> LENGTH: 17213
<212> TYPE: DNA
<213> ORGANISM: Artificial Sequence
<220> FEATURE:
<223> OTHER INFORMATION: PN1137

<400> SEQUENCE: 1

aacttctatt ccaacttatc taacctatta catattaatc aaatacattt attatacatc     60

tattgacttt tatcaaaatt tatgattgga acataaaatc taatttcttc tattaaatag    120

tagttttaaa ttatttaaac ttttttaaga aaaactgttg acaaaacttt taaacgtttg    180

ctatactaat tatgtaatca aaacaaggag gtaacaaaaa tggttaatgt tgataatgca    240

ccagaagaaa aaggacaagc ctatactgaa atgttgcaac tattcaataa actgattcaa    300

tggaatccag cttatacatt tgacaatgca attaacttag tagcagcttg ccaacaacta    360

ttattaaact ataacagttc tgttgttcaa ttcttaaaag atgaactaaa caatgaaatt    420

aaaccagaat caatattatc ttacattgct ggtgatgacc ctatagaaca atggaacatg    480

cacaaaggat tttatgaaac gtataacatt tacgtttttt agaaaggaat gatataataa    540

tgaaagctga tgacattgtt gttttacgtg ttaaaggtta tatacttcat tacttagatg    600

atgataatga atacattgag gaatttgttc cacttcacga gtatcattta actaaaacgc    660

aagcaaaaga gttattacca gaatcatgta cactattatc cactacacgt acaacgaaaa    720

caattcatgt ttattacaat gatttactac aaatcgcaat tgcagaaagc aaataattta    780

aataagagga gaaattaaaa tgacaaacgt aaaagatatt ttatcaagac accaaaaaac    840

attagcgaga tttgaatttg aggaaaaaga aagagtattt atcaaactat cagaattagt    900

agaaaaatac ggtatgaaaa aagagtatat cgttagagca ttattcataa acacagaatc    960

ccaattcggt gaacagggtg ttattgtcac tgacgactat aatgtaaact taccgaacca   1020

cttaacagag ttaattaaag aaatgagagc agacgaggac attgttgaca ttatcaacgc   1080

tggtgaagtt caattcacaa tttatgaata tgaaaataaa aaaggtcaaa aaggttattc   1140

aatcaatttt ggtcaagtat cattttaata caatttcata gggggtattt atcccctatt   1200

tttatgaggt gctaaacaat ggaaaaatat acactgccgt attattatac aatgtatcaa   1260

ttaatgaaac atatgaacat gaaattgaac aattcgaaaa aataaataaa gttaaggtaa   1320
```

-continued

```
tatatagtta ttttgacgca aacttttaca aaaaaggtgc atataatctt tgtgtaaaat   1380
atattaagga gctataaaat gaaaattaca acaacattaa acacaaacaa attaattaat   1440
tacattttaa ctaatagaga gtgttttata aataaaataa caaaatttac atcactaagt   1500
gataaatgtg tcgtttttgt tagatacggt gatatttcta ttgaatacta tgatagtgat   1560
acaaaaaaca ataatgattt atttacttta gacattgacg ttgatattaa taaacatgtt   1620
tttaattgtc ttgtggtttt ttatcgagaa catttaaacc cactatataa aaaagaagtt   1680
ttcacgggat gtactattga tgatgtatta gaaaattttg agaaaccatt agaaagttat   1740
attactatta tataccaaaa aaaagtcata tacgataatg ggaaagtgat tgaacatgaa   1800
taacctatta aacatagcca ttgtattcct tttagcgttt ttaattacac tgattatact   1860
tatgacactg catatacgcg tgtcatttgg tgttttattc actacattga ttatattcta   1920
cattatcttt ttagtggtta tatatgggtt atatggaggt cgttagcaat ggttagacat   1980
acgtccgaaa tggataaatg gaaaaaagaa agagacgcaa gaaaagagca ggaaaaagaa   2040
ttgtttttaa atgattttag tactgttaat tttaaatttg atgataaaga tttacaagag   2100
gcgtatatag acgcatggaa acatttcgca catttgccct attttccaaa agaaagaaac   2160
gtgtcatatg taaatgcggt atcattggta agaggtaaaa gacatgaaca attaaactat   2220
atacttgaaa tatataaccg taaagatgaa tctaataata aaaacgctaa aaaacataaa   2280
tatgctttat atgaattaca agctaaaaat aataattctt ctatgtataa atatataaag   2340
gaaattgaca ctttatacaa agaaattggt aaatcagaca gaccagtgac aactattgat   2400
gatgaagatg tgaggtataa ttttttatat tatgcaacat ttgaagacta attttaatac   2460
tgtaaacgac atcataaact attataagga gcaaaaaaat ggtaaaacaa aaccgtttag   2520
acatggtaag agattatcaa aatgctgtca atcatgtcag aaaaaaaata ccagataact   2580
ataatcaaat agaattagtt gatgaactca tgaatgatga tatagactat tacatatcta   2640
tttcaaaccg ctctgacgga aaatcgttca actatgtttc atttttttatt tatttagcta   2700
ttaaacttga tataaaattt actttattat cacgtcatta tacattacgt gacgcttacc   2760
gtgattttat tgaggaaatc atagataaaa acccactatt caaatctaag cgtgtcacgt   2820
tcagaagtgc tagggactat ttagctatta tctatcaaga taaagaaatt ggtgtgatta   2880
cagatttgaa tagtgccact gatttaaaat atcattctaa tttttaaaa cactacccta   2940
ttattatata tgatgaattt ttagcacttg aagatgacta tttaattgat gagtgggata   3000
agttaaaaac aatttatgaa tcaattgacc gtaaccatgg taatgttgat tatattggtt   3060
ttcctaaaat gtttttacta ggtaatgctg tcaacttttc aagtcctata ttatctaatt   3120
taaatatata caatttatta caaaagcata aaatgaatac atcaagactt tacaaaaaca   3180
ttttttaga aatgagacga aacgattacg tcaatgaaaa acgtaataca cgtgcgttta   3240
attcaaatga agacgctatg acaactggtg aatttgaatt taacgaatat aatttggcgg   3300
atgataattt aagaaatcat attaaccaaa acggtgattt tttctatatt aaaactgacg   3360
ataaatatat aaaaattatg tataatgttg atacttttaa tgctaatatt attgttatac   3420
cttatacaaa acaatatgag ttttgtacta agatcaaaga tatagatgac aatgttattt   3480
atttaagaga agacatgttt tataaagaaa acatggagcg ttattattac aatccaagca   3540
atttacattt tgacaatgca tattcaaaaa attacgtggt tgataatgat agatatttat   3600
atttagatat gaataaaatt ataaaatttc atataaaaaa tgaaatgaag aaaaacatca   3660
```

-continued

```
acgaatttga aagaaaagaa aaaatatacg aagataacta tattgaaaat acaaagaagt   3720
atttaatgaa acaatacggc ttataaaagg tgtgtaagat tatgggatta cttgagtgta   3780
tgcaatatca taaacatgaa cgtaaaatga tattgtattg ggatattgaa acattatcat   3840
acaataaaat aaacggacgt aataaaccaa cgctatataa aaacgtaacg tattcagtag   3900
cgattggttg gtttaatggt tacgaaattg atgttgaagt attccctagt tttgaagctt   3960
tttatgatga tttttacaag tatgttaatc gccgtgatac aatcacaaaa tcaaaaacag   4020
atattatcat gattgcacat aactgtaata agtatgacaa ccatttttta cttaaagata   4080
ccatgcgtta ttttgataat atcacacgtg aaaatatata tttaaaatct gcagaagaaa   4140
acgaacacac actaaaaatg caagaggcta ctattttagc taaaaatcaa aatgtgattt   4200
tagaaaaacg tgtgaaatcg tctattaatt tagacttaac catgttttta aatggattta   4260
aatttaatat tattgataac tttatgaaaa ccaatacatc aattgcaaca ttaggtaaaa   4320
agttgcttga cggtggttat ttaacagacg accaacttaa aacagatttt aattacacga   4380
tatttgataa agataacgat atgaatgata gtgaagcata cgactatgca gcgaaatgtt   4440
tttcaaaact cacacctgaa caacttatat acattcataa tgacgtgatt atattaggta   4500
tgtgccatat tcattatagt gatatatttc caaattttga ctataacaaa ttaacatttt   4560
cattgaatat tatggaatcg tatttaaata atcaaatgac acggtttcag ttactcaatc   4620
aatataaaga tattaaaata tcatatacac attatcattt ccatgatatg aatttttatg   4680
actatatcaa atcattttat cgtggtggtt taaatatgta taacactaaa tacataaaca   4740
aacttattga tgagccttgt tttctattg atatcaattc cagttatcct tatgtgatgt   4800
atcatgagaa aattccaaca tggttatact tttacgaaca ttattcagaa ccaacgttaa   4860
tccctacttt tttagatgat gacaattatt tttcattata taagattgat aaagatgtat   4920
ttaacaatga tttattaatt aaaatcaaat cacgtgtatt acgtcaaatg attgttaaat   4980
actataacaa tgataatgat tacgttaata tcaatacaaa tacattaaga atgattcaag   5040
acattacggg tattgattgt atgcatatac gtgttaattc gtttgtgata tatgaatgtg   5100
aatattttca tgctcgtgat attatttttg aaaactattt tataaaaaca caaggtaaat   5160
taaaaaataa gattataatg acatcaccat atgattataa aattactgat gatatcaacg   5220
aacacccata ctcaaatgag gaggttatgt tatctaaagt cgttttaaat ggattatatg   5280
gcatacctgc attacgttca cattttaact tattccgttt agatgataac aatgaactat   5340
acaatatcat taacggttac aaaaacactg aacgtaatat attattctct acatttgtca   5400
catcacgttc attgtataac ttattggttc ctttccaata cttaacggaa agtgaaattg   5460
acgacaattt tatttattgc gatactgata gtttgtatat gaaatccgtt gttaaaccct   5520
tattgaaccc cgatttattc gacccgattg ccttaggtaa atgggatatt gaaaacgaac   5580
agatagataa gatgtttgta ctgaatcata agaaatatgc atatgaagtg aatggaaaga   5640
ttaaaatagc ttctgctggt ataccgaaaa acgcctttga tacaagcgtc gattttgaaa   5700
cctttgtacg tgaacaattc tttgacggtg ccattattga aaacaataaa agtatctata   5760
atgagcaagg tacaatatcg atatatcctt ctaaaactga aattgtatgt ggtaatgtat   5820
atgatgaata ttttactgat gaacttaata tgaaacgtga atttatatta aaagacgcta   5880
gagaaaattt cgaccatagt caatttaatg atattcttta tattgaaagt gacatcggtt   5940
cattttcact taacgactta tttccagttg aacgttcagt acataacaaa tctgatttgc   6000
atatattaaa acgtgaacat gatgaaataa aaaaaggcaa ctgttaaaat aacagttgcc   6060
```

```
tttttttat tgagataaca tgaaaaatgt gtacgaaaat tgattatgtt ttgtatttta   6120
tttactagca ttactagcat gtgttcatta tagcatacat ctttatgcaa tgccactaaa   6180
gaatacaata ttatcaccag cattatttgg tacaccatta atgagtgaat acaataccac   6240
acgtgacggt gcaacgtatg gtggtacatt atagtttgct actaagaatg aaccatcgtc   6300
aaatactgcc actacaacac ctgtgtgacc aataccataa gctgttgctt gtaagtatgg   6360
tggtttactt gaaaaaccat aaccaacagt agggttgtgt gttgttttag cacctaactt   6420
tttataaaca taccacacac gttgaccgtt tgttatttgt ccgtcgtcgg taggttgtct   6480
tttaccatgt agttgcgaca tataagccca tgttaattct gtacactgtc ccgcattacc   6540
cgtttgagga aatatgttac cgggtttgta taagtattct tttttgaata aaggtacacc   6600
aattgctttt ttatattttt ctggtaactg tgcatacgtc cagttaccac caatgacgcg   6660
accactttta ccattaggtt tgactgattt accactaatt ggtttatgat ctccgtcatc   6720
atcagtaggg tttgaactac tacccccact atctacttgc acgctatcaa tcagtttttt   6780
taatgaatcg agtagcccaa tagtcatttt aatatgatat gtgttgttaa atgtttttttg   6840
taatgtaaaa taatcattac taaaaaattt gtcgctacct atactgtgta catcccattg   6900
taatgcgtct tgtacttttt ttaataattc ttgcatggct tgttttgcta aagcgagtag   6960
tgaactacca ctgtcaccac tactaccact gtcagacgtg tcactaggtg aaccaccttt   7020
accgtctaat tttccacccc atgctagaat agcatttgca ccgtctaaaa atggattacc   7080
atagttttgt actttattat atgatgcttt caaacctggt ggataatatg ccgcccaagt   7140
agctgcagct gttaatggaa tatacgcacg tccaattgta cctgctttca tatttttagc   7200
aaaatctgca ttaccttttc tttgtacgtc ttgtggtaca aaatgcactg gattaccgta   7260
atcataccaa gacggttgcc cagcttgttt tgattgtgat actaattttc ttgctatgaa   7320
tttagcgtct gttaaataat caccacgtgc agacgtatga tttaaccaac ctaaaccagc   7380
actataaccc tcattttttt catatacggc aaaaagagta ggtgatacac ctatctcttt   7440
tactgctttt aatacttgtc tgattttact ttcattacca ccaagccata cattaaagcg   7500
cccatatcct tttactttag ggactaactg gtctatcgtt aaaccgaaat catcattaat   7560
atacgaatgc gtaaatttat ctatcttctc ttggttgttc attattatca ctcttttcag   7620
aatcattttt aattactctt aatttatctt taatttgttc tgggactaac acgtccattt   7680
ctgcacaatt ttctacgata gataacccct cattagcgat ataatagaaa atcgtaatca   7740
tgagtaagcc accttttaat tgtaaaatct ggtcaatgat gttagctaaa atgataatac   7800
agaatatcaa taatttttta gcaaaacctt tcattgattt tttagaccat aagttattat   7860
ttttaatagc tttagcaaaa cctgtgataa catcaataat cattaaaaca aataaaaagt   7920
atagtaattt taaatcccca gcatatataa acatgtgaaa cgcttctgag tctgtaaatc   7980
tgaattttac ttcgttcata ttataccccc tctctaaatt tgttatttaa tggattttgt   8040
aacattggat tacctgaacc gtcattatgc caaaatctca caccagattc taaaattgct   8100
tttaattgtt ccattaacat ggggtcaatg tcacgtatgg tatacgtacc tgtacatttt   8160
aaatagttgc aaacagtcat actgttaatt ggttcaataa atgaattata gtcattcact   8220
tcaaaaccaa acaacatata atatttttgt aaaaatgtaa tttctttagg tgacggtaca   8280
ctaattttca tcgttaaacc gttaatactg tttgcaattt ggaatgcgtt gcccatttcc   8340
gactctgtca ctgacggtgg ttgtaatgct aaatctttat attctgcttg ttgttgtttg   8400
```

```
tagaaattat attcttcatt aaacttacca aataaagcag tcggacttaa attacttgct   8460
acgctcactg cgtcataaaa acgtgatttt ggatcacttc catttaatac attatttata   8520
cgacttgtga ttaattgact ttctgcatta cgctgtctat tggcttgttg tgattgtcct   8580
aaaattccgt tattaattaa tataggtact tgcgcaaaac tattaaatgt tatatttgta   8640
tttaagaatg aacctgtatc aattaatata tctttatttt tagcaagtat cggtctatcg   8700
ttttcagcac tgttataatc tactggatat actcgcactt cattatgata accaatgatt   8760
gactttgtac gtaacttaac acctgttttt tgcgaaatct taccagcgtc tagtaacatt   8820
gtattaccgt tccagtcata aaattcaatc gtcatatact cattacgtat catatgttta   8880
aactcttctt ttttagacaa catcatttct tgaagctttg tgaaacttaa tgataaatcg   8940
tttaaactcc attcttttga ttttccacct tgttttaacg tctttaatcc agtaattttt   9000
tcacttgtct taacgtcctc taaatctttt gtattaataa agtctttagg taacatttga   9060
accttttgaa agttttgtgt aatccatgga tatgcactca ttttatccat aaaattgata   9120
aaatccccgt attccataac gtataagttg actggtgatg tgatattgtc atatatcgta   9180
cctttagacg tatctaagtt tggctctttt ttcgtaccaa atttctttga taaatcagcg   9240
cttgactgga ataacactaa attttctaaa tactgttgca tttggttata cacatagttt   9300
ttatttgata cttttaacac atcatcattg ttacgtaaca ttggtaacat atagttatac   9360
gtgcgttttg ataagtgttg acgttcaata ttaacgtttg agagttgctc taatacatta   9420
ccttgtgtat acgtcataat agtatcaatc acaaaatata tttttaccac aacatcattc   9480
acatattcga tttgattcac aaaagcataa taacgtctgt cctcaaaatc tgataaaaac   9540
gtcatatagt taatcccttg tgcgtcatgc cactgcatat caacattgat ttccattcta   9600
tcacgtataa aattatacgg ttgtttggaa tagtctaatg atttaaaatg acgaccattt   9660
aaaaaataat catcacgttc tttattacta ttaaaatgaa tcgtgttttg ataatctgta   9720
aacggtgtgt tatagaaaaa tttaaaattt gttaattttc tcatttttac ctccataaaa   9780
atagtcgtat aaattattta tacgactatt ataacatttt tattcaatga tttgtgtgtc   9840
tattgcaaaa cgtttatcac catttgttaa gtcactatcg ctataatttg atgtaacaaa   9900
atgtaagtta cccttaaagt ttaaatacat tcttgtattt atcattttat tatcaacagc   9960
acattgcgtg taatgatgtg ttgattttaa atttgcgtta atcgtaccta atttaatatc  10020
accgttttta ttaatccctt taaatacacc ttttaattgt attgttttta tgtcattgat  10080
tgtaacaatg cgatatttta aaggtggata agcattacta ttataatctg ttgtaatacc  10140
actttctaat tgtatatttt gccaacctgt atcattaaat tcaactttta cactgttaat  10200
tttttgatta aaattttgtt caatttctga tttggattgc gcaattttag tatcaattaa  10260
attaatttca tttgtattac gtcctacact atctttagta gcgtttaatg attgtgtaag  10320
tgtgttatat ttatcatcat actgtaacat tgatttttca aattcattta attgtttttg  10380
atgttgttct aaactttcaa ttaatatgac atctttttct tttaatgcgt caatgttatt  10440
tttattacta tcaatcattg gttgtaattt ttttatcttc tctaaaaatg ttgatatttt  10500
ctctttgtta tcattaattg caatatcatg tttatctatt tgaccactat atttatcaat  10560
caatgttttt aaatcattat aaaacgttaa cttataataa cttgaatcag tacggacata  10620
aatatgtccg tctgatgtac taatcaagtc attttcttct gttaaaaaat ctgctaaacg  10680
ttctatatct tcgacacgtc ttaaacttct tacgattcta tcagccattg tttacacctc  10740
ttatttatat cgtttccaac taaactcaaa gaaaaaacct aaaataccca ttatgagaac  10800
```

```
accccccaag gaataccaac actgtaacta ttacctgttt taccattcca ttgccttact  10860
ggtaaataat aacgtgtacc ttgccagttg taaccaatcc aaactaaccc atctgataaa  10920
catacttcgt catatggtgt atatccacca ggttgaaacc agtagccgtt aggttctgat  10980
aatttaggac taccaacatg tgcaaatatt ggtaaaaagc cacatgtaaa tgttgcattt  11040
tcatttctgt aatatgtacc gtattgattt tgtttccagt tgttagtttt ttgaatattt  11100
tgttctaata ctttactatc actatttgaa aattttggac gaataaaatg cgttacaccg  11160
tcataataat gggtgcgtat tgtcgctttt tcccaaccgt caaaaccgcc attcaaccag  11220
ttttgctcta aacatgtata ataatctaaa ttcccactta ttacacattg gatatgacca  11280
tattgagaat tagtataaac agcaacatca cctaattgag gtttaaagct cggtgtattt  11340
tcatacaccg ttgctaaacc tttaaagtta ttattaatag cgtctttggc gttaccccac  11400
atgcgaactt taccgtcggt aatgtaataa acataagcaa ctgctaagtc catacattga  11460
aaaccatatg cgccatcaaa gtcaacgcca acaccctcat gtttatatat ccaatctttc  11520
gcttgttgtt gtgatttcat ttatatcact cctatttttg atgttttggt acccaatcat  11580
attcacgatg tgtatttttt actgttacaa gactataaaa ctctttatat gttgatgaat  11640
ttattaataa cgtttgtcta acttcacctg aaacgttacc acttgatact tgtaaccatg  11700
caccagcttc accaatatct ttaggtttat ctttaaagtt attcatttgt gttgatgtaa  11760
tgtaatattc acctggtaat gtaattttag caatccaata accaaaattt ttagcctcta  11820
cgtattcttt ttcagttgaa ttagtatcaa taacagacca gttaccaaat tcaaattttt  11880
gtgtttttaa gttatatgtg aaacttctta ttagtttcat catttttctt aatcctgagt  11940
ttcttgttaa ttcttgatat ccacctaact gttgtgtttt tggtgataca aataaaaacc  12000
aaccggcatc attattgata tatggaaaat catccataac tttagtatgt tctgtcatca  12060
tataataaaa tccagtttcg gtaatttggc ttaaacttgt tacaccatct cttattgata  12120
aagctctacc gtcatctttc gttagtttat agttttgccc accttttaac gttaatccta  12180
caaaacgctc atattcacca gtttgaaaga aaccatacaa taagttttgt ctttttccac  12240
caccagcagt tgtatatgca attaataaag attgtttttt agttctagga ttaacgtata  12300
aatataatcc ctcaggttct ctaaaattat ctctaggatt ttcaacacca tgttcaaatg  12360
aaacatcgtt taaataataa tcgtatactt ttgattttgt tttaaaacta tatttttgaa  12420
ttaatgtttt actatctagt tctgaccaac cacttaacca gtataaatca tcaccataaa  12480
ctgcaatacc ttgcataggt ctgtctggtg tgtttttcttt tacatcaatt tgtagttctt  12540
tttctacatt gtcaatgtga ttaattacat cttctcttga ccgtacttgt attaaaccac  12600
caccatatct aaatactaat ttgtcatttt cttcatccat aataggcgta aaatattcat  12660
gtgacgatgc tggcgtgaaa tcagttaatg ctttcgcatc atctactgtt aatgttgtat  12720
tatctctata agcgatttgc acaagttttg aaagtgcaac atgatacaac catattttta  12780
tctcaccgtt actttttctt tctaaagcaa tattagtacc atgaccaccc tctacaatat  12840
gcatactaga aattaaatca ccactaggcg taaatttgtt aatccaaaaa ccttcttttt  12900
cttgtgagtc ggattgtgta gagtacattt gatttgtttc tctatcaatt aatatacttt  12960
ggtttacagc gttacgaaca ccaccaaagc cagttacaaa ctttggttca agctcattta  13020
attcaaaccc attaacgaaa cggtcaatgt ctttaattaa gtctttcact tctgctttaa  13080
aatcattcat ttgtttcatt tctgcaactt taaataatgc aaacgccgat gttaatcctg  13140
```

-continued

```
cactatattt tttaaactcg tcatgaataa tgttatcaat cgtaccatcg tttaaccaac  13200
ctctaaataa gtctttcgct tggtctggga atgctttcat taagtcgtcc cagtttctaa  13260
aacgtttttt taactcaccg tcatagtccc aaatacgacg tgctaatact tcaattagtt  13320
ttgataatct tgaaatataa tcataatacg attttgaatt tgtattataa tctgctctat  13380
catcgtaaaa cggtgtgtaa cgttctctag ttttatatat ttcgtctaaa aatggacgaa  13440
tgtcatcaaa atatttaaaa tcgttttcat tatatgccat aattttccac ctttaccaaa  13500
tttgtaaaaa acattttta tcaaattcat ttaaaatttt ctttcttaaa tcgtatactt  13560
tatcaatatt atcaattaaa tactgctttg aaaattgtgt acctttcgca ttaccttttt  13620
gattttgatt acgttttgcg ttttgattac tttcgttact tgatttattc acagttttac  13680
cgttatcgat tgtattatta tcagcaaatc gtaacgttgt attatcaaca tcaatgttaa  13740
cctcactttg tggcagtgac acataagcat ttctgtttgc tgtcatccca gttgaattgt  13800
ctaaagatgt agcattttga ttcgatgttt catcagtatt gcttgttgta tcttcattat  13860
gttctgtaaa accttgtgat tgtagatatt tttcaacttc tcttgatgaa taaaccacat  13920
tcaaataatc ctcatgtgtg atacatacag taatcacttg catgccaaaa gcttcaactg  13980
tttgtctgtt gatttctcta tctaaaaagt gtattgtaaa tgattttta aaaagtaagt  14040
cagataagtc atctttaagt ttaaaacctt taaacacttt ttcattaacg atggctaaaa  14100
cgtctttgtc aaacttcaac attttttgca tgaattgaaa ttcatcatca taaaacgtta  14160
atttatcatt atttacaaat tcattaaaac ctttttaat taattctgat ttaataaaat  14220
caaataaagt cattgtatat ctagccattg tattcactac tttcatcatt agacaatgta  14280
tctatcattg ttatttctga agtaacttca tcgtcgtaat acggtttaat atctaaacca  14340
taacgttttg ataagaatgt aatcggttca cgacctttta aataaatatt actatttgat  14400
gtggtaaaac ctcggttgct ttttgcctct tcgtccgaaa caccgctttc cttatccact  14460
gctagtgaat taatacctaa atagttactt aattcactaa ttttattttg gtattcgcgt  14520
ttcatctcag ttagtgctgg aatcacacta ttactggtta aatctatgat atcatcatcg  14580
gcgttaaaca taggtgacat tttaacaaat ggtgcaccgt tatatatttc cgatacaagt  14640
tgattaactg actcatcatt aatgtctgat ttaaatattt tgctaaattt tgcttgcata  14700
attaatgaga atcgagataa aacaacctca gataattcat cagtataatg ttctatgatt  14760
tctatatcac tattatattg aattggttta ttttgcatga caacaaagtt accactcata  14820
cagttatcat atattttatg aatctgtaag cattcatctg gtattaaata ctctggtaca  14880
atgaaataaa tatcatcttt tgttaatcgt ttttgaaatt ggaaattaaa gtttgatgaa  14940
aaatttggtg cttgattaaa gtaagtgtta tttacataac caagaatcat aatttgctta  15000
tttctagctt caccaaccac tacattgatg ttttgtctta aagctgattc taactgaata  15060
aaatctatac caaccgtatc acgattggta tagttgatga gtagcggtaa aaattccaaa  15120
taacgattaa acataagacg tttaaatctg ttgcgatgtt ctacaacacg tttattgatt  15180
tctttagata attcaacctg tacgccttta ttatgtttag tcatttatag cacctctatt  15240
attctgttct cggtgtaaca tcttggtcag taattaaaat tttattaaag aatgggctaa  15300
tggctttaaa tgaataataa tgaatccagt gtgtgacttc atcaaattca ccattataga  15360
atggttgttt taacatacct tttgtgtaac gtttatattt aattgaatta atatccaaaa  15420
taaacgcata taaatctgat tttggtttaa tttcttcaac gttagactta aattcagata  15480
aatttgaaac atcataagtg aatactgaac caactggaat tgtatcacct ttatgagttt  15540
```

gataatcacc gtaagcacgt aagaaattaa ctgattcgtc acttgatacg acaatatctt 15600
tagtaacttt aaatactcca cctaaatcat caaaactaat aacgtggtct gtaaagtcaa 15660
tccctgctac ttggaacgtg tgcgcaatct ttgtatctaa aagataagat tttaagctat 15720
cagtcgttaa aataacaata tcttttaatt ttgaaactgt tgtatattgt ccaatagcac 15780
cacctgaagc acgatgaact tcattatatt tagcactgtt gttttgtaag ttgagaatag 15840
cttcaaaaac tttacttgct aaatcttctt ttgatgttgc tttacgtaca tttgattcag 15900
ataattgatt caatgagtaa tcaactaaca ttgctcgcat ttctttttct tctaatacgt 15960
taatatcaga aattttcttt ttatagacac ctaatgcata attagttgcg tctgctaatg 16020
tttggaaatt gaaacgtgta tcattgttat ttaatgtgaa tttttgtttc ttcacaatac 16080
cactaccata taacttagta gccatacgtg gataattacg ttttagcatt aattcttcat 16140
ttttagataa atccatgtta ataggtacag tatccataat tacatattct tcactgtatt 16200
gtccgataaa gtcttgttct ttagctaacc aattaaaacg gttacctaat gcaatatcga 16260
ttaataacgt ttcattaatc ttagggaata aaaatttatt tacaaatgtt tcaaacattg 16320
tatttgagtt atcccactta tcgccaaacg tccatgattt tgaataagta tgattaaagt 16380
cttgtaatgc agatttagct gacttagcaa ctaatagtgc tgtttcgttt tttgtaatat 16440
tttctgccat gatttattat tcctcctcta catcgccagt aaatgactgt tttgaaagtg 16500
aatgaatttg tacaccataa ctatcttcac ttttgtttgt gtcaattgac atattttcat 16560
ttaattctgt tcgtttattt aatcttgaat cttcatatga tgtacccatc attgaacgca 16620
tattgtttcc ctcatacatg tttaaattcc tcctaatcta aatctaactt ttctattaat 16680
tcttcatctg aatagtcgtt atcttctttg tctgattctg ttacatctgg ttgtgtttgt 16740
tgtacttgtt gtggttgttg catttgtgaa gataaataag tagttacttg ttgttctaat 16800
gaagtaatac gctgctctaa tacaacaggg tcaaatttag aactatcttc atctgttgta 16860
gtaggttcta atttgttttc attttcttct tcgattgttt ctactgtttt atcttcagtt 16920
gattcttcag ttgattcttc agtagattct tcagttgatt cttcagttaa ttcttcagtt 16980
gattcttcag ttgattctga agtttcttct ttgtcgtctg gttttacgat ttcatcaaat 17040
tctgtcattt agacacctcc aaatatttta taactaatta tatcatagaa tatttaaata 17100
agtaaaataa ttttattata tgttcaaacc ataatttttg ataaaagtca atagatacat 17160
aaattttgta tttgatgaat atgtaatagg ttagataagt tggaatagaa gtt 17213

<210> SEQ ID NO 2
<211> LENGTH: 134876
<212> TYPE: DNA
<213> ORGANISM: Artificial Sequence
<220> FEATURE:
<223> OTHER INFORMATION: PN1483

<400> SEQUENCE: 2
aaaacctata gaacctgaaa aacctataga acctgaaaaa cctatagaac ctgaaaaacc 60
tatagaacct gaaaaaccta tagaacctga aaaacctata gaacctgaaa aacctagctc 120
agatactacg atacctttag ttccattgga acctagcaca cctgtagatg aaagtaatga 180
tactaatgga gagggataac ctctcctttt tttgctatat taaaagagta ataaaataaa 240
cattatagtt ggtgattttt tgataggatt aaacgtactt acagctatat ccgtagtttt 300
tgcttgtgta agtctactag cactaatgat atttgcgtat attaaaactg aaaaaagtag 360

-continued

```
taagttggtt ctatacttga tatatgctat aatttctata ggttcttatg tagtattaac    420
aatgtttcaa gccacgtcaa tcattataaa aaatgatgtt atagactcta ttgagaatac    480
agagcagtat gtagggttta ataacccttt aattgttttt ggtataagtt tctttggagc    540
tgtaataggc agtttttggt ttttagttat gaagattgta aatactagga atttaaaaaa    600
taaaaaatta aaggattgaa gcatttgcta ttttcaaaag acgataaatg ggatgaagca    660
aaagacttta taaaaggtca aggattagca gataattgga tagaagtagt ggattactat    720
agacagatag gtggtaaaca tgtagctatg tttattgcta ttgataaagt taaatatatg    780
gtactagaag ctacaaagga taataaagta atattggtag ataaggataa taatattgtg    840
ttagaggatt atgatattgt tatggaaagt aagaaaatgt tttactatat agaagaacca    900
ttcgaagtaa agataaatat tcctaaacat atccaagaca ttacctataa taacactgtt    960
atactaacta ctattcgagg aggtaaataa aaagttgcct gatttattta aaagtctaag   1020
gttaggtagt atgtataaag aagacactga agaccttatg gttcctatag atgacggaat   1080
acaagctaac attagacaaa tagaacaaga tacaaaagag atgcaagaaa ttactaaatc   1140
tttgtatggt aaacagcaag cttatgcaga accattttta gaaatgatgg atacaaatcc   1200
tgattataga gataagaaga gttatatgag aaatgctcat aatttacatg aagtgttaaa   1260
gaaatttggt aataactcta tactaaatgc tataattatt acaagagcta atcaagtatc   1320
tacatactgt aaacctgcta ggtattcaga aagaggagtg ggttttgaag ttaaattaaa   1380
agacttagac gctacacctg gtattaaaga aaaagaacag atgaaacgta ttgaagaatt   1440
tattcttaat acaggtacag ataaagatat agacagggat tcattccaag agttttgtaa   1500
aaaaatagta agagatactt acacgtacga ccaagttaac ttcgaaaaag tttttagtcc   1560
taaaaacaaa actaagatgg agaagtttat tgcagtagac cctagcacca ttttttatgc   1620
tactgataaa aacggtaaga taattaaagg tggcaatcgc tttgtacagg tcatagataa   1680
gcaagtagta gctagtttta caagtagaga acttgtcatg ggtattagga accctaggtc   1740
agacttaaat tctagtgggt acggattgtc agaagtagag attgcaatga aagaatttat   1800
agcttataat aatactgaaa gttttaacga taggttcttc agtcacggtg gaacaacaag   1860
aggtatctta cagattagag ctgaccaaca gcaatctcaa catgcgttag agaactttaa   1920
aagagaatgg aaatctagtt tttcaggtat aaacggtagc tggcaaattt gcctctatat   1980
aaagtaattt gtatagatga agggttaact gctaagaaca cctaaagctc aatacactac   2040
aaagtaaccc gaaagggtag gcttgaatgt tacgaaagta gaaaaaagat attgagatac   2100
gttaaggtta aatcctaaga cgaagaacaa tggttgttta gcatcgaaag tcctaaagaa   2160
ctgaaaggtc tatggaatac gttcaacgac tatcccgtta caagacggga gtaaagctcc   2220
aagctattgg gagaagaaaa atccttaccc tacacaatag ggataacaaa tagtctagtc   2280
tcgtactgaa aggtagagca tgtgaaataa cacaggttta caaagtagcg tttgtaaata   2340
aataaaacta aggtttataa aaaaaaatta ttcctttact agttgacaag taatcttttc   2400
tatgatatac ttaaaccata gaaaagaggt gaaagtcaat gaagaaacta aaattaagat   2460
tattaccaac tccagagcaa gaagacttaa tgtgggttca tgtaaatcat acacgtaatg   2520
ttaaaaatat atttttagct aaatgttttg aactaaaaga aacaggagaa tttataagta   2580
aaaccacatc aaataaacta agattagaat taacggaaat gttgaaaaca gataaatata   2640
gttatttaaa aagtgtatca agagatacac tagatagagc tgtaaatagt gtagttcaat   2700
cttatgttga ttggtgtaga ggtactcatg gtaaacctaa attcaaaaag aaaaataaat   2760
```

```
gtacaaaata ctttgatgtt agggaaaata gattaaaaag gtatggacat acttttcata   2820
tacctagtat aggaaaagtt aaagtatcta aaaatacttt aaagaataat tttagtatta   2880
taaattctat agaaagttta gataaattta gaaaaacatc tattaagtat gatggtaagt   2940
attggattat gtttattact tatgatgaca caatagttac ccctcgaaaa ccaagagaat   3000
tatctaatga aaccataggt atagacttag gtattaaaac attagccact tgttctaatg   3060
gtaaatctta taaaaatatt aataaaagtt ctaaagttaa aaaactagaa aagaaattat   3120
ctagactaca aagacaagta agtagaaagt atgaaatgaa taagcaaggt aagaagttta   3180
ttaaaactaa taatattatt aagttagaaa aagaaataaa actcttacat agaaaactta   3240
gtaatattag aaataatcat attcatacta tgactaaaga aatagtagaa caatatccta   3300
gtgaaatagt aatagaagac ttaaaggtaa gtaacttaag aaaaaataaa catttatcta   3360
atagtatttc taaagctaat tggtatacaa ttagagaata ccttacttat aaatgtgaag   3420
atagaggaat attacttact attgctaata cttactatcc gtctagtcaa acatgttcta   3480
attgtggtaa tcgtttaact aaacaagata aactatcttt atcacaaaga acatataaat   3540
gttcttgtgg aagtagtata gatagagatt taaacgctag tattaactta aagaactata   3600
gatactccaa ttggtatcac aatcatgttt taactaaatc aaacagtaaa catgatatgt   3660
aggattccgt aaatccgaat taacgccttt ggagtatcac acaaacctga gtagagtata   3720
taaaagtagc tagtaatagt gaagatactc aaaaagggat acgttgaaaa aggaataaaa   3780
tttttataaa attttagatt acgaagtccc cgtgatgatg gctgatgatg ttaagtttgt   3840
taatatgaca ccaacagcaa atgatatgca atttgagaaa tggttaaact ttttaatcaa   3900
tattatttct gctttgtatg gtatagaccc ttctgaaata ggattcccta atagaggagg   3960
aggagccaca gggtcaaaag gcggttctac attgaatgag tcagaccctg ctaagaagca   4020
acaacaatct atgaataaag gtttacaacc tctattaaga tttatagaag aattaattaa   4080
cagacacatt atatctgaat ttggtgataa gtatactttc caattcgttg gaggagatac   4140
taagtctgag ttagataagc ttagtatttt acaaaaagaa gtacaagtat ataaaactgt   4200
aaatgaagca agagaagaac agggattgaa accaatagat ggtggagatg taattcttga   4260
ctcagcattt ttacaaagta cagcacaaga aatacaaaaa gaccaatacc tagatactaa   4320
acaaaaagaa agacttcaat tacttatgag ttatacacaa ccacaaactg atgagcctac   4380
agatgatagt aaacaagaaa ctactaatca agaagtaggg acagataacc agttaaaagg   4440
tgatgataac gtatatagaa cacaaacatc aaataaagga caaggaagaa aaggtgagaa   4500
atcttccgac tttatgtaga taatattagc aacctaatta atacttaggt tgttattttt   4560
taatttggag ctacatttat actatgttat actatgtgtg tagtaatgaa taatgttgat   4620
gatatacttt ttgttatatt atgtatgtac atataaaata acaattaagt gaggtgtata   4680
atcactttgg aagaaatgaa atttaatgct tttgttccta tggacttaaa gaaatccata   4740
gatacggaag atgatacaaa taaatattct atcgtatctg gttgggcttc cacaccagct   4800
gttgatttgc agaatgacat tataaatcca aaaggtattg atatagaata ctttaaaaaa   4860
aatggatata ttaactacga acatcaacaa gataatgtag taggtatacc tacagataac   4920
tgttatgttg atttagaaaa aggtttattt atagaagcta agctatggaa agatgatgaa   4980
aatgttataa aaatgttaga cctagctgag aaactagaaa agtcaggtag tggtagacgt   5040
ttagggtttt ctatagaagg cgctgttaag aaacgtaaca taaatgacaa tagaattgtt   5100
```

```
gatgaactta tgattacagg ggtagcacta gtaaaaaacc cagctaatcc tgaagctaca   5160
tgggagagtt ttgttaaatc attccttact ggaacggaaa caacaccaga cacacaagta   5220
gatgcaggag ccttacgtaa agagtcatta gcaagctcta ttactaattt aacctatgta   5280
acaaaaatta aagatgttaa agagtataat gatatttgga ataatgtagt agaggactta   5340
actaaatcta ataatatggg ttatgaagaa tcagttatta cattacaatt agccaaagga   5400
ctatcaagaa aagatgctga gatagcagtt atgagtatta ataaaaaaaa tttagaatag   5460
gggattatat tatatgccta cggaattaca aaatattcta caagaatatg ataacttaga   5520
caaagaagaa gtatcaaaat ctgtagaaga gtctaaagaa gaagtaaaag aagataaaac   5580
agaagacact aaaacagaag acactaaaac agaagaaatt aaaaatgaag tagaagctac   5640
agaagagcaa gtagcagaag ctaaagaaga accacaagaa cctgcaaagg ttactgaaga   5700
agatgctaaa gaagcacatg aacaagaaga aaatctagaa gaagaagtat ctaagtcagc   5760
taaggagtcg aaagaccctg tagataaaaa agatactaaa acagaagaca aagacaacga   5820
gaaacgaaaa aataaaaaag acaaaaaaga agaaaaagat gaagaagagg aagaaaaaac   5880
atctaaatct atttctgata aagatattgt agatggtttc cgtactatct tgaaatcatt   5940
ccaagacatt aaaaaagaaa atgaacaata tgtgactaaa tcagatttag aagaagtaac   6000
taaatctatt caagctttaa ctgataaaat taattctaat gaagaagttt ctaaatcagt   6060
tgagagcaac caagaagata aagaagaagc agtagaaaaa tccgtaacga ctaataacac   6120
ttcgaatgaa caagatgtag ttggttatgt agctaaatca gtacaaacag aagaacaagc   6180
agaaactaca gaagataaag aagaacaaga agtagaagtt aaagaagaaa gtagagactt   6240
atctgtagaa gcccgtgaaa aattcatgag tacctataaa gaaaaatctc aaaacccaca   6300
tacgaatcgt tcagaagtat tgaatgctta tcaagcttac ttaaatatcc gcaacaatcc   6360
agagcaagca agtgaaaaag actttaatat tgtaaaagaa tttgctaatc tttaattaag   6420
aaacaaagtt gtgttatatt atagtgtgta aaataaaaca ataaaaaaaa gagcatatat   6480
gaaaggtgat atatataaat gaaccaaaat gaactttcaa aaaagcaaca tgcagttgct   6540
gatgaattac aagaaaaatt atcgaaatcc ttccaaactg gatatggtat cactcctgaa   6600
acacaagtgg atgcaggtgc tttacgtcgt gaaattttag acgaccaaat cactatgctt   6660
acatggggaa ataatgattt agtattttac cgtgatgttg cacgtagacc agctgaatca   6720
acagtaatta aatatgatgt tttcttacgt cacggtaaag taggtcattc tcgttttgta   6780
cgtgaaatcg gagtagcgtc agtttcagac cctaatatcc gtcaaaagac cgttacaatg   6840
aaatacattt ctgatactaa aaatatgtca ttggcatcta gtttagtaaa taacattgct   6900
gaccctggtc aaatcttgac tgaagatgct atctcagttg ttgctaaaac aattgaatgg   6960
gcttcattct atggtgatgc ttcattaact tctgaagttg gtggagaagg actagaattt   7020
gatggactag ctaaattaat tgatgctgat aacgttatcg acgctaaagg tgctcactta   7080
gatgagaaat tattaaactt agcttcagtt aaaataggta aaggttttgg tacagctaca   7140
gatgcttaca tgcctatcgg tgtacattct gactttgtta ctaatatttt aggtcgacaa   7200
atgcaattaa tgcaagacaa tagtggtaat gtaaatactg gtttcagtgt taacggattc   7260
tattcatctc gtggattcat tagattacat ggttctactg taatggaaaa tgaattaatc   7320
ctagatgaaa ctttaatccc acaaccaaat gcaccacaac cagctacagt aactgctact   7380
gtaaaaacag accaaaaagg taaatttact aaagaagaag accgtgcagg tttatcttat   7440
aaagtagttg ttcactctga tgaagctgaa tcagcaccat cagaagcaca agttgctaca   7500
```

```
gtaacaaatg ctacagatgg agtagaatta aagattactg ttaactctat gtaccaacaa   7560
agcccacaat tcgtatctat ttaccgtcaa ggtaaagaaa caggtatgta ctacttaatt   7620
aaacgtgtag cacttaaaga tgcacaagaa gatggttctt tagtattcgt tgataaaaac   7680
gaaacattac ctgaaacagc agacgtattc gttggtgaaa tgtcaccaca agtattacac   7740
ttgttcgagt tattaccaat gatgaaatta ccattagctc aaattaatgc tagtattaca   7800
tttgcagtat tatggtatgg tgctttagcg ttacgtgccc ctaaaaaatg ggctcgtatt   7860
aaaaacgtaa gttaccttgc attaaaatag taaatacaat taaaaattga atacaataga   7920
ataaggagta tacctaaggg ttgctccttt tttattacta cttatagtat acacgaaagg   7980
aatttaaaaa tcaatgttaa cttataaatt aaaaaatatt aaaatggcta ctgtacatgg   8040
tcaagtagaa gtagatgata aaggcgtagt taaaggatta actgctaaac aagaaaaaga   8100
ttttgctaat ttaccaggtt ttacacatat ggaagacaag aaaacaacaa agaaagaagt   8160
aaaacctaag gaagaaaaag aagagaagag accaattaaa aaaacaacta aaaaagaaga   8220
taagtaggtt gatagaatgg taaacagtat gtttggtggt agtttagacc cttacgaaag   8280
ctctttatca tatgagtatc cttatcaccc atctggaaac ccaaaaacata tagataaaag   8340
agaattagat agtattactc tagctgatta tggttggtca gcagatgctg tgaaagccta   8400
catgtttggt ataacagtac aaaaccccga tacaggacaa cctatgggtg atgattttta   8460
taatcatata ttagaaagag ctataggtaa agcggaaaga gctttagata tatctatttt   8520
acctgactta caacatgaaa tgagagatta ctacgaaaca gaatttaata gttatatgtt   8580
tgtacacgca tataaaaaac ctatattaca ggtagaaaat ttacaactac aatttaatgg   8640
tagacctatg tatgattatc cagctaactg gtggaaagtg gagcatttag caggtcacgt   8700
acagttattc cctacagctt taatgcagac gggtcaatct atgtcttatg atgctgtatt   8760
cagtggatat cctcaattag caggaatgta cccaccaagt ggagcaactt ttgcacctca   8820
aatgattaca ttagattata ttagtggtat gttacctaga caaagagcag gtagaactaa   8880
accatgggaa gtaccaccag aattagagca attagttatt aaatatgcac taaaagaaat   8940
ttaccaaata tggggttacg atgatattac cctgtgtgta gcgtaagttg cacattttca   9000
aaggttaact gctaagaaat cctaaagcta actaaactac aaagtaagtc gaaagactaa   9060
gcttgaatgt tgagaaatca gaaaaaatta gttagatact ctaaggttaa atcctaaaga   9120
gaagagcaat ggaagtttag catcgaaagt cctaagtcaa tagataagga atacgttcaa   9180
cgactattct gtatagacga cagaagtaaa gctccaagtg attgggagaa gaaaaatctt   9240
taccctagtc ttagggataa caaatagtct gcacacgtct tgaaaaggag tgctaggaat   9300
tgacctagac ttatttagta gcgtaagtaa ggaaacaatg ttaattaaat gaaaacttcc   9360
tattgaaatt accccaagta tatgttatat tatagatata atatataagg tggtgaaagt   9420
aaatgaaaaa aacggaaaat acattttata gaggtataac actaaaagta aaccctaccc   9480
aagaacaaga agagttaatg tggaaacatg taaaccattc tagatttatt tataattata   9540
tgttagaaag atattggaaa gctctcgata acggtaaata tatagaccat aaaaatatga   9600
tttctatatt aaaagaaata aagaatgatg ataagtatag tttcttaaat gaagtatcta   9660
gaaaaacctt agttggtaaa atagatgact taagagaaac attaataaaa tatcataatc   9720
atgaaattag aaaacctaaa tttaagtcta agaaaaggga atctaagagg tttcctatta   9780
gatatgaccg aatgcacttt aacaaagaaa aacatgttaa agttgaaaaa ttaggttact   9840
```

```
taagaatttc taatggtaca tataaaaata ataaatcagt actagagaat gaaagcatta   9900
aacctttaaa ccctaaatgt tactatgatg gtaaatattg gtatatatct ttttcaattg   9960
aagtagataa tcaatacaag aaagaaaagg ataatactaa cgaagtcata ggtatagact  10020
taggtagtgg taaaaaacac gtaatttgtt ctaacagaaa aatatatggt aatattattt  10080
attccaagaa aatgaaaagg ttagaaaaaa aattatctga cctacagaaa agattaagta  10140
ataaatatga tattaatcac accaaaacaa ataatgtttt aaagctagaa aataagatag  10200
ctaaagttta tagaaaaatg tcaaatatcc gtaaaaatca tgtacatgaa ataacaaaag  10260
aaattgttga aaagtatcct aaagagatta ttgtagagga tataagagtt cgtgatttaa  10320
taaaagacaa aggatataca ggacaaaaaa gaaaacaaat acagttttct aatttctata  10380
tgattagaca gcaattacaa tataaatgtg aagatagagg tataaaattt acagtagcta  10440
gtacttatta tccatcatca caaatatgca gtaattgcgg agaaagaaaa agaaatgctt  10500
taaaattaca gttaggtgat aaagtcttta aatgtaatgc ttgtggatat gaagaagata  10560
gggatataaa tgcaagtatt aatttaaaaa attaccataa ttcccaatgg ttaaaagaac  10620
aaaaccaata atatgtttgc ttttagtagg gttccataac ccgaatgtat aatgcccttt  10680
attttacaaa ggaagttaat ttaattaaca tatggtaatc tcattatcgg tgcaggaata  10740
gcaaacaaaa ctctagatgt agatggtatt acagaaacaa taggtactac acaatctgct  10800
atgtatggtg gagcaagtgc tcaaatacta caaattaatg aagatataaa agagctatta  10860
gctgggttaa aatcttactt tggctccaat atgataggca tatagtagga aggagatatt  10920
aaatgcaaaa accttttatg ataggtacta ataataatac ttctaatata attaataagt  10980
ctactatgta tacatctaca acacaagcag atgaacaaga acaaaagtta tctacagcta  11040
gactagagtt tgacactaag gatatgagaa gatttgtcaa tgatagaggt ataaaggtac  11100
tgtgggaaag agcttacttt tgtccttgcc ttaaccctga cacaggacat cctagagtag  11160
attgtcctag gtgtcacggt aaaggtattg cctatttacc tcctaaagag acaataatgg  11220
ctattcaatc tcaagaaaaa ggaactaaca atttagatat aggaatttta gatactggta  11280
cagctatagg aactacacaa ctagaaaaac gagtatctta tagagacagg tttactgttc  11340
ctgaagtatt gatgccacaa caacttatat accatgttac taaagagcgt atacaaaaag  11400
gtattccttt gtattatgat gtcaaagaag taacttttat tacatctaac gatggtaatg  11460
tttatgaaga tgactataat atagagaaca atagattatt catggacgct aagtttgaaa  11520
acaaaactgt atccttaaat attttaatgg tacttagata tgtagtatca gatatattaa  11580
aagaaagtcg atatcaatat actaaattta atcaacctaa tacaaagttt gaaaatttac  11640
ctcagaagct attattaaaa agggaagacg ttattgtact acctgagcca tttaaagtta  11700
atgatggtat agaagaggac ttagagatac aggtagaaga ccctaaaaaa gaatctaaag  11760
ataatcattc aggtggtttc tttggaggaa tgctataatg cctataaaag caactagacc  11820
taagttattt agagacacga actataaaaa tataggtaag agaacagtag atgttatgcg  11880
ttctgatatt ttagatagat tacaagctac agcattacaa gtagataatg taagtgtcaa  11940
acgcatgcct acttatctac aaataactga gaaaaagcta gagaagcaag gtgtaataga  12000
ccttaagaaa gcttttgctc attcacctaa aaagaaaagg actaaagatg gtggttggta  12060
tctaacggtg cctataagaa taaaaacaag taagatgaat aataaaacat accaagactt  12120
aaggtcttta aaaatagaca gttcaagtaa ttcagtatct actcttactg attatttaga  12180
aggtagacga agtaatatta gtcacccatc actaaagcct gctagtaaat caagtagaat  12240
```

```
tactaaagta agaaatggta aaaaatctag ttactttatg tttagaacag tatctagtaa  12300
atcccctgca agttcatgga tattaaatag agataaggtt aatgaaaaca acttctctaa  12360
aacaacatta aagtatgtta gaaatcttat gaactggaag attaagaatt taatgtagaa  12420
aggttatgga agtaggatgg caataacatc agtagactca tatttactag agcaaataaa  12480
gcccagatta catacagtac taagtaattg ttatattata gatgaagttt taaaagactt  12540
tgattatcaa actagggaaa tgttcaaaga ggctttttgc ggtaagaacg caaagcacga  12600
agtaacagta gggttcaatt tccctagctt taaaaacaac tacgaagctc attacctaat  12660
acaactagga caaggtcaag aggttaaaaa ctctttaggt agtatacaag ggtcttatct  12720
agaagcttcg ggtaacacat atagtgaaca atcagtagct aaaagagaag gtaatcgttt  12780
agtatttcat gtatctaaac ctatttctaa tgtaataaga gtagaagaca tagcgtttga  12840
ttcttacgat gatgttaaag tatcagataa cactgtatct tttaattata ctaacaatga  12900
gacttatgaa ggctacaacg caaatattgt atatgtagaa aaaacaaatg atagtaaagg  12960
gttagtaaaa ggtattacca tagaagaaca agtaacaatt gtgggtatgt cgtataatgt  13020
agatgttgct agatgtttag atgccgtatt aaaaatgata ttgatatcta tgagagacag  13080
tatagaagaa caacaaacat tccagctaca aaatcttgca tttggagata tcgcacctat  13140
attccaagac ggtgagtcat ctatctttgg tagacctact ataattaaat acacaagttc  13200
attagattta gattatacaa taacacaaga tattaataag attactttca agaataaagg  13260
agcaaaaaga taatggctaa gaaaacacct aaaggtaaaa cctttacagg ttatgtacat  13320
atagatacat ttttaaaaac agcacagacc ttgtttaata tgaaagagtc acaggtagca  13380
ggttttaaag cctacatgga aggtaaacac tacctgttca atgaaaaaga ctttattcca  13440
tttttagaaa agtatttagg tagagaatta gaaatttaat atatagatag gagaattata  13500
catggcagtt gaaccgtttc cacgaagacc tgtcactcgt ccacatgcag tcattaatgt  13560
agacagtaca ggtatcggta aatcagctag ctccagtgaa aagattttat gtttaattgg  13620
acaagctgaa ggtggtaaac ctgataccgt atatgaatta agaaactacg cacaagctaa  13680
aagactattc cgctcaggtg aattacttga tgcaattgaa ttagcttggg gttctaatcc  13740
acaatacaca gcaggtaaga tttttgctat gcgtgtagag gatgctaaac cagctacagc  13800
tgaagtaggc ggattgaaag ttacttcaca gatttatggt aacgtagcta acaacattca  13860
agtaggatta gaaaaaaata caatcagtaa ttcattacgt ttacatttaa tcttccaaga  13920
tgatagattt aatgaaacat atgataatat tggtaatatc ttcactatca aatataaagg  13980
tagtgaaagt acagctactt tttctgtaga gcacgataaa gagacacaaa aagcaaaaag  14040
attagtatta aaagctaata gcacagaagt taagtcttat gacttaacag gaggagctta  14100
cgctactact aatgccatca ttaacgatat taaccaatta cctgattttg aagctaagtt  14160
atcacctttt ggagataaga acttagagtc ttacttatta gaccctatga cagatgttaa  14220
cattaaggat aaagctgagt atgtaaaagc agtatttggt gatttagaga aacaaacagc  14280
ctataacgga cttgtttcat ttgaacgatt agtatctgaa caagcaccta aaaacgtaga  14340
agtagacgca catgaagaat ctgctactgt aacagctgtg tccccaattc aagaaatcac  14400
accttttgaa ttaacaaaac tttctggcgg tacaaatggt gaaccaccag ctacatgggc  14460
agataaaatt gaaaaatttg cacatgaagg cggatactac atggtacctc tatcatctaa  14520
acaatctgtt catgcagaag tagcttcttt tgttaaagaa cgttctgatg caggtgaacc  14580
```

-continued

```
tatgcgtgct attctaggtg gaggatttaa tgaaacgaaa gaacagttgt ttggtcgtca  14640
atcatcatta tctagcccac gagttgcttt agtagctaac tcaggtatat tcacaatgga  14700
caatggtcgt aagttacatg taccagctta tatggtagct tctgctatcg gaggtttggt  14760
aagtggttta gctataggtg agtctattac ctttaagcaa ctacgtatta ataatgtaga  14820
ccaattatat gaatcattag acttagatga gttaaatgaa aacggtatta tcaccgtaca  14880
atatgttcgt aatagagcta atacattctt tagattaaca gacgatgtta cgacatttaa  14940
tgataaaaat gaccctgtta agtcagaaat ggctgttggg gaagcaaatg acttcttatg  15000
ttctgagtta aaacttgagc ttgaaaataa ctttattggt actcgtacta tcaatacaag  15060
tgcttcaatt atcaaagact ttgtacagtc attcttagga cgcaagaaac gagataacga  15120
aattcaagac ttcccacctg aagacgtaca agttattgtc gagggtaatg aagctagaat  15180
ttcaatggtt gtataccta tcagaagctt caagaaaatt tctgttagct tggtatacca  15240
acaacaaaca ttaagagcct aaactaggac aaggagtacc tagtttaggt actcctatta  15300
aatttaatag gagagtgaat taatatggct tcagaggcta agcagtctgt ccatactggt  15360
aataccgtta tgctaatggt aaaaggtaaa ccagttggaa gagcacaatc tgctaaaggt  15420
caacgtgaat acggaactac tggtgtatac gaaattggta gtattatgcc acaagagcat  15480
gtttacttaa aatatgctgg tacaattaca ctagaacgtt tacgtatgaa aaaagaaaac  15540
ttcgcagatt taggatatgc ttcacttggt gaagagattc ttaagaaaga tattattgat  15600
atcttagtag tagataactt aacgaaacaa gttattattt catatcatgg tttaattaaa  15660
cagacccctt gtacagtgat gtgcattgaa taatacctta aattgctaga acaccgtaaa  15720
gctaactaaa ctacaaagta agtcgaaaga ctaagcttga atgttgagaa atcagaaaaa  15780
attagttaga tggtataagg ttaaatccta agtactacat aattggtaat tagcatccaa  15840
gctcctgtaa aatggagaag gttcaacgac tataataggt aagtcttagt tacatattaa  15900
gattatggca tagtctagtc ccttaaaata tatcgaaaga tagggtataa acggttcagc  15960
aaacaactac aacgagactt ggcagacaaa tgaaattgta acagaagaaa ttgagtttag  16020
ctacctttaa ctaatagagg ctatgtttgg tgacaagcat agaaaacact ttaaattgcg  16080
tgaaagtctt aaagactaga taactacaaa gtaacctgaa agggtaagct tgaatgttga  16140
gaaatcagaa aaaatatcta gtatagtata aggttaaacc ctaagtacag taaaatagat  16200
gatacgcagg caagcctacg agagtgggaa gcttcaacga ctataataag tgagtcttag  16260
ttacacatta agattatggt atagtctact ccctttaaaa tatatcgaaa gatagggtat  16320
agaggacagc atcagataag gctagaactt aaatttcgta ttaagaccta acaataaaag  16380
ttaggtcttt ttttatactt gttttattag aagtactgta ttataattaa aaataaaagg  16440
aggtgtacta aatgacaaac aggaaaacaa taggtaaagt aagtaattca agggcaacat  16500
ggaaaattaa accaacaaca agaattaaaa aagataaaac aaaatattct agaaaaaata  16560
agcataaagg tattgacaat tataaataac tgtaatacta tagttatata aggagatgat  16620
gaactgtgaa aactttttat tcaggtagaa gaacaacaag taaaaacagg caagtaaaga  16680
agcattataa acaaatgact aatcaagaaa taattatatg taggaactta ctaaaagagg  16740
cttataataa aaataattac tttaagttaa caaatcactt caaaggtaaa tgtaagaaac  16800
cagtaaattt taaagcgttt gttcattata tacataataa gaacttagat attatagaat  16860
ataatgaaac attatacaat aacaaaatac aacgtagggt agttgttaga caccccttatg  16920
tagtaaaagt aaataataaa ttatcttacc aatatttagt tatagaagtt gaaacaggtg  16980
```

```
aagttgtaac tatgtactat aacagagtca cagataacca caaaacatta aatttaaatg  17040
attattatga taaaaattta aaaataaagt attgacataa gtaaatacat aatatatact  17100
aaggttacat taataaagag gagaataaaa aatgacaaat aaattaagag ctatccatga  17160
agaaatgaaa attgagttac ataaattccc acagaatgta gatttaacaa gtaagacaac  17220
tgctattgca atcaatcaaa ttcttgacaa gtttaaaacc ttaacggaac aagcaggtaa  17280
aatcactaaa aagtattttg agggtcaaga gattttgacg attgattttg aatattatga  17340
ctcacttcaa gattactaca tttacttact taaaaatagt gaaacaattg aacaaaggtt  17400
acaagaaatt gaaaaaagag tagctgaata tgttaagtaa tttggagtta taaccacatt  17460
atgttatact gtatgtgtat aaaaaacata agttagctgt tatattaatt atgagaaaat  17520
aataaaggat ggataaagaa ttggaaaaag aacaaaaaga tattaaagat atgacacctg  17580
aagaaattga tgaattaaaa tatcagcaac aaaaagataa agagcgtgtt attaacaaag  17640
taattaaagg tgttaatgat gtatgggaga aagaatacaa ctttgaagaa ttagatttaa  17700
aattcaaagt aaaaattaga ttacctaatg ctagagaaca aggtaatatc atggctttac  17760
gttctgcata cttaggtgga atggatgctt atcaatctga ccaagttatt aatgcttatc  17820
agatgttagc tactctacaa gaagtagggg tagaagtacc taaagaattt agagaccctg  17880
aagagattta taacctaact ccacttgcta ttatgtggga tgattggtta gactttatga  17940
cgtcctttcg ttactagtaa cgtaaagaag ttaaatgaag atatagaacg gttaggtgga  18000
ctttcacata tagctagaga gcctttatca agaaacttat gggctatcat gcgtgagttt  18060
aatgtgctac ctaccgaaca acgttttaaa gatttagatg actatcaaat agagtttatt  18120
atagctaaca tgaatttaga tacaaaagaa atgatggaag ctagagacgg taaaaactat  18180
gatatgaaag cggaagacgt agacacatca tggttcgaag cgccgacaga tgaatttgat  18240
gttgttcctg atttcttaga cttagatgat ttaaatacac aagtagataa aagtttaagt  18300
gagaaagaaa agatagaaag agatagacga gttgaagctg agttagaaga tgaaaccgag  18360
ggattaacaa ctcaacattt agctatgatg gaacacataa gacaaaaaca aaaagagctt  18420
gatgaaagtt taggtattga taacaaagaa acaacacaag aagatataaa caaagcaata  18480
gaagatgtag atgattggta catgtagggt aatggtataa caccaatacc cttatttttt  18540
gattaggtgg tgaatactgt ttggcaatga atgacgatta taggttggtc ttgactggtg  18600
atagttctag cttagaacaa agtttaaaag ctatagagat gtacatggat gcgttagagt  18660
ctaaaaacat agatgcacca ttaacaaact tcttagagaa attaaaagta atagcaaaag  18720
aagtaaaatc tgtacaaaac attatggata aacaaagtga taagtcttta atatcaccaa  18780
aagctatgga tgaggctatt agttctacac agaatgtaac taagaatata aacgacctaa  18840
agaaagcttt aaatgacata caaacagata atattacaaa gggtatagct cctgaccctg  18900
aagtagagaa agtatatagt aaacttaata agacactaaa taatacacaa acagaactag  18960
agaaagtagc atctcaaaag attggttcag actcagatat aacaaacaga ataaaagaaa  19020
tgaaaacact gaaccaagtt acagaagagt ataataaatt agtaaaagat gccagttcag  19080
ctaaggagta cacaaagcaa ctaagagcta atcgtaatat ggttagaggt catatatcta  19140
ggtctgaagg ctctaataga atgtcctatg accaaggtgc tagagtacgt tctgaattag  19200
gtaaagtaga cacttttgaa aagcaacgag aagctaacaa tagaagaata aaagaaaacc  19260
aagatagata tagaggttat agacaacaac aacaagattt agtaggcaaa agagctcgtg  19320
```

-continued

```
gtgaaataag ttctgaggat tataaaaaac aatcagcttc tattaaaatg atgattgatg  19380
aaagtgaaaa gctttctgaa gtttatagaa aaacaggtgc tgaattagac aagtcaatca  19440
actactataa aaatagtgct aaaaaacagt ttgctcagcg tgagatagaa cagcaacgag  19500
gaacaatggg taaattgttc caagatagat taccatctat tggtgcacat gctactatgg  19560
cagtaactgc tcttgcaggt ggtatgtata tgaaaggtgc ctccttatcc gaggcaaata  19620
gacctatggt aacatcatta ggacaaaatt cagataatat ggatatagac gcagtaagaa  19680
atacatatgg agatttgtca atagataata agcttggtta taattcaact gacatgctaa  19740
aaatggctac gtcatatgaa agttctatag gacataaaag cgatgcagat acgtataaag  19800
gagctaaaca gttagctgta ggtggtcgtt cattaggtat acaagaccaa gaagcttatc  19860
agcaatccat gtcacaactt atgcatacag gtggcgtaaa ctcagataat atgaaagcta  19920
tgcaagatgc tttcttaggt ggtatacgtg aatctgatat ggttggtaga caagacgagc  19980
aattaagagc tttaagtact attgccgagc agtcaggaca aggtagaaca ttatctaaag  20040
gagaaatgtc taatcttact tctctacaag ctcaagtagc gggtacaggt agtaaaggtc  20100
tacaaggtgc acaaggagct caagccttaa gtagtattga ccaaggtatt aaaaatggta  20160
tgggtaattc ttatactaga ttagcaatgg gatggggtac taagtaccaa ggattagaag  20220
gtatgcatga cttacaagca caaatggata aaggtatatc agaccctaat aacttagtta  20280
atatatttga ccaagctaat aatataggaa gtacaacaaa agaaaaacaa gccatagcta  20340
aaaaaggctt tgaaagcatg ggagctaact taacacaaga gcaaacagat gagttgtaca  20400
atctttacgc ctcaggtaaa ctatctaaag aagagttagc tagtaaagct aagagcatgg  20460
aacaagaagg ctctaaagca ggagataaaa ataaggataa gtattccgag tctaaagcag  20520
gtagaaatga ccataacaaa gctaagacag atgataaagc tgaggatatt tatgacttag  20580
ctcaacctat tagagatgtt catagtgcta tggcaagctt gccagctcct ttatacctag  20640
cttcaggagc agtacttgcc tttgtagcat ctttagctaa atctactgcc atgatggctg  20700
gtggttcttt attaggtaaa ggtcaaaaag gactaaaaga ttggtttaat aaccgtaaag  20760
gaggttcaac aggtaagact ggtggtagta aacctggtgg taatcctaac ggtggtggac  20820
gctttggagg acttaaaaac ttagctgaca ctatactagg tgataaccct agaggtggag  20880
accgaccatt taaagaccaa gcaaaaggag caggacaaac tgctaaaggc atgggtaaaa  20940
ccttgtttga tacctttgga aaaagagatt ttacttttgg tgaatatatg ggaagaacca  21000
aagacctagg taaaggtgca tggaacaaag gtaagggagc ttttggtaaa gctaaaggta  21060
aatttagcgg taaaggttct gacttaggtt ttatgtcaca agcacctact gctaacgcag  21120
gaggtcttgg taaactaggt ggtcttacaa gtaagctagg ttggattggt gcaggtctat  21180
cggcgtttga tataggtagt tctttaatac aaggagatac taaagaagct tcttctaaat  21240
ttggtaatac tataggaagt attatagacc cgttaaattt aggctatgga gatggcttaa  21300
gagattatgc tacgaaaaca gcggaaggtt ctatgacaag tgatggttgg aaattatggt  21360
ctaatggaga taaagatggt aagaataaat tccaagactc tcctgtaggt aaactatggg  21420
gtggcataac agatttcttc acaccagata acccttctaa attagacgag acagtgaaaa  21480
ataaaaaagg taacataatt agttatatac taattgcctt gcttatagag caatctgtaa  21540
gtaccgagtg ttaactgcta tgaaactact aaagctaact aaactacaaa gtaacctgaa  21600
agggtaagct tgaatgttga gaaatcagaa aaaattagtt agatactcta aggttaaatc  21660
ctaaggagaa gtacaatggg tgtatagcat cgaaagtcct aaagacctga aaggtctacg  21720
```

```
gaacacgttc aacgactatt ccgtataggt gacggaagta aagccacaag tgattggtgg  21780
aagaaaaata ctcaccctat actaataggg ataacaaata gtctgcgcac gtaccgaaag  21840
gtagtgtcta gaaataacta gagaatatac agtagcgtgt atatttaaac attgttaaaa  21900
tatataaata attaaaattt gtattctact tctgcatata aacctttctt attttgtaag  21960
gtaaacttgt tattaaataa atatacataa ctaatacgat aggttatata tgaaagtata  22020
ctattgttta tatgttttaa cttatggtat taatgataaa tcacaaagta aagacaggca  22080
aaaagcagaa gaaaaaagag aaaagaataa tgattctaga gaaggaaatg taacagtata  22140
ctcacatttc ttagaccatt tagcagataa cctaacaaat aaaggtagta gttctaacga  22200
cagttcatca ggaggaacac ttgactacct tgatggtaaa aactttacgg ataaagacgt  22260
aactaagcat gacttaggta aaactgctaa aggtgtaaac gccgaaatgt taaataaatg  22320
gattgagtct caagcaccta gtaattctaa aatgcgcggt ttaggtgagc tttatatgaa  22380
agcaggtaaa gagtcaggac ttgacccaag gtatttagta gcacatagtg ctgttgagac  22440
aggctgggga acatcaaatc tttccaaagg aggagaccct aacaaaggta actggttcgg  22500
tataggtgct tttgataaca atcctaataa tggttttaac tatggtttgg gtattgttgg  22560
tggtgctaaa tggattagag acaacttcta caacaaagga caaaagaact tacacgatat  22620
gagacacaac aatggtgttc atgaatatgc aacagcaggt aattgggata ctatgattgc  22680
cagtattatg aaaggttcag acaagttcat aggtggcgga ggtggaggca gtgatgttat  22740
gcctagacat gctctaaaaa acgaccatca accaaagaat cttaaatata acatagaagt  22800
acctaaaagt aaaaacccta atgaaacagg gaaagcaata ggtagaaaat taaaacaatt  22860
attagaatct aatttttaga atacaattat aatacttata tattttaaca aatggtataa  22920
ataataaaaa acagaaaatg tctacagaac aactaagaga aaagaataat aaatcagaaa  22980
ctaaaaactt aaaaacttac agtaacctat tagatagagc acaacaaatt atagaagatg  23040
ctaaagcgct agactcagga ggttcagaca gtagttctga ctcagggggt tcagcttccg  23100
atgtagatgg agaaggtgcg ggtaagattt acaaattcct taaaggtaaa ggtttatccg  23160
ataaccaagt aggtgccgtt atgggtaacc ttaagcaaga atcagggctt gaccctaatg  23220
caaagaacgc ctctagtggt gcttttggca ttgcacaatg gttaggtagt aggaaatcag  23280
accttgatag ctttgctaaa tctaaaggta agaagtctaa tgacttagac gcacagttag  23340
atttcttatg gaaagaaatg agttctggtc aaaatagtga tatgcttaaa aatgcaggat  23400
ggagtaaaag tggtagttta gaaaaaaata caaaagcttt tgcacaaggt tttgagcgta  23460
tgggtgctgg agaggctatg atgagtactc gagtaaataa cgctaaaagt tatgtaagca  23520
aatacggtaa gtcaggtggc ggtggcggtg gagctatacc atcatcatat acgtccgtat  23580
taagaaaccc gatacttagt agtgcttcag gaagtactgc atctcaaaat aatgtatctg  23640
tgaatgttag cattacagga acaaatgaca aaagggatgc tgaagaaata ggtaaaggca  23700
ttaagtctac ttttggagat gacttagata ttttctcaaa cacatataaa cgtaattact  23760
agggtagtat tattaagtac taccctttat ataaagaaaa aggaagtaca agtatgtata  23820
gaattagacg tcctaagata cgaatagaaa tagtaacaga tgataataca tttacattaa  23880
agtttgaaga tactaaagat tacaacggca atcaatttgc ttcaaagtta cttagttttc  23940
aaactaagaa tgctatggaa gatgatagtg ctgtattcca aataactatg gcaggggata  24000
cgtattggga taagctagta atggcaaatg atattattaa gatatatatt acgcctaata  24060
```

```
atgaccataa agataaagag ggaaaccaag agaaacttat acaagtaggt atggtatctc  24120
aagtatctaa agtaggtagt tatggtaatg accaagtaca atttagaata acaggtcaat  24180
catttgtaaa accttttatg aagtttggtt taggtgttat tcaagaggta caagctgtat  24240
taccaactgt tggttggtta gttgatggcg atggagagaa tcaggttaaa tttacaggta  24300
gttccgctaa agatgtaatg caaggtatta tacaacgatt tattccttac atgaagtaca  24360
attatacgga taaaacatac aacacattag agagttactt agattatgat gatttatcta  24420
gttgggatga gtatgaaaag ttaactgaag tttccgcttt tactaacttc gatggtacat  24480
taaaacaact tatggactta gtaactgcta gacctttttaa tgagttattc tttagaaatt  24540
cagataaaca taaaggtaaa gcacagctag tattaagaaa aactcctttt aatccaactg  24600
aatggaaagc actagaatac atagttgtac caactgatga ttttatagag gaggatgtag  24660
gtaagagtga tgtagaaacc tactctatct ttacagtaaa accagcaggt atgttaaaag  24720
aattaacagg ggatgtattc tctaaacctc aatttcacca agaattagta gatagatacg  24780
ggtattctaa atatgaaaca gaaaacctat acataggaac taagagtggt agtgctacag  24840
aagatagtga aactacaggt ggagataacg gtcatgaacg agtaacttat gacagactac  24900
ttaaagattt aaataactat ggtagagagt ccatatctaa aggattagat aaatactcta  24960
gtaagatatc atcaaagtac aacaatatta ctaaacctga agtaaagagt attttagagt  25020
cttacataaa aaaaggtaat ttaagtaaag aagattatga aaagataaca aagaataata  25080
cttcaagaga atcagtatct gatactagac caaagttaac aaaagaaaaa ttaaagtcta  25140
tattagcgga aaagtttaat aaaaaagaaa cttttgatga taaagattta aataagaaaa  25200
caacaaaagc tgtaatagat gatattacaa agaattataa atatggtaat cctgcacatg  25260
ctaagaaact actagaggat tacactagat ttaaaggcaa cccacctaca agtaccacag  25320
gtgatattta tgataagtat cttaaagccg tagaaggagt agctaatgtt gctagagata  25380
caggttctga cgcaagtgat gaccctttaa ttatatttac taaaatgcta tttaattggt  25440
atcactcaaa ccctaatttt tatgcaggta atattgttgt attaggtgac cctaagtatg  25500
acctaggtaa acggttattt ataaaagata aacaacgagg ggatatatgg gagttttaca  25560
tagagtccat agaacataag tttgattata aacaaggata ctttactaca ataggagtaa  25620
caagaggact aaaagatgct attataaaag atggtgaagg aagcaaacat aggtttaaag  25680
gactatggaa tcagtcatct gactttatgg gtggtcttat gggtgaagag acatctaaag  25740
aattaaaaga aaaaggtgta gccgagaaga aaacaaaagg aaataaagat ggagattctg  25800
acggaggcgc acaagatgga ggtaccttag cttcactaga aaaatataat ggtaagttgc  25860
ctaaacacga cccaaatttt gttcaaccag gaaacaggca ttacaaatat caatgtacat  25920
ggtatgctta taatagacgt ggtgagttag gtattcctgt tccgttatgg ggagacgcgg  25980
cggattggat tggcggtgct aaaagtgctg gttatagtgt aggtagaaca cctaaacaag  26040
gagcttgtgt tatatggcag agaggcgctc ctggcggaag ccctcagtat ggacatgttg  26100
cttttgtaga aaaagtatta gacggtggcg ctagtatatt tatatcagaa cataattatg  26160
caactcctaa tggctatggt acaagaacaa tagacatgag ttcagcaata ggtaaaggtg  26220
ctcaatttat atatgataaa ggataattga tatggcaacg gataaacaag ttaaagatgt  26280
tatagataaa tttatagata atcttttcaa ttttgaagta ttaaccaaag aaaaggttga  26340
agaaaaagat agagaagtta aaaagataac tacagaagac gtatacaata aagttgttta  26400
tattagacca tatgtaggtg ttatacaaag tataacacct agacaggtaa catatgatag  26460
```

```
ttttactaat aatggtacag atatagaagc taaactcaca tttagaaaaa taagttatac  26520
tacagataat ctcacagtac ctactgatgc attatcaact tgtatggtgc atatggtaga  26580
aagaaatggt gtacttgtta tagattactt tgatgagtta cagaacatac tgtatggtag  26640
ctacatggag aatgagcata tatttgatga agatgttcca gttagtacat tagtaacatt  26700
agacttgaaa gagaatttaa ataattataa acatatacaa tatatgttta aagggaatac  26760
ggataaaaat ccttttgaaa gtaaggatat agtaccttta gatacataca acttattata  26820
ttggatgtat aaaaagagaa atgtagagct aaaaaatcca ttaacagtta actacttctt  26880
cacaggtaaa agcttctata ccatatttgg taaaggacac aaatataaag ttggtattga  26940
caaattcaaa ataggtgata tactattctt tggacgtagt gatgataata tagggatata  27000
catgggagat aagaagttta tttctcttat gggtacattt cctaaagata acacctctat  27060
tagtacctat gagttagacg attattggga tgactttaat ggtagggtta tgaggtttga  27120
tgaggatgat atagcatggt agtaagatta caatcttctt taggtagaag tttaaaaaag  27180
atagactcag aagaacttaa tgttaaaggt ctattattag gtacagtaag caaaataaat  27240
tataagtacc aaactgtaga agttaaaata aatagtttaa cattaggaca taaccctagt  27300
gatgatggta agttagctgt tccttatcct aaagattatg taggaagaac acctgaaggt  27360
agtatgtatg gcagtaatac tttaataacg gaaggaacta ctgtactgtt aggatttatt  27420
aatgatgaca ttaattaccc tattatacta gctatctacg gtaatacaga agcaaaccaa  27480
ctcataaata cgaatccttt agagggtggt aaaatgagta atgatgatgt ttataaatat  27540
agtagtgctt tgtattctat attacctgac ctaacttata catataaaga tggtgaaggt  27600
acatctataa aaacattcaa tggtaaatct ttcttatcca ttacttcagg tgataaagaa  27660
aaacctttat cttcagactt ttatacaggt actgaatacc aagacttatt cccatcatac  27720
tatagtaaca aaaatttaat agaacctaga atacaaaagg cacctaacat gttatttaaa  27780
caccagggtc tatactttga tgatggttct gaagataatc atgttacaac tttatttatt  27840
tccgaaaaag gtgatgtaag agcttccgta ttagacaaaa gcacacaaaa aagaacaaca  27900
caagagatgt ctcatgatgg ttcttataga gttataaagc aagatgatga cctattatta  27960
gactcagcgc aagtatgggt agagtttggt ataaatgata ataatgtgtt ttatataaaa  28020
aaccctaagc atatgtttga atttaatgat aaaggtatat atttagatga taagccaatt  28080
ttagatacgt tagatgctag cattaccgag tctatagata ggcttaagga agtacagaaa  28140
gaattagatg acattaacta cttacttgag ggtgtaggta aggaaaactt agaggagtta  28200
atccaagaga ctaaaaaatc tatagaagtt tctagtaaag caagtagtga tgttacgact  28260
atgaaatctc aaatatctaa tgtaagtagt agagctgagg gcattattac acagtttcaa  28320
gagtttagag acaaaacatt taaaggctta tatgaagatg cttctactat gataaataaa  28380
tacaaccaag aaatacctga gttaaaaagc agattgaata ctctaggtac aattacatta  28440
cctaacatta ataatacctt attagagaaa tcaagtaaga cctatgttaa taatagttct  28500
caaagtgtta gtagtaatta tctaggttca ttactgcaat tagatagtaa ccttactatt  28560
tatccgtaca cacctacacg tattatatgg aataagatag tttttaataa ttctgagttt  28620
gtaaataaga ctaaggatgc ttttgttatt ccgttaggtg tatctaaagt taaagtttct  28680
attaatctta aatgggatat attacaagat aaagtaaaaa ctattgcagt caagaagaat  28740
agtaatacat acaaaactat aaccaatggt aatacacacg ataatataat tacaaatgtt  28800
```

```
atacctgtta aacaaggaga tacattcaca gtagaagtac aacaagataa tgatattaac  28860
cttacattac tacaagataa tacaatgttt agtatagaag tattagaaac tactttagca  28920
cctactaaca ctgagttatt aggtacagta tccgaacaaa cagataagca actacaaaca  28980
cttgtaaatt ctaatgttga tttattgagt ttgacaacac aagttactaa agataatcag  29040
ttagtctgtc ttaatgattc taaattagat actataacaa caggtaaagg taatgtgtct  29100
gattacactc tacaacaaat aaagtcattt tcttctaaga gtggagaaag tattttatct  29160
ttagaagaag tattaactaa atataaaaat tctgttagat acagtattaa tttaccaact  29220
actgcaaaca tagtagaact actgaaaaaa tataatttaa ttggtataag agcacctagg  29280
aatcaagtgt atttgaaagt taaagattta acaatcacac aagaaatatt aaataatttt  29340
tctaacttac cagtattata taatacttcc tatctaacaa gtacagatat taacaaaggt  29400
atatatacaa atatatacgg agtactacta ccatatacta gcatcactca agatacagta  29460
aatacagcac ataataataa cctatctata tatgctagtg gtgatatgac aagtgatatt  29520
ataaataagc ttattttata tggtatagat ggtgtagaaa caaataaaat attagagttt  29580
aaaaaagttt aaaagtccta ttaatagggc tttttatat atgtcatgtt atattaaact  29640
tgagaaagta gttgtattta aatcctatat atgatataat acgatataga aaggtggtaa  29700
gttatgcctc aatcagatgg aaagaataca ataagacgta ttgcattacg ttttccaaca  29760
gcaagcggta aatataatat gtaccgtttc aaagtaaacc ctgaaagtta tgaaatagat  29820
gcaccacaaa gaacatctat aactaaaact aaatcagaca ttattgttga agactacggt  29880
aaagatatag agacaataac tttttctggt actactggat ttagacctgt aaaagaagta  29940
gatggtacta aaacaggaaa acaaaaaata gaggaactac aagaacaagt agaagcatat  30000
gctaagcagg gtggagatgg tagcgtagca ggagcttata tagagttcta taactttact  30060
gatgataaat attacaaagt acatctagca ccgcaaggtt taaaaataac aaggtctaaa  30120
gatgaatcct tgttatatag atatgaaata actttagttg tgataggtaa ccttgctgaa  30180
gcagatagag gttccgtaac atctgctgag tttggtaatg taaaacctaa tgctaaacaa  30240
agagttgatg agggtgttaa tgatttagat agtaacgcac gaaaaacaag aaacaaaaat  30300
aatcaaatag tatcacaatt tgaaaataaa agcagtcaaa gctcttctaa ttctagtagt  30360
agcggttcac gatatggaac ggcaggaaca ttaagaggag gtagtggcat aagaacaggt  30420
ggttctgagg gtaatagaga cggtatgagt aatataggta tatataaccc tagacagaat  30480
actaacggtc ttagtagtac tgttgatgat atggcactta aaataggata cggtgatgga  30540
ggtgtatcta ggtaatgaat aattatatac ctcaaccaca aggactatta aggtttttaa  30600
atggattaga gttagacatg tcttacacac atatgaactt attagatgag gaagtacctt  30660
ttgtttctaa attctataca ccacaaatac aactaagtga acttgcaaga ataaaattaa  30720
aagagattaa gtctactgat atccctactt tagaaagaac atttaacaac aatacaatag  30780
ttaataaagt agaacaaaca agtttaaagt tacaatcacc tagaatgtat ttaattatgc  30840
aatctatcgt aatggaagct tacgctattg taaactgctt tgtagaaagt cctgaatact  30900
taaaatattt aacagaaaaa gatgtatcta tagtaagaag taatgttaac tacgtagctg  30960
actacttaag tgattatgaa gaatacaata gtattgttct cgatttaaga gacttagact  31020
tatgttttgg ctctttggaa ttacaactac cactaattaa gagtgaggtg gtataatgag  31080
atttagaaag catgaagtcc aaccagaaga aaccttacaa gctatatcac aaaggtatta  31140
tggtgatgtt agttactggt tagatttaat agaacataac aacttacaat atccttatat  31200
```

```
tgtagataca gatgaagaaa agaaaaagaa ccccgagcat ttaataacta aaggtgatat  31260
tattattata cctttagatg ctgagttaac agactcggtt tctaaagaaa taacatcaag  31320
agacaaagat gtattagtag aattagcttt aggtagagac ctaaatatga cggataataa  31380
agagtatata gacgctcatg gaacagatga tgaaatatta gccctatctt cagatggtag  31440
aggagacctt gatatagtta aaggcataga taatattaag caatctttaa gagctagact  31500
attgacacct aaaggttctt tattattaca tcctgaatat ggttctaaca ttcataattt  31560
atttggttta aatatacctg aacaagctac gttaattgaa gtagatgtat taaagactct  31620
aacatcagat agtagagtta aatcatctaa cttaaaaggt tgggagataa aaggtaatga  31680
atactatggg tcatttaatg tagaaatcaa gtccgtagaa gaatctatag actttgtatt  31740
aggtcaagat gattcaggtg tctttgcttt atttgactaa gaaaggaaat ttatatgaga  31800
acaagaaagt taacacagat attatctagg ttaatggata agacgataca aggtacaagc  31860
aaaataacag actttacacc tggttcagct gtacgctctc ttttagaagc agtagcttta  31920
gaaatagaac agtattatat attaacaaga gaaaacatta attggggcat tcaagaaggg  31980
attattgaag cttttgattt tcaaaaaaga aaagctaagc gtgcttatgg taatgtaaac  32040
attcaatttt accaaccttt agacatgaga atgtatatac ctgcaggtac tacattctca  32100
tctactaggc aagaataccc tcaacaattt gaaacactag ttgattacta tgctgaagaa  32160
ggaaccactg aaattacagt agaagtttat tgtaaagaag ttggtattgt aggtaatata  32220
cctgaagata tcattaatac aatagcctca ggctctagtt tagttcgtac aattacaaac  32280
ccgacttcct ttaatacagg aacaaaagaa gaatctcaag aggattttaa acgtaggttc  32340
catatgtttg tagaatcgag aggaagagct actaataaat ctattagata tggtacatta  32400
caagtacctg atgttgatgg tgtttatgtt tatgaagaag taggtcatgt tactgtatat  32460
gcgcatgata aaaacggaaa tttatctgct actctaaaaa atgacataat aacggcatta  32520
gaagattaca gacctagtgg tataaaatta gatgttgtag gcgtagagaa agaggaaata  32580
gatgtgtctg cagtagtaac aatatctaat aaagctagga taggtgacac attacaaaga  32640
catattgaaa gtgttattag agggtatcta aatagtttga ctacttctga tgacttaatt  32700
attaacgatt taattcaagc tattatgaat atagatgata atttaattta tgatgtagca  32760
tttaagaatt tatctacaaa tatagaagta tcttcgaaag gtattattag agcaggagat  32820
attaaggtag aattaatata gggggtaaac aatggctaat tttttaagaa acttacaccc  32880
tttattaaga agaaataaga ataataaaga taaccaagac cctaactatg ctttaataac  32940
agcacttaat gatgagatga acaatataga gttagacacc attaaaagca aacttcaatc  33000
atcattaaaa actgccacag gagattactt agataagttt ggggattggt ttggtgtata  33060
cagaagaata aatgagaatg atgacagcta tagaaaaaga attataaaat acttattatt  33120
gaaaagaggt actaataatg ctatcattag tgctattaaa gactacttag ataatgagaa  33180
tataaatgtt agtgtatatg aaccttttaa aaatatattc tataccaata aatcaaaatt  33240
aaatggtgaa gattatttaa tgggttatta ttatagattt gctgtgataa atgtttctgt  33300
tgatggctac tttcctttag agattataga tgtaataaat gaatttaaac ccgcaggtgt  33360
taagttatat ttaacttatg atggtgctac taccataaag ggtgatggtg ttgttaaatg  33420
gcttaaaaat ctacctaaga ttgaaacata tatggattta gatagattat taggttatga  33480
tgaaactttc tatggacatt taaacatggg tgaagcaaca gctgaacaat ctgataaaac  33540
```

```
aaggttcaga acaaataaga gtacattaaa tagtgaagat attctatcag gctcttctaa  33600
tattggacgt agatttataa attatgctta tgttacgaca tatgcatatg aacctactag  33660
tacatcagcc gtcacacata tagcttcttt aaatgataaa ggaaaagaac cacctttaga  33720
ttattactta tatacatcct taaagaatac taatgatata aatatatcaa tggaaacttc  33780
ttacggtgta tcttatttat acaataactt taatgtaggg gagtttatca gtagatacaa  33840
acctaatata gatataacta gagataatgc taaaaaacaa atatccgatt ttgtaggga  33900
actaacaatt gatttctttg caaaagcttt agtttcacct gatgaatcat tacctattaa  33960
gttacaaata tttgattttc gtactaatga atggttaact gtatcagaaa cagaactatc  34020
tttttacgag aaaaacatag gtgtaaacat aggttatata agagattact taaatgatga  34080
ccttaattta tttacaagat tagaggttaa tataggtaaa gatgagcaaa aagatataag  34140
tattaactac atggatttac atttttataa ttataaaaaa gatgtgtata ctatcaaacc  34200
ttttaaggca ctagttgaaa actacataga tttgactaaa gatacttata ttgaaggctt  34260
taaagtagcc tcattattaa atggagacat aattaataaa aatggatacc aacccataaa  34320
atatttaagg ttacatgcta cttatgattc aactaaacct attgtaagta ttacaggtaa  34380
aaacagcaat aatgaggtac aaaataatac acctatagat ttatataaaa atgcaactaa  34440
tagaaactta ttgcaatcat ataaaggtga tagtagtata ttcaaggatg ttgtaagcac  34500
aaaagagttt tatatctcat catgggctga caccttatat aactcaacgt atttatctaa  34560
agtactagaa ccacaaaaat tatatacttt gtcattcgag atggaaatca cagatgctaa  34620
tatggactta aaaacatatt ctgacaatca tggtatatat ttatatagta gtactaaagg  34680
tattgttgct aatggtgtta aaagcatgca aagaaagata ggtaataaga ttgatgtatc  34740
taccacattt acagcaccta caattacaga ccatagactt gttgtttaca caggtagata  34800
tacagcagat ggtactgcct ctaaaacacc tattgcttct aatacggtaa aagtaacaaa  34860
ccttcaacta aaagaaggag ctactaagaa ggactacacg gtagcacctg aagatgtaac  34920
taatgttata gacaaagcta ttgtgtttga taacatatta acagatatac aaacaatagg  34980
aataaataca acaacacctc ttagaaatat tgagctaagt tattcttact atggggataa  35040
ttggacaaac ctaaaaacaa taagtaattt aagtcaaggt gaaacaataa cacctaataa  35100
cctagtagat ttatatggct tagaaacaat agattattca agtattacac ctttctctag  35160
ggttatactt aaaactatat ggaatgctaa cctgaataat ttaacaaata aaaaaggtag  35220
tatttctaac atgagtaata actatttcaa tgctgtgtgg caagaggtag atatgatata  35280
taacactaca ttaagtagca tgagcatact tactgatagt gaaggtaatg tatttgatag  35340
ttcaacagga caggtaataa aattagcacc taagatatac caaggatata ctgatgtaga  35400
tagattgcta acgtctacta ctctatataa cgagaatatt acattaggtt caaatagatt  35460
tatttatgac ttacgggata tgttactatc aagtgataca ttcacagtag ataataaaat  35520
taaagtaata gatacataca cagaagtaca gtaaagatat tgacaataaa gtattaatat  35580
gatatagtaa ggtatgcgta ttatagtata ccttgttata ttaatacaga atactagaca  35640
tgaaaggaat aaaaaatatg gctatagcaa caaatgcttc acatgtagaa ttagctaaat  35700
acattgtaag taaggctgac tctatttatt taacaattgg taaaagtaca gcgtggtcta  35760
atgaaacaag tccacctcaa cctgaagaaa cagcaacatc attacaagaa gttatcggat  35820
ataaaaaagc aactaaggta gcattagtta gacctgcaaa aacaacaggt gatgaaaata  35880
aaaaagaaat tacatatggt aataaacgat gggtagaaat tgattcagct aatgcagttg  35940
```

```
ctgaaggtgc taagtgggtg tacttagaaa gtagtattgt tggggatgaa ttacccttag  36000
gtacatatag acaagtagga tttgttatgg atttgttagc taaagataat atttctaaat  36060
ttaacttact acctagtgaa gtgcaatcta caggaacctt attattttat gataataaac  36120
aattccaaaa tagaagtgaa caaacaactg taaaagagcg ctttatcatt gaagtttaaa  36180
aaggagaatt gaatatatat ggcaattaat tttaaaagtt ctccatactt agatagattt  36240
gaccctacaa aagatagaac aagagtacta tttaatccag atagaccact acaacaatca  36300
gaactaaatg aaatgcagtc tattgaacaa tattacttaa aaaatttagg ggattctatt  36360
tttaaagatg gagataaaca atcaggatta ggttttacat taactaaaga taatgtacta  36420
caagttaatc caggttatgt gtatataaat ggtaagatac gttactatag tagtgaagac  36480
actgttaaga ttacgggtgt aggtaaagaa acagtaggta ttaaactaac agaaagaatt  36540
attacacctg atgaagatag tagcttatta gaccaaacaa gcggagttcc tagttatttt  36600
tctaagggtg cagaccgttt agaagagaag ttatttttaa cagtcaatga ccctacttct  36660
gctactattt atacttttat ggatggagac ctctatatcc aatctactaa tgctgagatg  36720
gataaaatca acaaagtatt agcagagcgt acttatgatg agtcgggctc atataaagtt  36780
agtggatttg agctattttc agaaggaaac gccgaagatg ataatcatgt atctgttgtt  36840
gtagatgctg gtaaggcata tgtaaaaggt tataaagtag ataaaccagt ttctaccaga  36900
attagtgtag agaagtcaag ggaattaggt aaagcagaga atgaaagtac tgtatttaat  36960
aaatcatcaa ataatattac tttagctaat acccctgtaa aagatgttca acgtgtaaca  37020
gcacaagtat tagtagataa agagcgtgtt acaagaagtt caacaggaga ttctcaagac  37080
tatttatcta ataaaacagc ttttgaagta gttagagtat ggacagaaac aagtccaggt  37140
cagacaacaa aagaatacaa acaaggagaa gactatagac ttaccgatgg tcaaacaata  37200
gactggtctc cttcaggtca agaacctaat ggaggtacat cttattatgt ttcgtataag  37260
tacaatagaa agatggaagt aggtaaagac tatgaagtat ctacagtagg tgagggagta  37320
ggtaaacgtt ggtctattaa tttcacacct gttaatggta ctaagcctat tgaccaaagt  37380
gttgtacttg tagactatac ttactactta gctcgtaaag atgctgtttt tattaataag  37440
tttggtgaca ttgctattct taaaggtgaa cctaatatta tgagattagt aacaccacct  37500
ttaaatacag accctgagaa cttacaatta ggtactgtaa cagtattacc tgattctaac  37560
gaagcagtat gtatttcata tgctattact agattatcta tggaagactt acaaaaagta  37620
aaaactagag tagataattt agagtataat caagctgtta atgctttgga tgatggcgca  37680
atggaaaaac aaaacccatt aacattacgt tctgtattta gtgaaggttt tatatcttta  37740
gataaagccg acattacaca ccctgacttt ggtattgtat ttagttttga tgatgcggag  37800
gctactttag cctataagga agctgtgaac caacctaaga ttattcaagg agacactaca  37860
gctcatgtat ggggtcgatt aatttctgct ccatttacag aagaacgtac aatttaccaa  37920
gggcaagcat cagaaacctt aaatgtaaac ccatacaaca taccaaataa acaaggtgta  37980
ttaaaattaa ctcctagtga agataactgg atagatactc aaaatgtaac aatcacagaa  38040
cagaaaacta aaaaagtaac aatgaaaaga ttctggagac ataatgaaag ttattatgga  38100
gaaacagaac attacttata ttctaactta cagttagata aaggacaaga gtggaaaggt  38160
aagtcatacg catatgatag agaacatggt agaacaggta ctctattaga ggctggagga  38220
cagcgtacac ttgaagaaat gattgaattt attcgtgttc gtgacgtatc tttcgaagtt  38280
```

```
aatggtttaa atcctaatga taataatttg tatattttat ttgatggtgt tcgttgtgct  38340
attacaccag caacaggtta tagaaaaggt tctgaagatg gtacaattat gtctgatgct  38400
aaaggcacag ctaaaggtac atttacaatt ccagcaggta ttcgttgcgg taatagagaa  38460
gtaacattga aaaatgctaa ctctacaagt gctacaacat atacagctca aggacgtaag  38520
aagactgtac aagatgttat tatcaaaaca cgtgttacag taaacttagt agacccatta  38580
gcacaatcat tccagtatga tgaaagtaga actattagtt ctttaggttt atactttgct  38640
agtaaaggag ataagtctag taatgtaact gtacaaattc gtggtatggg agatacaggt  38700
taccctaaca agacggtata cgctgaaaca gtaatcaact cagatgatat taaagtatct  38760
aataatgcta gtgctgaaac tagagtatac tttgatgacc ctatgatggc tgaagcaggt  38820
aaagagtatg ctattgtcat tattacagaa aatagtgatt atactatgtg ggtcggaaca  38880
agaacaaaac ctaagattga taaacctaat gaagttatta gtggtaatcc atatgtacaa  38940
ggcgttctat ttagttcatc taacgctagt acttggactc cacaccaaaa ttcagattta  39000
aaatttggtg tatatacttc taagtttaat gaaacagcta caattgaatt tgaacctatt  39060
aagaatgtat cagcggatag attagtttta atgtctacgt acttaactcc tgaaagaaca  39120
ggatgtactt gggaaattaa aatgatttta gatgacatgg ctacatctac tacatttgac  39180
caattaaaat gggaacctat tggtaactac caagatttag aggtattagg tttagctaaa  39240
caagttaaat taaaagctac atttgagtct aataaatata tttcaccttt attaagttct  39300
aatgacttaa cgtttactac attcttaact gagttaaaag gttcctatat cggtagagct  39360
attgatatga cagaagctcc atataacaca ataagattta gttatgaagc attcttacct  39420
aagggcacta atgttattcc taaatattca gacgatgatg gtaaaacttg gaaaacattt  39480
actaagtctg ctcaagtagt taaggctaat agagacttta atagatatgt tattgatgag  39540
aaagtaaacc aatctactaa gaataacaaa ttacaagtaa gattagactt atcaactgaa  39600
aatagtttct taagacctcg tgtacgtaga cttatggtta caacaagaga tgagtaagtt  39660
taaagagggt ttcataccct ctttttattt aactaaggaa gtgatattat gcctacagaa  39720
tatagagacc cttactcaca agctaaactc tttattccta ctgtagaaga aaaagctata  39780
aaagaaatgg aacaaacata taaagataaa ctacaagaag ttaatgagct tattgatgag  39840
cttaaaaaat tgaaaggtga ttacacacat gacgtttaac tacacacctc taacagaatc  39900
acaaagatta aaggatatgt accctaaagt aaatgaaatg ggtaaatact taaaagaaga  39960
agttaactta tctgatttaa aaacgattag ttatcctgac ttaaataatg ttctaaattt  40020
catacaagac tcaggtgact actttgtaac acaagccaga aacaccccac aaggtgtaag  40080
tactacgggg tttttacact tagataaaaa gggtagtact tattataagt tatattatgc  40140
cccatctaac acaaataaat tgtttgtgaa aacttattat aatggtactg tctatgattg  40200
ggttagtttt aaactagatg aaggtacact atacgattca ggaaatacaa ttaatgtaaa  40260
agatttaaca gagtctacaa ctcaatttgc aacactcata aatcctccta aaagtaattt  40320
aaacacagga tggataaatt ataaggaaag taaaaatggt acctcagctt tagctgagtt  40380
taatcctatt aattctactt caacatttaa aatgattaga aagttaccac gccaagacca  40440
acaacctaac ttgttaaggg atagtttatt cacattacca atgacggatg tagctaatat  40500
aagaacgtat tatatagata atacatcttt ttgggggttt actaataatg catctacctc  40560
aacagttaga tatatgggtg aaaatactat tcaattagat gatgggggg aatcatatcc  40620
tactgttata tctaaacgtt ttagattagg gaatgattta tatgtaggtg atacagttac  40680
```

```
aatgtctgta taccttaaag taaatgacac tagtttatta aatggtaact tcccttactt  40740
tgaaatagcg ggttatgata atgtatctca aacaaataac ccttacacag gaggaaggag  40800
agaagttaat tactatgagt tatctacaga atggaaaaaa ttctcattta cttttacatt  40860
gcagtattat aaccaagagg ctagcagtga cactgttaat tatatatcag cattattaag  40920
atttaactgt tctaactcta aaaataatgg tgctattgta tattatgcac taccaaaatt  40980
agaaaaatcg tactcggtaa ctccatttat tacaaatact tatgataaaa gaaaatatga  41040
tgagatatgg agcaattgga tagagacaac aagcaaggat gaacttcaaa cacatagtgc  41100
tgtagatacg tacaacaatg actactacaa atatgtatgg aattatcaaa acgcaaacgg  41160
tagaagttta caacaattag caatgtctgt acctcaaggt ttttatactt tttattgtga  41220
tagttctata agtggaacac ctaacaataa aactatacaa ggtacgatac aagtagcata  41280
taagaataat aatataaata ctacaaataa aataatacaa atggatttta gtgaccctaa  41340
aggtaaaaga tattctttaa catataataa agatactaat ggttggcaag atatgaaaat  41400
tcaaatgtct agtaatagtc tttgggaagg tactcttgac ttagcttcag gtaatacagt  41460
aaacttatcc tcttcattag ataattatga ttttattgaa gtagtatact ggactagaag  41520
ttctggacat aatacaacta aaaggtaccc agcaagtaca tctagtattg taattagaga  41580
ttttaactta gtaaatgatg gttctaatgc tagtgtagac ttttttgaag ggtattgtga  41640
cattacagat agagtgaatg ttactgctaa aatgtcaaaa acaaatacaa tagatgggaa  41700
tagaaatact atgtctgttg ctcagtttaa tcaaactggt catattgaag tattaagagt  41760
tgtaggacta acgtatattt aataaggagt tttgtaaatg ataaaaatatg atattagtaa  41820
agatgaaatt gtgttacatt tagaagatag taagtatatc atgggttaca ctattgttgg  41880
agggtatgat gagaacaacg gtgacgtaaa aatttctagg tcaattcttc ctgacgggtt  41940
ttttactgag tttgttagta ctaagtatgt atactataag aatactaacg aagtaatata  42000
taacaaaaat tttaaggata atgctaagag tattgaagat gctgattacc aaccacctaa  42060
agagtatgtt cctaaagaag attataaaaa gctagaaagt gaagtagaag aattaaaaag  42120
aatgctacaa gaattgttat ctaagaaagg ataaataata tggcactaaa ttttacacct  42180
attacagaaa atagtacaat agcagattta acaaaacaag ttaataatat aggtggtgta  42240
ctaactgagg acagaaatgt ctttgaagta acaacagact tacaagcaga tgtaagtaga  42300
acacagaaag ttaagttaac aacagataga gggttagcta aagatattga ttatactaat  42360
tacttaagag atattagaaa ggtaggtcta tattatatag gagctcgtac attagctact  42420
atgtatgata aacctgatat ggaaaacatg gatgtactac ttcaagtact aaccttagat  42480
actgaggata gagtagtaca gatattacat acattatcta ccgctgattc taaagtaaaa  42540
gtactatata ggtttgttaa caattatcaa acatcacaat ggcaagtagt acaaagtcta  42600
ccaaataata aatacacatc tcaaataggt ggaagtcctt ttgatattaa cacacaaggt  42660
atatattatg tgtctagtat gtcggatatg ccaaatggtg tatatgaagg gtttttacag  42720
gttattatag acaataatga aaatagaatg ttaagattaa cggatattag cacaggaaaa  42780
gaatatctta atgttaaaaa atcgtatggt agctggggca catggaaaac tgatttagat  42840
gtacaaaaaa taagtaagta tttattatct aatgtagatg gtgatgctga aagtaataac  42900
tactctttat ctgtatatac tacagacaac ataacatttc aacaggcaat agctaaacat  42960
attgaagaaa caagtaaaac tgtttttact ttttatatac aaggaggtgt tgtagggtct  43020
```

```
ccgtcctcgg ttagttgtag aggtgtattc atatcagatt caactaactt tactaatcta  43080
tatggtgttt atactgctat aggtactgat ggaagaacta ttaatggttc tgtaaatggt  43140
aatgtgtgga acacaacaaa aacactacca ggatttaaag agctgtggaa tggtgcacat  43200
aactttaaag atacaaataa aaaagaaacc atgtctgatt ctatatctaa ctaccagtat  43260
gtagaagtat acacaagata tagagctcta caaaatacaa aaggtactga taaaacaggt  43320
acactatgtc ataagttcta tatagacgga gacggtattt acacatgttc aggagcttat  43380
gtatcaggag actctaatat tggagtagag tattatagag taacactatc tattagtggt  43440
gatacttgga caattaaaga tagtgcagta aataataata aagaccaata tgttacacgt  43500
gttgtaggta tctctttacc atagactagg ataattccta gtcttttttt cttgactaac  43560
tttaataaat atggtaagat aataaaggac taaaaagaaa ggagaatata tgcagttaag  43620
acaacagaat atatatacat atgtagattt tgacgaaagt gatgggtata ttaaagatat  43680
catacttaag cgtgttcata aaacattagg agctaaaaaa gatggttatc aacatagctt  43740
agcttttaaa cgaggtgtgt gggatggtta tgtagatttc tatgattatt ctgagaacaa  43800
attccccagt gggttgttac ctaagatgat aacattacta ggtgagttac aatcaagaca  43860
taactttcaa tacgaaatta ttgatgaaaa atctgaaagc tttttagctg aagaagatat  43920
tgatgatgaa atacaactac tagataataa cgtaggtaag attacattac gtgactatca  43980
gtacgaagct gtatttaata gtctagtcaa ttataatggt atatgtaagc aagctactaa  44040
tgcaggtaaa ttttgcccct tatagtagaa atattataag tgtgactcct ttaattcatg  44100
ggaactctct catttgagac aatcatgagc caagcctata aataggaagg tgcaacgact  44160
attatgtaca tccaagtgga tggaaacggg gagaacctaa gtctcattag atatggttaa  44220
gatatagtct gaactttgta ggagactaca agaaggttag gagtaacgaa cctaaccgta  44280
acaaaattga aaacagaggt tgctagcggt atcatagacc aactattacc acaactagaa  44340
aaaggagagc gtgtagcttt ctttacaagc tctaccgaga tttttaatca atctgctgac  44400
cgtttaagtg aacgattgaa tataccagta ggtaaagtag gttctggtaa gtttgatgtt  44460
aaacaagtaa ctgtagttat gattcctact gttaactcta acttaaaaga ccctacagaa  44520
ggagtaaaag tatctgctaa agtaaactta agtaaaaaga tagctaaaga gatacttcct  44580
aaatttgaag gtggtaaaaa tcaaaaaagg ttacttaagt tattattaga aagtacaaca  44640
cctaaaacta aagtagagca gaatgtgctt gatatacttc aagatattta tcataattca  44700
aagacggatg ctgaagtatt aatggcatta aacaatcata atgttatttt ccaaaaagaa  44760
gtaagaaaga aaaatcaaaa gagctatgat aaatatcata aaatgcgtga gttcctagac  44820
tctatagctg taatgatagt tgatgaagca catcacagta aatcagattc atggtataca  44880
agtttaatgt cctgtgagaa tgcactatac aggatagcac taacaggctc catagacatg  44940
aaagatgagc tactatggat gcgtatgcaa gcattattcg gagatattat tgtaagaaca  45000
tctaatgagt ttttaatcga gaatggctat tcagctagac ctacaataaa tattatccct  45060
attgctaacc ctgatgatat agataatatt aaggattaca gggatgcata taataaaggt  45120
attgtacata acgagtttag aaatacactt attgcaaaac taacagctaa atggtttaat  45180
caagataaag ctacacttat tattattaac tttgttgaac atggtgagat actatccact  45240
atgttgaatg aaatgggtgt agagaatttc tttttacatg gtgaaataga gtcagatatg  45300
cgtaaacaaa agttagatga aatgcgtaat ggtaaactta aagttatgat tgctacaagc  45360
cttattgatg agggtgttga tatcagtggt attcgttcat taatcctagg tgcaggtggt  45420
```

```
aaatctttac gacaaacact acaacgtgta ggtcgtgcgt tacgtaaaaa gaaagaagat  45480
aatacaacac agatatttga ttttaatgat atgacacata agtttttata taaacattct  45540
aatgagcgta gaaaaatata tgaagaagaa aaatttgaaa ttaaagaatt aggaaagtag  45600
gtatgggtag tgactaagac agaaagaaga ttatatgatt acattgaaaa aaaatcaaaa  45660
aataatactt atcaaataac tactaaaaaa gagttagcag aagagctaga tgtctcagtc  45720
tctactttat ctaaaaacct taaaagatta gaacaggata acaaaattaa tgttgtttct  45780
aaaagaggaa ataaaggtgg tattgttata tcactagtaa gagattatga tacagatagt  45840
ctcttacatt ttaatgctac agatgataat gttattactt ctaatctaga atacgctact  45900
gaattacgaa atagattttt tcctagttac gtatatgaaa gaaaagaaaa taaacgtaga  45960
acaaaactag aaatggttca atataatgct attaaagata aaaacaggaa aataatatca  46020
aatatgaatt tttatagtag tagcttacct taccctacta aagatatttt taatatgtct  46080
tatgaccctg agggttttta taaagcttat atattatgta agttatatga ccaatatgct  46140
atagcacaca tgaatgctaa atatatacaa catttaacat tatcaaatgg taatgaagac  46200
gtagatagac ataagcattt atctgagtac tacagaaaga aaatgttaca gaatttatca  46260
cgagatagta tttgtaaaga cttctttggt agtaagacat ttaatacatt ctacaacttt  46320
tacttaaaga taaaagataa gaacattaat gtttttaaat acatgcaaaa tgtttttaag  46380
aataccacat ttgggtttga gaataaaaca caaccttacc ctatacctgc accaaatttt  46440
tttagttccg ataaatactt aactaattat gaaaattatg taaaaggtat taaacgaggt  46500
gtaaataaaa caaatagaca aattggggaa gtagagtctt taattaagtc atctgattac  46560
ttattaaatc ctgctgtagc acaattacat caactatata caacaccttt aaatgaagag  46620
atacatgata ttgatacaat gtttaaaaca gctttaaata tagaagatac tatttatggt  46680
atatttaatg gcatgaaaca tattatactt ttatcatata ataaatatat agaacatcta  46740
atagaaaaat tacctagtaa acataaaaac ttattaaata aatttattaa acaatgtatt  46800
gtaaatgagt attcacctac tacaatacct aacaatgcta gactatctat gtttttaatg  46860
caaaaagagt ataaagcaaa tatcgcagaa ttaaatggtg gtatagatag aagagactta  46920
ataggtataa gtttagtaaa cactacagac ttaagtaaac aagatattgt aaatatagaa  46980
caaacaacaa tgaattatct acatatgaga agatttactt caacatcata tattttacaa  47040
atgtatagta attacttagg ttatgaggtt aatttaaaag aagttaagtc tataattgaa  47100
aaatataatt taattgataa aataccattg acaaaagaag gtatgttgaa ctataataag  47160
gttattgata tagtaaagga tgacacatat gagtaaacga attaaggaga ttatcctaca  47220
taagtctatg aaggatatac attttgcaag agaagtacta gataagttac ctaaaagtct  47280
atttgctaca gaatcggaag acatgggtta cttattcaca gctataaaaa gaacagcaca  47340
cattgctgat aaaatgtcaa atgaatcttt agctattaaa gtagagcaat taatgggtag  47400
tgataaacaa gatgatgaaa aagtaacaca aacattaaaa tatttagata gcttatatac  47460
agtagacatg aataataaag acgattctgt aaactatgaa gtagaaaagt atattaaaac  47520
agaaatgtct aaagaagtat tagttaagtt catagctgag aataagcaag aggactcaga  47580
taacttacct gaactagtag agaaactaaa acaaatagaa gtcagtgaca ttaatggtac  47640
tgacggagaa tttattgact tttttgaaga cgtagataaa aagagagaac tattaagcaa  47700
cttaagtatt aataagtatt ctacaggttt ccattctata gaccagcaaa ttgaaggtgg  47760
```

```
tataggtaga ggggaagtag gattagttat tgcacctaca ggtagaggta agtctcttat  47820
ggcaagtaat ttaggtaaga actatgttaa acaaggttta aatgttttat atattgccct  47880
agaggaaaag atggatagaa tggtattaag agcggaacaa caaatggtag gtgtacaaaa  47940
gaatcaatta cttaatggtg acttatcttt aaacacagat gcttataata agatacaaga  48000
acactataaa aagaatagac aactgctagg taacttttat atcgttaaac atatgcctgg  48060
tgaggtaaca ccaaaccaat tagaacaaat tataattaat acaacaatta agaaagataa  48120
acatatagat gttgttatta ttgattatcc taaacttatg cgtaaccctt accttaagta  48180
tcaaagtgaa tcagatgctg gtggtcgtat ctttgaagat attcgaaaat tatcacaaga  48240
atacaatttt gtttgttgga cattagcaca aacaaacaga acagcttacg gttcagaaat  48300
tattacaagt gagcatgttg agggaagcag aaagattgtc aatgctgtag aggttgcttt  48360
tgccgttaac caaaaagatg aagaatttaa aaatggtttt ttaagattgt acttagacaa  48420
agtaagaaac agttcaaaca caggtgagag atttgttaat cttaaagtag agcctactaa  48480
aatggttgtt agagatgaaa caccagaaga ggcagaagaa cataagcaaa tactagcgga  48540
acttaatggt gaagataaaa gtagatttaa agaaaaacct aataaagctg aagctattaa  48600
taattctttt ggagggttga gtttttaatg gatgacttta ctaagcttta taaaaaagta  48660
cgtagaacat ttacacgtaa taaagcagaa tgggattata caaatacagg attaagaacc  48720
ttccaattaa aggaactaa tgtatgtgtt acattactag actctatagc aaggaataat  48780
acaacaggat ataagtacaa cgttatgtct aataaagtac ctgctatacc ttgcaataca  48840
catcaagaag taattaaagc aattgaatat aagttaaaaa attgagaaaa agccttgaca  48900
atgtatttgt taaggcttat acttttatta taaacaataa agaggtggta agatttgaac  48960
ttaaatgaag caaaagtaaa attaaaaaac tttaaagtca ttaataagca cggatttata  49020
gagactataa acacaaagta ctctgaaaag gagttagagg atgtctcaac cgatatattt  49080
aatacattag ataattacgt aatagataag tatggttgta aattgtttaa tattaagcct  49140
aaaagaagta ttatagagtt agaattaaca aacaataaaa ttaaacactt aagaaagtag  49200
gatattaata tggaattaga attaaataaa atatataacg aagattgttt agaaggtatg  49260
aagaaaatac ctgacaatag tatagactta atagtaaccg accctcctta tttaattaat  49320
tataaaacca accggagaaa aaataaagag catagatttg gaaaagttat tttaaatgat  49380
aataactaac aacttattat aaattatatt gaggagtgtt acaggatatt aaaaaacaat  49440
agcgctatgt atatgttctg ctcatcagag aaagtagatt tttttaaaca acaattagag  49500
aagaaattta aaataaaaaa tatgattata tgggtaaaaa acaatcatac agcaggagat  49560
ttaaaaggtt cttttggtag aaaatacgaa atcttatttt tagtagtaaa gggcaaaaaa  49620
cattttaatg ggagaagatt aactgatgta tgggaatttg atagggtaag tggtaaaaaa  49680
caattacacc aaaatgaaaa accattagat ttaataaaac aatgtattat gaagcatagt  49740
aataaaggag atgtggtttt agatgggttt attggtagtg gcactactgc tattgcttgt  49800
atgagtacta accgcaatta cattggtttt gaattagacg aagaatacta taatttagcc  49860
agtgaaagaa tagaaaaata taaggagata ctaaacaatg aaaatgacaa tacaggaact  49920
acaagataag actgaatttt taagacacgt aaaggtatat acggaagaag caatggatat  49980
ccttgaagat atattaagag gagagcctta cacagatgag gtatgtgaat tgatacattt  50040
ttattcaagt aagctactaa atgagattaa tgacaatcat atgtttaaat tacaggagtt  50100
tgctaatcat gatgttatag aaattagtga agagggagta aaataatgat aaaattatta  50160
```

```
cagggggatt gcttagagtt attagataca attgaagata gtagtatcga tgctattgta  50220

acagaccctt catataacat ttcaaaagaa aacagattta caactatagg tagagctggt  50280

attgattttg gagagtggga taaaaatttt gaatctactt tatggattaa taaagctata  50340

ccaaaagtta aaaaaggtgg taatatcgtt gtgttttgtg acatgagaca attcacaccc  50400

atcattaata ctatggaaga attaggctgt gaatttaaag atgttattcg tctgaaaaaa  50460

tctatcccta tgcctcgtaa tagggataga cgatttattt ttgatactga atttgctctt  50520

tattttgtta aaaaaggaga taaatggact tttaaccgtt tagatgaaaa atatgaaaga  50580

ccttgtatta aaacaagtgt aacacctaga agtgaaaagc agggcaaagg acacccaaca  50640

cagaaacctt tatatgctat ggaatggttg ttagagtgct taactaatga aggagacatt  50700

gttctagact gcttcatggg aagcggaaca acaggtgtcg catgtaaaaa gttaaataag  50760

aattttattg gttgtgaatt atcagaagaa tacttcagta tggtacaaga tagattacta  50820

aataatacaa attaaaacaa aacccttgac aacatgtttg ttaagggtta tacttttatc  50880

ataacgtact aaaggaggac actaatgaaa tttatatttt ttacagatag ccattttcat  50940

atgtttacga attatagtaa acctgatgaa gaatatggta atgatagatt taaagaacaa  51000

attgagacat tacaaaaagt atttgattta gctagagaaa ataaagctaa agttatattt  51060

ggaggagatt tattccataa gagaaatgcg gtagatacta gagtatataa taaggtattt  51120

gaaacctttg ctaagaatca agatgttaaa gtctatatgg ttagaggaaa tcatgatgct  51180

gtgtctaatt ctttatatac ggaatctagt attgatatct ttgaaacatt acctaatgtg  51240

gaagtaacta aagatttacg tagtgactca ctttctagta aagtacaatt aactatgtgt  51300

gcttatggag atgaaacaga agaaattaag gagtatatta aaaaatatta ccaaaaagat  51360

aaagtaaata tattagtagc acatttaggc gtagagaata gtttaacagg taaaggctca  51420

cacagattag aaggtgcatt tggttaccaa gacctattac cagaaaaata tgattttatt  51480

cttcttggtc actatcatag aagacaatat ttaaacaata accctaatca tatgtatggt  51540

ggttctctaa tgcaacaatc cttttcagat gaacaagaag ctaatggtgt acatttaata  51600

gatacagata agctaacatc aacgttcatt ccattagata ctagaaggtt tattacagtg  51660

caaggtgaca atgtaccaga taacatgaat gatttagtaa accaaggtca ctttattagg  51720

tttattggta ctccagaaca agctaaagta attgaattag ataaaacaga agatgaatct  51780

aatgtacaag tacaaatgaa gaaagaatac acggtagaaa agagagtcga cgctgacgtg  51840

tctgacagcc ctataacgat tacttctagc tatgcagaca aatactatcc agaagcaaaa  51900

gatgagattc tagagtgttt aaaggcggtg ctgtagtatg atagatatta ttataaagaa  51960

tattaaacca agtatatata aatctaaacc tattttacag ttcttacata ataaaagaac  52020

atatgatgta tgtaatgtta aaaatattga tgatgcgatg taccttatta acaaagtatt  52080

agaggaagct aactatgctc attattatac gaggattatt gaacaagaag attgttatat  52140

tctagattat ggttcacatc aatgtttctt taaattgtta aaagaaggtg gtacaaatgg  52200

ttaagtttaa ttatgtagag atgaataact ttttagctat tgagcatatc aagctaaatc  52260

tggataagca aggtcttgta cttattgagg gtattaataa aacaaatgat agttttgaaa  52320

gtaatggaac aagtaaaacg agcatgatat cttctattac ctatgcactg tttggaaaaa  52380

ctgagaaagg tttaaaggca gatgatgtcg ttaataagta taagaagaaa gacacctacg  52440

ttaagctttc tttcaacata ggtaaagacg agtatttaat cgaaagatac cgtaaacata  52500
```

```
aagaacacaa gaacaaggtt aagctgttct gtaataacaa agagataaca ggctctacaa  52560
atgatgttac ggatactcaa atacaagagt tatttggtat tccttttaat acatatgtaa  52620
atgctattat atatggtcaa ggagacattc caatgttttc acaagctacc gacaaaggta  52680
aaaaagaaat actagaatct attactaaga ctgatattta taagcaagcc caagaagtag  52740
ctaaagaaaa ggttaaagaa gtagaagaga aacaaagtaa agaacaacaa gaaatagaaa  52800
aactagaata taaaagaaac ctaaaacaag aacaatataa taatgaagta aataaatata  52860
ataacttatt agagcgtaag aagcaagaag aggaacagtt taatcaaaag aaacaagagt  52920
acgagaataa attaaaagat ttagacaatc agattggtgt atgtaaaggt agtattccta  52980
aagttgaaga ctttgaattt gtatttagtg aaaattatac aaaagctaac caaggtattg  53040
aaaagattaa cacaaatatt aatgataaat tattgccatt attgagtcaa gaaacaacaa  53100
ataagaatac aactctaaat ataattaatc aattaaaaca atctattaat aaactagata  53160
caaatgacca ttgtcctgtt tgtggttctc ctatagataa tacacacaaa ataaaagaaa  53220
aagaaaactt agaattacaa attaaagaag aacaagctaa aatatctcag tacgaacata  53280
atgagcaggc tataattaat aagaaagaag agctactaac taaatctaag gaactacaac  53340
aatttataca gcaagaagat atagaaaaga aaaaacatga tgatgatatt caacggcaat  53400
atagagaaca gcaagaagta tatgatgaaa ttagccaatt agaaaacact aaagctaatt  53460
taaaagaacc aacattaaat gattactctt atatagaaga acctaatgaa gaattacaca  53520
ataaagaact aaaagatact gacaatacta ttgacaaaca taaggaaaat atagtacaat  53580
tagagagtaa gaaaacaaaa tataaacaag ctgtagatgc atttagtaat aaaggattac  53640
gttctgtaat attagacttt attacaccgt tcttaaatga gaaagctaat gagtatttac  53700
aaatattagc gggttcggat atcgaaattg aatttcaaac acaagtagaa aatgctaagg  53760
gagaacttaa agataagttc gatgttattg ttaagaataa caatggaggg gagtcttaca  53820
aatctaattc agcaggagag caaaaacgta ttgacctagc tattagtttt gctatccaag  53880
acttaattat gagtaaagaa gatatatcta caaatatagc cctttacgat gaatgctttg  53940
acggactaga cactattggt tgtgagaacg tagttaaact actaaaagat agactaaaaa  54000
cagtaggtac tatttttgtt attactcata ataagagtct agcaccttta tttgagaata  54060
caattacggt agtaaaagaa aatggtgtag ctacactaag aaaggaatta aataatgaaa  54120
ctaaagatta aagataacca gtttgcatct ttaacagtaa attacacaaa caatgcaaag  54180
ttacatatag ataatattcc tgtttctact ttagtagact ggtacccttt aagtaatgca  54240
tacgagtata aagctagtaa tgactttgga tatattgaac taaagagatt acgctctagt  54300
ttacctatgt cttatggatt aacacaccga actttatata aaggtgaaac tgttaaatgt  54360
aaactaggat tatggtataa tgaaaaaata aaagaagata atgagaaaat tattgagaaa  54420
gctaagttgt acggtttacc tactatagat gaacccttca caagtaaaga tgtaaagcaa  54480
ggatttagtg acttaggtgt tattttccaa acactaaaaa caatcagtac aaacgagtac  54540
ttaaaagata aaacaattga agagattaac atctttagta agaaatcaga ggattatcaa  54600
ttaaatgaag tactcaagta cagtacaaca ctggtagatg atacttatag tgacttaagt  54660
caaatctata atatgttact attaatgaag aaaattgttt ctatatagga agtgactgaa  54720
aatgaggttt gaagactttt taagtcaaga gattggaaca cccaaagaga atactgtagg  54780
agaattacga tattgttgtc ctttttgtgg ggaacagaaa tacaagtttt atgttaaaca  54840
gtctttagac gctactaatg gtatgtatca ttgtaagaag tgtggagaac atggtaaccc  54900
```

```
tattactttt atgaagtctt attatagtat tacaggtaga caagcttttg agttactaga  54960
aacaaagaat attgatatac aattctcacc aacattagaa atatataaca cagatttaac  55020
tgaaagtgag aaattattac taaggcttaa tggatataca aaagataata gtagtataaa  55080
atcaaaagca cctgaactac ctatagggtt taaattgatt aaagataact taaataataa  55140
agaagtagta ccgtatttaa gatatcttaa gaatagaggt attacactac agcaaatcct  55200
agattacaac ataggttata ttacagatgg ttattgttat tcttatggta ttaataatga  55260
gaaaaagaaa atagtactta gaaatagtgt tatatttttt acttatgaca atgaaggtaa  55320
gtatatatac tggaatacaa gaagtattga aacaaatcca tatattaaat ctataaatgc  55380
accttctaaa cctaatgagt atggtaaaag cgatgttata tttaatttaa atatagctag  55440
taaacaaaag tttgttgtta taactgaggg tgtttttgac gcccttacat ttgataagta  55500
cggtatagct acgtttggta aacaagtttc aaagatacaa gttaataacc tcatttcaag  55560
tattcctaaa gaaacaccta tatatattat gttagacaca gacgctacag actttagtat  55620
taatttagct aataagctta tctcacattt caatgtagtg tatttagtac cacatggtaa  55680
tgaagatgct aatgatatgg gtatggaaaa agcttttagt actttgaaac acaatagatt  55740
tttagttaca cctgaaagta ttcaaagtta caagttacaa caaaagttaa aactttaatc  55800
ttgcattata atgtatagta tgttacaata catatataaa aataaaggaa gtgttatttt  55860
ggaagagaaa gatattctac attttgtaga tgagtatgtt acagcattac gtgtaggtaa  55920
tgaacagcgt atgcaccaat tagaagagtt aggtaaagaa caaacagcaa ctttaacaga  55980
tgttatgaaa gctattacta acttattgtt aggtgttaat aaacaaatgg ttgacctaga  56040
gcaaaataca gagttaaact taaacattct aattgatgct ttatacaaag ctgagttagt  56100
taacgatgac gtattaaaat atattgagga agcaattgaa gaatcaaaag aaaaggatga  56160
agaataatgg aaaaaaatat tagtacacat acaaaaggta tttcacaaaa agatatggac  56220
atgtggttag aagctattac acaaggaaca gtagaaggca aggaattaac tgaggacact  56280
gctaagcaat tacatcgtat tggagcacgt agtgtatcgt tagatgaggc tactagaatt  56340
gcacgagcaa ttaatgccgt tacagttcaa gagtatgcat ctgcctttaa tgatgctttt  56400
aatgctattg atttgttaat gattgttatg gaagataact tagatgtaac tactgagcaa  56460
gtagagaagg cgcaacttaa attaaaagaa aaacgtgaaa agtatttaga agaaaaacaa  56520
gaagaagtaa gaaaaaaaca agaagagcat aaagcaaaag aagataatga aaaagtagtg  56580
cagttgaaga aacatgacaa atagtaaaaa aaaaggtgat gtattcgaaa gaaagattgc  56640
caaagaactt tctgattggt ggggttatcc ttttagtagg tctccacagt caggaggtgc  56700
ttcatggggg gctaataata atgctgtcgg tgacattgta gcacctttag agtctaattt  56760
tccattagtt gtagagtgca aacatagaga aaattggatt atggacaatg ttttacttaa  56820
taataaagaa cctcatacat ggtgggaaca agttatagga gatagcttac aagttaataa  56880
aactccttgt ttaatattta caagaaatag agcacagtca tatgtagcat taccttatat  56940
agaagatgta tatgtaaagt taagagatga agaataccct attatgagaa cggattttat  57000
tgtagaaaat gttagaaaag ataaacattt ttatgatgtt cttataacta cgatagatgg  57060
gttgactaac ttaacacctt cttatattat atcttgctac aacaaaaaag agattaaacc  57120
atatagagtt gtcaagtcta aaatatctaa agttagtaaa aaagaagata agttgattga  57180
tgatttactt gatggtatat aaggaaggga tactagttga ttacacaaat aaaaaaacgt  57240
```

```
gatggttccg ttgtagatta tgatttaagt aaagttacta atgctatttt aagagccaac  57300
tcagaaacag aagaatatat tgaagatgtt attgattctc ttgtagatga tgtagactct  57360
ttactagaag aacaagacac tatcattact gtagaattaa tacaagatat agtagaagaa  57420
gttttattta gtagtatgta taaagatact gctaaagctt ttattttata tagggataaa  57480
aagaaaagag agcgtaaaag agacttattc aaaccaagaa aagaattaaa accctatgaa  57540
taccctgaat tattagaata taaagatgct atacgccaaa gttactgggt acacactgag  57600
tttaactata catcagatat tcaagactat aagaataacg ttaaatacaa tgagcaaatg  57660
accattaaaa aagctatgtt agcaattgct caagtagaag tagcagtaaa gactttctgg  57720
ggtgacctat atcatagaat gcctaaatgg gaaacaggag ctgtaggtgc aacttttagt  57780
gagagtgaag cacgtcatgc agacgcttat tcacatttat tagagatttt aggtttgaat  57840
gaagagttta aaacaattga cgatattcct gctcttaaag aacgtgttga tgagttagcg  57900
atgcatgtaa aactaagtaa gagtgaggat gatagagatt acgtactatc tgttttatta  57960
ttttctatat ttattgaaca tgtatcttta tttagtcaat tttaattat gatgagtttt  58020
aataaatata aaaacttatt tagaggttta tcaaatgcta ttgaagctac atctaaagaa  58080
gagcaaatcc atggattatt tggaacagaa atcattaata ttcttagaga agaaagacct  58140
gagtggttca acaaagaaat ggaagatgca gtttacacag cctgtaaaaa atcttatgaa  58200
tcagaaacac ggttacttga ttggatgtat gaagatgggg aactagagtt cttacctaag  58260
aaagtagtac aagaatttat taaaaataga cttaataact ctctagtagc tgttgggtat  58320
aataaacttt ttgatgttga tgaagagtta ctaagtgaag tgtcatggtt tgatgatgaa  58380
gttattagta ctaagttaac ggacttttta tctaaacgtt ctgtaaacta tacaaaattt  58440
agtaattctg taacggaaga tactattttt tcaacggaat ctgattttga aaatactggt  58500
aaacgagtta ctaaagataa agtaaacgct attttaagac taaaaatgat ataaaggcag  58560
tgtatataga tgagtaattt tgaatggtta aataatgatt ctagagtttt tctagaacgt  58620
ggttatttaa gtgatggtga aacaccagaa caaagaatta aagatattgc agattatgct  58680
gaagatattt taggtattga tgggttttct gacaagtttt atgattatat gagtaaaggt  58740
tattattcct tatccagtcc tatatggtct aatttcggga aagatagagg atttagtatt  58800
agttgttttg gtagttgggt agatgatact ataccatcga tacttaatac tgctagtgaa  58860
gtaggtatga tgagtaaata cggtggtggt acaagtggtt acttcggtaa catcagacct  58920
agaggctcag aaatcactga taatggactg acaagtggtt ccgttcattt tatgaagcta  58980
tttgagcaaa tgacagatac gataagccaa ggatgttatg atgataaaac tgaaatactc  59040
acagagaatg ggtatgaatt attatctaat gtagttagta gaaaagatgg aacaaaagtt  59100
gcacaggtaa cagataatga tgaaatagag tttgtagagc ctacaggtta tatggaattt  59160
gtacctgaag ataatgaatt agttcatttt aaagatagta aaaatattga cttattagtg  59220
actaagaacc ataatatggt ttttaaatac agaactaaaa ggactaataa agaaacagga  59280
aaaagagaaa gtgttttagt acctgagtat agaaatagat tagcagaaga tatgccatta  59340
catagagacg tttatttagc acattcttca tttgctaaag aaggcagagg actcacattt  59400
aaagaacgtc ttttggtagc cttgcaagca gatggtagta ttattaaaaa ataccctaaa  59460
tctttgaagt ttagatttag taaagaacgt aaaaaagata gactattatg gatattagat  59520
ggtctaggag ttgaatacac atataatgta gacaaagaca ataatcataa tatttatgtt  59580
aatatgggtg aagaattacc taaagaattt agtaaatggg taaatttaca aaatgtcaca  59640
```

```
caacaatggg cttatgattt tattgatgag ttgtctcatt gggatgctag tagaagaacg  59700
gataaatcat ttatctacat gagtgtggtt gaacataatg tagacattgt tcaagccata  59760
gcttctatgg taggttataa atctcgtaaa tcagttgatt taagggaaag agaacctaat  59820
aaagccacta tgtataaaat atatctatct gaaggtcaat tatttggagg ctcaaatgtt  59880
actgtggaaa cggtacaata taaaggtaaa gtatattgtg ttgaagtacc tactcataaa  59940
cttgttgtaa gaaggaaagg gcatacatta gtttgtggta attctacacg tagagggcgt  60000
tttagtcctt atttacctat agaacatgag gatattgatg agtttttaga gattggtacc  60060
gaaggtaatc caattcaaaa cttaacacat gcagtaacag ttactgatga ctggttatta  60120
gacatgatta atggggataa agaaaaaaga aaaacatggg ctaaagtatt aacaagaaga  60180
acacaaatag gataccctta tatcttcttt catgataatg caaatagtaa tacagtagat  60240
gtatataaag acaaagggtt aactattaat aactcaaatt tgtgtaaaaa tttgcacctt  60300
tagtaagtaa ttactatcga aaaatccatc taaacggtga atatctaagt taaaatatat  60360
gacaacaccg tgctaaatca gattataaat ctgtaaatgc ctaacgacta tctgtaacct  60420
attcacataa gtgaagggat aaggttagag ccaagtggta taagtattga gtaataatca  60480
agtaaatctt atttaaatcg aaatggtgga cttccttatt aaggaagatg atatagtctg  60540
ctctatatgg aaacatatag aagttcatat taacaataat aattaagagg gtcgaaaatg  60600
gagtaccata tttataaaat tacaaacaaa aacaataata aaatatacat cggaattaca  60660
tcaaaaacag ttcaacatag atttaaaaat catattagaa aagctaagat aggctcaaca  60720
actaatttac accaatcaat gatgaaacat ggtgaagaga atttttatgt agaagaatta  60780
tacactttta gtacagagga taaaaagttt gcttacatgg tagagcaaat ttttatagac  60840
atgtacgaat ctgtaaaaaa aggttataat atggagatag gttttgggtg gaatataatg  60900
gatagacgag gaaaaaacaa tccgatgtat ggtaaagaaa gcgctaatgc taaaaaagtt  60960
attgttgatg gcgtagttta taaaaatatg ggtatatgct ctgaagagct aggaataaac  61020
agaaatacat taaccagaag atgtaattct gaaaaattcc ctaactataa atattgttaa  61080
ttagagaact ggtagtgatt aacgaccact attgaacatg taggagtgaa ataatgttac  61140
ctaataaaga agattggtca tttgtatgtg acctatctag tatgaacctt gttaagtatg  61200
atgaatggaa acacacggat gctgtagaga cacttgttta ctttttagat gctgttatgt  61260
ctgagtttat tagagactta gaatatctaa gagactcaga tgaaaaagat aaacaagaag  61320
catttaaatt tatggagaga gcttataact tttctgttga gaacagagcc ttaggaatag  61380
gcgttcttgg ttaccattca tacctacaat caaaactcat accttttgaa agtattaaag  61440
ccagtcaaat taatgaagag atatttaaat tattaaaaga aaaaacttat aaagctagtg  61500
agcagttagc taaactttat ggagagcctt ctattttaaa aggttatggt agaagaaatt  61560
catgtttgat ggcggtagct cctacgactt cgagctcatt tatcctaggt caagtttcta  61620
aatcaattga accttttatg agtaattatt acgttgtaga cactgctaaa gtaaagaaaa  61680
ctatgattaa tccttacctt aaaagactat taaaagaaaa aggaaaggac aataaaaaag  61740
ttattgagag tatcagagat aatgatggtt ccgttcaaca cctaactttc ttaagtgatt  61800
atgaaaagga agtatttaaa acatatggtg aaattaatca atataatata ttagaccaag  61860
cttctacaag acaaaaatat attgaccaag gacaatctat aaacattatg attaacccta  61920
aacatgttac agcagaggag ttaaatgaac tttatctctt tgcatggtct aatggtatta  61980
```

agtcattgta ttatcaacat ggtacaaatg catcacaaca attcaattta tctaaaattt 62040
gtattaattg tgaagcctaa agaggtgact aaatgaataa aaaagaagcg tttggattac 62100
taagtagaac tgaagatata ttcaaatcaa atgatatttt ctcacaagta agtaatgtac 62160
aagaccctat taagatgttt aatagggaag atgatactaa agcagatagt aaatcaagta 62220
aatttcagct agagtttatt tataatacat atgtgtacat tcttatatat gaaggtacat 62280
taaagctatt taaagctgat ggtacggagc agttaacaca tgtagctgat attgaaacat 62340
ttaaagatat tattgacaca ttagaaaagg atgatacaga aaatggaaaa agtgaatagt 62400
ttattagagt taaatacaac aatcagacaa aaacaggatg ttattgtcat ggttacacaa 62460
gatgagtgtg ctaaatgtga aattttaaaa agtgtgattc ctcttttcga agcagaagga 62520
gatattacta aacctgttta tgttattaac ttagatgata aagatgtaga tagagaaaaa 62580
gcggtcaagt tatttgacat tatgagtaca cctgtactta ttggttataa agatggagaa 62640
cttgctaaga agttcgaaga ccaagtaaca cctaaaaact taatggaatt agatttactt 62700
taatttgtaa ttacctacta cttatgctat acttatatta gtaaaaggta gtaggttttt 62760
tcatgaaagg atgaatagtt atcgcaaaaa ataaaacatt aactatatat aatagtgata 62820
gatattttaa tatacatgta aaaaacaaag atgaattatc taaagctatt aaagttacaa 62880
ctttaaatga agatgagata gaaaaagata tggacaactt agctaataaa tcaactaggt 62940
atatactaag agatgataaa cattacatgc tatttaatga gaagtataac aatgataagt 63000
tgattgaaaa aatatgcaag cacggtggac aagtaacata ctataccgat tcagtaattc 63060
cttactatgt gcttaaagat ttatcagctc accctaaatc atcagttgta tatagaatgc 63120
gtagtaagtt tagtaacaaa gagatggata atatagcttt gagtttcatg ggaacaaaag 63180
tcattattga tatttcagtt gtatttcctt acgtcaatcc ttacgatatt attagaagtt 63240
tatacgatgt taaaacgaat gtagacgagg ttcatctatc attccctcgt attagttcta 63300
tagacgctaa acaaggtaag tactacacgt atgataaaga agcttataaa ctaaaaccta 63360
ggtatacgct tgactttgca gacaaattaa gggtttcttt gtccgtgtgg aaaatgtata 63420
tctatattct tgctagtaaa gaaaataaag attatgaaac aatagaagac ctacttactg 63480
aattaaaaag acaaagaaag attaagattt aggtgatttt gtgagtacag caaatagaag 63540
agatatagca agaaagatat ctgagagtac agggtattat atccaagacg tagaagagat 63600
actagaagca gaaacaaaag ctatttctga attactactt gaagattacg ataaggtaaa 63660
gaatcataag tactttcaaa tagaagtagt agagcgtaag ggtaaaaaag catgggatgg 63720
actaaataaa acatacttca ctttacctaa tagaaaggca ctaaagttta aacctttgtc 63780
tgaattagat aaagttatag atgtattaaa caaagaggaa gaaaacagtt aaatatttta 63840
tatagcataa gatttagtat ctactcttca tgtatttagt tggtagtata tgttttgcta 63900
ttatatacta tttatttaac agagattgag tcaagtttat acttgactct tttttttatg 63960
ttatgttata gtttaactat aaggagctga ttgaatatga aaatgaaaga tttagataac 64020
ttacatattg ttgtagtatg tattaagaat gatacattac ctgatgtagg gtatatggtc 64080
ttagaaaata taaaaagaaa gtaaaagaaa atagtgacat acaatgaaat catataaaac 64140
agaagtaaaa ccaaataaac aacaaataat tgagattaat aaaacaatta atgcttgtag 64200
aagtgtttat aataaattta ttgaagtaaa taaatttcgt tatgataacg ggttgaaatt 64260
tttaaaccat agaaagttta gtgtttggta taataatgat tttattccta ataataaaga 64320
taaaaaatgg actaaggaag taaatactaa agcaactaaa caagctatgg caaatgctga 64380
ggatgcatat aaaagattct ttaataatat atcaggtttt cctaagttta agaagacaca 64440
aagtaacggt tcttactatt taataggtac tatacatgta gaacgtcata gaatacgact 64500
acctaattta aaatgggtta agttaaaaaa aaaaggatat ataccggaaa acaatataaa 64560
atcagctact attattaaag aaaatgatag atattatgtg tcagtgttag tagatgaaga 64620
acctaagact atacttaaaa aaccacatac tgaaggtatt ggtatagacc taggattaaa 64680
agatacacta tttacacctt caggcgttaa gattacagat ttaaggaaaa ataaaaaatt 64740
agttaaatta cataagtctt taaaacgaca acaaagaaaa ttatcacgaa aacaaaagaa 64800
gtccaataac tggtctaaac aattattaaa agtacaaaga ttatatcgta aaataagcaa 64860
cattaagaag gatattaaac aaaagaaaat actagaaata gtacaggaaa acccacaatc 64920
tatcacaatt gaaaatttaa atattaaagg tatgatgaaa aataaaagat tgtctaatag 64980
tttccaacaa ataggattag gctacattat tgaatggctc aaatggaaat gttatcaata 65040
tgatatagaa ctaagacaag tagatagatt ttacccttca agtcaaatat gcaatcaatg 65100
tggaaataga caaaaaatgc ctttaaataa aagaatttac gaatgtgata attgtgatat 65160
gatagaagat aaagatataa acgcaagtat taacttaaaa caagcaaaag aatatacaat 65220
actagtataa aagaaaaaga gaagttactg agaactagta tcttacttaa agtctaaaca 65280
aatacggtag gctatatcgg aattaacgct ctgggagagg tttttagacc tgattgttaa 65340
tacaatcaac ctcgttgaat ggagaaactt tctaaatata catttaagta tgtttttagt 65400
agcaggatta agttcctctt ttttttattg actactatga ttagatatgc tatactgtat 65460
ttaagttaaa gaagggattg gtaataacat gaaagtttta attttatacg actatatcag 65520
agaggaacac ttttcagtta gtaatgatgg tagtgttaag aatgtactat taaatacacc 65580
taatggtaga gtactaaaac aactattgtc taatatttct ggtattaata gagataggag 65640
cacaaaggat tatgacattg attttttata tcctaaagta cctacaccta ttaagaataa 65700
ctatggtaaa acaattaagt accaagacgt taagttatct gaagttaaac cttactatga 65760
aagaatgagt caaataatca taaacaataa gtacgatatt attattcctt taggtaagct 65820
aggggttaaa tatttattaa atgtatcagc tatcggtaaa gttagaggtg tacctaataa 65880
agtaactatt actagtgaag ataaaaaaca tgatgtttgg gtattaccta cttatagcat 65940
agagtacaca aacgttaata agaatagtga gcgtcatgta gtagctgacc ttaagttatt 66000
aggtaagttt gtagaacaag gtgaagatgt atttaaacct aaagaagtta agtatgaact 66060
tgttacaagt attgagcgtg taagagaaat atttaataaa gaagtaaaga atgataatca 66120
tgacggtgta gacattaccg catgggattt agaaactaac tcacttagtc ctgatagaga 66180
aggaagtaaa cccttagtat tatcaatgag ttgggagaat ggtcaaggtg ttacaatacc 66240
tttatataaa tcagacttta cttgggagaa tggacagcaa gatattgatg aaattctttc 66300
cttattaaaa gaatgggtag ctagcaaaga agacattaag gtactacata atgctactta 66360
tgatataaat ttccttatgg caacgcaagg tttcacaaac tttgaaaata atcaagacac 66420
taaggtaggt tggtatttag ctgtaacaca agaacaagca gagtctctaa gattatcaga 66480
ccttgcttac gaagtaacag atgtaggagg atatgacaaa ccccttgaag attttaaaga 66540
gtggtatgta ttgaagctac taagattctt atcagataaa ctaaaagata ttaaaaaaga 66600
aaataaaaaa gttgctaaga aagaatataa cataaaagca aatgagtatg atacttggtt 66660
gaaaaataaa ctcgataaca ttgatataga actaacagat gaagataagt attatggtat 66720

```
cacagaagag caaaaaagat atttagagtt aaaactaaca cctgaggtta ttacaaagaa  66780
tatgcttatg gattctgaat ttaaagaagt agccgaatca tcacctgagt atatgagttt  66840
atctaacaaa gctaaagatt atgtattagg tacatctatt aatttaatta acacgtataa  66900
agacaatact aaagttatta atgaggtaga tggaggtgac tttaattatg attggattcc  66960
attagagctt atgcatcctt atgccagtgg tgacaccgat gtctgtagaa gaatatactg  67020
tgatgttatt gaaaagttaa aagaacaaaa tagacctaaa gcattggact taatgtcaat  67080
aagttaccct agattaatta gaacattagc tagaatacaa tcaaatggtt tacattgtga  67140
cctagaatac atgcataaaa atgatgaatt ttatattaat gagatggaaa aaacccacca  67200
agaaattaga gaacattggg ctatccaaga atttgaggag actaggtata atttatacca  67260
attagcctta gcagaacatg agaagaaacc atctgataga aataaagaaa tacatgagta  67320
tagagctaaa tttaaagatg aaggttggaa gtttaaacca agctcaggtg accataaagg  67380
tgaagtattg tatagcattt taggtataca gttaccttat agtaaagaga cagttaagga  67440
taaacctttc agtaatggta ctaaagaaga tgagttatca tggaaagatt acaaaacaga  67500
tactaagtct ataaagatgg cattatcttt ggttgagaat gaagataata aaaagctact  67560
agacttactt atttattatg cctctttgca aactaaaaga aattctttta ctaagaaatt  67620
acctaaaaga gtaaataaga atacacataa tttacatggt aactataata gtacaggaac  67680
tgcatgtatt acaggtgatt ctttagttat tactgataaa ggtataaaaa aaatagaaga  67740
cttatcaaat aatagaaaag aaaaagtatt tagtagtatt gatgtaggta ttgttaatag  67800
acagggaaat ttagaaaaag cttcacactt ttattatagt ggtgtaagaa atggattaaa  67860
gattacttta gaagatggta ctacattaac tactacttta aaccacccct tattacgaaa  67920
taattattat agtaatactg gtagggttct aaataaaaca aaacaaacaa ctaagcattt  67980
actagataat gattgggttg tagctgaaga tttaaaaata ggtgattata taaaaatgtc  68040
ttataattct aatctttata ataatagtta tattgattta gatactaaag attttatata  68100
tagtaaagaa aaaagtatta caaacacaaa aagctataca ctacctaatt atgtatctga  68160
agattttgct gaatggtacg gtatgtatac agctgatggg tctttttcta caaataacgg  68220
ttcattcagt ataagattaa ctaatagtaa tcttgaagtt aggaatagat tctttaacct  68280
aactaaagat ttatttgata ttacaccata ctacattagt aataaagata gaagtgattc  68340
tattgaattt tcttcaattg gtttaggtag atggttagaa catattttta atatgcaaag  68400
taaagcatta aataaagaaa tcccacaaca aatattagat agccctaaaa gtgtacaaca  68460
agcatttctt aagggtttaa gtttagatac tgcaacagaa aagaaaaagt atcctagttt  68520
gtactataat actgtatcta ataaaatgtc tttacaaata agaacaatgc taatgaatat  68580
gggtatctat tgtaggtatt ctataggtaa agtttataaa aataataata gaaaagtaca  68640
aaatgaatgc tattctatac aaataactta tgatgcatta gataaatttt acgatgaaat  68700
agggtttatt gaaagtatta agcgtgatag agtaaagtat aaatcagaaa atctaaaggc  68760
attaggcaga agaaacggta ttcttttata tgataatgtt ttattaggta aaataaagaa  68820
aattgaaaaa ataaaagata tggaattttt tgatttacat gttcctagta gccattcatt  68880
tgtagctaat aatattgtaa atcataatac tagcaggctt tctagtaaca accctaacct  68940
tcagaatctt cctgctcata catctgatgt aaataagttt gattatcacc accctattaa  69000
acgttctttt atctctagat ttaaagatgg tgtaatttta caagccgatt acagtgcctt  69060
agagatgcgt attacggcac tatatacaga tgataaagaa atgttagaga tgtttttaac  69120
```

```
aggacaagat attcataaaa atacggcaag tattatgtat ggtaaaagta tgaaggacgt  69180
aacagcagaa gaaagacaag ccagtaaagc tgtagccttt ggtttaattt atggtgaatc  69240
ggaattttcg tttgcaggta aaaataatat gacagttgat gaagctactg aaatatttaa  69300
taagttttat tctaataaac ctgctattaa gaagtctata gatgaaactc atgagtttgt  69360
tcaaaaacat ggatatgtag aaacaatgaa tggacacaga agatatatac actcagcaca  69420
atctagagat aaaaagatta aaaatgaggg tcttagacag tcctttaaca cgattattca  69480
aggtacaggt ggttacctta ctaacatggc tattacttat attgacgact ttattcaaaa  69540
taagaatatg aaatcgaagt tagtagctac tgttcatgat agtattgtag tagactcacc  69600
tcctgaagaa gttaatatta tggctaaagt tattgtccat gtaatggaga accttcctta  69660
tgatttccta aaaataaaaa ttaatggtga gttaaggcag tatcctatag atgctgatat  69720
agaaataggg ctaacatata atgatatggt agaatacaac gaagagttaa taaataaatt  69780
taattcatat aaaggatata ttaaatataa actagcctta cagcaaatta aggactacta  69840
tgaatcaggt aaactaactg aagagcagta caaacaaaaa acggaatata ttaaaaataa  69900
tattgacagt ttcaaagtta tatagtatag taacctatat cataataaaa tagaggatgg  69960
tattatggag atacatttag atacattaga tttcaatgag ttaaccttaa aagataacaa  70020
tggaaacaca cagacgttta atattcatga tgaactaaaa cttagtgagt atacaattca  70080
agacgaaatg taccaacagt cgtctaaatt tgcatggtgg gcttccttaa aagaacgtgt  70140
gagtaattat gccgaagcag agcaacgtaa gttagaaaaa ataggagctc aacttaatct  70200
acaaattaga gctcagtacg aacaacaggg aaagaaacct acaaaagacc aagtagagtc  70260
tgctgtattt ctttctgatg aatatcaaca gcaagcaaag gttgtagaag catggaatta  70320
tagagaaaaa caattacatt atatcgtaaa agcttttgaa acacgtacaa ctatgttagt  70380
acagattagt gcggaactaa gacaaacaaa taaaaatggt ggtgttacta acccatttac  70440
acattaggta ttgacaaaca aaagaaaaca tgttatacta attaagtaat ttttaaaata  70500
aaaggagaaa agatattatg gattttaatc aatttattaa tcagcaatca gaaaagctac  70560
aatcaagtgg ttttgacaat gaggtagaga cgtacaaacc aaagaatccg gttttgcgat  70620
taggaaagat taaggacgtt aacaataatc aaattaataa agagtctgca cttgtacgtg  70680
tactaccgcc tgtagcaggt tctaatgagt tctttaagga atttagaaca ttaggtatta  70740
actatgttaa aaaagatggg gcacaaaagt tctctatgct tactttaccc gagaaagtta  70800
actcatctgt tgtagaccct tatgtaaata catggttaaa gcaaggtgta caatttagta  70860
acttccctaa taaacctgca cgacgagcat atattcatgt gattgaatac tttaatcaaa  70920
acggacaatt agttcctaac acagatgaac aaggtaatgt tgttattcaa cctatggagc  70980
tatctaatac gggtctgtct caattgattg accgattaaa agataaaatg ttatcaccat  71040
cacctactgc tacacacagc tttatttcag ccgatgatgc attccctatt aatattgcta  71100
aagctaaaaa aggtgaaaaa tcatggaatg taactgttta tcctacagta aaattaggtg  71160
ccttacctca aggttgggaa cagcagttat cggatttaga taagttagct acaccaacag  71220
aagaaaataa ccctaacttt gtaaactggt tgattaacaa tgttaataac acagaagttt  71280
ctcatgataa ttttaaattc agtagagaaa caaacacatt aggtgaagaa tcatcaacac  71340
aagagcaaac acaagctcct acgcaacaaa gtgtagagca acaattacct agtaatttag  71400
gtggacaaaa taacacacaa ccaaacttta ataatgtaca acaaccaaca ccacaagttc  71460
```

-continued

```
ccccacaaca aaatacacag tttggtcaag gaacacctgt gcaacaagca ccacagcaac  71520
agacatcaca gcaaccaaca caacaagaac aaagtaatcc atttgagaac tttgatgcta  71580
ataacattga cgattctcaa atcccattca acacaaatga atcaacacca gaaccaccta  71640
aacaaaatca acctaagagt gtagatgatg tattagcagg tttagattta taataacttt  71700
atagagtgct atcttagcac tcttttattt aaatttcata taaaaggatg atataatggc  71760
tagagcaaaa aaaggtaaag aagtagatac tacaaattta aatactattg acttaggtaa  71820
agaattaggt ttaactttac tatcagatag taatagagca gatattaaga atatcattcc  71880
tactatgatt ccacaatatg atagaatttt aggtggaggt attcctctag gaagacttac  71940
agaagtttac ggattaactg gctcgggtaa atcgaccttt gcagtacact tatctagagt  72000
agcaacacaa ttaggagtta ttacagtttg gattgatatt gagggaacag ctgataatca  72060
acgtatggag cagttaggcg tagatgtatc taaattattc tcagtacaat caggtgaagg  72120
aagacttaaa aacgttactg aattatcagt agaaactgtg ggtaaagagt tagagtactg  72180
gattgataca tttaatgaga aagcaccagg tattcctatt ttatttattt gggattcact  72240
cggagctaca cgtacacaag atgaaatcga tgcaggagta gaccataaaa aacttggaac  72300
aaaagcgaca tctactcaaa aagtagttaa tgctatttca cctaagctta atgatacaaa  72360
tacaggatta attgttatta accaagcacg tgataactta aatatgagta acccttatga  72420
tgaccctatt aagtctacag gcggaagagc ctttgagcac ggtgctagtt tacgtattaa  72480
agtatctaaa ggaaaagaat cggaattaaa gcaaaatgat tctatgacag gtaaacctac  72540
gtataaagga catgttatgc gtattgaaac taagaagtct aagttatcta gacctggaca  72600
aaaagcagaa gttgatttat tatcaggtta tgaagtaggt tctgaggaag acactgttca  72660
attaaatggt gttgaccctt atcatactat ctataaagaa gctgttgaac gtggtttaat  72720
tacaaagggt acatggcgta attatgttac gttaaatggt gaagaaatta aaaagtacga  72780
taaagactgg gtaccaacat taatggataa tcatgaacta tatttagaat tatttaatag  72840
agtttatcat gaaaacttcc ctaataagta tgtaccttta agcaatacaa aagtagacat  72900
tacccaacta gaagagttta aagcattaca agattactac gaagagctta gctctactaa  72960
taaagagact aaggaagatg taaatgaata atctaataga tagaaatatt aatagtgtta  73020
aagaagcatt aggcagggct aatacaaatg acgtattgcc cttaccttat attgaaatag  73080
cagaacgttt taaaaaagct agagatacta aggaagctat tattgtagaa gaagcaggct  73140
ttccttacac tgattctaca gttatgtata ttgagcatgt agagtcaagg tgggcagggg  73200
gttactcttt agtacgttat aatggttctg aagttaaagt acctaaaaca atacactatt  73260
ctgatatcta tgtatcaaat gatgtacaca ggattaagat tgtatttgag ggagcacatc  73320
cttatgaaga aagttaataa tgggaataga tatattatag acttagatgg tattcctact  73380
gactttggta gagacttaga catgctttta aagagatata aaaaccttag atggtcatta  73440
tttcataggt actctagagg tatgagtcat gactttgaaa aacaagagtt acgggaatac  73500
atagatgagc agtttattaa gttagttaag gagtatgata tacaaagtaa agtagatttt  73560
ccagggtata ttaaaacgaa actaacacta cgagtacaga acagttatgt taagaagaac  73620
aataagtata aacgtactga acttgtaggt aaaacagatt atacagtaga gtccttaaca  73680
caggagttaa atgtgggatt agaagaaaat gaattactta attatgtctt tgatgataca  73740
caatttactg aagtacaaag tgaactgcta aaagaactcc ttattaatac agataaagaa  73800
gacaacgcat ttattgtttc aactgtagct aataggttag aggtagagcg ttcagaaata  73860
```

```
actaaggagc ttacagaact taaagattat gttaaattta aaataaatgc ttaccacgaa  73920
caaaacagta gaagatacat tagagacaac aaaatagata cacaaaatca tgtatgggaa  73980
taacacaaat aagccttcct tttgttatat tattaatgaa aataataaca tagggaggtt  74040
ttttctatgt tataatgtaa aaaataatga ttggagctta attattatgg ctaagaaaaa  74100
tattaatgaa gtattaaaac aagctaccgc tactgtagca gataagtatt tacaagttca  74160
agtagagcaa gatggttata cacgtacaca ccgtggtcag tataactaca aagtagtaga  74220
taataaggga gaattattct tatacccgat tgaaacagat ggtagaggaa atattaaaat  74280
tatgaaaaag gctcctgttg cttatacaga tggagaccaa attcattttg tagttaatac  74340
tgttaaagac ccttacaacc atgcttttat tagaactgaa aatattaaag gtaaagataa  74400
aggtaaacaa ttaattcaag cgtttttagc attcgttgaa gaccgtttca gctttggagt  74460
atacaatgta ttccttgcta ataacaagaa ggatgttttt gctttagttg atgctgaaag  74520
taaagatgct aaaaaagtag tagatagtaa tgagaaacct catgaagacg tgagcgctga  74580
gtttcctgct agtccgctac gtaaagacgt taaaggagta gactcaggag aaggtcaagg  74640
agatacttca gaaccttcag tacctaaaaa tgtaacagta accgctaaag aaacaacagc  74700
tgatattaca gctgaataaa catataaagg atgacttagt ttggataaat taaatttata  74760
caaaggtgac cagctattaa aaagtgaaga gaaacaagca ggtaaaacat caattacaat  74820
tgataactta actgctaaca cagactaccc acaaggtaca tataaagtat ctttctctaa  74880
tgaatcagga gaatcagaaa aagtagatgt tcctgcgttt aagactaaag atattaaagt  74940
agtatctgtt actttagatg ttgaaagttt agatttaaaa gtaggagaaa cacataattt  75000
agtagctacg attgaaccta gtaacgcaac aaaagctact tatacattta cttcagaaca  75060
tgatgatatt gctagtgtat caagtaaagg tttagtagaa gctaaagcaa aaggtcaaac  75120
tacaatcact gttactactg atgatggtaa tcatacagat actgtaactg tagttgttaa  75180
agataaagta cctgaagctc ctacagatgt aactgtagac cctaaagaaa caacagctga  75240
tattacagca taatcggagg taaaaataaa tggaaaaaac attaaaagta tataaagatg  75300
gtgaagtagt aggtactaag actgctgaac aaacaggtaa aacaactatt tctattagtg  75360
gtttaacagc agatactacg tatcctaaag gaacttataa agtagcatac tctaatgagt  75420
ctggtgaatc agaaaaggta gatgtacctg aatttaagac atcaccacat agtgagctat  75480
aataaattaa agtccaactt aattgttggg ctttttttta ttgacttata tttatttata  75540
tgctatagtt aaacaagaat taataaagga ggtactatat ggatattaaa acagtatact  75600
taacttcaga taacgaccat ttgaaagtta aaaaattaat ggaaagtaag gaaaagtata  75660
ttgcagttac gtatgataat aaatcagtaa gtaaggtcaa tgtcgttatg gttattaatg  75720
ttattaaaga cctagtgcat atgtataggt ataaaattgt tgagtatggg ttatctaata  75780
atgataagga taaggaaatg gtagggtatt tattagaaag gattgaggat tgatgttatt  75840
tattttaaat gaagtagctt cacacacaga acatttatcc gaaggtatag atatgttcga  75900
cgttgaaagt gtagtatctt ttgactcggc attacattta gctagtgata atacgtatga  75960
ttctgttatt tttttaggtt ttatatacaa taatgaggat tacttaaagt ataaagaatt  76020
attaaaggat acaaaattat actttgtttc taatataaac ttacctgaca ataaggagtt  76080
tattacagta ggtgatgact taaagtacct atccttatta gagcaacttg tagtattaga  76140
agataaagac ctagacatta actttagtca gtatactaaa gacacggctt ctaagtacac  76200
```

```
tgagttgttt agctttaaat ctacttatga ggaggcaaaa gaaatgggtc tagtaggtta  76260
ccccgcagat atagtattac ctattatgac tgacaagttt tacaacgtaa atgatttgta  76320
tgtactatac gaagtagcac ctgagtataa attaccttta gcatatgaat gccttaagga  76380
taaagaaaaa ggtattgttg ttataggttc acaaacaaga ggtactagtg atatccttac  76440
tttctatgta aaaggttatg atgttaatag tgttgctaaa acattcggag catcttataa  76500
tgaaaattct aatatattca gtatatttat tgatagtcat atccatgtgt taggtgagaa  76560
tatgaataag tatttaataa cggaaggaag tatttatgag taattataaa acagtagaag  76620
agttacaagc agttattgta ggtgtgtttc ttaaagatga aggtaaagta gttacctcta  76680
aatttaataa agtattagca agttttggta ttgatagagt aaatcgcaat gaattaaaag  76740
atattgtaga taatattagg aaagacacat acttaaatga cttgaaaaat aaagcagtta  76800
aaggtgaagt gttattagag gacttaagag atgtagaaga taaacaagta tttgagggta  76860
atgattatca tgaagaagta tcatcttatg tagtagcaca tgaaaaagaa ctatctagac  76920
taagggaatt acgaaagatt aatagacaaa ctgcataccc tactattttg tttgatgaat  76980
taaagcgtac tatggttaat gagctaaaag ggaataagtt actagaccat aaagtaagta  77040
agtatacttc tactgaggaa gaagaagagc tggttatctt actgtcggac ttccatgtag  77100
gttgtgcttt tcaagattta actaatgagt ataactttga ggtactaaaa agaagattaa  77160
atcagctact acaggaaact attaaggata ttagtaaacg tggtattagt aatgttacag  77220
tatactttgt aggtgattta atagagcata ttaatatgag agatgttaac caagcttttg  77280
atactgagtt cactatggca gagcaggtag caaaaggaac tagactatta attgacttct  77340
taacagaatt atctccatat gtatggggta atttacgttt cggtatgata gcaggtaacc  77400
acgaccgtgt acagggtaat aagaaccaaa aagtatacaa tgatagtgta gcttatattg  77460
tattggattc tttactgctg ttaaaagaaa acggtgtatt agaaggtatt gagattatcg  77520
acaatagaaa agatgtatat actattaaag acacagtatg taacttaaat attattataa  77580
accatggaga tggacttaaa ggtaaaggta agcatattcc taaatttatt gagaacactc  77640
acattgactt attaattaca ggtcatgtac atcacttttc agtaacacaa gaagattaca  77700
atagaatgca tattgtagca agtagtccta tgggatataa caactatgct aaagaactac  77760
acttatctag aacgaagcct tcacaacaac tactattttt aaataaaaaa aataaagaca  77820
ttgacattaa aactgtattc ttagattagg gagagataat atggacattc tatcaattat  77880
agccttaaca ttgcttatca ttattattgt taataccaca atgaactttg taggtatgtt  77940
acgtggtgag cgtgatttag taaaaaaagg aggtaaccct ctacccaatt ggcagtacta  78000
taatgtgtta ttacctaatt tatgtggtat tatcctctta ggtattgttg tttattttgg  78060
agattcgatt tataaaatta caacaaggtt agaggttctt tttgctatta ttgcgcttat  78120
tgtaatagat gtattgttaa cagcgttagt attattagta ttgagtttcg taacaaaaaa  78180
taaagaatag taaagaaggg agtctggttt atacttgact ccctttgtta tttatggtat  78240
attagatatg aggtgatttt tgttgcaatt aaattttggt aaatttgata atgaaattat  78300
taagacaaaa gtaagtgaag gtgtttactc ttttagaggt gttccttatt actacataga  78360
acatgtccaa gatgaaactt ctgagtatgt attagtatat aacatacata gtgttgatga  78420
tgaagtacca caaaagaaat ataaaataga aacagtaagt aaaactatta gaggcggtac  78480
gatattaagt aatacaatta agtcaatgct acctaataat aagaagtata aaaaagtata  78540
tgaacctcct atctttttag ctaatattat acctttaggt acagatacaa ctacaggtgc  78600
```

```
tgtaggtaaa gggtttttcg aaagagaaaa agatagagta actattacac aaaaagaagg  78660
cactaaagtt atacatggtg aatatacagg agtatttata tgtttatcta atattaaatg  78720
gattaagtcc tatactcctt tagacagtat attacaatat tatcaacgta ttaaagggga  78780
tagaataaat gtctgagata actaaattct atgagcagga cattaaagat ttaattagaa  78840
ctaagagaca tatgtttaaa gatgatgaga taacaagtaa tatacaagat attagaatat  78900
ttaatgaaaa agctatttgt caaggtaaat gtagaactga ctgtttaatt cttgatagaa  78960
acggtactgt tatgggtata gagataaaaa cagaacgaga ctctacacaa agacttaata  79020
aacagttata ctattatagt ctagtatgta agtatgttta tgtgatgtgt catgataagc  79080
atgtacctaa agtagagcaa atactaaaaa ggtataaaca ccatcatgta ggtattatga  79140
gctatattaa ctttaaaggc agtccagtag taggtaagta taaggaagct acgccttcac  79200
cactaagaag tccttatcat acactaaata ttttatggaa gcaacattta atgactatac  79260
ttaaacagtt aagagattat aatacatacc taactggata taactatagg gagcacggta  79320
aaaatactaa caatgaaggc agttatatag aaggaacaca acgtatgaga atgaaaaagt  79380
cagctattat taaccaagtt attcattatt taggtgtaga gaactcttat aagatattta  79440
ctagaggtgt tatctatggt tatagtaata gatggcagat attagaagat gatttcttta  79500
aagttataca gaacggagtg agggtattat atggcaaaga ggaaacctga tgcatttaaa  79560
cctaaatcta acggatataa acatcaacct gttaactttg ctcctacagg taacttatca  79620
ggtagaagta cttctttttt taataaaaaa agaaaagata tatcagatga aagtattgtt  79680
gttaaataca aacctttgtt tgttaaaagg tttgataatg ttactgctac cgacattaaa  79740
atacaaaaga aatatgcgtt agacttaatt agtgaagctg tgaatataaa gaagaaatat  79800
cttgtaatga agcaaaaagg taaattaaca caaactattt tacatacgga tagagtttat  79860
tatgtttata gaggtaagaa attaataggt aaatgtagca ttcgtgaaca acgtacattt  79920
agaggtacac atttaatcta catttttagt actagacata gaatatctat acgcaaaaat  79980
agtagattag ataagaaaag aacaccaaag aaaatgatat ataaaggtgg taaataatgg  80040
ttaaatattt aagaacaaaa gctaaaaaaa caaatataag tactttattt aagaaactac  80100
aaagtaaaga tattacacta ttaggagtgt cctatgatag tgattatttc cctagcggtg  80160
taacaataat accttattta gaggacatat cacaagtaga agatggtata gaatttacga  80220
ataaagtaat agttactgag aacttaaaac ctgctattgt aggtatgaat aatatgataa  80280
gtgattcagg actaggttat gttaaaacag agcagttaaa taaaagatta gaaaatactg  80340
gattaatgac agatttatta tctaaaggaa cagaattaac ttcaacaaag aaagtagaca  80400
ttgtatcaac ttttattgaa cctactatta tgtaccaaga tactactatt aataaagaat  80460
taaaacttag attatacact atcgaagatg tatccccttt aaatgattac acacatgttg  80520
tatacttact agtaactaat aagcaatatg acggtcaatc attcataggt acattatgta  80580
accaaggtac attaaacaaa ttagatactc taaaagttct tacattcttc aagggtaata  80640
atttaatcaa tagaagtgtg ttttctgtta agttagatac gaataaatat cattatagtt  80700
tatataatac acatgagacc ggtattttct ttttagatga tgataaagac ttaattattg  80760
cttgtggtca atcctatgta aaagttaggt ataaagatat tgttagtagt aaaatagaga  80820
aagttagtga taataactat aaaatgattg ttaatcttgt tggtaatgat gagctaacaa  80880
ttctcttata gtataatact cccttaaata tgtatactaa ggtataaata tacgtatcta  80940
```

```
agggattttt tatacgtatt tttttcaagt agttagttaa tttttaaaag gtattattct  81000
tattttaaaa ttatatttat aaaacattaa aatatctttt aggtataggg ttttagaaaa  81060
aagatttata ttgcttaaaa tagttacact atagtgtaaa aaattagaat atcctttatg  81120
aaaataaaat agatgcagaa attgtgatat attatatagt gtaaagtata aaacagttga  81180
tttgataagg ttatgtgaat acacatactc cttattttag ttcacacata tgtaaagaca  81240
cttgagacaa gaagggaata tataatggct agaaaaaaga atttaagaaa taaaaaatct  81300
gatataaagg tagttccaga taaggaaagt attctatcta aactatataa taataaacta  81360
ttaaggtcta aagtggataa tgctatagat gaagatgtta gttatgatga tattatagac  81420
ctatgtaaag agtatgactt agagttatcc aaatctgcca ttacaagata taagagtaaa  81480
cgtaaagaag ctattgaaaa tggatgggat ttaggagaac ttattgataa aagaaagaaa  81540
gttagcgcta ctcaaataca gaaaaaagaa aaccctatga aagaattaga tagtgagaat  81600
tatacacctt ttgaactggc tacacagaat gtacaaacaa tatatgatga tattcaaata  81660
ctagatatga ttattcaaaa aggtgctaaa ggtttaaact ttgtagaaac attagaccct  81720
gctttaatga ttaaagctat ggaaacaaaa gatagaatta cgggtaacca actaaaaggt  81780
atgtcattca taggactaag agaactaatg attaaacaac aagcacaaga tactgctatg  81840
acagaagtta tgcttgagtt tattcctgaa gataaacatg aagaagttct tcaaagaatg  81900
gagcaattac aagaagagtt ctataaaaac ttagatttag atgaagaagg aagaaagtta  81960
aaagatacat tagatagagt aggctataca atatagataa tgaggtaata catatgacag  82020
aagaaattag tttaattcca ataaaagatg ttaaaccact tacagatata gtagatatta  82080
taacacacct acataaaggt gatgtactta gagttaaaca agagaaccaa ggagatatat  82140
tacttagact aagtactgga aaacataagt ttactgaagt gtcaagagac ttagataaag  82200
aaaccatgtt ctataaaagg tattgggtac tgtataatgt atctattaat tctttactaa  82260
cttttgatgt ttatttagaa gacgattatg tagaatctac aaaagttaag ttccctaaga  82320
acacaattgt agaatatgta agagataatc aagaatcaga tgtagccaag gttaaagata  82380
ttttagtaga tagtaaaggt aattatttct atgcactttc aggagaaaca tctttatata  82440
atgaagataa acttaataaa attaaaaatt aatgattgac acactcatat gggtgtgtta  82500
ttcttttatt acaaacaata aaaggagcaa ttgattatga ttattacatt aaatgaagaa  82560
gagaaagcat tattagaaaa taaaagcaac tatacgccat taagtaagaa taaagagttc  82620
aatacaccaa aagaagaata tattgttaca agttataata aaggtgtacc tgtgactgat  82680
attgctaagg aagctaaagt aagtatgggt ttgatttata cagtgttaaa cttctataaa  82740
gtaccaaaga aacataagaa atctagagta gcaaaacgtg taaagcatat tactaatgat  82800
aagaataaag tacaagcctt aattaaagat tatcaatata tagacttaca aagtatttat  82860
aaaaagtata acattcataa gaatggttta tattatattt tagatttgta taatattgaa  82920
agaaaatcag atttaaaaga gaaagcctta gaagatacta tcgaggtaga ataagaggtg  82980
tcatatgcgc aaagaacgaa ttgtagatta cttgtataat gtaaagaaca ttgataataa  83040
tttaactata caaggaatag aaaatagttt atttaacaaa gaatctttac aagacttaat  83100
acctgatttt gatacttcta gtaaagagat taatgaaagt aatttatacc tatgtacaat  83160
accagaagat tataactccg accacgtaga aagtggtcag tatataggta tagatgttgg  83220
gtatgtatct gaagaccctg cttttgacca tttaataggt caagttccta gaagtgtata  83280
tgagaaagcg catgttatgc aaccactaat taagatagaa aatactgata tagattatac  83340
```

```
tcaggctgat atgattaatg acattaaagt aggtacaagt attagtgatg taaagattaa  83400
agataaatta agtttaatgt caaataatct tattacacat ttagaaattg ttgataagca  83460
ctactttgat agtagtatgg aagaagcact actaaagtat tatgagttaa aaaatcctga  83520
ctattattta aaacattttc ttaaactaaa agaacttgtc ggagacaata gaatgatata  83580
ttgtccttta ctgttaaaat gtattaaagt tatagactaa gttattatat tataagtagt  83640
aaaggatggt gcgctatgag taaaaaagca ataattgctt atgtaattat cttagttatg  83700
ttagccttat ctatatctac ttattacgta tcctcatact tatatcatga aaaaaccaaa  83760
tcacaagtta cagaccaatt aacacatcac ggtaaactaa aaaaagataa gaatgtagag  83820
tacgtaggag attacacgct taagaaagta gtagacaaca aagcatactt tatggaaaaa  83880
ctacctacct atttaccagg aagaacaagt gataaaagta ttgatatgag atattatagg  83940
actagtaaat ttagagaagg tgtaaacttt aaacttattc gtgtgtatac ggaggataat  84000
gacaataatc cagtacataa gtataggttt gaagcagtac taaataaaaa gtaaaggtat  84060
gatagtctat gacagtagta attatactag tatgttttgc tattatatac tatttattta  84120
acaaggattg agtcaaggtt atgcttgact ctttttttat gctatgttat aatttaaata  84180
taaggagatg ataaatgatg aaaaaaagtg atttagataa tttgtatatt gtggtcgtaa  84240
gtattaagaa tggtgtttta cctgatgagc gtataattcc aattggttta gatgtactaa  84300
gtaaagtatt agagggtaaa actatatgga cagttaagaa agaaattaaa catacatttg  84360
gtaaagatga attaaaaata tttaaagata attacaagtt cttgcaacat aaaattgtag  84420
accttgctac aaaaggatat aggtaggtga tataaatgga tatagtagat aaactcatgt  84480
taggttttat tttattgttt tatgtaggtg tatttatttg gtacttatgg gaagtctgga  84540
aattaacttc tttaatatct gatatagtta ttaagtatta tgttcgtaag gagtgggtta  84600
aaggtttatt accttatttg attcatcaag ttattattac gttagtttgg gctactctag  84660
tattagtacc ttttatactt agctatataa tgataaaata tttgatagga ggttactaaa  84720
tggaaatagt atatgagaat gaatgtagag gatattatat ttgtgtcata gataatgaag  84780
gtaagtatga agtatcatct tttaaaaaat cagtaaacaa gtatacccct gaaattacag  84840
ggtatactac agaaaagtta ctcttggaat taaaaatacc atgtacatat gtaaatgcta  84900
gtgaagtaga aagttttatg caagaattaa aagtagcacg tattgcgctt gacaagttta  84960
ctaaagattt atataataaa ggcataacaa atattatatt ctaaagggtg gttagtatgt  85020
atacagaaaa atatagaaat ttaatccata ttacatatag tatcttggtt agtattcaag  85080
aattagcaag taatttatta aataaagaag taaaactagt tacaaaagaa aataagtact  85140
tatgtgttgt agatggtatt attatgttaa ttgttgagga aggattagta tacacctatt  85200
ttgataaggt aggtttaaaa gtgcctgaac gtattgcact tggtcattta gcaaaaagtt  85260
tacagtttac aatatcggaa tcaaataaag atttagaaaa tcaaaaataa gtgttgacac  85320
ctttaacatg ttgctttata ctaagagtaa caaaacgtta gaggtgattt tttatgtgta  85380
aagaaaaagt tcatagacag ctatctaatg ctatagaaat attagcaact tacaaagagt  85440
ggtggtcttt tccaaaagaa ttaagtccca cagaaacatt taagattatt aactggaaag  85500
aagatacatt agtatttgaa gttagagata acggtaatta tataggtagg tttagtgtag  85560
caactcctat tattgacttt cattatgata gaattaaaaa aacgacagca caatacatga  85620
taaattattt tgctaaacta gtatgtaaag atatgtatac gtattataaa ttacagagag  85680
```

```
gacagtaaaa atgaaaaatt taaataaaca aaaacgcttg acgttggaat tgattagtga  85740
taatctaaat acacaacata acttaaatac atcggttagt cttgtagatt atagtataaa  85800
agactttaca aatagaaaag tgtatgtaag aactaaaaaa ggtttagaac ttactaatat  85860
gaaaagttta aaaagtactg agtcattaga tttattattt aagtatctag aattaatttt  85920
aaaaggagat gtataacatg ctaacaccag aacaaagaac acaattaaaa gagtatcaaa  85980
ataaaatgac aaaaaagaaa aaataaatgt tgacttacta aataacaagt tgtataatta  86040
acttaacaaa gaaaaaggag attgataaat atgaaaaact tatataaaat tttaacagga  86100
gtattcttta gcactacact attattagga ggttgtgctt actactcaca agcagataca  86160
ccgacacaca attataagga agacaagaaa gaaaataaga aaaatgattc atctaaagta  86220
gaagaacaag aaaataaaca aattcaagaa gacaacactg ttcaaaataa ccaacaagat  86280
aaccaagtac aaggtaacca agcacaacag aacgaacaaa tgcaagaggc aagcagaagt  86340
gaacataatg gactatctaa tgctgagtat gcggacaaat acaatcagta taaagaagct  86400
caacaagcac aagcagaatt agaaaacaga actgaagcag ataaagctag tggcggtgga  86460
ggcggaggag cctcatggaa ttatgcaggt gctaatgaga gctttgagca atggttacaa  86520
cgctcgcaac aagaaaaggc tgaggctgga gtacaagcaa attaataaaa ggtataggag  86580
aataacaatg aaaacaataa caaaagaaga actacataaa gttttagaag agcataaatt  86640
atggttagat agtaatagtg aagaaggagc taaagcagat ttaagttata ctattttaag  86700
aaatgctaat ttagtagatg ctgacttaag gagtgctaat ttaagaggtg ctgtcttaag  86760
gtatgctgat ttagaggata ctaatttaag aggtgctacc ttaaaaggtg cggatttaac  86820
aagagctaac ttaacatgtg ctaacttaag ctgtgttgat ttagatgatg ctaacttaga  86880
aggttctgtt ttatatggaa ctgatttata ttatgctgat ttaagaaaag ctaatttaac  86940
agattccaga ttaaatgagg ctaatttaga atatgcagac ttaacaaata ccaatttaac  87000
agatgctaaa ttatcccaag caagtactca aaatatcaaa ggactaaaag tatactctat  87060
agataatatt ggaacttta atggtaaagt gacttatatt cctagcttag atagagtata  87120
cgcagggtgt tggataggta gtttagaagc gtttttagaa aagggattag agatgaatga  87180
aggaaataat agtaaacttg aggaaataag agatgcttac tgcttttta gtaaacgtaa  87240
atagatataa ggatgattaa ttatgaacat tgtagaacaa cgaaaaccca taaagagtaa  87300
gcatattaac ctaactaaac atgcgtatga acgttatact ttaagagtta gtaacgatag  87360
taaagaacgt gcttgtcagt ggtttgctag tgctttaatg caagctactt ttgaacatac  87420
acaaaaaggc ggtaatgaag tatatgtatt taaaaattat agaattgtta ttgataagca  87480
tctaactatt attacagtta tagatactga agatgataat tgggaaggta taaaagaagc  87540
aagagaacaa atagatacgt atattaaagg taagctaaaa agaactgtta cacctctatt  87600
tactaaatta gatagaatag atattagtat ccatgaagca catatcagca tgattaaaac  87660
aagaaaccct aagacaaaag atataattaa caaaaatatt gttgaacttg aaagaaataa  87720
atctttacta ttaaatagta tagaaggtgt aaagaaaaca gcacataagt attatgtaga  87780
attaaaagac attcataaaa gattaaagga ctgataataa tgtgtttaaa agatttaatt  87840
gaagattata taaatcaaga taaagaaata attataacag ttacaagtac taaagtaatt  87900
attgaagcag actatgatgt tatttgttta cctaaaagta aaattgatat tgacgattta  87960
aaagcttatg tatatggatt taatagattt aatatagagc aaattgtatt aaaggacgtg  88020
gaataatgca agacttaaaa aggataacac aacctgaatt agatttattg atagaaaagc  88080
```

```
atgaacaatg gctagctaca aatgaaaagg aaggagaaaa gctcttttta cagtgtgtag  88140
atttaagaaa tcttgacttt cattccgctg accttcaata ttcaactatt gtaatgtcta  88200
gtttaagtga tgctaaccta agttattgtg atttaagtta ttctgattta agttacagtg  88260
agtgtatatc tacgagattt acacatgcta gaatgagaga tactgagttg cctcatacta  88320
acttagaagg ggctaattta ataaaagcca acttagaaaa tgcctgctta gctgaagcta  88380
atgtaagtga agcagacgct aggtgggcta atatgaaaaa tgctaactta agtatggcta  88440
atttaaaagg tgcagatttc ggtggtacaa acctaactaa tacaacatta tattatgcta  88500
atactcttga cgtatttgga ataagtatat atactataag taatgtactt gattttgatg  88560
agcatgtaac ttatttacct gattatgata gaattattag taattataat gaatataccc  88620
ttgaagagtt tggtaaacta gaacctacac ttgagtacga agaagataga ataaaagaag  88680
tctcaaagaa aatagaataa aagaagtctc aaagaaaatt aaattatctt acgatttctt  88740
taaaggagtg aaagaaattg ataaaattta attcagacga acataaacat atacttaatg  88800
ttatggatag attaccatat acttgctggt tagatactgt agatggtgag tcaggtgctg  88860
actttttatg tgtattaaat aggacacact atgaacttac tgaactaggt ataatgattt  88920
atagttatga tagttggtat atgataccat atgacaaaga agatttaatt gaatatgcaa  88980
taaaaagaga tatagaggag gaaggggaat ggtaggtatg gtgattacat ttttaattgt  89040
tttaggtatt atattgctaa gtgtactaat tattgttata ccagatttaa gcaaagcaaa  89100
aaaacgtaaa gaagacgcag atattaacta tagccaatat actaaagaca tggcttctga  89160
gtactatgaa aagtatataa cacctactga acacattatt caaactaaag tagaagaggt  89220
aattgaaaac ataaagaaag agtatactgt ctctactgta attattgact cttctagtaa  89280
tgaagacaaa attatcttac atgttaacga taagtactta aaaaaggtag tgtataaaga  89340
tacgtatgaa tacatctacg attctaatac aaaataccaa tacattatta ataatgtaac  89400
atatgagtcg agtatcttat taaaacaaga tgaagtaaat aaattaaaag atatacttaa  89460
taaagtacct gtcacagcta agcatacatt taaaaatgag ttgcttaatc gtaggaatga  89520
atatgtgtta ggttatatta caatatatat ttatgatgat ttaactgcta aaattacaaa  89580
gaatggttat gtacaagact ttagtacact agaagatttt tgtgataagt atgaagctta  89640
ctgtagattt gttagaattg atttatatga ctgggtaaaa gaagtaagaa ctattaatgg  89700
gtataaatta aaggtagata ttaaacctta ttttaaaatt actgctacta aaacaagtaa  89760
atacgaattt gtagtaagtg atgatgtatc taatgttaag gtatatagag atgatatgct  89820
actaacaaac aggtatgtgc aaaaagcaat tgatatacag gaaatagtag aggaaacatt  89880
gaataataat actgtggtat tttaaaaaag gaagaagtag ggaaattccc tacttttttc  89940
atatataagt gttgacatga ataagtgtaa ggtttataat aagtatataa gttaaataat  90000
tatagaggag acattaatca tgaaaaaaat attaagttta gttttatccg tactaattgt  90060
actaacaata atcaatgtgt tgaaaaacca agagcaagta gaacaaagta accaagaatc  90120
tcaaaataat gaagatgcag atgaccatac ttcatacgta cctgagaata atggagaaca  90180
caaagatgtt agtggagaac acaaagatgt tagtgaagaa cgtaaaagat tatggggtac  90240
agagtatcaa gaaggtgaaa cacataaccc aaatgctaaa gtgtttaatc aagatacagg  90300
agaacaggtt caataaagag taagaggagc acttattatg gaatactgga aagaacaaga  90360
catatattat tcaaaaacaa aacaaggtgt tataagctat atagacttat cttccttgct  90420
```

```
ctaaacaatg ttcaacatta ccaagaagtc agtggataca tgaaccacca gaaaacaaaa  90480
ttatcagaca tagaaaagag agaatattgt aaagaaaata gtatacaata tatatagaga  90540
ttgatgctag aaagtctacc tttaaacata tattaagtaa cctacaaaga acatttaaat  90600
actctaatat agatagtaaa gaagtaatta aaagatatag acatgtatat aggtaagtgt  90660
agaagagtaa acaaccaaac agacaaacaa ataggtatag agattgatgt aggtagaagt  90720
tatataagta agtaataggt aaaagaaaac aatatatata agtagataaa gaaatcagat  90780
aagtaacaca taaagaaaca actgatatta taagtaccta tatatcaagg aaataagtaa  90840
tagataaaaa aacaataatt gatagcacat agataagcag taggtagtat ataagtaata  90900
gctaaataga taagtaaata aatactgtat aacagtttga agatatgaat aagaagaaag  90960
aattattaag taacttaagt attaatagat attctaatag taagtaatag atattaagta  91020
gtaggtaagt aactaaaaga aagtagctaa aagaaagtag ctaccactat cacttaggtt  91080
aggtaagaac agttacctag taatttcttt acatcttcta gatagataaa taagtagata  91140
ctaagtaata gctagtaagt aattaaaaga aaacaggtac atggtatacc tatatactaa  91200
gtagcaagta gcaagtagca agtagcaagt agcaagtagc aagtagcaag tagcaagtaa  91260
gaacaggtac atgggaattt ctctgcttcc ctccttcata gtgtatatat agttaggtgt  91320
ctaactatta gatatctaac tatttatttt tatatagttt taactactgt gaactatgtt  91380
tatgtagtat taaactatgc tgattatatg ctaaactatt ctaatgtata gttaaactaa  91440
gctgaagtag tatttactgt gtataaaggt atatttagta ttagatattg tgtatatggt  91500
atactataat tctgaacatt acttatttaa tatatatata gtttgtttct gtggtagtat  91560
tgacttaatt ttccctagag taaaagttta atatatttag taatttccga acaataaaga  91620
aattttaact attttacaca tatgtgttga cagtatatta cttatggttt atactaagta  91680
tataaagtta aaggagatga tttattatga agattaaaag agaagtttcg tttatagaat  91740
taatgtatat gtattataaa ggtgatataa aaaaaggtcg acactattct actgatagtc  91800
agtttattgt tgttataact gttgatgata tatcgtttta taatgcattg tatcctaata  91860
aatctattac tattactata cctaatgaca ctaagtttat tgtagaagcg gttatagatg  91920
cttctactga gttaagtagt atagtagtta cttataagca aggtaacagt gtattaaact  91980
cagtatggta tagaagtagt attaatgaag ttattgacta ctatgtcgaa ggtaaaaata  92040
catggttatt gtctgttagt actgttgtag ataatgagtt agttactata tggaaagatg  92100
gtaacgtatt gtgatttggt atatagtaat attcagtata cttatatatg tacagcactt  92160
gtattattat gtgtagtact agtatataga ggggttaaat aaccgcttca ataaaaaggg  92220
ggattagttt atgagtatat ttataagtat cgttgctata tttttagcta ctattagtat  92280
tgtactaagt ataaggtttg gtaagaagta ttataagcat gtactcgata attatgatag  92340
tgttagtgat ttagaatcag cttgtgtgtt tggtttatta tttatgagta tttgtattgg  92400
tactatttct attgttttga gtttaggtta tctaatagtt aatttgttac attgttaggt  92460
gtatttaggt atatagagta gggcatatta agtaagggta tttttagatg ttaattttaa  92520
gttggtttat tatcggcata tatcttgctt gtttagttac tattacactt ttttctatta  92580
aagataggga tattattcct gctacactag gtattgtagc tcttattata gttattattc  92640
ttatatctac caaagtgtta aatatgtagc ttaagtgaga ttaagtaagg aggattataa  92700
atgttaagtt ttattttgtt atgtgttgct ctaggtattc cagaactttt cttacttact  92760
attttaggtg ttatcttagt gatatctatt aaagatagga atatagtctc agctatattt  92820
```

```
gctattgtag tttttattat aatgagtata cttatatccg cttcagtact acgtatgtta  92880
ggtatgtaat ttaaaaagga ttaaataagg agggttagag atggaaaaac tacaagtatt  92940
aaataaggta ttagaaaaca ggttaggcat aaaagcgttt acgtattctc attatagtaa  93000
gcataacagt aacggatata tttacagttt tcatatgaaa aaagaatctt ttacttgtca  93060
tattgttgta tatgatgtta gttgtgaagg tttagataca tatagagtaa aagtactaga  93120
caaggatgat aaggtaaatg tttcaacttt atatacttta atagaaagta tgtatgatat  93180
actactatat gaatatgata agtacctaaa agacaaagaa catcaaaatg aaatttactc  93240
tatgtttgat aaacaattag atactattta agaagaggtt tttctctagg gaaaagtagt  93300
caaaggtaaa aatagggctt gaacccgcat tctatggttg acatttaggt aaaattagat  93360
aggttttccc tagaagaaaa gtttaaaagg taaaaaagga gttggttact atgtcaaaat  93420
tagctaagtt ttgtaggaag tatggagaag ttactggcat aatggagaat attacagatt  93480
atgagatgta cttaggtagg ggttataaag taaggtgtag agtaggtaat agccttattt  93540
atgttcttgt atataaagac aaccatatca ttgctaggtt tgaggaagcg gataatatag  93600
tatttccttt gagtgatacg cttgaggtgg ggacaattaa agacttagag gagctagaag  93660
agttgtataa taatatctat acattattag ggtatttata tacagaatat gaaaataaag  93720
ttatgtatga gtatgggagg ttagaataat ggatattacg gtaagtgagt tatttgagta  93780
tatattaggt cattatacct ttagtagtgg ggattggtat acttatgact taggtgaagg  93840
ttactgtatt aaatttaatg atgggtattg taggagcatg cattttatca aaggtactag  93900
agtagtaaaa gaggttctta tcgatgataa acagctcttt aaagggttta gtagtattta  93960
tgattttatt gattactgtg aggaagcttt agatgaaaag tgcagaaaag aaaaagagcg  94020
cctaaaggaa attcgtacgt tcttaggtaa gtagagtatt atttattatg tataaccgct  94080
tctatatgaa actttatacc tatagttatt atacctatag ttattatacc tatagttatt  94140
atacctatag ttattatacc tatagttatt ataactacag gtattttttt atatttctta  94200
cataaatgtg ttgattttat gtgtgttaag gtttatactt aatatataat taaaggagtg  94260
aagttaatat ggatatgaat aaagaagtat tagaacgttt agatagttta ggtggtaagt  94320
tagagcaagc aggtacacat ggttatgaat ccttaattaa atacacagtt actcaaggta  94380
ttatagattt atgttcaata agtatattat tatctataac agctatctta tgggtggctt  94440
tgtataagtc agataaaaag tctaatgaag gtcatagtac cttattattt gagtttgttt  94500
gtaagaatga aaaagagctt tctgctgcag gatgcatagt aattatattt gctgttacta  94560
tgtctattat ttcttttta gtgctattaa taggcttgcc tattgctatt caagagattt  94620
ttaatccaga aggatatttg attaagagta cgatagataa tttaaaataa ttgtaaaaat  94680
aaggaggaaa atataatgtt agaacaagct aaaggtataa ctacagatta tattatggaa  94740
tttattgatg aacatgagca ttattcctat gaagacttac acaagttagc aggggagtta  94800
gtgttaaaag atacacatga cacaaaccct attgttatta atgatggaga tggttactca  94860
ggtactatta tatctaaatt taaatcaaag gtagagggtg ttccagatat cactgttagt  94920
gatttttacg gttcatgttc tttctgtgat actttatcta atatctatga aggtagtgat  94980
gaacttgaga taattagaga tttagctact atggtactac atacaattca atctatggaa  95040
gagcaagtag aataatgtat aagggagtgg tatagtgttt agtaagagaa aagaaattaa  95100
agagtataag aaacaaggtt actctgttga gtatatagga agtattttag gtttatttgg  95160
```

```
tattggcgat gttttatact atgtagaaac taataagaaa tacttaaagt caattagcgt  95220
aggtaaagat gacaaccaat atgtatatga ctttaatggt tatgaatact tatcaagaca  95280
taagttaaat atcaaagaag aagaactaat gtctaaagct attgctcagt taagtatcaa  95340
aggtttaaag aattttaatg gagttaagca taaatgggat gtaggtttct tagagcaatc  95400
ttttaatgta catcgtaaag ctattgatat ggttaaactt aaactaagtt ttgatgaagc  95460
gggtaaccta tattatgaat tagaattagg ttggattaat atttataaag agtatacagg  95520
tgtaaaagac tttcttaata cagtagataa ctatctcaac ttcttctata aagatatagt  95580
cactagtggt cttgaattaa aacaagtact atataatact tttattggag gagattatga  95640
gtttgtagta tctccatata aggttgaagt atatagagaa gctgagttaa ttgatgtaag  95700
agattttaat tatagcttct gggaatatgg gtacggcact aatgtacata aacctttaca  95760
aacaattaag tattatctgg aataccctat gaatgaagtt gacattaatt aagtataggt  95820
gtatgataga tatataaaga ttaaaggaga atagataatg agtagtaaca aaaaatagca  95880
gaaagagtta ttgagaaatt tttagatgag actaataaag gtgtagattt tactaatcaa  95940
gatgaattta accgcttctt agataataca gaagacttgt atgaagtatc tgaaactcaa  96000
agagataaga ttattaaatg tttacaaaac attgtagtta ctgtatttat ggataaggat  96060
aaataataag gagaaataac aatgaaaaca ataaaaagaa aaatagtaca agaaggtatg  96120
aacaaagaag aaactatgag ggaagacgat tctgttgtaa tcaaaaaaat tcaaaaaata  96180
acaggtgggg ctattcttcc tttatccaat ggcaaggaat atgtagtagt gtttagtaaa  96240
gtagacccta ctaaattaat tgtatttaat gtggaaaata atcaaatcta tttaagtggc  96300
tctggtttcg atagtgaact gtcttatgta gacagtaaaa gcaaccctat taccttagaa  96360
acagttaggt taatcactaa tttattgtaa ttattatttt gaagcgggta acagtccgct  96420
tctttttta aataagtagt tgacaagtat attagtatgg tttatactta gtatataaag  96480
attaaaggag ttggttatta tgaaaacaat tacacaagaa gaattagata aagtattaaa  96540
agaacataaa ttatggctga acagtgatgg cgtagaagga actagagcaa atttaagtta  96600
cactatgttg agacatgtta atctaagagg cgctgattta agaagagcta ttctccgtaa  96660
agctgactta agtcatgctt acttaacagg ggctatctta agagaagttg atttggatgg  96720
tgctatttta agtcatattg atttaagtaa cgcggattta acacacgcca gcttaaaata  96780
tgttgattta agatacgctg atttaagcta tgctatttta tcagctacag atttaagtag  96840
tgctgatttg agattttctt atttagataa tgctatttta aagtttacta atctaagccg  96900
agcaagtata acaggagtta taggactgaa tatttactct atagataata ttggaacttt  96960
taatggtaag gtaacttata ttcctagttt agacactgta tttgcaggat gttggaatgg  97020
aaatttagaa gcgtttttag aaaaaggttt agaaatgaat gaaggaaaag aagcggacaa  97080
gattaaaaaa gcatatgaat tttttaaagt gtgtacagat taaagattat taggctttta  97140
aagattaagt tattttatag gataaatact actagaaaat gattaccgtt taatacagaa  97200
ttttaacgta cctagtttag aggtcttaaa tataaaggag ggtattagaa tggctaaagt  97260
tgtaagtaga ggatatagtt ttgaagaaca agaagtaagt atgaattata accaagggca  97320
atggattatt tacgcaagta ggaaacctta tattaccgat attatgaaaa aatatccgga  97380
taaggtagaa gtactagagc aactagataa tggtacacct gtactcgtta aagttatatt  97440
agatgaggat ttaattacgt taagaaaacc tgtaagtaac gagcgtaaag aacaaatgaa  97500
aaagattgct aaagaaagat ttggtaaata attaaatata ctagtgaaga agaatctgac  97560
```

```
attaataaac accaacgtga taccgtaaca cttgtaggaa ctagactaat gttacaagat  97620
atctagtatg gttatggtct tattgagaat gagtatgctt taactaaact agttaaagaa  97680
gataaacagt atttacaata tcatatcgaa gaagtagaag cggtattaaa ccgcttcttt  97740
tttatacatt atttacattc tgagtaaata tactgtattt aatcttggct aataattgta  97800
tatcaatttg agcatagtat gcccgtttca acatagttaa tctaataatt tatatattta  97860
tctgttagtt atgtataaat atttgttatt acttatttat atatttgtat ttcgtactaa  97920
ccgtacgact tatcttttta aaaagataag aacaaaacag cgtatacctt gttgttttac  97980
gctacgctac aacaaggtaa cgcctgtaat aagttattcg tattaaaata ctaacaacta  98040
attacttgtt gtttagatta taacatatgt ttatgagaat tagatgagaa tttagttaca  98100
acagcattat aataatatta cagttatgtt acaagttgct aagtatgttt tgttactaca  98160
atatattgaa tatgaaaact ttagaccttt tctgcagaca agtaattatt acaggtatgt  98220
atgataaaag gtaagtatca gggattaaat taaggttgga ttaatgaagc ggataagtta  98280
gatactgatt aaaataaaat actttacatt acctaaaact tatgatacac ttaggatagg  98340
ataaaggagg aatatcaatg aatattcaag aagcaaagga taaattatac gatgaattac  98400
tttatacagt aagtctttgt gagggaacag aagaagattt actagaactt attgagaatt  98460
tattttatat ttacaatgac gagcctgcat ttttaagtaa agacggtatg caatatacta  98520
ttaaagagtt tatggagaga agaaaaacat tagaacctat cttaactgaa ttaggtatag  98580
ggtacgcaat gatagaatat aacacacata cagaatacga gttagttact cattcagtac  98640
ttaaagttat acagtatgat gtagataact atactgtaat tattgatact aatagtgata  98700
agaatattaa gttatcagat ttaacattag aagctgttaa ggacattttg aatcaaatta  98760
agtagctagg gttgttttta ccctagcttt tttatatgct tgtattgcct atttaactac  98820
attatataag caagtaagta ttataggata aatactacct aaaaagtatt accgttgaat  98880
atagacctat aagattaagg ctctcttact gttataaaca tcataagtat aaatctatga  98940
ttttcctaag tagcaggcgc tgtttttact aaaaaatgta aatatcgtaa gtatcaggcg  99000
ctgttttccc tttatattaa ccgcttcaaa caacataaaa aaagattagg ttaatagcct  99060
aatctataac tcttttatat aattcttgta attctttttc taactttttt attgtttcta  99120
tatcattatt tcttttaata gactgacata taaatgcaat acctttaatc aaattaaatg  99180
gttagtttta cactgcattg tatacaatta aatcgattga ttataataat taatttaagc  99240
tgtactttct agtttcttct atataatggt aagaaaacat ttatttaaaa aactttcgta  99300
taacctattg acattaaata caagatactg taatataata agcgtagtaa acaaaccgaa  99360
aggaattgat aggatatgaa cgtaaataaa attggggata tacttgtaga acttttagac  99420
atggacggtt acaaaagcaa taactactat agaaatgact taaaatactc tacacattat  99480
caagttaaat atttagctta cattgatgat agctatgaaa cattagaact atttaaagaa  99540
acgaaagtct ttagcgtatc acattcaaat aggttaccaa ttaacattaa tattaaggta  99600
gtaaacaaac acttatttat agagctagat aatacgttat acctagtgaa cgagaatgca  99660
gaaattatta aagaaaaaaa gttaaaataa tagttgacac tagaattaat atagtgtaat  99720
ataataggtg taatacaaat aaactaaaag gattgattaa ctatgaaaac attaattact  99780
aatagtaagc cgtataagaa ctacggctat gaaatggaac aattcgagag agaaaacaac  99840
gttattatca cacgagcata ccacgaacca acaaaacaag gctatgacct tgtagtacat  99900
```

```
tatacggagg ttaaataata tgaaatacgt agactacatt agaggcacgt acaacagaat  99960
taaagcacaa ggatatatta cgaataattg tagtttgtgg tctgatatgg atgaatgtga 100020
cgacttatat tactatatca ataaagcttg ttttaactta tacggtcaag gcgtacaagc 100080
aataacaaca acgccaaaat gtgttaaaat gatacttaat gacggtcaaa caaagtttgt 100140
taaaaaaggt taaaataatg tttaacatta cacttaagat actgtaatat aatagatgta 100200
gtaaaaaaac aaatcaaaaa gggattgata cacatgatta aatttaaata taacggcaag 100260
aaataccgtt caacacaaaa gacagatgct attgtaacta ttataggtgg tacagcagta 100320
atcacattga tagactggtt tattagatta caagataata ttaatatatt tattaaataa 100380
gggttaacca ccccttattt tttttgtgct tatataaccg cttcacatta gtgtaaaact 100440
tcccttattt ctttgctaaa atactttaca aatatgagct tatactgtaa tatataaagt 100500
gtagtaaaga acacgacaga gaacactaaa aaaacttaaa aaagttttaa aaaagtgttg 100560
acactaacat taatatagtg taatataata gatgtagtaa acaaaaacaa acagaaaagg 100620
aattgattaa ttatgaaaaa tacagtaaaa gaaatggcaa acggaaacac taaacttgaa 100680
agattattag ttttagcaat tgaggaagcg gttatgacag agcttgttga atatgatgca 100740
ttagataaat acaaccactt agaacagcag ttattaaaca atgaaacatt aacacaagca 100800
gaacgtaaac catctaacat tgactatagc acttacgagg gggctatatt agcacaagac 100860
aaagcagaac actttactaa cgttatctta aaccacatga acaaagaaca atttgaacaa 100920
atgattatgg atattgaaac actagaattt aatgcagaac aaatgctatt ctaaggagac 100980
attacacatg aacttatctg agaaagaact tatagatata atggacaacg ttaatagctt 101040
cactggtatt gatgaagcta ttaacgaaat ggaaaacaaa caaacaacta aaggcagtga 101100
caaagacgca ggagcaatta agaaatataa tagtttagat gagttaagac aagactatga 101160
cataacaaca ttagcaccag atgtaataaa agaattactg aataatcatt agtgtaaaac 101220
ttcccaaaat aattaactaa aactattgca attaactgta gatttgatat aatgtaatta 101280
aggaaaaaca aataaaagaa aaaggattga taaactatga aattacttaa ccaaatgaaa 101340
caaacagcag aacttgaagg aattgaattt gacttattat taacagctat ctatgaaaca 101400
atagaggtag aagctgttga acatgattta ctatgtaaat acattcatat tgtaaaccaa 101460
ttaaaagaga ataaagacat aacaccatta gaatatatac cttctaacct agactttaca 101520
gacaatacaa caataagact agttgataat aaagtgtttg agttagcaga ttatataatt 101580
gaacatatga gtgttaaaga gtttagtaaa cacattaaag actatgaaca aattaaagca 101640
aaagctatag aaatgatgta aaacaaattg aaagggaata aactcccttt ctttttttta 101700
ttattaatta ggattgtata caataggtta atataaatat attatacggg ggcaggggta 101760
aaatgccact aaagtgggtg ggtcttacag ggctataggg ctacctaagg aacctaatta 101820
gtgagtaata ttatataact tattattaaa agtcaacatt aaccattact ttattaaact 101880
atgtcaacat tactaataac taattgtatt cattttacaa taaagttagt aatatgtttc 101940
cttactctct tacacttaat tagagtatta gtatattacg acatataagt agtttagtat 102000
ataggagcct ttccttatat atagttttct atggtattct atggtattct ttagtatacc 102060
attttaataa ctatttatgt aagataccat cagttagtat gggatattac ataacttatt 102120
attaaaagtc aacattataa agtacagtgt actaaaaagt caacatagta ttattactat 102180
taaagtcaac ataataggat ttccattatt gttcttattg tcctacctat ccctattgaa 102240
ttactagcag tagtgttact ctatttctta caatataaaa aacacctata gtaattaata 102300
```

ggtgtttaat gtgaggtatc atatccatac tcaaacaatt ctttatctac ttgttcgaaa 102360
cctttctttt tatcttttat aatatagtta ccgcgtacaa ctttctcaat acctgaaggt 102420
gttttaataa acaggctatt gtctccttgt ttatctactg ctctaaatgt ttgaccttct 102480
gtccactgat taataacatg cttattatat cctgtatatt gaatatactc tactacgtct 102540
tccatatcga ttaagacttt tagcatatac tctcttactt tagcataatc atctgtagtg 102600
gtatctaagt ctaatggttt taattttgct atattgctta tattacgttc tcttacaggt 102660
gtttttgaat attctaccat taaatctagt aattcttcac ttgcacctaa actcctaaaa 102720
gaatattgtt cgttgagaaa cacccaagca ataggttgtt ggttttcttt tttaataagt 102780
atttttcttt ttctcttggt agtattttta tttgctaagg taacagtata ttctaactgt 102840
tttacatttt caataaattc atttgtatac ataggtggta cttcctttgt ttaattatta 102900
tccactatgt ctatttcatg gattgtaatc atgtcatctc tatactcatc tatatgctta 102960
aggtaactga cgccatcatg ttttctagac attccttgta attctctata tccttcggct 103020
ttaatatctt taacaagctg ttctttgtta gtgtatactt tatcttctct atatgagtag 103080
ctatcctcat aaggctcaca atagtcatgt tctacttgat atagtttcat attattttta 103140
ctccttttta attttatctt ctaattctgg taatacattt tttgaaatat atttatttaa 103200
gtcatttatt gttttaactc tataagtacg catgtttctg ttactaatat ataaattata 103260
taaatcctct accttacttt caatataata gaaaggatag cttatacaac tcattaatag 103320
agatatacta tacagtatat tttcaggtaa ttctctagta aattttttaa ttttatttac 103380
ccttttttct cttcttaatt ttttatatag ctttcttagg ttgtgctcat gtttttttaat 103440 tacaagtagt tgattttggt taagtaagct atcgtcgttt ttgtttatat agtttaatat 103500
tcctttatat aaagttagta attctctatc atccatatta atattatctc cttatgttct 103560
acatttaacc agactaaagt ataaatgact tgaggctcta tatctcattt attctatgtc 103620
cttcttttac tgattggttc catgatttta gtttttcaaa gaacttggag tctactttac 103680
cttctaattt ttggttagta taatcatcat agaaactaaa tgttccgcct ttaaaaaagc 103740
aataatacgt gtctgtcgta tagttaatat taatgtactc tatatagtct tttgttactt 103800
ctggtttgtc ataacgtaag actggtattt cttgacgtaa caattttatt ccttctttac 103860
ttaaacctgt atatcttttt agcttgaaac cgaacctcaa ccaaaagtct atttcattga 103920
ggttaaaagg ttcatttact tttttaccta aaatactatg cataaatagc atataaacaa 103980
gttctatata ctctatacat gttgttaaaa aatgttgttt gtcttcaaag tgatggtaag 104040
ccaacaaata caaaaacgta aaagggaaaa gaacaatgga cattaaaaaa tataaaaatg 104100 atttaatct tgtgttcatt actcagacac cttctctaca tcatatagta ttgggtatag 104160
attgaagata tgaactctat atccaatagt tttaactttt actttatctc ctacttttaa 104220
tctagcttgt atgtctgcgc tatcaaactt tcttttgaag aataagtctg agttttcaat 104280
gacttgtttg ttgtctaata caatatagaa cttgtcttct ttatcttgtc ttttgttata 104340
tttatctgta attgttcctt ggtgcgtttc tttgtgttga tagctagcca ctgtatagat 104400
aggtaaagtg ataacaagta gcaatacggt tataccgaat aatgacagta ttccaaaaat 104460
aaagatatcg aaccaattca tatttttaag ttttttaatc attgttacag caatctccca 104520
tcttcccaaa ttagtcttaa cttactttga tgcataatat agaagcgctc agatttacta 104580
gatttaactt catttattga catattatga tgagtgagta tattttcgtt atctagatac 104640

```
tcgtatagct tagtaaatac catgtcttcg gtatagtcaa taactgatag ctctttgatt 104700
aaaacatggt cttccttata atcatttata tttttgtaat acccatatcc ccttactgca 104760
tcccataccc tttcgtaccc ttggtctaaa agtgagttta ctacttgttc tttatcccta 104820
tagacttttg tttctgtata tgtttcttga tattcacgag gtttacaatt atcatgttct 104880
agttgataca gtttcatagc taccccatcc tttccaataa gtatggattt tcatatatat 104940
ttcctttaac ttgtaactct aaagtatctg tgtatggttt tatggagaaa tcactaagta 105000
aagtaagttt acaccctgca tacctcacta tatagaaaaa tcccttaccc ttcttaatta 105060
aacctaggtc actataatta cctttggtat ttagtatttc tataatatct ccttcatata 105120
tatcattacc gtttacatct ttaacttctg tgctttgcat aatttcaagg ttttctccta 105180
aataaccttc acaagcaaat agatgtgaat atactgtgta atctgcaaaa tcaaatctat 105240
caatattaaa cattctttgt gattcttcat cccatgctct aaatttcaac atcatactac 105300
ctccactttt tcgatttcta tgcttacagt tttgaatagg ggctttttac gagtcagttt 105360
taatgccata ttcttagctt cttcctcatt tatactttgc acaaaataat gctttttat 105420
tttgtaatca catttagata ctaagaactt gatacaaaga cttactttat aggtttgcat 105480
cattctacca actccccatc tttccaaatc aatgtcatcg tcatgtcatc gtttaagata 105540
tagaatgctt tggtagggaa agacgcgttc tctaaacgtt ctttgatact ggtattgtgt 105600
gcagcgctga catataggct ctttctcgaa actcatatac ttcaaacaac ctatcaaact 105660
tagtatcttc tgtgatttcc tcttcaactt tgacttcgaa aagagtatcg atagaaataa 105720
aacctcctag agtaaaacat ttatttgtat ctttttgaaa acataccgct tcataacttt 105780
cacctgttgt acaatatttt ttgccttgtg atagctctgg attttctcta gcccatttaa 105840
ttaactcgtc taatggcatt tcttttttag ttttgatttt catttccata tctcctaatt 105900
atttaatttt tctatcattt tcacaatctt ttttgattct ctaatgtcag ctttctcaca 105960
gtttttttaat atgaaattaa ttttgttttt tacaacatta acgataatgt ccacttcttt 106020
ttctgttggc tcggtaggga aaagcaaccc tacaactatc tgaatttgat ttttatttag 106080
tgagtaaaca ctaatgttac atttctcatt aaagtcaata tgtggtttac ttgaattaaa 106140
tacctcatct acaattgtat ttaattcttg gataggttta aaataatgtt gttttctttg 106200
tatcattacc tgtgacatta gtttatatag tttctgttct ttatcaagca tttcttttgt 106260
aagtctttta acttccccta tctttatagt attacctcgt gcatcataat tatttttaat 106320
atactcagct tcttctatgt tagtagtata tcctattact tctgaggtgg gttcctcatc 106380
gtagtaacag tcctcttcta catatatagc atatatctta ttcatatcta tcaaaccttt 106440
ctttaagtta aattaactat aacatataag cattagggtg tcaactacta atatacactt 106500
tttacagtaa acaaaaaaaa gaaccttttt acaggttctt tactaggtta ttaatttttt 106560
aaatcttgat ttccttttat tagcttctta tcatcaatag gatgaccatt gtataaatat 106620
tttacttcca tatatacatg attatccgta gccgtaaggg catctaggat atccggattt 106680
gtgttaattg catttgtatc aggaaacgaa aattttcttt tatcagactg gattgtatct 106740
acatgaaatt tttcttgttt tggtaaagag taattaaggt cttctaaatt ttgtaggaat 106800
ttagtaagag aaaagggttt gaactttcct tgtaaattat tatctatata atcatttaat 106860
agtcttgtca tttcctcttt atttaaagtc attgtttcat aatcgttaac atcataaaaa 106920
acaacaatat taggttgctc aatacttgta tctccatctt tgtacttagc aatgtaatag 106980
cctatttcac ctttatgagc taaataatct tctttcatga tattaaatac ttctctagca 107040
```

ataggttttg tatatagttc ttcccattca tttgtttctg tgttgtaaaa atgtggtaat 107100
aagtttgcca ttatagttta tcctttctta ttccgattta agccatattt tgttagtgtc 107160
tttaggtggt tcattgctga ttgtgtaccc gtcggtaccc atatctaatg tgttaacaat 107220
gacaggctga gctacagctt ctttttcact ctctaatgtt ttgaaactag gcacatctgt 107280
tttattagat tcttgtccat cgactaacca agagacttta aagtcacctt tattataagt 107340
agtattaggt tttaaatctg ttaatgttac ttttactgtg ctacctgtaa cttcatcaga 107400
agttaaaata agctgttcct ctttgttgta gacctttaat tttttagtca taatgttatc 107460
cctttctgtt gtgtaataca ctaataatat agcatataaa aaacaggtaa gggctttcaa 107520
aacctttacc tgcttattct ttactgataa tcataccaat caagaaaatc atctgaacag 107580
cttaactcta tagttatatc atttataagt tcagtagctt catctttact taatgactct 107640
atatcaaaag taaactcatc atataaacaa tctatatgct tataaataaa atatttttgt 107700
ttttccgtag ctttgtttaa ctcattgctt tttttactta taaattgact aaagttatca 107760
ctcatttaaa tcttcctctt taataaaggt accattaact gtttttcctt tacgaccttt 107820
aatttcaccg taagcaaact ctaaacactc ttgtaatgac atgtcgtgtt gctgagctaa 107880
aataattaaa gtaactacag tgtccccaat accatcttta agagcttcta ggttaccacg 107940
tgataatgcc gatgctactt cacctgcttc ttcgtagaat ttaagagctt gtctatcagg 108000
gttgttattg ttcaatcctt tatctttact ccattcctct acttgactaa ttaaaccttc 108060
tagcgtgcgg tcttctgttt caccttcatt aaagttaggt ttttcatcat ttggtacatg 108120
ttcttcttgt tctctatcct ctattgtaat aaataaagtg tctatttctt tttcgtactt 108180
atttctctgc atataattat actgcccata ctcaggataa ggtacatata cagtatcgtc 108240
tgtaccatcc tcataattca aacaaacaca aacaatatct ttgccactta atctatcata 108300
taatgtcatg ttgtagggct catctaagaa accatgaaac tcttcaaagt attcatcctt 108360
cataccactt acctcaatag aaactttttt tgctgactta cttgtatcta cttcactatt 108420
tccatatatc atagtttttt cttcactaat accttctagt atcaactcta cattttctgg 108480
ttctaacacc gcactatcta agttttcaaa aacaatttca atatttttaa tttttttagt 108540
cattaataat cattcctttt ttttagtata tagtaaatat aacacataag taaatagaag 108600
tcaataaaaa aaaacaccta ctttaaaaat aggtaggtgt aagatatttt agtaggtatc 108660
ttgtggaaaa aaatcctgag cagggactcg aacccctcga ctaggtagct acaactagcc 108720
aatgccatta ctcaggattg ctagtaacgc taaatagggt cataacgtta ccgtagacct 108780
tttctacgat ggtagatagg tagaatataa tgatttcaca gtacccatat ggttaggctg 108840
ttactctcat tataaggtta aaaaatgcta actgtgtttc gcattgttaa gaggcgttag 108900
ttaactacta taataatata gcatatattt tattgtttgt caagttcttt attccattta 108960
ctttttcttt ttagtaatcc ttttttaatt aattcttcac taatattttt atactcttta 109020
ttttctttgt agaacacttt agctaaatat ctaccaaaag aatcatcttt gtatgtttga 109080
attaaaacat cttttccttc taacatagtt gttgtaaatt ctttagcttc ttggtaatta 109140
ttttgtttct tttctggtgt gtcgacacct agtaatctta ttctttgttc agaatatgtt 109200
ctcattccgt ggtcaatagt tacatgtata gtatccccat ccactacttt gtccacgtgt 109260
gctttaaata aatataaatt gtcttctatc atcattaaat cccctttttta ctaatttaaa 109320
attatccaat cagtattgct tgatgtacct ttagctacat atacagatga gcctattata 109380

```
gcaatttgac ctttgtataa aggtatatta ctaatgcttt cagttacacc tatttggctt 109440
atgacttcaa aattagcttt tgtggatata aattcccaca gtatagagcc atctgatata 109500
acaccgttat tatgagtagg ttgtgttcca ccacttgtac ctgaagctac tgctttatat 109560
acataattcc cattataaac aatttgacct tgtgtataat ccgtattaga tgtccacttc 109620
atattagtag caactccatc gctagtacat ctccatttct caggactacc tgatgttagg 109680
gttctactag tattaacaac aatatctccc aatctccaac ttcctgtagt tggtattgca 109740
gtaccgttca gtactttagg taaattataa gctatattat ccttacttat aacattaaat 109800
gcattactag aaatacttaa gtttttattc atattgttat ttaatacgaa tagattacta 109860
caagaacctt gaacacttaa tgaatcatta cctttatctg tttttatatc attattagta 109920
attgtactat ccataacaaa atttaagaac atagctttat ccaaagcagt atttgtactt 109980
cttaatgtat tatttttaaa gttaatttct gacacaggtt tactagttgt tcctgaaaca 110040
taaataatac ttgtttttaa acttgttgta tcttgtttta atacattatt ttgtatatct 110100
atgttattaa ctcctggata aaggtacaac tcgtaaccct cattacctga tacattattg 110160
ttactaataa ttcctttact acctcctgta atagcaatac cattagatgg tttattactt 110220
aactctcctt tattactatt accataaatt acgttattag taattgtata attagtacct 110280
gatatactca gtcctgagta cttattgttt gtatgtatgt tattacttat aataacattt 110340
tctgttcctg attcaaaacc gcttgaacca ttccctgtag atacattatt aacatagtaa 110400
ccatttttag tgccacccat aaagttaaaa ccattctcta aacattgtgt agctgagcaa 110460
ctatctatag taatgttgtc tgagtaatca taaacaccat ctaccgcttg catagtgttt 110520
actgcattta caacgttacc cataatatta taaccatgta cattatatgc tttacagttt 110580
ctacttcctt taaatgctat tccaatagaa cgaggtgacg catatctaaa ttcaccttta 110640
ccatcccatt cccctttaaa tgttaatcct tctacaagaa tgttatcaca gttgataaat 110700
gagaatcctg taaacatatc tctaccacta gaagaaacat catctataga gtctagatag 110760
tttttagtga ttcctgacat aataaatgta ggattacctt cacctttaat gtatatatta 110820
cttcctgtta cttttacacg tgatgggttt tgtacagtag gtgttttagt tttgaataaa 110880
tagtcctctg ttcctttagg tactataaga gttccaccct tagtacttat taaataatct 110940
aaagctcttt ggaatctagg gtaatcatta tcttcatcat taattcttgg gtaatcttct 111000
atattaatta ttactttact cttagaatta gtatctttac ctagttcttt ccaatcatta 111060
ccttttagta cccaaccata tgcttgtgtt gtaccattgt tgtatacctt ttcatcatat 111120
ttaaaatctt caacactaga aggtttaaca tgagaataaa aaacatcagt tttattctta 111180
ctactatcgt ttgaagactt aataatatta gatggattag ttgaagctac aagtaaacct 111240
tgcatagttc cagatattaa aataacgata gacttaacat cttcactatt aacagtaaaa 111300
gtatcttttt gggtgttatt gaaagtgaac gctttatatt tatcgttata ataaccatcc 111360
agtaatattg tatcataatt attagatatt ttgtctaata tattaccgtc tttatcaaaa 111420
catttaataa atataccact agaattacct ataaatgata acttgttaat aattaactcg 111480
tcaccaacac taacattatt aacatataaa gccatagggt acgagcctgt aaaggtaagt 111540
aatcctttat tatctactaa actaggtgta gtactgtagt cataagatac ttcatctgtt 111600
agagaagttg actgtaatgg ttttctaaat acatttttga ctgtgtgata gttacctcct 111660
aatcttctat agtctttgct aaaatcatta tttttataca ataatgttgt tttgtattcg 111720
tctactattt tagcaatact acttctaggt attttagcag tattaatatt tgtaaacgtt 111780
```

agtttatgtc cattacctaa aacaaattca ggaataaact taatatcttt actatgtgtt 111840
acataagatt ttgtcatatc ttgagtttct aaatcaacaa ccgcaaaagt agctttgtta 111900
ttaaattcaa atctgtaatt cttaaatata aatcctactg ctttcttaag ataaaccata 111960
acataatttt cagatgttgt ggaagcagtt tcaaatttaa gtgaatcgaa tacattgcta 112020
tttcctccat aggtattacc atttgttaga gtttgtttga tgttatagta tgtgttaggg 112080
tgtttattaa actcagtgcc actatatgaa aaagctgatt tatagaagta attactattc 112140
atccaagatt gctcaccatt agaatctata ccatctgtat ttaattctat atgtgtttca 112200
ttattaataa agaaattaat aatagtatta ttaaaccaat gacctctacc accagtagct 112260
ttatgtttat tacctactgt aaaaccaata atttcattaa tattagtatt aacatttcta 112320
cagttaacta attctagtcc tatatagttt tgactcttaa aaccatgata gcctccacca 112380
taagttggat aagaactatc atcataaata cctttaattg taacattaga atatgataaa 112440
ctatctagtt taatagctgg tttatcctta ctaccattat aaacaatctt agcatcagat 112500
acaatattaa tattcttatc tattatcaaa gtatcatcta ttttaatagg tgattcacta 112560
gaaggaatgt gtagggtatt accttcactt gtatctttaa tagcacgtct taacctttga 112620
acatccgaag tatcatcttt ttgctttata tactcgttag agtatacata aggactttta 112680
cctgttttaa gccaatctgt agctgaacct gtaaaaccgt tatttacagc tacttcataa 112740
gcacttaaac cttgcttacc ttgttcccct ttctcccctt tttctccttt aatagactta 112800
acccattctt cttcagaacc gacaaaacca ttatctactg ctacatcata agcagattta 112860
gcatttacaa gtatatgatc tttaaaatat aatgttattt ctttgaatga tgattctagg 112920
gttgtaaaac caggaactac tactttatcg gtttcatatt tttcagcttc ccatgataca 112980
tagaactcac cttgagggta atgtgtgtga ggagctaagt taggtatgat tacagaccct 113040
acttcttcat gtaactctac attgtaacct attgccaata tattaccgta tttatcatat 113100
gcttttaaat gaggcattga aaatctcctt tgctattagt caatgttaat atatcataaa 113160
acacaaaaaa gggcaaattg ccctttagtt acagatatca tttagatgaa tatggtcttg 113220
tactgaatag tctacaatga catgtgtatg ctttttcttt tttgttaaca ctttatatgt 113280
gataaagaat gatacaatag ttaaacatat atttaatttt ttcataaaat ttctccttta 113340
aagaaagtat ttaccatctc agtagttaat tctttgcttt taaagataca agattctgta 113400
ttgttattca atatttctaa catattttgc atactacttg ctttttgtaa atccgttaag 113460
tctataacaa ctgttatttc tgcgttatct attagaatat tacctatgta ataattttta 113520
actccgttct ccgtagcatg agaggtgaca ttatgattta aaacaactat accttttgat 113580
ggtaagtaat ctgaaaagta taggtaacaa aagtatttat gtatcttttt tttattctct 113640
tccattacta ttaccatatt ctatgaagtt taacaacctt tcggtatagg ttttaatttt 113700
ctctacttct tttctttcat cgtcttttct tcctaatctt gttgtatatt taacaatatt 113760
aaatagcatg cagtctataa agccaataat gtagaaatat tcttctaaaa atgatataac 113820 atctttttttg cctttataat ggtttggtgt attagtggta gaattgacat tatagtataa 113880
ctctagttgt tctacatttc tcataagctt tttagcataa tataatgtgt catctaaaga 113940
atgtgtcaca tctaaagatg attcaataat gtttatcttt agttctttta attctgttgc 114000
ctctttgtta cttccaattt gtgagtcaat aaattctcta gtatccatat tggtgtcctt 114060
tcgtatctaa aataaaaacc ctatctagaa tatagatagg gaaaaggaaa gatattatgg 114120
aagtgtacta taaagtacac atataatata acagttcctt tgccttttaa tctatatcat 114180
ttattttaac ttcttgtact ttaacataat ctgataaact attaacgacg atattatctt 114240
ctactaattc gtttctatta tttgtaacat catatgagtc tctataaggt gtttgtacta 114300
atgctctaac tgtaatgtct atatctacat attctttact atacctttcc attactcaac 114360
gtagtttcct ttagcaagct gatacttttt gtgtaattct tcatataatt tctccatatc 114420
tttatatttt cgtacatctt cttcaaaatg acttaaatac tctattaatg tcttaacttc 114480
tttaggttct aaagttataa ctggttttac cattacgcaa catcctcact aaattgttta 114540
tttatatttt taatatcttt tattaattcg tcttttaatt ctttaggtaa ctcatgactt 114600
tttaaagatt gttgttgacc taacgtatat ccatattttg ttatccttac ttctacagta 114660
taccatgatt tttctaaatc gtcaactttt ctagctagta atattaaaca tctgtcattt 114720
ataatattcg aagcataact gccgacacaa tgagatagct gttcaccttc tctttttaat 114780
ttttcagtag tatccgcagg taaaaattta actttagagc catcgtttaa cttatattct 114840
ttatttgtga tattatttaa tttattatca tatttttgtt gtaactttaa gtcatcgact 114900
tcatctttaa ctgttaaata ctcatcagta acaatatcat gctctagttt taaagaatat 114960
ggtgttaagt taatactttc tttagttcta tatccaagaa gtactaggtc tgaagcaaag 115020
tctatataat ctctatataa attattaaca gcgtatgaat gtatacgttg tctgtttctg 115080
acatcatagt ttatataatt caccattttt ctaaagtcag aaaatgaaaa gttaagaact 115140
tctttcgtag tacctttaaa agataaagca tttcctattg aatatgaatt agtcaccatt 115200
ataaagtcgt catcgaatag tttgtgtaag ttagactcat tatataaact aggaaattta 115260
tttatgataa ctcgaagtat attaaggtaa ttttcttgct cttctttact aagagtaata 115320
aacttattat atgtttgttt acttaaattt aaagcttcat gtaatttcca tttatttttg 115380
tttggtatta ctagaaactc tttgtgttct ttaaatatat cacaatcttc gttgttataa 115440
actttatcaa tattagacac aactaatttt aacagattgt ttaaattatc agtagcattt 115500
tcacctttac taactgtgcg ataaccatca ggtctatcta tcatagagta tacatcaaag 115560
ttttttacat taagtctact tagatttaag taataatcat tattctttag tgtttggatt 115620
attatgttaa aagctaaatt ttcctttcca tatttactta aaataatatt taaaaggaca 115680
ggtaaagtaa tgttattttt taatttatcc ttattaaaat catcttcata catattaaat 115740
ttaaattctt tatgttgtag tgtatttgat aggtgtaggt atacatttcc atttttatta 115800
ttaaagtcac cgtttactat actccaatct gttgttacta tacttatgtc ttttaaataa 115860
caagtcttaa ttaaaaacgg agtattatta tcttttatag gtgttaattt gttaagccct 115920
atttttatat tttttaaaac ttcattgtag tattcgtagt tattatcata agatttacca 115980
aatgcataag ggtcaatatt aataccaaat atactatagt cacccattaa taatacatca 116040
agtatatcat tagttgtagt atttatttgt ctttttaaat ctcttatttt ttttgtaagg 116100
tagttattac tgctcttatt ttgcatactg tcaaattgtt ttaattcatt ttcatagttt 116160
gcacggcagt atatcttatt acgatagtgt cttttgttat ataaaggaaa ttcagaccta 116220
tcgtcacttt ctatatactc actatataca gtatttacat ctgtaactgt tttacttaac 116280
tcttgtactt ttttatatgg gtctccctta aacgtagtaa gttttttatt cccacataat 116340
gctataaata aaagcaaatt taaagcacta gaataacaaa aggtattatt aatatctctt 116400
aataattctt tagagccaat atctacaata tttttattat ttatttttaa atatactctt 116460
tcttcaccta taaatatact atttctattt actttagata atttaagaat ttcttcttca 116520
gttaatcctg tttctttata ttctactgac atgtgtcatc acctcattta ttattatata 116580
agtatggtaa catagttaaa cttaatagtc aacaaaaaag aagaactttt ttacagttct 116640
tctagataag tttcatattt aattttttta gttcttctta cgggtacaat atcgggatta 116700
ctcattaagt ctttgtactt cttagaattt ttaaagttaa tagtattagg cattgctaat 116760
acttcctcta actcatctgt gtacatagta actttagata ttatatctat gtcactaatg 116820
tataaatttt tagatttact tttaaaaata atctcatcgg tactagttac ttctttatta 116880
tctattaaat ccatatagaa gtcctttcta gtctacataa acaagtatac aatctttgtc 116940
tgataaagac accgaggtca tatcattaag ttcttgtagt tgtttaatag acacatcata 117000
tttcttactt atagtccata aggtatcacc atttctaacc ttataataga atttattacc 117060
tttttgtatt aagtctttca ttgttatcta cgcctttata ttcataataa gatgcctgta 117120
ggtaacatat cgtaataaga ataaagttag ctacttctgt atatattaca tgtggtgtcg 117180
tatttgttat taacatacta ataattaaac aagctaatgc aatacctata ataagaaata 117240
aatatttgct agttccattt gtacttttag ttttataaaa tttatttatt tgggataaat 117300
aagctacgat aatactaata gtagccatta tctgtccata ttcaacactg tagttagcta 117360
ctgaatagcc gatataaata acaattataa acataaccat ttctaaaaga ctaacttctg 117420
ttgttctaaa taagtatata ataaaacaaa taatccctag taataaacta atacttactg 117480
atataatttg aaataggggt gcatgtgtta caaataagct tgttaagcta atacttactg 117540
taacaacaat ataaaaccaa aaatagctat ctacaccttt aacattctta tcttttatca 117600
aacctactaa agcaggtata tatcctacag taactaatat agcatatagg atgcttaata 117660
tatgagctaa attagacatt agatgcacct aacttttcta attcccctaa aacttcttcc 117720
catgaaataa cacctttacc gtctgttaaa gataaagcta ctccgtatac gtaagcgtta 117780
aaggaatatg gaactctatc catatcatca tgcatatctg ttgtgttcca tctgatgtca 117840
ctagagtaaa ttaaaacagg tttatttagt attttctcgt taatttcaag ctctttatct 117900
aaaactgttg ctacatctgt taattcacca tttacatcaa ggtaataaat atcatataag 117960
tcgtttagcc tgtcaatagt aatttgtgct tgtcttttca tttgaaaaat ttgacctaac 118020
tcggtgatgg ttcctaaacc tccattaccg ctaataggca aatcaataac ataaatatca 118080
gattcctcaa tagcacacgt gtcgttttct acaattcgtt ctgccaactt atgtgagtct 118140
gtattctttt tatcgttaaa tgattgtgag ctagggtcaa aaactttaat accaacaata 118200
ctttccatct cttcttttg tttgattcta tattctttta acccttgcat caacatatcc 118260
gatgcatgat acacctgaag ttctttcatt aaatttgtca ttctacttct ccttttcttt 118320
ttcaaactca tcttttagtg tgatgatatc tttattcagt tcttctgagt ctttcatttt 118380
agcccaataa taaaaatctc taagttcagg gtttcttgtt aaaatatatt gcttaggtct 118440
tacatctctt ctttgtgata aggagtaagc tatatctctc atatatttcc agtctttgta 118500
atagtcagac ttatatttaa acataaatcc tttcaaatct tcaaatacat acccttcatg 118560
caatatatta taagagccat tattatcctt ataccattta taaaattctt cccaactagc 118620
aaactccaac tctttttctt ttagttgtaa tcctacttca tcagcaacat atttcaaata 118680
atcataatct ttctttttca tatttaaagt atttgaaata atatcaagta agaatatatc 118740
gctttttcta tattttatga tatgtgggtc ttcttcaata tcaactacct cgaacactag 118800
ggtaaaacta tcgtcagcaa tataatagtt ttcaaggaat gttgctagta tttgtatttg 118860

```
tcttttggtt aaagtttttt ctactaactc tttaaatagt agtgcatatt tatttccatg 118920
tccacttaaa tgggttttag atttacttgc atatataatt ccttctaacg ggtcatagaa 118980
cattagtcct aaaaatccat tttctttctt atatccagtt aaagggaatt ggatagtgtc 119040
tggcatattc tctaatttgg tttcttctac ttcattgata ttaaagaact tattatatcc 119100
tcttcctagt actgtgtttc tatcttcatc aatataaaga cctctagaac tcactgttaa 119160
ttggttccat ttctttttag aaaaagctct ttttgtaaag ttaactgaga acacatctct 119220
atattgttga ttggttttga tggttttatt ttcttttctg gctatatcta ggtattgatt 119280
aggagtgagg tctttgtcaa tactatcgtt ccgtctgttt gataaaagga atttagggtc 119340
gtaaatagtg ttttttactt catgcttctc aatactgttg tttttattta tcgttatagc 119400
tcttaagcaa ccaccttttt ctacacgacc ttctaaatta actgaatttt tagtagtatc 119460
taaaggctct ctatataaat tcctatgtcc atgtatttgt attgtattag aatgttccca 119520
ttggtcatca acattaaaat catatccccc gattccatta ataagctgac ttgttgaaat 119580
cttatttaaa ttatcaagaa cttcaggaag gactccgcca tgattaacaa tgtagtcttg 119640
acctttaaaa ctaaagtaag ccacctgctg taactttcta agaatagact ttactctatt 119700
ttgagttatt ccgttctcta tgaaggattt caaggtaggt ataaatcctc ttgcatgaaa 119760
tatttttaaa gcttgtttat aaaaatcttt ttcactaata tctacccaac tataggctaa 119820
acaaatatta tcatagtctt ctttttctaa ctgagtatat ctgcgaaggt gtctttcatg 119880
atttccttct aatagaatga cgttttttaa tttataaata atctcaagat actcaaacat 119940
ttgcttcgat tctaatcctc tatcaaaata atctccgaca aatatgaaga gttcattttg 120000
attatctata atgtaatcag tagggaaaag agaatgaagg gctgtaaaac aagaatggac 120060
atctccaatt acatgaattt tctcatatga atcagtattc atgagatttt tgtcccactt 120120
aatagtattt aacaaatcat ttttatctac ttcttttgca aaacttggga tattctcatg 120180
ttttaaacgc tcatagatat tttcaataac atccacagga actttcttta gttcttgtct 120240
attattatta cgttcaaaaa gagtgtctag ctctgcttct atgttaacca catatactct 120300
atatccgtat ttttttgata acttctcata ttttttaatt agtttagccg tagaatgtgt 120360
agcatctatt acagtaaact ctccattttc catacgcttt tctaatatgt taaataataa 120420
atcccatacc ttgttgtctt cttcttgtga tattctaagg tttccttctg tatcatatac 120480
aggtgcgctg tattgcgttc taaggatatc agggctaaga gaatatccct ctaatccatt 120540
ttcttttata tacgttgttt tacctgagcc tggagcacct ctcattagta ttagttgtct 120600
catatttcat tctccttgag tgattttata tgttattgct tatacatcat ttttcctttt 120660
cttttatata ctatagcagg acaaaacaaa tcctctccta tcctatataa aaagtctcct 120720
tcttaatatt cctttccttt attttaatta tcaagtactc ttaagtcact tttaagaaca 120780
tccatgctag aggtatgtct atttatacca tctagatttc catcttttaa cttattatct 120840
ttcatgattt ctttttaat ttgtttttct gtttttttat ttgtcatagt gttttcaata 120900
tcaaaagaca tctcttcaat aataagtgtt ttaataaaat caataaattc cttaattgta 120960
tatctactaa aataatcttt atcctcaaag tacgtagcac aaaaactttt acgtcttgtt 121020
agtacaccta ttgacttatt ggaagtagca atataaacat gatatgtttt tccttttact 121080
tttattttaa atcttgtatt atctaacaaa tggttatagt ctttaaataa gtaattgttc 121140
aaaattagcc ctcctttgcg ttaacccaaa tttatagtat tttattgtag ttttctctcc 121200
gctgtagtaa aggtgtcatt attccaacca ccatcatgat taataaactc taaatcacct 121260
```

gtcacagtac ataagacatc aaaactaata ttttcttttc taccttttga aatacctgtg 121320
taaactattt taggtataca actaagggtc tgtaatccta aaccatctat atattctcta 121380
aaagatacat gaggtaataa ataagcactt aattcactac tgatacttct actaaaataa 121440
atgataatgt ctccaacagg tagttcatcg ttatatagat ctacaatatc atcttcttca 121500
atagtccatg ttgtatgttc tatatctgca ggtgctacat gaacaagttg tttaacttca 121560
ccatgtataa tggactcctt atagaaacct acagcgtttg ctttctctaa atactgtgca 121620
ataaaagtac cgtcatcact aattaaatat ggcgttctat tttgaaaatc tatagattgt 121680
tccatatcta gtttttcgta ggtatccttt aagtactccc taattttatt aacatctttt 121740
gttttaactt tatttgttcc taccttaact tttaattctg tcattatttt agtctcctta 121800
taagtacttt ctaactggtt ccgagtaatc attaatatcc tttactcttg gatactttaa 121860
aatactaaaa gcaataatac ctagagctac aataggtgct aataaaacca agccccagaa 121920
tgttaatact gtttgtaaga aaaacattac actatctact aaaaaccatg tagctactac 121980
tagtaatgtt gtaactgtaa ataaaaataa cttttcccaa aatccacctt tttgaaactt 122040
ttttgataat tttttcatca taatatttct ccttatattc caattgcttt ttttgctaat 122100
acatctacat attcattcca tttgttatta tcatgagcct ttacttttat aaaatttata 122160
tctataaact ttgagtattc ccttagcata ttaatatatg ttttacttaa attgttttta 122220
gttttccacg aaccttcata ccattgaata agtcctatat aatctacatg aataatagcc 122280
tgcttataac ctagttttat agcctcttca ataccataac aacaagctag tatttcacct 122340
gcaacattat tatacttaat taaactacta ttttcaatag gtttactgat ttcttttaca 122400
atgttctcat ttttatctaa aataatagct cctgctccaa caagaccttt attataagat 122460
gagctaccat ctgtatatat taatgcagtc ttatgcatat ttatgccctt ctacaaagca 122520
agggaacatc tcacttgtat aaatctcttt gtagtcttgt aattttatag tagagaaatc 122580
aaaaaactta taacaatgtt cttctgcttc gatatagtca tctgcaataa cattaacttc 122640
aaaaccatca actaaaataa cgaacaattt cttaaacatt taaaaaaccc ctttataatt 122700
taataaggta cttaattaaa tcaatttcag tgtacttttc tgagtgttct agctcttcta 122760
atttttcttt tacttcttca agtctgtatg actcttctaa aagttcaaac tgctctaata 122820
atgtgatact atcaaattca ctactattaa tgatgttgtg tatatattct agatgtgtgt 122880
ctttaataat gtttgttaag tcatcaccag tataataatc ctcgatatac gataggtctc 122940
ctaataactc agccgtactt ctaataatac tatatttaga tatattaggg taagattgat 123000
ataaacaatt atctaattta ttacttaaat gctctactac tttttgcatt gtattacctt 123060
tttcttcagt actatatgaa attctaatat tagggttttt agaatcataa tcaactaaag 123120
aactcctatt agtgtttaat aacttatcta aagaagttaa aataatagct ctatcttcta 123180
tattatctaa ggttaagata atatctataa tagtataaaa tgctttgtct cctattgctt 123240
tattaacatc ttgaagttca aaaatattaa tcatatcctc aatctcatga cgctcaacaa 123300
agttaataat agattttgta aatttattca tcaacatcaa cctctttaaa taattctaca 123360
ctattagtat ttaaagcttt ttctaatttc ataagattag cactcttagg ttttctttta 123420
ccactctccc aataagaaat aagtgagtag tgaactccaa tctcttgtgc taaacttcta 123480
actgtatgac ctttttcttc tcttactttt tttaaattta atactttagt ctcttccata 123540
ataaaccact acctatcttt cttcaatttt taaaatacta tagttatttt tattataagc 123600
atacttattt aaaacgtcaa gcgtttttttc tttagcctct actttacctt tagctttcat 123660
attaacatag aaaacattac ttttatttga acgtgtgtgc ttaatatata ctttgtactg 123720
cgtaacctca ctttttaata cattacgttt aaaccatttc tttaattttt ccatttatta 123780
taaccacctt taaaacttat atatgtattg tagcatatga taaatacatt gtcaacttaa 123840
aaataaaaaa atactaggga aaattcccta gtacattatt tccagttaat acgaccccaa 123900
tacttctctt ttagcatacg ttcccacttg tcagtgattt tacatactgc catatagaag 123960
ttaccagctg acgggtttgt aggatattta aacctaatcc accagtagcc gtctgcttta 124020
ataacttggt caaagtttac atattgacca ctataaataa atgattcagc acctactatt 124080
gaacccctta aacctggtgt gcgtcttacc ttaatcgttc tatcagcagt aaatttacct 124140
ccccaattcc aagttgtttg tacctcgtct ttgaaattag gttctataaa ccacatagga 124200
aagtcgtaac catgggctct aacggtagct ttctcccagc caccgcctcc ttgagcatct 124260
ccccaagtcc aacctccacc taaccaatta ttttcaatta ctataatttg gttttggttt 124320
gcacttagta cccatgcgac atgaccataa ccgcacccgt atgaattatt aaagataacc 124380
atagtgcctg gtttaggaat gtaggatagt gtattttcta ctactctagc tttatctttt 124440
aacatagctt tattatccca tggaatgtta catgcacttg ctccacctaa agaataacct 124500
gggaagagct tgttaaatcc atagttagct aagtcgtaac attgctgacc ataccaacca 124560
tcaaagtcta ttgctttgcc ttctagactt tttaaaaatc gaacaaattc acttctagtc 124620
atcgatgctt tcaaaagttt tcactcctta tttccaatct atttttccaa aatatttttc 124680
tttcttaata cgctcttgtt tatctgttat ctcacataca gcacaataga aataattttt 124740
actagagcct ggttttggat atttaaatcg aatccaccag tagccgtctg ctttaataac 124800
ttggtcaaac tcaacccaat catccttatc gtatagccat gaatctctat ttactatagt 124860
gcctttaagt cctggagatt ttctaacttt aatagctcta tctggataaa aagtaccttt 124920
ccagctccac atagttttag tagattgtgt ttttactcta ggctcagcat tacctgattt 124980
ctttacatct actgacttaa taactttctt gtaatactta gctacttcct tatctaagtt 125040
actagtgttt ctacctaatc cacatgcttc taataagtta cctgggtctt gtttgtcgtt 125100
ttggatgtct tggtgacctg gcatatttgt tttgtaatca acaccccagt attcagctaa 125160
ataagctaag acacgagctc cattgtctaa tgattttttta gaacgttctt tatcactaaa 125220
gtaacaaatt tctacaccaa tagcaccatc attagcgtta attccgtacc ataggtcatc 125280
cataggagcg ttatacaaca catgccaagc tttttctgta gtaggaacac atatgatagc 125340
ttctttatca tctacaaaga tatgtgcgga tgcagtagaa gcccaatcaa tgttatatgt 125400
atttttgtaa taatctacat tattttgagc tgtagtatta atattccctg tatcatgagc 125460
tacaataaaa acgggttttt taaccgccat agcttgacct gtgcgtcttg ttccaatagg 125520
tagtaaatca tacctaacac ttacaccttt ccaaatttct atcattactg ttcacctact 125580
tcttttgggt tatcttcttt atctaattca gacactaagt ctttttctac tttaccatgt 125640
tctaatggtt ctgcatgact tgtatctatg tcttcattat taactccttc aggagccatc 125700
ggcatctttg taggaggtaa ctctgaggta ctattcattg cttcactctt gtatgttaaa 125760
gctttatctg ggtcattata atctctaggt ttgttaaagt cctgtacaat agggctatcc 125820
gctatacctt tagtgtcatg acttacaaga acacctaaac cagtcaagaa actaataact 125880
acacctgcaa ttgcagtgcc ttggtttaca atatcttctg cacctttgat tcctaataaa 125940
ctacatacac tgacaataaa cgtagctaaa acaggtacaa aacctgtcca aaatgtagcg 126000
ctttttgctt ttgcagtaat attgttacct gctattaata atggtttttt atcttttttt 126060
gacataaaaa aaataccatc ctttctgtta ttgtaaagct aataataata taacaaaaag 126120
aatggtttta gttattaaat tttaagttat tgttctttaa tttgagaaag tgttttgatt 126180
acttctgaca tttgtttatt atctaagtct tctaacttag tgtgtggaag taaatctaat 126240
ttatcccaaa tatctttttt agttgtgaat ttttcattaa taattgctct accgattaaa 126300
ctttcggtat aataaatttg ttttgcagat gccatattag tatctaccct tctatagtat 126360
aattaaacat acatacataa accgtctcac tggtaagtaa catactagac ctattgttaa 126420
gttaatcact acgcttgact ctattaggta gctaacctaa gtccatctca cgtaacctat 126480
taaagcagta caaccgtagg gttgattctg tttaatattg taatgtgata ctaacatatt 126540
aattagtaac tttcacatgg tatgaagaat tttagcggta ttctataatt tgaccaatta 126600
ttattttgca ggtttatgct acttgtacta gtatcgtatg ttatcaaaca tttttcaatg 126660
ctccaactgc atatacttgt taaggtgtat ttgtaaagga ttccaccaag accctttaca 126720
aaaattaagc ccatcagata ctatacttta taaacctaat atgttactgc tgagtattcc 126780
gattgtaata agcattacta ttgacgaatt atctcaccga tataaaccga caagttttaa 126840
ttcgttcgac aatctcacgc cttacaggta ccaccctgtt taaatcagcc attatgtatg 126900
tatgtttaat aatactactt ttaaagtata acatatattt attcggttgt caagaaaaat 126960
ttataacttt ttatagtttt tttatactag ggtaaaaaag ttttaaaaga cctagtttcg 127020
acaaataaaa ataaggagga ataacacttc aatttgacaa caaattaatc tctatgcaat 127080
cttaactata atataacata atattctaag tttgtcaagt tctttttct ttttatcttg 127140 ataattcttc ttgtatttta tcccaatatt tttctgattc tgttctatta tcctcaatgt 127200
gagcagttgt acatttacac ctgatacaat gtaaatgttt tatgtgtcct tcttctcttc 127260
tttgagctct ttttcttggt actgtaaaag tattaccaca ttctgaacaa actaaattac 127320
tgtggaacat tttctgtctt tttttcatga ttatcaatcc ttttaaaatt ttttgtatag 127380
ctagtatatc atataattat tttgatgtca atacaaatac tgttgttttg ataaaagctt 127440
attactagtt atatttaact attctgaata tttagatact ttacctattt ggaaaataag 127500
gaggattcct tatatatata ataaataatt ataaatacta aaataataat actagttata 127560
ataattaata atatatatag gaaagtcaac aaagagtaat aaaaaaaagt gacttactta 127620
aaagtcacta attttcaaat actaacttaa atgattctat gaataaaggg ttaatgaata 127680
ctgtatcaga attaatatcc tcagagactc taactctaac tgatgcttgt ccatgtcctc 127740
taattgttcc atttatctct ctttgtgtat actcaatact atcgtcagag attaaataat 127800 attttttcc actaatcatt gttacctcag catgttttac catatcaaaa ctcctaacta 127860
aatttattga aaatgaaagt tataatagaa cctaacacta gtagtagtac tttctcggta 127920
gtatccttct ttcttgtgtc cttaacaact gtattgttag tgagttcttt tatcttttcg 127980
tctaatctat ctagctgtat gtagatagac gattgtttct cactattaac agctacttct 128040
ttgtctaaac taactaccat ttttcttagt tcatcaactt cattttctaa ttccttatac 128100
gtatttttat caatatagct accatcttgt attttatctt ttatcttatc tacttgtccg 128160
acaaggtttt ttagttcttc attcaactaa agtcacctct taatgtctaa cttttcagat 128220
tctgaatgga cgtcatagtt ttcgaaaaag tcattaataa tttgcatata atcctcagta 128280
actatctcac catatgacgt tttagtattt atttcaaacc taagcttacc aaactcatgg 128340

```
aggtctattt ctttaataac ggtattagga ttatcagatg gtatgtaata ataatcaaaa 128400
tatataatag agccgttgat aagcaaccta tcaatcctat agacgtggaa gaattttcta 128460
tctcgtctaa agtgagctaa ggcatcttta aactctaatt ttaatatatc tttatactta 128520
gtcaaatcaa cttacccccct tataattaat tttgagctac actagttttg tgttataata 128580
gttattgtag tagcagatat gagtattacg tttaataaaa ttagcaacca ccaactacct 128640
gtacttatta accataatga aaaacaagat aatatataaa caaccaccaa gtagcctata 128700
tatttcatag tgtttttaca ctcttttaat actactacgt atgctagtga tttagataag 128760
ctaaacagaa agtaaaaata aaaaataaaa agaggtatag ctataatgct tgctagtata 128820
atcactaatt acacctaatt tcttttagct agataataaa atcttatata atacaacttt 128880
aatataacat tgaaacctgt ttataaatca acaatgttac attaatagtg tacggtatat 128940
tttaaattag gaggactgaa ctaatagggt gaataataac atagctgtat ttatatttaa 129000
aactctaata attattattt ttattttgtt tattttgtct attattaact cactgtcatt 129060
aatatactct attcgaccta gtacagttat gacttacttt atatttggtg ggatagtttc 129120
taatgtggca ttaacaataa ctgataaatt attattacac aaagaagacc ccttacccga 129180
ttatattcta aaagaagtag agctaaataa caatgaatta caagtattaa agaaaattgt 129240
agagtcacaa actaatgttt ctgctgagga agtaagagta agagcaaaag cacaacgtcg 129300
agtactaaaa gataaaaaga gagatgctgt caatgaaaac gaagaaggac attaaggaac 129360
aacgtaaaga gctgaaagat aatgcaaccg ctgtttcctt aacaaaaaga ggagataaac 129420
gtattgcaag tcctagtagg gtgtgttgtt tgtgtggtca gtctctttca ggaatgaatt 129480
atactaaagg taaagctata gctaaagtta atcattttca tttacagtac actaagtact 129540
tatattttga catgtgcgca gatattaata actgttacaa gaatttaaag aaagtaggtg 129600
aattgataga gtgagcgctg aaagtttaag agatatgtta tctaagaaga aaattgaaga 129660
cgaagataaa cgtaaatata tagctgatgg atttatgtca ggtattacta aacttatgta 129720
tgactttaat aaaaagattg acagagggga aatagaagta aaagacccta atgatttgta 129780
taaagtgttt gttatcttcc aacaaatgca aaacttaatt acagatggtt ctgatggtgg 129840
cggtgctata ccgcaattat caagaccaca acaagagctc tttgatgaaa taacaaatga 129900
gaatagtaaa ggtgagaaag aagtagattt agagaagtta tctcaactat ctgctgatga 129960
tattactgct atgattattg ataaagaaaa ggttatgaac gaagagaact caaatacatt 130020
ctaaagaaag gtgtatatga atggatggta aagaattatt aaaaataaca caagaaacat 130080
tcggtacaca aaatgttacg caagaacaag ttgaccatat tatcaacatg ttaaacccta 130140
gtacttatat gctaaaatat catacgttac gaggtcaccc gataactttt agtattccaa 130200
acagggacag aagtaaagca caagctcata gaccataaac tagtgctgtg gtctttaaac 130260
tctgttaaac ggtcatagga aaataaagaa tatcctggta agaaaagcta agtcctaatg 130320
gatagagctg ataccgtagt aaagaatcta caacatgtag aggaaaaact ctaacgacta 130380
aatttctagg tagttatcta aatggagata gtgagaacta gataagaaaa ctctttatag 130440
agaagtaaag cagagaaccc ttaaccaaaa ctaagggcta taatatagtc taaaccctta 130500
ataaatatcg ggaaaccgag ggtagtagtg ggcaagttaa gattgtcaac gatagtcacc 130560
ctaataaagc ggtaattaag agtagacaat taggactcag tgagatgtca gtaatggaaa 130620
tggtacactt tgctgacatg tatagttaca gaaatgtaaa gtgcctctat acgttccctc 130680
gattaaacag tgtgggggaa ttaaaacctt gttaaacggg catagtaaaa taatgtatag 130740
```

```
aaaaaacaat atactggtaa gaaaccctaa atctgactat acacagacag tgggaaccaa 130800
ccgtgctaac tgttgacttt atatgtagtg tatgttatac tgtatttata aagttagcta 130860
aaagcctaac gactaaactt actaataact atataaacgg atatagtgaa aatagtataa 130920
gaaaatttta actaaacatg taagaaagaa aaggtatatt gtaatgacta aaaagaaaac 130980
acataaagag tttgttcaag atgtgtataa tctagtaggt gacgagtata ctgttatata 131040
tgccaaagat aacaacatat cattgatacg aataccttac tattataaca tggatgaaat 131100
agacaatata ctttcgtatt tagttaaaaa agtaaagcaa ggagctacta accaaaatta 131160
gtagctatga tatagtctaa tcccctaata aatatcggga aaccaagggt aaaaaatgac 131220
acaagagcag ttaaagaaat ttgtacagtc acgtcttaat cctgtattag ataaaactta 131280
ttttagagat attgtgaatt gggataaaga ctccttaggc tataaacaaa ttagaaactc 131340
aagtttgttt tttagaacta gtagtaaacc aggttcagtt gagggtgttg acatagactt 131400
cctcgcaatg gacgaatttg agagggtgaa ctcactagcc gaaagttcgg ctttagagtc 131460
tatgtcaagt tcacctttta aagtagtaag aagattctca actccgtcag cacctggggt 131520
aggtatacac aaattatatc aacaatctga ccaatggtac tatgctcatg tgtgtcaaca 131580
ttgtcaatat gaaaacgaaa tgaaatatgc tgattatgac cctaatgact taaataagag 131640
tggtaatctt ttacttttaa acccagatgg tattgatgaa caagctaaaa cagtacaaga 131700
aggtacatat caatacgttt gtcagaaatg tggaaaaccc ctagaccgtt ggtataatgg 131760
catttggaaa gtaaggtatc cagaaagaac aaaaaaataat tcaggtatta gaggttacta 131820
catttcacag atgaatgctg tatggataag tgcaagccaa ttagtagaga aagaaatgaa 131880
tacagattct aagcaagcat tttataacta ttctttgggt atgccttatg aagatgttaa 131940
aatgcgtgtt ttaccagaag acatctttga caataagtca gaaattgcaa aaacacagtt 132000
atttaataga gataaataca aatttatttc agtaggtata gactggggta acttccactg 132060
ggtaactgta catggtatga ctgaggaggg taaagtagat ttaatacgtt tattctctat 132120
taagaaaaac agtagaccag atatggtaga agcagattta gaagctataa tattagagat 132180
atctaaatat gaccctgata ttattgttgc agataatggt gattcgggta acaacgtact 132240
taaattaatt aatttctttg gtaaggataa agtatttggt tgtacttata agtctagccc 132300
acgctcatca ggtcaattat atgcacaatt taatgaaaac agtaatacag taactgtaga 132360
taaattaatg cataataaac gatatataca agatttaaaa gctaaacgta taagaatgta 132420
ccaacaggta gatgatgaat taaaaactta tcttaagcac tggcaaaatg tcctaatcat 132480
ggacgaagaa gatgaaaaaa caggagaact ttatcaagtt attaaacgta aaggcgacga 132540
ccattattct cagtctgcct gtattggtta catcggtctt actcgtctaa aagaattata 132600
tgacaaaggc aacggtacat ctttcacatc cacttttata tcaacggatt acaatactac 132660
acaaaacaac tcgtctaatg agttctattt tgatgactaa gaaaggactg acgacttgac 132720
aagtatatta aattatgata caatacaaga agatgatata agtaaagaga catttaattt 132780
attaattgaa gaacctttaa ctttatctta tgtttctaaa catagtgatt ctttagatag 132840
taaatatgac tacatatata aatcactagg ctttgataac ttcatggact gttatttata 132900
cgtaacaaga gaaccagaac gtatatacaa aggtggagct aaagatataa gctcattgaa 132960
taaagtaaaa agaactgtag tacgtaatgg gaaagaaatt gaaatgacag tctatgaaga 133020
taataaaaat gatgataaac ctaaagagaa aaatggtgaa gaaccaaaag aacctaaaac 133080
```

tgctaaaggt tcaaaggttc ttactcatgg tgatgctgag aaacctaacc ctaaaaagat 133140
tgccagttct ctttctactc taaagaataa gggtgtgaac actgaccaca tagatggcaa 133200
cgcatcaatg tataaagaat ttgtagatga tagtaataac acaataggac tagcttcctt 133260
taaagaaact gattacgata tcatattaca tggatatgta tcagacctcg aaactaatgg 133320
ggtaggtgct aggtctattc tagagttaat ttctttagca ataaagaaga acaagaacgc 133380
tgttgtttat gatatagaat tatctcaagc catagagttc ttaaagtctt tagggtttat 133440
taaacgtaaa gatgagtatg tgttgaaaaa acaagatata aagttatttt taggtgagta 133500
cagtgagctt atttagcact gtactcattt atacgattat atatgtaagt attattatat 133560
tagtagttgt aaatgtaata gtaaaagaaa aaagattgaa taatactaag cagttactta 133620
tacaagtaaa aaaggatatt ataaataact taaaaaaggg agatatgaat gattaaagat 133680
aataatacaa aaacattgga agagttaatt acacctattt ctacaaaaga aaaagaaaat 133740
aaagttaaag aatttagtaa aacattatgt gaaatgatta gtaagttata tgagtcttat 133800
aatgtgttaa gacaagaccc tattgatgaa acacaaagat tagatggttc tctaatggtg 133860
tttcaaagta gattagatga tacattaaca ggtgaggaac accaaaaact tttcaagtta 133920
gcctttgatt ataacattaa tatctttgaa gctaacaaac aatttaaaaa agatgtgcaa 133980
aatggaaatt ctattaagtt aggtgatgtt gttgtaaccg acacagcttt aagtaatgtt 134040
ttatctagta atgagcttaa tgttagtatt acatttatgt taagcaaaga ctatgaagaa 134100
aagaaacgta ttgaagaaga agaaaaggaa aaactagata agttataata gatattatga 134160
gacctttatg gataggtagg aataaataat atgaaacgta agtttagtag taatgagatt 134220
actataacac ttataactat tgtagttgct ctatttatag tattaattac agtagcattt 134280
aacaagtacc aaattgctaa agaagataag gacagatatc aaaagctagt agaaatttat 134340
caaaaagcag atgatgatga cggtaaaact aaaaaaaggt atgttgagaa gttaaatagg 134400
gctgaggaag aacttaaaaa ggttaaagaa gaaactaatt ataaaggtta taatgataaa 134460
acagaaaaag aaagagataa agaggataag agtgtaagag aacgtattta tggtaatgat 134520
aaggataaag atttagtatt agtaaataat aaggttgttg taagtaatga agttactaga 134580
cctaagataa tagaagataa tggtgtcagt acagttgtag tacctcctgt tgtaagtcct 134640
gttgagccac caagtgaacc tagtatacct tctcctacta tacctaaacc tattattcct 134700
aatcctatta accctaatcc tattctacct aaacctaaca tccctacccc taacccacta 134760
ccccctatag aacctgaaaa acctatagaa cctgaaaaac ctatagaacc tgaaaaacct 134820
atagaacctg aaaaacctat agaacctgaa aaacctatag aacctgaaaa acctat 134876

<210> SEQ ID NO 3
<211> LENGTH: 136156
<212> TYPE: DNA
<213> ORGANISM: Artificial Sequence
<220> FEATURE:
<223> OTHER INFORMATION: PN1815

<400> SEQUENCE: 3
ttgagctagg tttttcaggt tctataggtt tttcaggttc tataggtttt tcaggttcta 60
taggtttttc aggttctata ggtttttcag gttctatagg tttttcaggt tctatagggg 120
gtagtgggtt aggggtaggg atgttaggtt taggtagaat aggattaggg ttaataggat 180
taggaataat aggtttaggt atagtaggag aaggtatact aggttcactt ggtggctcaa 240
caggacttac aacaggaggt actacaactg tactggcacc attatcttct attatcttag 300

```
gtctagtaac ttcattactt acaacaacct tattatttac taatactaaa tctttatcct    360
tatcattacc ataaatacgt tctcttacac tcttatcctc tttatttctt tctttttctg    420
ttttatcatt ataaccttta taattagttt cttctttaac ctttttaagt tcttcctcag    480
ctctatttaa cttttcaaca taccttttt tagttttacc gtcatcatca tctgcttttt    540
gataaatttc tactagcttt tgatatctgt ccttatcttc tttagcaatt tgatacttgt    600
taaatgctac tgtaattaat actataaata gagcaactac aatagttata agtgttatag    660
taatctcatt actactaaac ttacgtttca tgttatttat tcctacctat ccataaaggt    720
ctcataatat ctattataac tttataactt atctaacttt tccttttctt ctgcttcaat    780
acgtttcttc tcttcgtagt ctttactcaa cataaatgta atactaacgt taagctcatt    840
actagataaa acattactta aagctgtgtc agttacaaca acatcaccta acttgataga    900
ctttccattt tgtacatctt ttttaaattg cttgttagct tcaaagatat taatgttata    960
atcaaaggct aacttgaaaa gtttttggtg tgcaacacct gttaatatat catctagtct   1020
actttgaaat accattagag aaccatctaa tctttgtgtt tcatcaatag ggtcttgtct   1080
taacacatta taagactcat ataacttact aatcatttca cacaatgttt tgctgaactc   1140
tttaatttta tcctcttttt cttctgtaga aataggtgta attaattctt ccaatgtttt   1200
tgtattatta tctttaatca ttcatatctt cttccttttt taagttattt ataatatcct   1260
tttttacttg tataagtaac tgcttagtat tattcaatct tttttctttt actattacat   1320
ttacaactac taatataata atacttacat atataatcgt ataaatgagt acagtgctaa   1380
ataagctcac tgtactcacc taaaaataac tttatatctt gttttttaa tacatagtaa    1440
tctttatttt taataaaccc taaagatttt aagaactcta tggcttgagg taattctata   1500
tcataaacta cagcgttctt gttcttcttt attgctaaag aaattaactc tagaatagac   1560
ctagcaccta ctccattagt ttcgaggtcc gatacatatc catgtaatat gatatcgtaa   1620
tcagtttctt taaaggaagc tagtcctatt gtgttattac tatcatctac aaattcttta   1680
tataatgatg cgttgccatc tatgtggtca gtgttcacac ccttattctt tagagtagaa   1740
agagaactgg caatcttttt agggttaggt ttctcagcat caccatgagt aagaaccctt   1800
gaacctttag cagttttagg ttcttttggt tcttcaccat tgttctcttt aggtttatca   1860
tcatttttat tatcttcata gactgtcatt tcaatttctt tcccgttacg tactacagtt   1920
ctttttactt tattcaatga gcctatatct ttagctccac ctttatatat acgttccggt   1980
tctcttgtta tatataaata acagtccatg aagttatcaa agcctaagga tttatatatg   2040
taatcatatt tactatctaa aaaatcacta tgtttagaaa cataggataa agttaaaggt   2100
tcttcaatta ataaattaaa tgtctcttta cttatatcat cttcttgtat tgtatcataa   2160
tttaatatac ttgtcaagtc gtcagtcctt tcttattcat caaaatagaa ctcattagac   2220
gagttgtttt gtgtattatt ataatccgtt ggtataaaag tagatgtgaa tgctgtacca   2280
tttcctttgt catataattc ttttaaacga gtaagaccaa tgtaaccaat tactgaagac   2340
tgtgcgtaat gcatttcata ccctcggttt cccgatattt attaggggat tagactatat   2400
cttagttatc taaattgata actcagtgct ttacgaataa aataatttat tgtttaacaa   2460
tttctctata cttttgtaat ccttagttgt atagaatatc tcaaaaagct cataaccgtt   2520
atcttttgca taagaacttt ttatactatc tatctttttt tgtagcttaa attgttcttc   2580
tcctccaaaa tgcttgacag gtttaacgtg ttgttcacct tgatattcga taagtaagtt   2640
```

```
atattcaggc aaataaaaat catatgataa gttatttatt aactttaagc cttcaaaagt   2700
tttttgtttt ttatatgtta taccttttg ctctagataa ctttctacta atttctcacc   2760
tatggaattt ctacagtgtg agcatcttct accttttcta aatttgcca tagttccccg   2820
atatgttttt ccgcactcat tatgctttat ttctatgggg gtgtgtgcat ttttataatg   2880
atttgaaact acttcatagt ttcctttcgt ttctttacgt acttcaaatt taatatcttc   2940
caatgtccta ttaaatctcc tgttacatct cgaacattgt ttatacttta aaatatctct   3000
tgcagtaata gtataagtac tatcacaaaa gaaacagtgt aaagttatct tcttaaatgc   3060
accttcatat tttgttatag ccattatacc ttcaggtaat tccttttggt attcttcatg   3120
tgtttttctt tgcttactat ggactctttt ttgagaacat gtattacaac ctgtcttacg   3180
tttactcata aatgttgatg gtgttataag tattttgtta ccacattttt tatgaatagc   3240
tcttagtttt gtgtactgat taacatagtc atctaaaaat tcatattctt catagtcctc   3300
tggtctaaca tctttaattc tattaataaa ccactcgtta tcataaacca cttaactacc   3360
ctccttttta gtatactcaa taaattattt taatctctta cgttaatagt aacgaattta   3420
gtcgttaggc ttttatctta atttaataat aacattaaaa aatataatgt taatatttaa   3480
attaagaatt tagcacggtt ggttcccact gtctgtgtat agtcagattt agggtttctt   3540
accagtatat tgtttttcta tacattattt tactatgccc gtttaacact gtttatagac   3600
gaccatatta caaaatcgtc tcctctgcgt ttaataactt ggtacatttc acctgtctta   3660
tcatcttcct catccatgat aataacattt tgccaatgtt taagataagt ttttaactct   3720
tcatctactt gttgatatac actaatacgt ttagctttta aatcttgtat ataacgtttg   3780
ttatgcataa gtttatccac agttactgta ttgttatttt cattgaactg tgcatataat   3840
tgacctgatg aacgtggact agatttataa gtacacccaa atactttatc tcttccaaag   3900
aaattaatca atttaagaat attattacca gagtcaccat tatctgcaac gataatatcg   3960
gggtcgtact tagagaactc caatataatt ctttctaggt ctgcttctac catatcaggt   4020
ctactattct tcttaacaga aaataaacgt attaaatcta catgaccgtc ttctgtcata   4080
ccgtgtacac agcaccagtg gaaattaccc cagtcaacac tgcaagaaat aaatttgtat   4140
ttgtctctat taaataattg tgtttttgca atttctgatt tattattgaa tacatcttct   4200
tctgttactt tcatttttac gtcgtcaaaa ggggctccga tgatgtagtt ataaaagctt   4260
tgtttagatt ctgtattcat ttctttttct ttaatctcat cacagcttat ccacgttgcg   4320
tttaattgac ttatataata tcctctgata cctttattat tttctgttct ttcagcatgc   4380
ttgcaatccc aacgaccagc gtaccaccta tcaagaggct ttccacattt ttgacaaaca   4440
tattggtaag taccatcttg gacagtttta gctatctcat ctatcccatc tggatttact   4500
agtaatacat taccactatt ttctaagtca tcaggtttat aatcagcata cttcatttca   4560
ttaaaatgac cgcagtgttc acaatcataa ccataaaacc attggtctga ttgtttatac   4620
agtttatcta taccataatc tcttacagtt ggtgtagacc accttcttac tattttaaaa   4680
ggtgaacttg acatagattc taaagctgag ctctcagcta aattatttac acggtcgtac   4740
tcatcaagtg aaagatagtc aatcaatttg taccccctagt ttcctagtac tttaacactc   4800
acttaagagt aggtttagac tatatcataa cctttctatt aggtgaaagg ttctctgctt   4860
tacttccgcc aagcggtttt cttatctagt tctcactata cccttttgta tagctaccta   4920
gaaatttagt cgttaggcat ttagctaacc ttataaatac attatatcat attcttttta   4980
taaagtcaac atttagcacg gaattgccct cgtctttacg ttaggggttt ccccgtttaa   5040
```

```
cagagtttaa tgtggacttg ttacctatcc acaccttcga cagtactagc tttactacta   5100
gttctgaaaa ataaactaga atttcttatt tgtttataac ctaatgagtc cttatcccag   5160
ttaacaatat ctctgaaata aggtttttct aatactggat taagtcttga ttgtacgaat   5220
ttcttcatct gttcattcgt cggaaaggta tacaaacatt ttacacttgc ataactatgc   5280
atgtcagcaa aatgtaccat ttccattaca cccatctcac ttacaattac taccgttagt   5340
ttcctaatac tttaacactt atttaaaagt cggtttagac tatatcttca atatataaat   5400
aataatttat aattacggat tatatattgc cttgctttac ttctattaac gaaaattttt   5460
tatctaagta agatttcata cttgaatatg tgtttatttt gtaggtaggc tcctataaaa   5520
caaagtcatt atctttagca aatttatttt taatattatc gttaacttgt tgttttttaa   5580
acctttcttt tgctaactct ttagatatac cttcaaattt cttctgttct tcgtacctaa   5640
tgttatcttc ctttaagtat gtttcaatat attcctctcc acgagacttt ttacagtaag   5700
ggcaacctga atggtgttga ataatatctg tatatctaac cttaaatgtc ttattacaat   5760
ctttatgtaa taattttact ttattaccag caccattata ttctgatact aacttataac   5820
ttgaccctaa atgttctttt atattactat ctatttcctg aggtgttaat ctttgacttt   5880
gatagtaaca agctatacat ctagaatgat acaaaaagtt accaggtgat actttatact   5940
ctctaccaca cttgttatgt ctcataagta taggtgttgc tctattaata taatcttcaa   6000
gtaccgtata ttcatcacct acaagggtat agacttcttt aataaattct ttatgcgtct   6060
tctttctcat attaaacctc ttatttacgt taatagtttt cttatctagt tctctttatc   6120
tccattcaga taaataccta gaaatttagt cgttaggcat ttatattaat tcaataataa   6180
cataagtatt ttatactgtc aactattaaa ttaagaattt agcaacggat tgtcatatgc   6240
ttctttaagc acttagagtt tcccgtttta acaaggtttt acttgaacaa agtttatcca   6300
agctgtctac ttttaattac tactttattt gggtgtgtgt catttactat catttactac   6360
cctcggtttc ccgatattta ttaggggact agactatctc atacatgtac cttttggtgt   6420
acatgccctc tttctttacg ggttttatcc ctcttatact gttctaccta atcccttttg   6480
attagttacc agtaagttta gtcgttaggc atttacgtaa ctaaggtata tatcctagtt   6540
cgatttagca attgattgcc ctcgtcttta cgttaggggt ttccaatttt agaaaaggtt   6600
tatagtccgc atagtatgtt tacggacttg ccaaggtcta tgagcttgtg ctttacttct   6660
gtccctgttt ggaatactaa aagttatcgg gtgacctctt aacgtatgat attttagcat   6720
ataagtacta ggatttaaca tattgataat atggtcaact tgttcttgcg taacattttg   6780
tgtaccgaat gtttcttgtg ttatttttaa taattcttta ccgtccattc atatacacct   6840
ttctttagaa tgtatttgag ttctcttcgt tcataacctt ttctttatca ataatcatag   6900
cagtaatgtc atcagcagat agttgagata acttctctaa atctacttct ttctcacctt   6960
tactattctc atttgttatt tcatcaaaga gctcttgttg tggtcttgat aattgcggta   7020
tagcaccacc accatcagaa ccatctgtaa ttaagttttg catttgttgg aagataacaa   7080
acactttata caaatcatta gggtctttta cttctatttc ccctctatca atctttttat   7140
taaagtcata cataagttta gtaatacctg acataaatcc atcagctata tatttacgtt   7200
tatcttcgtc ttcaatttc ttcttagata acatatctct taaactttca gcgctcactc   7260
tatcaattca cctactttct ttaaattctt gtaacagtta ttaatatctg cgcatatgtc   7320
aaaatataag tacttagagt actgtaaatg aaaatgatta actttagcta tagctttacc   7380
```

```
tttagtataa ttcattcctg aaagagactg accacataaa caacacaccc tactaggact   7440

tgcaatacgt ttatctcctc tttttgttaa ggaaacagcg gttgcattat cttttagctc   7500

tttacgttgt tccttaatgt ccttcttcgt tttcatcgac agcatctctc tttttatctt   7560

ttagtactcg acgttgtgct tttgctctta ctcttacttc ctcagcagaa acattagttt   7620

gtgactctac aatttttcttt aatacttgta attcattgtt atttagctct acttctttta   7680

gaatataatc gggtaagggg tcttctttgt gtaataataa tttatcagtt attgttaatg   7740

ccacattaga aactatccca ccaaatataa agtaagtcat aactgtacta ggtcgaatag   7800

agtatattaa tgacagtgag ttaataatag acaaaataaa caaaataaaa ataataatta   7860

ttagagtttt aaatataaat acagctatgt tattattcac cctattagtt cagtcctcct   7920

aatttaaaat ataccgtaca ctattaatgt aacattgttg atttataaac aggtttcaat   7980

gttatattaa agttgtatta tataagattt tattatctag ctaaaagaaa ttaggtgtaa   8040

ttagtggtta tactagcaag cattatagct atacctcttt ttattttta tttttacttt   8100

ctgtttagct tatctaaatc actagcatac gtagtagtat taaaagagtg taaaaacact   8160

atgaaatata taggatactt ggtggttgtt tatatattat cttgtttttc attatggtta   8220

ataagtacag gtagttggtg gttgctaatt ttattaaacg taatactcat atctgctact   8280

acaataacta ttataacaca aaactagtgt agctcaaaat taattataag gggtaagtt   8340

gatttgacta agtataaaga tatattaaaa ttagagttta aagatgcctt agctcacttt   8400

agacgagata gaaaattctt ccacgtctat aggattgata ggttgcttat caacggctct   8460

attatatatt ttgattatta ctacatacca tctgataatc ctaataccgt tattaaagaa   8520

atagacctcc atgagtttgg taagcttagg tttgaaataa atactaaaac gtcatatggt   8580

gagatagtta ctgaggatta tatgcaaatt attaatgact ttttcgaaaa ctatgacgtc   8640

cattcagaat ctgaaaagtt agacattaag aggtgacttt agttgaatga agaactaaaa   8700

aaccttgtcg gacaagtaga taagataaaa gataaaatac aagatggtag ctatattgat   8760

aaaaatacgt ataaggaatt agaaaatgaa gttgatgaac taagaaaaat ggtagttagt   8820

ttagacaaag aagtagctgt taatagtgag aaacaatcgt ctatctacat acagctagat   8880

agattagacg aaaagataaa agaactcact aacaatacag ttgttaagga cacaagaaag   8940

aaggatacta ccgagaaagt actactacta gtgttaggtt ctattataac tttcattttc   9000

aataaattta gttaggagtt ttgatatggt aaaacatgct gaggtaacaa tgattagtgg   9060

aaaaaaatat tatttaatct ctgatgatag tattgagtat acacaaagag aaataaatgg   9120

aacaattaga ggacatggac aagcatcagt tagagttaaa gtatctgagg atattaattc   9180

tgatacagta ttcattaatc ctttatttat agaatcattt aaattagtat ttgaaaatta   9240

gtgactttta agtaagtcac ttttttatta ctctttgttg actttcctat atatatatta   9300

ttaattatta taactagtat tattatttta gtatttataa ttatttatta tatatataag   9360

gaatcctcct tattttccaa ataggtaaag tatctaaata ttcagaataa ttaaatataa   9420

ctagtaataa gcttttatca aaacaacagt atttgtattg acatcaaaat aattatatga   9480

tatactagct atacaaaaaa ttttaaaagg attgataatc atgaaaaaaa gacagaaaat   9540

gttccacagt aatttagttt gttcagaatg tggtaatact tttacagtac caagaaaaag   9600

agctcaaaga agagaagaag gacacataaa acatttacat tgtatcaggt gtaaatgtac   9660

aactgctcac attgaggata atagaacaga atcagaaaaa tattgggata aaatacaaga   9720

agaattatca agataaaaag aaaaaagaac ttgacaaacc tagaatatta tgttatatta   9780
```

```
tagttaagct tgcatagaga ttaatttgtt gtcaaattga agtgttattc ctccttattt   9840
ttatttgtcg aaactaggtc ttttaaaact tttttaccct agtataaaaa aactataaaa   9900
agttataaat ttttcttgac aaccgaataa atatatgtta tactttaaaa gtagtattat   9960
taaacataca tacataatgg ctgatttaaa cagggtggta cctgtaaggc gtgagattgt  10020
cgaacgaatt aaaacttgtc ggtttatatc ggtgagataa ttcgtcaata gtaatgctta  10080
ttacaatcga aatactcagc agtaacatat taggtttata aagtatagta tctgatgggc  10140
ttaatttttg taaagggtct tggtggaatc ctttacaaat acaccttaac aagtatatgc  10200
agttggagca ttgaaaaatg tttgataaca tacgatacta gtacaagtag cataaacctg  10260
caaaataata attggtcaaa ttatagaata ccgctaaaat tcttcatacc atgtgaaagt  10320
tactaattaa tatgttagta tcacattaca atattaaaca gaatcaaccc tacggttgta  10380
ctgctttaat aggttacgtg agatggactt aggttagcta cctaatagag tcaagcgtag  10440
tgattaactt aacaataggt ctagtatgtt acttaccagt gagacggttt atgtatgtat  10500
gtttaattat actatagaag ggtagatact aatatggcat ctgcaaaaca aatttattat  10560
accgaaagtt taatcggtag agcaattatt aatgaaaaat tcacaactaa aaaagatatt  10620
tgggataaat tagatttact tccacacact aagttagaag acttagataa taaacaaatg  10680
tcagaagtaa tcaaaacact ttctcaaatt aacgaacaat aacttaaaat ttaataacta  10740
aaaccattct ttttgttata ttattattag ctttacaata acagaaagga tggtattttt  10800
ttatgtcaaa aaaagataaa aaaccattat taatagcagg taacaatatt actgcaaaag  10860
caaaaagtgc tacattttgg acaggttttg tacctgtttt agctacgttt attgttagtg  10920
tatgtagttt actaggaatc aaaggtgcag aagatattgt aaaccaaggc actgcaattg  10980
caggtgtagt tattagtttc ttgactggtt taggtgttct tgtaagtcat gacactaaag  11040
gtatagcgga tagccctatt gtacaggact ttaacaaacc tagagattat aatgacccag  11100
ataaagcttt aacatacaag agtgaagcaa tgaatagtac ctcagagtta cctcctacaa  11160
agatgccgat ggctcctgaa ggtgtcaata atgaggatat agatacaagc catgcagaac  11220
cattagaaca tggtaaagta gaaaaagact tagtgtctga attagataaa gaagataacc  11280
caaaagaagt aggtgaacag taatgataga aatttggaaa ggtgtaagtg ttagatatga  11340
tttactgcct attggaacaa gacgcacagg tcaagctatg gcggttaaaa aacccgtttt  11400
tattgtagct catgatacag ggaatattaa tactacagct caaaataatg tagattatta  11460
caaaaataca tataacattg attgggcttc tactgcatcc gcacatatct ttgtagatga  11520
taaagaagct atcatatgtg ttcctactac agaaaaagct tggcatgtgt tgtataacgc  11580
tcctatggat gacctatggt acggaattaa cgctaatgat ggtgctattg gtgtagagat  11640
ttgttacttt agtgataaag aacgctctaa aaaatcatta gataatggag ctcgtgtctt  11700
agcttattta gctgaatact ggggtgttga ttacaaaaca aatatgccag gtcaccaaga  11760
catccaaaac gacaaacaag acccaggtaa cttattagaa gcatgtggat taggtagaaa  11820
cactagtaac ttagataagg aagtagctaa gtattacaag aaagttatta agtcagtaga  11880
tgtaaagaaa tcaggtaatg ctgagcctag agtaaaaaca caatctacta aaactatgtg  11940
gagctggaaa ggtacttttt atccagatag agctattaaa gttagaaaat ctccaggact  12000
taaaggcact atagtaaata gagattcatg gctatacgat aaggatgatt gggttgagtt  12060
tgaccaagtt attaaagcaa atggctattg gtggattcga tttaaatatc caaaaccagg  12120
```

```
ctctagtaaa aattatttct attgtgctgt atgtgagata acagataaac aagagcgtat  12180
taagaaagaa aaatattttg gaaaaataga ttggaaataa ggagtgaaaa cttttgaaag  12240
catcgatgac tagaagtgaa tttgttcgat ttttaaaaag tctagaaggc aaagcaatag  12300
actttgatgg ttggtatggt cagcaatgtt acgacttagc taactatgga tttaacaagc  12360
tcttcccagg ttattcttta ggtggagcaa gtgcatgtaa cattccatgg gataataaag  12420
ctatgttaaa agataaagct agagtagtag aaaatacact atcctacatt cctaaaccag  12480
gcactatggt tatctttaat aattcatacg gaggcggtca tggtcatgtc gcatgggtac  12540
taagtgcaaa ccaaaaccaa attatagtaa ttgaaaataa ttggttaggt ggaggttgga  12600
cttggggaga tgctcaagga ggcggtggct gggagaaagc taccgttaga gcccatggtt  12660
acgactttcc tatgtggttt atagaaccta atttcaaaaa cgaggtacaa acaacttgga  12720
attggggagg taaatttact gctgatagaa cgattaaggt aagacgcaca ccaggtttaa  12780
ggggttcaat agtaggtgct gaatcattta tttatagtgg tcaatatgta aactttgacc  12840
aagttattaa agcagacggc tactggtgga ttaggtttaa atatcctaca aacccgtcag  12900
ctggtaactt ctatatggca gtatgtaaaa tcactgacaa gtgggaacgt atgctaaaag  12960
agaagtattg ggtcgtattt aactggaaat aatgtactag ggaattttcc ctagtatttt  13020
tttattttta agttgacaat gtatttatca tatgctacaa tacatatata agttttaaag  13080
gtggttataa taaatggaaa aattaaagaa atggtttaaa cgtaatgtat taaaaagtga  13140
gattacgcag tacaaagtat atattaagca tacacgttca aataaaagta atgttttcta  13200
tgttaatatg aaagctaaag gtaaagtaga ggctaaagaa aaaacgcttg acgttttaaa  13260
taagtatgct tataataaaa ataactatag tattttaaaa attgaagaaa gataggtagt  13320
ggtttattat ggaagagaat aaagtattaa atttaaaaaa agtaagagaa gaaaaaggtc  13380
atacagttag aagtttagca caagagattg gagttcacta ctcacttatt tcttattggg  13440
agagtggtaa aagaaaacct aagagtgcta atcttatgaa attagaaaaa gctttaaata  13500
ctaatagtgt agaattattt aaagaggttg atgttgatga ataaatttac aaaatctatt  13560
attaactttg ttgagcgtca tgagattgag gatatgatta atatttttga acttcaagat  13620
gttaataaag caagttgatt atgattctaa aaaccctaat attagaattt catatagtac  13680
tgaagaaaaa ggtaatacaa tgcaaaaagt agtagagcat ttaagtaata aattagataa  13740
ttgtttatat caatcttacc ctaatatatc taaatatagt attattagaa gtacggctga  13800
gttattagga gacctatcgt atatcgagga ttattatact ggtgatgact taacaaacat  13860
tattaaagac acacatctag aatatataca caacattatt aatagtagtg aatttgatag  13920
tatcacatta ttagagcagt ttgaactttt agaagagtca tacagacttg aagaagtaaa  13980
agaaaaatta gaagagctag aacactcaga aaagtacact gaaattgatt taattaagta  14040
ccttattaaa ttataaaggg gtttttttaaa tgtttaagaa attgttcgtt attttagttg  14100
atggttttga agttaatgtt attgcagatg actatatcga agcagaagaa cattgttata  14160
agtttttttga tttctctact ataaaattac aagactacaa agagatttat acaagtgaga  14220
tgttcccttg ctttgtagaa gggcataaat atgcataaga ctgcattaat atatacagat  14280
ggtagctcat cttataataa aggtcttgtt ggagcaggag ctattatttt agataaaaat  14340
gagaacattg taaaagaaat cagtaaacct attgaaaata gtagtttaat taagtataat  14400
aatgttgcag gtgaaatact agcttgttgt tacggtattg aagaggctat aaaactaggt  14460
tataagcagg ctattattca tgtagattat ataggactta ttcaatggta tgaaggttcg  14520
```

```
tggaaaacta aaaacaattt aagtaaaaca tatattaata tgctaaggga atactcaaag  14580
tttatagata taaattttat aaaaataaag gctcatgata ataacaaatg gaatgaatat  14640
gtagatgcat tagcaaaaaa agcaattgga atataaggag aaatattatg atgaaaaaat  14700
tatcaaaaaa gtttcaaaaa ggtggatttt gggaaaagtt atttttattt acagttacaa  14760
cattactagt agtagctaca tggtttttag tagatagtgt aatgtttttc ttacaaacag  14820
tattaacatt ctggggcttg gttttattag cacctattgt agctctaggt attattgctt  14880
ttagtatttt aaagtatcca agagtaaagg atattaatga ttactcggaa ccagttagaa  14940
agtacttata aggagactaa aataatgaca gaattaaaag ttaagatagg aacaaataaa  15000
gttaaaacaa aagatgttaa taaaattagt gagtacttaa aggataccta tgaaaaacta  15060
gatatggaac aatctataga ctttcaaaat agaacaccgt atttaattag tgatgatggt  15120
acttttattg catagtattt agaaaaagca aatgctgtag gtttttataa ggagtctatt  15180
atacaaggaa aagttaaaca acttgttcat gtaacacctg cagatataga acatataacg  15240
tggactattg aagaagatga tattgtagac ttatataacg atgaattgcc tgttggagat  15300
attattatta tttatcataa cgagaagtac agtagtgaat tagatgcata tctattacct  15360
catgtatctt ttagggacta catagatggt ttagggataa tggatagcat ttccctatct  15420
agagtagttt acacaggtat ttcaaaaggt agaaaagaaa atattagttt tgatgtactg  15480
tgacaggtga tttagagttt attaatcgtg atggtggttg gaataatgac acctttatta  15540
cagcggagag aaaactacaa taaaatacta taaatttggg ttaacgcaaa ggagggctaa  15600
ttttgaacaa ttacttattt aaagaatata accatttgtt agataataca agatttaaaa  15660
taaaagtaaa aggaaaaaca tatcatgttt atattgctac ttccaataag tcaataggtg  15720
tactaacaag acgtaaaagt ttttgtgcta cgtactttga ggataaagat tattttagta  15780
gatatacaat taaggaattt attgatttta ttaaaacact tattattgaa gagatgtctt  15840
ttgatattga aaacactatg acaaataaaa aaacagaaaa acaaattaaa aaagaaatca  15900
tgaaagataa taagttaaaa gatggaaatc tagatggtat aaatagacat acctctagca  15960
tggatgttct taaaagtgat ttaagagtac ttgataatta aaataaagga aaggaaagga  16020
aaggaaaata aaagaaagga aaataaagga aaggaatatt aaggaggaga ctttttatat  16080
aggataagat aagatttgtt ttgtcctgct ataatatata aaagaaaagg aaatatgatg  16140
tataagcaat aacatataaa atcctcaagg agaatgaaat atgagacaac taatactaat  16200
gagaggtgct ccaggctcag gtaaaacaac gtatataaaa gaaaatggat tagagggata  16260
ttctcttagc cctgatgtcc ttagaacaca atatagctca cctgtatacg acacggaagg  16320
aaaccttaga atatcacaag aagaagacaa caaggtatgg gatttattat ttagcatatt  16380
agaaaagcgt atggaaaatg gggaatttac tgtaatagat gctacacatt ccacagctaa  16440
actaattaaa aaatatgaga agttatcaaa aaaatacaga tatagagtat atgtggttaa  16500
catagaagca gagctagata ctcttcttga acgtaatgat aacagacaag aattgaagaa  16560
agttcctgtt aatgttattg aaaatatata tgagcgttta aaacacgaga atatcccaag  16620
ttttgccaaa gtagtagata aaaaagattt attaaacact attaaatggg ataaaaatct  16680
tatgaatact gattcatatg agaaaattca tgtaattgga gatgtccatt cctgttttac  16740
agccctctat tctcttttcc ccgctgatta cattatcgat aatcaaaatg aactcttcat  16800
atttgtcgga gattattttg atagaggatt agaatcgaaa cagatgtttg agtatcttga  16860
```

-continued

```
gattatttat aaattaaaaa atgtcattct attagaagga aatcatgaaa gacaccttcg  16920
cagatatact cagttagaaa gagaagacta tgataatctt tgttttgcct ataattcatt  16980
agataataac aaagaagatt tttataaaca agctttaaag atatttcatg caagaggatt  17040
tttacctacc ttaatatctt ttataggaaa cggaataact caaaacaggg ttaaagctat  17100
tcttagaaaa ctacaacagg ttgtttattt taactttaaa ggacaagact acattattag  17160
tcatggcgga gtccttcctg aagttcttga taatttaaat aagatttcaa caagtcagct  17220
tattaatgga atcgggggat atgattttaa tgttgatgac caatgggaat attctaatac  17280
aatacaaata catggacata ggaatttata tagagaacct ttagatacta ctaaaaattc  17340
agttaattta gaagggcgtg tagaaaaagg tggttgctta agagctataa cgataaataa  17400
aaacaacaac attgagaaac atgaaataaa aaacactatc tacgacccta aatttctttt  17460
atcaaacaga cggaacgata atattgacaa agacctaacc cctaatcaat acctagatat  17520
agctagaaaa gaaaataaaa ccatcaaaac cagtcaacaa tatagagatg tattctcggt  17580
taactttaca aaaagagctt tttctaaaaa gaaatggaat caattaacag tgagctctag  17640
aggtctttat attgatgaag gtagaaatac agtattagga agaggatata ataagttctt  17700
taatatcaat gaagtagaag aaaccaaatt ggagaatatg ccagacacta tccaattccc  17760
tttaactgga tataaaaaag aaaatggatt tttaggacta atgttctatg acccgttaga  17820
aggaattgta tatgcaagta aatctaaaac ccatttaagt ggacatggaa ataaatatgc  17880
gctactattt aaagagttag tagaaaaaac tttaaccaaa agacaaatac aaatactagc  17940
aacattcctt gaaaaccatt atattgctga cgatagtttt accctagtgt tcgaggtagt  18000
tgatattgaa gaagacccac atatcataaa gtatgaagaa agtagtattt tcctactcga  18060
tattatttcg aacacactaa atatggaaaa gaaagactat gattatttga gatatgttgc  18120
tgatgaagtg ggattacaat taaaagaaaa agagttagag tttgctagct gggaagaatt  18180
ttataaatgg tataaggata ataatggctc ttataatata ttgcatgaag gatatgtatt  18240
tgaggatttg aaaggattta tgtttaaata taagtctgac tattacaaag actggaaata  18300
tatgagagat atagcttatt ccttatcaca aagaagagat gtaagaccta agcaatatat  18360
tttagcaaga aaccctgaac ttagagattt ttattattgg gctaaaatga aagattcaga  18420
tgaacttgat aaagatatta tcacactaag agatgagttt gaaaaagaaa aggagaggta  18480
gaatggcaaa tctattaaaa gaattacaaa tctataatgg gggacatata ttgaacgatg  18540
caatggtaaa atatagaaac aaacaggcag accaaatcaa tggaatcatt ggtgttaaat  18600
gttataatgt attagatgat aaatcaatca atgacaaagc taacgcagaa caggttgggt  18660
tagctgaacg tatcttgaat aatgacttta aggctatgca agagtcagat atatttgtat  18720
tcgatgtatt gaatgaggga ttaggtacaa tagcagagat tagtattctt ttgggtatga  18780
aacaccaagc tcaacaaatt atcaacaaat atgaagatgt agattttaga gagttagata  18840
aaaacacaca agatgatata ttagaagcgt atcatgtcgt caataaacct gttttaattt  18900
attgctctga tattcgtcaa gggcacggga aaccatacac tgacccagac agagcagagt  18960
tttcaacgaa ccagtttgtc tatggcatgg ttttatcatt aaccaacggc aaaggcttta  19020
tttcatggga agaagtttta ggggaattag aaaagttagg tgcatctaat gtctaattta  19080
gctcatatat taagcatctt atatgctata ttagttactg taggatatat acctgcttta  19140
gtaggtttga taagagataa gaatgttaaa ggtgtagata gctatttttg gttttatatt  19200
gttgttacag taagtattag cttaacaagc ttatttgtaa cacatgcacc cctatttcaa  19260
```

```
attatatcag taagtattaa tttattacta ggtattattt gttttattat atacttattt  19320
agaacaacag aagttagtct tttagaaatg gttatgttta taattgttat ttatattggc  19380
tattcagtag ctaactatag tgttgaatac ggacaaataa tggctactat tagtattatc  19440
gtagcttatt tatcccaaat aaataaattt tataaaacta aaagtacaaa tggaactagc  19500
aaatatttat ttcttattat aggtattgca ttagcttgtt taattattag tatgttaata  19560
acaaatacga caccacatgt aatatataca gaagtagcta actttattct tattatgata  19620
tgttacctac aggcatctta ttatgaatat aaaggcgtag ataacaatga aagacttaat  19680
acaaaaaggt aataaatttt attataaggt tagaaatggt gataccttat ggactataag  19740
taagaaatat gatgtgtcta ttaaacaact acaagaactt aatgatatga cctcggtgtc  19800
tttatcagac aaagattgta tacttgttta tgtagactag aaaggacttc tatatggatt  19860
taatagctaa taaagaagta actagtaccg atgagattat ttttaaaagt aaatctaaaa  19920
atttatatat tagtgatata gatataatat ctaaagttac tatgtacaca gatgagttag  19980
aggaagtttt agcaatgcct aatactatta actttaaaaa ttctaagaag tacaaagact  20040
taatgagtaa tcccgatatt gtacccgtaa gaagaactaa aaaaattaaa tatgaaactt  20100
atctagaaga actgtaaaaa agttcttctt ttttgttgac tattaaattt aactatgtta  20160
tcatacttat ataataataa atgaggtgat gacacatgtc agtagaatat aaagaaacag  20220
gattaacgga agaagaaatt cttaaattac ctaaagtaaa tagaaatagt atatttatag  20280
gtgaagaaag agtatattta aaaataaata ataaaaatat tgtagatatt ggctctaaag  20340
aattattaag agatattaat aataccttt gttattctag cgctttaaat ttacttttat  20400
ttatagcatt atgtggaaat aaaaaactta ctacgtttaa gggagaccca tataaaaaag  20460
tacaagagtt aagtaaaaca gttacagatg taaatactgt atatagtgag tatatagaaa  20520
gtgacgatag gtctgaattt cctttatata acaaaagaca ctatcgtaat aatatatact  20580
gccgtgcaaa ctatgaaaat gaactaaaac agtttgacaa tacgcaaaat aagaatagta  20640
ataattacct tacaaaaaaa ataagagact taaaaagaca aataaatact acaactaatg  20700
atatacttga tgtattatta atgggtgact atagtatatt tggtattaat attgaccctt  20760
atgcatttgg taaatcttat gataataact acgaatacta caatgaagtt ttaaaaaata  20820
taaaaatagg gcttaacaaa ttaacaccta taaaagataa taatactccg tttttaatta  20880
agacttgtta tttaaaagac ataagtatag taacaacaga ttggagtata gtaaacggtg  20940
actttaataa taaaaatgga aatgtatacc tacacctatc aaatacacta caacataaag  21000
aatttaaatt taatatgtat gaagatgatt ttaataagga taaattaaaa aataacatta  21060
ctttacctgt cctttaaat attattttaa gtaaatatgg aaaggaaaat ttagctttta  21120
acataataat ccaaacacta aagaataatg attattactt aaatctaagt agacttaatg  21180
taaaaaactt tgatgtatac tctatgatag atagacctga tggttatcgc acagttagta  21240
aaggtgaaaa tactactgat aatttaaaca atctgttaaa attagttgtg tctaatattg  21300
ataaagttta taacaacgaa gattgtgata tatttaaaga acacaaagag tttttagtaa  21360
taccaaacaa aaataaatgg aaattacatg aagctttaaa tttaagtaaa caaacatata  21420
ataagtttat tactcttaat aaagaagagc aagaaaatta ccttaatata cttcgagtta  21480
tcataaataa atttcctagt ttatataatg agtctaactt acacaaacta ttcgatgacg  21540
actttataat ggtgactaat tcatattcaa taggaaatgc tttatctttt aaaggtacta  21600
```

-continued

```
cgaaagaagt tcttaacttt tcattttctg actttagaaa aatggtgaat tatataaact  21660
atgatgtcag aaacagacaa cgtatacatt catacgctgt taataattta tatagagatt  21720
atatagactt tgcttcagac ctagtacttc ttggatatag aactaaagaa agtattaact  21780
taacaccata ttctttaaaa ctagagcatg atattgttac tgatgagtat ttaacagtta  21840
aagatgaagt cgatgactta aagttacaac aaaaatatga taataaatta aataatatca  21900
caaataaaga atataagtta aacgatggct ctaaagttaa atttttacct gcggatacta  21960
ctgaaaaatt aaaaagagaa ggtgaacagc tatctcattg tgtcggcagt tatgcttcga  22020
atattataaa tgacagatgt ttaatattac tagctagaaa agttgacgat ttagaaaaat  22080
catggtatac tgtagaagta aggataacaa aatatggata tacgttaggt caacaacaat  22140
ctttaaaaag tcatgagtta cctaaagaat taaaagacga attaataaaa gatattaaaa  22200
atataaataa acaatttagt gaggatgttg cgtaatggta aaaccagtta taactttaga  22260
acctaaagaa gttaagacat taatagagta tttaagtcat tttgaagaag atgtacgaaa  22320
atataaagat atggagaaat tatatgaaga attacacaaa aagtatcagc ttgctaaagg  22380
aaactacgtt gagtaatgga aaggtatagt aaagaatatg tagatataga cattacagtt  22440
agagcattag tacaaacacc ttatagagac ttatatgatg ttacaaataa tagaaacgaa  22500
ttagtagaag ataatatcgt cgttaatagt ttatcagatt atgttaaagt acaagaagtt  22560
aaaataaatg atatagatta aaaggcaaag gaactgttat attatatgtg tactttatag  22620
tacacttcca taatatcttt ccttttccct atctatattc tagatagggt ttttatttta  22680
gatacgaaag gacaccaata tggatactag agaatttatt gactcacaaa ttggaagtaa  22740
caaagaggca acagaattaa aagaactaaa gataaacatt attgaagcat ctttagatgt  22800
gacacattct ttagatgaca cattatatta tgctaaaaag cttatgaaaa atgtagaaca  22860
actggagtta tactataatg tcaactctac cactaataca ccgaaccatt ataaaggtaa  22920
aaaagatgtt atatcatttt tagaagaata tttctacatt attggcttta tagactgcat  22980
gctatttaat attgttaaat atacaacaag attaggaaga aaagacgatg aaagaaaaga  23040
agtagagaaa attaaaacct ataccgaaag gctgttaaac ttcatagaat atggtaatag  23100
taatggaaga gaataaaaaa aagatacaca aatacttttg ttacttatac ttctcagatt  23160
acttaccatc aaaaggtata gttgttttaa atcataatgt tacctctcat gctacggaga  23220
acggagttaa aaattattac ataggtaata ttctaataga taacgcagaa ataacagttg  23280
ttatagactt aacggattta caaaaagcaa gtagtatgca aaatatgtta gaaatattga  23340
ataaaaatac agaatcttgt atatttaaaa gcaaagaatt aactactaag atggtaaata  23400
ccttctttaa aggagaaatt ttatgaaaaa attaaatata tgtttaacta ttatatcatt  23460
ctttatcaca tataaagtgt taacaaaaaa gaaaaagcat acacatgtca ttgtagactt  23520
ttcaatacaa gaccatgaac atttaaataa tatttgtaaa taaagggcaa tttgcccttt  23580
tttgtgtttt atgatatatt aacattgact aatagtaaag gagattttca atgcctcatt  23640
taaaagcata tgataaatac ggtaatatat tggcaatagg ttacaatgta gagttacatg  23700
aagaagtagg gtctgtaatc atacctaact tagctcctca cacacactac cctcaaggtg  23760
agttctatgt atcatgggaa gctgaaaaat atgaaaccga taaagtagta gttcctggtt  23820
ttacaaccct agaatcatca ttcaaagaaa taacattata ttttaaagac catatacttg  23880
taaatgctaa atctgcttat gatgtagcag tagataatgg ttttgtcggt tctgaagaag  23940
aatgggttaa gtctattaaa ggagaaaaag gggagaaagg ggaacaaggt aagcaaggtt  24000
```

```
taagtgctta tgaagtagct gtaagtaacg gttttacagg ttcagctaca gattggctta  24060
aaacaggtaa aagtccttat gtatactcta atgagtatat aaagcaaaaa gatgatactt  24120
cggatgttca aggttaaga cgtgctatta aagatacaag tgaaggtaat accctacaca  24180
ttccttctag tgaatcacct attaaaatag atgatacttt gataatagat aagaatatta  24240
atattgtatc tgatgctaag attgtttata atggtagtaa ggataaacca gctattaaac  24300
tagatagttt atcatattct aatgttacaa ttaaaggtat ttatgatgat agttcttatc  24360
caacttatgg tggaggctat catggtttta agagtcaaaa ctatatagga ctagaattag  24420
ttaactgtag aaatgttaat actaatatta atgaaattat tggttttaca gtcggtaata  24480
aacataaagc tactggtggt aaaggtcatt ggtttaataa tactattatt aatttcttta  24540
ttaataatga aacacatata gaattaaata cagatggtat aggttctaat ggtgagcaat  24600
cttggatgaa tagtaattac ttctataaat cagcttttc atatagtggc actgagttta  24660
ataaacaccc taacacatac tataacatca aacaaactct aacaaatgct aatacctatg  24720
gaggaaatag caatgtattc gattcactta aatttgaaac tgcttccaca acatctgaaa  24780
attatgttat ggtgtatctt aaaaaagcag taggatttat atttaagaat tacagatttg  24840
aatttaataa caaagctacc tttgctatta tagatttaga aacacaagac atgacaaaat  24900
cttatgtaac acatagtaaa gatattaagt ttattcctga atttgtttta ggtaatggac  24960
ataaactaac gtttacaaat attaatactg ctaaaatacc tagaagtagt attgctaaaa  25020
tagtagacga atacaaaaca acgttattgt ataaaaataa tgattttagc aaagactata  25080
gaagattagg aggtaactat cacacagtca aaaatgtatt tagaaaacca ttacagtcaa  25140
cttctctgac agatgaagta tcttatgact ataatactac acctagttta gtagatgata  25200
aaggactact tacctttaca ggctcgtacc ctatggcttt atatgttaat aatgttagtg  25260
ttggtgacga gctaattatt aacaagttat catttatagg taattctagt ggtatattta  25320
ttaaatgttt tgataaagac ggtaatatat tagacaaagt atctaataat tatgatacaa  25380
tattactaga tggttattat aatgataaat ataaagcgtt cactttcaat aacgcccaaa  25440
aagatacttt tactgttaat agtgaagatg ttaagtctat cgttatttta atatctggaa  25500
ctatgcaagg tttacttgta gattcaacta atccatccaa tattattaag tcttcaaacg  25560
atagtagcaa gaataaaact gatgtttttt attctcatgt taaaccttct agtgttgaag  25620
attttaaata tgatgaaaaa gtatacaaca atggtacaac acaagtatat ggttgggtac  25680
taaaaggtaa tgattggaaa gaactaggta aagacactaa ttctaagagt aaagtaatag  25740
ttaatataga agattaccca agaattaatg atgaagataa tgactatcct agattccaaa  25800
gagctttaga ttatttaaca agtactaagg gaggtaacta aacagttgca atagaaatat  25860
aaaaatatat aaaatacttt gtattttatt aaataaaact gtttgccttg cttatagagc  25920
aatctgtaag taccaaaggt taaatgctaa gaaatcctaa agactcaata actaaaacag  25980
aatctgaaaa gataaatggt atagttacga aagtagaaaa aatattgagt atggtataag  26040
gttaaatcct aagtactgtt acaatggaag tttagcaggg aaagttctaa gggattatta  26100
atcctatgaa agaccctcaa cgactattcc gtataggtga cggaagtaaa gccacaagct  26160
attggtggaa gaaaaatctt taccctataa taatagggat aacaaatagt ctccgcccgt  26220
actgaaaggt agggcttgga aataaccaag aacatagaag tagcgttcta ttgttaaaga  26280
aagttaaaac ttataaataa tttaaatttt attctaaata actgttgaca ataattctac  26340
```

-continued

```
cttatggtat attatatact ataaggaggt gggaataatg tcagaagaaa aatataaacg  26400
tattaatatt agactattac caacaaaaga acaagaagaa ttaatgtgga aacatgttaa  26460
tcattcgaga ttcattaaaa attattttat tcagtattgt attgataaaa gagaaaatga  26520
aagtatttat tatagagata ctattaaaca tttatcagaa ttaaagaaac atttaactca  26580
actacaaaag caaaaatatt ttaaatggtt aaaagaaaca agtagacact ctaaaaatga  26640
agctattaaa gatgtactag tttcttttga aaaactttac actaatcaat ctaaatcagt  26700
aaggtttaaa aagaaaggta aagtatctaa tacttattct atcagaaatg atttattgcc  26760
tagtggttta tgtaggttta gaagagtaga gaatactttt cagatagaaa agttaggtag  26820
agttaaattt tctcaaaaac agtataaaaa gaataaacat atttttgatg aaatagaaag  26880
taaacataag tttataaacc ctattattac tcatgatggt aaatactggt acgtatctat  26940
gctatataga gatgatttag taagcaaaaa ccaagttact gagttaacta acgaaaccat  27000
aggtatagac ttaggtatta aacattagc cacttgttct aatggtaaat cttataaaaa  27060
tattaataaa agttctaaag ttaaaaaact agagaaacgt ttaaaacgat tacaaagaca  27120
agtaagtaga aagtatgaaa tgaataagca aggtaagaag tttattaaaa ctaataatat  27180
tattaagtta gaaaaagaaa taaaactctt acatagaaaa cttagtaata ttagaaataa  27240
tcatattcat actatgacta aagaaatagt agaacaatat cctagtgaaa tagtaataga  27300
agacttaaag gtaagtaact taagaaaaaa taaacattta tctaatagta tttctaaagc  27360
taattggtat acaattagag aataccttac ttataaatgt gaagatagag gaatattact  27420
tactattgct aatacttact atccgtctag tcaaacatgt tctaattgtg gtaatcgttt  27480
aactaaacaa gataaactat ctttatcaca aagaacatat aaatgttctt gtggaagtag  27540
tatagataga gatttaaacg ctagtattaa cttaaagaac tatagatact ccaaatggta  27600
taacaatcat gttttaacta aatcaaacag taaacatgat atgtaggatt ccgtaaatcc  27660
gaattaacgc ctttggagta tcacacaaac ctgagtagag tatataaaag taactagtaa  27720
tagtgaaggt actcaaaaag ggatacgttg aaaaaggaat aaaatttata attatttata  27780
agttttaact tacggcactc ttatagtacc taaaggaaca gaggactatt tattcaaaac  27840
taagacacct actgtacaaa acccatcacg tgtaaaagta acaggaagta atatacacat  27900
taaaggtgaa ggtaatccta catttattat gtcaggaatc actaaaaact atttagactc  27960
tatagatgat atttcttcta gtggtagaga tatgtttaca ggattctcat ttatcaactg  28020
tgataacatt cttgtagaag gattaacatt taaaggggaa tgggatagta aaggtgaatt  28080
tagatatgcg tcacctcgtt ctattggagt agcgtttaaa ggaagtagaa actgtaaagc  28140
atataatgta catggctata atatcatggg taatgttgta aatgcagtaa acactatgca  28200
agcagtagat ggtgtttatg gttactcaga caacattact atagatagtt gctcagctac  28260
acaatgttta gagaatggtt ttaactttat gggtggtact aaaaatggat attatgttaa  28320
taatatatct acaggaaatg gttcaagtgg atttgaatca ggaacagaaa atgttattat  28380
aagtaataat atacacacaa ataataagta ctcaggttta agtatatctg gcactaatta  28440
cacaatcact aataacgtaa tttatggtaa tagtaataaa ggagagttaa gtaataaacc  28500
atctaatggt attgctatta caggaggtag taaaggaatt attagtaaca ataatgtatc  28560
aggtaatgag ggttacgagt tgtaccttta tccaggagtt aataacatag atatacaaaa  28620
taatgtatta aaacaagata caacaagttt aaaaacaagt attatttatg cctcaggaac  28680
aactagtaaa cctgtgtcag aaattaactt taaaaataat acattaagaa gtacaaatac  28740
```

```
tgctttggat aaagctatgt tcttaaattt tgttatggat agtacaatta ctaataatga  28800
tataaaaaca gataaaggta atgattcatt aagtgttcaa ggttcttgta gtaatctatt  28860
cgtattaagt aacaatatga ataaaaactt aagtatttct agtaatgcat ttaatgttat  28920
aagtaaggat aacatagctt ataatttacc taaagtactg aacggtactg caataccaac  28980
tacagggagt tggagattgg gagatattgt tgttaatact agtagaaccc taacatcagg  29040
tagtcctgag aaatggagat gtactagcga tggagttgct actaatatga agtggacatc  29100
taatacggat tatacacaag gtcaaattgt ttataatggg aattatgtat ataaagcagt  29160
agcttcaggt acaagtggtg gaacacaacc tactcataat aacggtgtta tatcagatgg  29220
ctctatactg tgggaattta tatccacaaa agctaatttt gaagtcataa gccaaatagg  29280
tgtaactgaa agcattagta atataccttt atacaaaggt caaattgcta taataggttc  29340
atctgtatat gtagctaaag gtacatcaag caatactgat tggataattt taaattagta  29400
aaaaggggat ttaatgatga cagaagacaa tttatattta tttaaagcac acgtggacaa  29460
aatagtggat ggggatacta tacatgtaac tattgaccac ggaatgagaa catactctga  29520
gcaaagaata agattactag gtgtcgacac accagaaaag aaacaaaata attaccaaga  29580
agctaaggaa tttacaacaa ctatgttaga aggaaaagat gttttaattc aaacatacaa  29640
agatgattct tttggtagat atttagctaa agtgttctac aaagaaaata aagagtataa  29700
aaatattagt gaagaattaa ttaaaaaagg attactaaaa gaaaaaagta aatggaataa  29760
agaacttgac aaacaataaa atatatgcta tattattata gtagttaact aacgcctctt  29820
aacaatgcga aacacagtta gcattttta accttataat gagagtaaca gcctaaccat  29880
atgggtactg tgaaatcatt atattctacc tatctaccat cgtagaaaag gtctacggta  29940
acgttatgac cctatttagc gttactagca atcctgagta atggcattgg ctagttgtag  30000
ctacctagtc gaggggttcg agtccctgct caggattttt tttccacaag atacctacta  30060
aaatatctta cacctactta tttttaaagt aggtgttttt tttattgact tctatttact  30120
tatgtgttat atttactata tactaaaaaa aggaatgatt attaatgact aaaaaaatta  30180
aaaatattga aattgttttt gaaaacttag atagtgcggt gttagaacca gaaaatgtag  30240
agttgatact agaaggtatt agtgaagaaa aaactatgat atatggaaat agtgaagtag  30300
atacaagtaa gtcagcaaaa aaagtttcta ttgaggtaag tggtatgaag gatgaatact  30360
ttgaagagtt tcatggtttc ttagatgagc cctacaacat ggcattatat gatagattaa  30420
gtggcaaaga tattgtttgt gtttgtttga attatgagga tggtacagac gatactgtat  30480
atgtacctta tcctgagtat gggcagtata attatatgca gagaaataag tacgaaaaag  30540
aaatagacac tttatttatt acaatagagg atagagaaca agaagaacat gtaccaaatg  30600
atgaaaaacc taactttaat gaaggtgaaa cagaagaccg cacgctagaa ggtttaatta  30660
gtcaagtaga ggaatggagt aaagataaag gattgaacaa taacaaccct gatagacaag  30720
cccttaaatt ctacgaagaa gcaggtgaag tagcatcggc attatcacgt ggtaacctag  30780
aagctcttaa agatggtatt ggggacactg tagttacttt aattatttta gctcagcaac  30840
acgacatgtc attacaagag tgtttagagt ttgcttacgg tgaaattaaa ggtcgtaaag  30900
gaaaaacagt taatggtacc tttattaaag aggaagattt aaatgagtga taactttagt  30960
caatttataa gtaaaaaaag caatgaatta aacaaagcta cagaaaaaca aaaagatttt  31020
atctataatc atatagattg tttatatgat gagtttactt ttgatataga gtcattaagt  31080
```

```
aaagatgaag ctactgaact tataaatgat ataactatag agttaagctg ttcagatgat  31140
tttcttgatt ggtatgacta tcagtaaaga ataagcaggt aaaggttttg aaagccctta  31200
cctgtttttt atatgctata ttattaatgt atcatacaac agaaagggat aacattatgt  31260
ctaaaaaatt aaaggtctac aacaaagatg aacagctaat tttaacttct gatgaagtta  31320
caggtagttc tgtaaaagta acattaacag atttaaaacc taatactact tataataaag  31380
gtgactttaa agtctcttgg ttagtcgatg gacaagaatc taataaaaca gatgtgccta  31440
gtttcaaaac attagagagt gaaaaagaag ctgtagctca gcctgtcatt gtaaacacat  31500
tagatatggg taccgacggg tacacaatca gcaatgaacc acctaaagac actaacaaaa  31560
tatggcttaa atcggaataa gaaaggataa actataatgg caaacttatt accacatttt  31620
tacaacacag aaacaaataa atgggaagaa ctatatacaa aacctattgc tagagaagta  31680
tttaatatca tgaaagaaga ttatttagct cacaaaggtg aaataggcta ttacattgct  31740
aagtacaaag atggagacac aagtattgag caacctaatg ttgttgtttt ttatgatgtt  31800
aacgattatg aaacaatgac tttaaataaa gaggaaatga caagactatt aaatgattat  31860
atagataata atttacaagg aaagtttaaa cccttttctc ttactaaatt cttacaaaat  31920
ttagaagacc ttaattacgc tttaccaaaa caagaaaaat ttcatgtaga tacaatccag  31980
tcggataaaa gaaaatttc atttcctgat acaaatgcaa ttaacacaaa ccctgatatc  32040
ttagatgccc ttacggctac agataatcat gtatatatgg aagtaaaata tttatataat  32100
ggtcatccta ttgatgataa aaaattaata aaaggaaacc aagatttaaa aaattaataa  32160
cccagtaaag aacctgtaaa aaggttcttt ttttttgctt actgaaaaaa gtgtatagta  32220
ttagttgaca ctatattgat tatatgttat agttaactta acttaaagaa aggtttgata  32280
gatatgaata agatatatgt tatatatgca gaagaagatt cctattatga tgaagaacct  32340
accttagaag taatagggta cactactaat atagaagaag ctaagtatat taaaaataat  32400
tacgatgcat ggtgtcgtat tataagagta ggggaagttg aaagacttac aaaagaaata  32460
cttgataaaa aacagaaact atataaacta atgtcaacgg cagtgataca aagagagcaa  32520
cattatttta aacccataca agaattaaat acaattgtag atgaggtatt taattcaagt  32580
aaaccagata ttgactttaa tgagaaatgt gaaattatcg tttattcatt aaataaaaat  32640
caaattcagg tagatatagg tttacttttc cctactgagc caacagaaaa agaagtagac  32700
agtatcgtta atgatgtaaa aaacaaaatt aacttcatat taaaaaactg tgaaaatgct  32760
gacattagag aatcaaaaaa gattatgaaa atgatagaaa aattaaataa ttaggagata  32820
taaaaatgaa aataaaaact aaaaaagtaa tgacgctagc cgaacttatg gaatgggctt  32880
gggaatatcc tgatttaaca aaaggaaaga gattttacac agaaaatcaa gataatgaga  32940
actttgttta tttttcttcg gaagacggaa gaaaatgtct tgccagtgaa tttatatcag  33000
ctgacgacac ttttgaagtt gaagtcgaag ttgaagagga aatcacagaa gagactaagg  33060
ttgataggtt gattgaatta ttcgagattc aagaaggaga ctataactct acactatatg  33120
agaacactag tataaaagaa tgtttatatg gcagatgtgt gcctaccaaa gcattctaca  33180
tcttaaacga tgacctaact atgacgttaa tctggaaaga tgcggagttg gtagaatgat  33240
gcaaacctat aaagtaagtc tttgtatcaa gttcttagcg tctaaatgta attataaatt  33300
aaaaaagcat tattttgtgc aaagtacgaa tgaggaagaa gccacgaata cggtattaaa  33360
actgactcgt aaaaagctcc cgttccaaac tgcaagcata gaagtagaaa aagtggaggt  33420
agtagaatga tgcctaaata tcgagtgtgg gacgaatata caggaagaat acacgatgtt  33480
```

```
gtaggattcg acttcatcga gaatgaagtt cactatgaaa actacgcgga agcagaagct  33540
ttaatacacg caagagattt caaagatgta gaacttatgc aaagtacagg acttaaagac  33600
aaaaacaaca acgaaatata tgcgggagat atagttgagt ttgaagatga aatattagag  33660
atgccagacg atgaatctgt aataggaaca attaatagag cagtaatatc tattgatgtt  33720
gtaaatggta ttcaattaaa agattttatg tttgagagcg caatctccga aaatgattac  33780
tttgagtata cagacaaaaa atctttcctt atgtacgact gtgaggttaa aggcaacgta  33840
tttgaatcat ctcatttatt ggaggtaata gaatgatacc gaaatttaga gcatgggata  33900
aagaatcaca aagaatgttt aatattgcta gatttgactt tgcagaccat acaatatatt  33960
cacacctatt tgcttgtgat ggttacttag gagaaaacct tgtaattatg caatctacag  34020
gacttgaaga taagaatggt actgaaatat ttgaaggtga tatacttaga tattgggggg  34080
attgtagacc tgtaatattt aaagaagctt cttttggatg ggttgaaggg ggagattaca  34140
taccattctc tatgatgtgc atttcagaga ttggtaatac tgaagttgta ggaaatatct  34200
atgaaaaaag gagtaaaaaa gaatgaaata ttaccaagta gagcatgata attgtgagct  34260
atacgaagac agctactctt atagagaaga taaaatatat actagtaaag aacagcttat  34320
taaagacatt aaatctgaag gatacaaaga agtacaaggc atgtctagaa atcatgatgg  34380
tattgcttac cttaaacata tagatgaatt tagagatgat atgattacaa ttcatgaaat  34440
agaaattata gataataaat aaaggggtat tatttatgta tactaatgaa tttattgaaa  34500
atgtaaaaca gttaggctat actgttacca tagcaaataa gaatactacc aaaaggaaag  34560
aaaaaatact tattaaaaaa gaaaaccaac aacctattgc ttgggtattt ctaaatgaac  34620
catattcttt tcgaagctta ggcacagata gtgagttatt tgatttaatg gtagaatatg  34680
caaaaacacc tgtaaaagaa cgtagtataa gcaatatagc aaaagtaaaa cctttagact  34740
tagataccct tacagatgac tatgctaaag taagagagtt tatgctaaaa ttcataatag  34800
acatggaaga catagtagaa tacattcaat atacaggata taataagaat gttattaatc  34860
attggacaga aggtcaaacg tttagagcag tagataagca aggagacaat aacctattta  34920
ttaatacacc taatggaatt gaaaaagttt taaaagataa ttatatcata aaaggtaaag  34980
agcaaggttt cgaacaagta gatagagaac tgtttgaata tagatatgat atttcacatt  35040
aaacacctat gaactattgt aggtgttttt aatattataa gaaagatatg taactactac  35100
tactataaat tcaacaggga taggtaggac aataagaaca ataatggaaa tcttattatg  35160
ttgacttttt attatattgt actttataat gttgactttt aataataaag tatataataa  35220
tactaactac taatagtaca tagtataact agttattaaa atagtatact aaagaccact  35280
atagcaacct catatataaa aaaaggctcc tatatactaa actacttata tgctgtaata  35340
tactaatact ctaattaagt gtaagggaag aaggggatat actactaact ttattgtaaa  35400
atgaatacca ttagttatta gtaatgttga catagattaa agagtaatgg ttaatgttga  35460
cttttaataa taagttatat aatattactc actaattagg ttccttaggt agccccatag  35520
ccctgtcaga cccacccacc tatattaaaa taaaggaacc tttaatttag gctccttata  35580
ttttttaaat actcgtccct ttctttttc attcttgata gtttttcttc tacttgctta  35640
atattatggt caaaaggtgt atagtctaca agaccaagac tagatgcttt ttttaatcta  35700
tccgtaatta ctgaagtaga agtacttaat tctttactaa tttttttaat accataacct  35760
ttactgtata aatctataat ttcttgaata aatccgtttt ccatatattt atatacttct  35820
```

```
ttccaatcta tacattcggt aggtaaatca ctgcttataa tactttgttt aatatagtca  35880
aagctgtgtt ctcttacatc tatttctatg tattttagtc cgtgggaaag tgcttgactt  35940
ttcttccatt catcgttttt cttattttct tctaacgtta agtgaaacct ttgaccctct  36000
ttttgctcta gataatgctg tacaccatga acttctataa cacaatcgta ctcaggtaaa  36060
taaaaatcat aacgtttacg attagaccaa tcaaatgatt tttcagcagt ataaataata  36120
ttttgttgtt ttagtacctg ctctaccatg gactctcctc tacttctgtg tttattaagt  36180
tccttaaggg atttcttcat agaagaacag tccgcacaat aatccctaga gtaattattt  36240
atgtgacttg tttttatttt ctttatcata ccacattcat tacattctac tataataaaa  36300
cgtgttgttt ctatcttacc atctttagct atcttttcct ccgttatatt ttcctttaca  36360
gtgaattttc ctaaagtact acctacatca taagggtaaa cataagggtc agcaactcgt  36420
tgtaaattac ctataataac attaagagca ttatacaaga aagtatcccc attactattt  36480
tctaatctaa catattcaat aaccttacct ttgttatttt gtttagaaaa agcatctata  36540
atttaagtt ctcctttatt atcttcaaaa cgatatgtaa aagaaagacc tatactattt  36600
ttaaaatcta tatcataaga taccttacca taatactttt ctttatcaag tttaggtagg  36660
ttatttaagt ccacagaacg tttaccatta aatcttttaa ttaaaccttt tcttttacgt  36720
tcactgtatg ttactttatc taatgctact ctattaagag aacttatagt tattgttcct  36780
ttttcatttt tgtacacata atcataagtt acctcaggag ttttagactt taaagttaaa  36840
tacatcttat cctctaaacc tttataacta aaaggaactt ctatattttt catttttttct  36900
ataagactgt aattatactt tgtatactta gtctttttta aaggtaggtt agttaagtct  36960
acccacacct cgtgattact cttattaact tttataaatat ttttgtccat atttttaata  37020
cctcgttttt tactatctac ttataatata acacatataa aggtgataca agaggtataa  37080
aaaaaatcgt tgacttatat taaaataatc attcttttat ttattgtttt gttgactttt  37140
gtattactac tatgtagcta taccatttac atagtacctg gacagaccga tataggtata  37200
taaaaggtgt ggtattagtg gtattttacc cctgcccccg tataatatat ttatattaac  37260
ctattgtata caatcctaat aaataataaa aaaaaagaaa gggagtttat tccctttcaa  37320
tttgttttac atcatttcta tagcttctgc tttaatttgt tcgtagtctt taatccattt  37380
attagattct tcaacactca tatgttctaa catataatca gctagttcaa acactttgtt  37440
accaactaat cttgttgttg tatcgtctgt aaagtctagt ttagaaggta tatgttctaa  37500
tgctgtgata gctttattct cttttagttg gttaacaata tggatatatt tacctaatgc  37560
gtcgtgttca ataacgtcta tgtctattgt ttcatagaaa gctgttaata gtaagtcaag  37620
ttcgattcct tcaagtttg ctgtttgttc cctttggtta attaatttca taatttatca  37680
atccttttcg tttattgtgt tttctttata tttatatatt accatgtatc ttagtaagtg  37740
tcaacacttt tctttaactt tttttaagaa gttttacact attataagtt aagtaattct  37800
tttataacgc ttggtgctag tgttgttata tcatagtctt gtcttagttc gtctaagctg  37860
ttgtaatgct taatagttcc agcgtctttg tcactgcttt ttgttgtaat tttttttgtta  37920
atagccttgt ctatatcctc aaggctatta acgttgtcca ttaggtttat taaatcagtt  37980
tcagttaagt tcatgtgtat tgtctcctta gaataacatt tggttagcgt taaactctag  38040
tgtatcaaca tccataatca tttgctcaaa ttgttctttg ctcatatgat ttaaaataat  38100
gttagtaaag tgttctgctt tgtcttgtgc taatgtagca ccctcgtaag tgctaaagtc  38160
aatgtttgat ggtttacgtt ctgcttgtgt taattcttcg ttgtttaata attgttgttc  38220
```

```
taagtgttcg aatttgtcta gtgcgtcgta ttcaagtatt tctgtcataa ccgcttcttg  38280
aattgctaca actaataatc tttctaattt aatgtttcca tttgccattt ctttaattgt  38340
gtttttcata atttatcaat ccttttcgtt tattgtgttt tctttatatt tatatattac  38400
catgtatctt agtaagtgtc aacacttttc tttaactttt ttaagaagtt ttttaatgtg  38460
ttgctgttcc ttacatctat tatattacat gataatctag tatatgtaaa gtgttttagt  38520
aaagaaataa tagcaatttt acactagctt gaagcggttt aaaagcataa aaaataaggg  38580
ctaataaccc ttatttaata aagatattaa tattgtcttg taacctgata aaccaatcaa  38640
ttaatgtaat tattgtcgta ccgcctaata tagttacaat agcgtcagtc ttttctgttg  38700
aacggtagtt cttacctttg tatttaaatt taatcattat agttagccct ctttataatc  38760
ttcctgtatt aataaataac tctaattgtt tgtttaactc gtccatgata aagttatcaa  38820
gttcatgagc agtaatgttg tattttttgt ttcctgttgt cattgaaact acattgtaca  38880
cgttgtcaaa tttattaaag taaatgccgt actgtagtaa accccaatca ttgacataga  38940
tatcagtaac atctaaatca ttatgtttgc ttgaagcttc gttatatgtt ctaacaactg  39000
tgtaatcttg gtttaattcc tctaaagttt tataagtttt cataatttat caatcctttt  39060
cgtttgtttt attacatcta ttatattaca gtatcttagt gataaagtca agtgtttgtt  39120
taatattttt taataaattt tgttttgtta ttatcaagtg ttagcttaac acatttgtct  39180
gttactgtaa tttcttttac acctttatta taaagactat gacaagcctt attaatatga  39240
tagtataagt catcacattc atcaatatct gaccatagtc tatagtcatt tgatattgtg  39300
ccttgtgttt taattctgtt gtaagtacct ttaatgtatt ctaaatatct gttcatttct  39360
catcaatcct tttcatatta tttattacgt ctattatatt acagaagttt ctatataaag  39420
tcaataggtt attttaaatt tttttcttta attacattag cgttgttatc cactaagtat  39480
aacatgttat tcatttctat aaataagtgt tcattaactg ctttaacgtt tatattaata  39540
ggtagcttgt ttgaatgtga tacgctaaag actttcgttt ctttaaatag ttctaatgtt  39600
tcatagctat catcaatata agctaaatat ttaacttgat aatgtgtaga gtattttaag  39660
tcatttctat agtagttatt gcttttgtaa ccatctatat ctaataattc cattagtata  39720
tctccaattt tatttacgtt catatcctat caattccttt cggtttgttt actacgctta  39780
ttacattaca gtatcttgta tttaatgtca ataggttata cgaaagtttt ttaaataaat  39840
gttttcttac cattatatag aagaaactag aaagtacagc ttaaattaat tattataatc  39900
aatcgattta attgtataca atgcagtgta aaactaacca tttaatttga ttaaaggtat  39960
tgcatttata tatcagtctg ctataatagt atttgtaaga taaataaaag aaaagggatt  40020
gattacctat gaaagaaaca cacggatata aatttgataa aagaaaaagc atgctacaaa  40080
atgcaaaaga aaaaggcatt aaaaaacatt aaataaaaac agtgacatta taagaataaa  40140
agaaagtaga ttaaaaatag ccaaaataaa taatgatata gaaacaatta aaaaattaga  40200
aaaagaatta caagaattat ataaaagagt tatagattag gttaatagcc taatcttttt  40260
ttatgttgtt tgaagcggtt aatataaagg gaaaacagcg gctgctactt aggaaaatca  40320
tagatttata cttatgatgt ttataacagt aagagagcct taatcttata ggtctatatt  40380
caacggtaat actttttagg tagtatttat cctataatac ttacttgctt atataatgta  40440
gttaaatagg caatacaagc atataaaaaa tctagggtaa aaacaaccct agctacttaa  40500
tttgattcaa aatatcctta acagcttcta atgttaaatc tgataactta atattcttat  40560
```

```
cactattagt atcaataatt acagtatagt tatctacatc atactgtata actttaagta  40620
ctgaataagt aactaactcg tattctgtat gtgtgtgata ttctatcatt gcgtacccta  40680
tacctaattc agttaagata ggttctaatg tttttctttt ctccataaac tctttaatag  40740
tatattgcat accgtcttta cttaaaaatg caggctcgtc attgtaaata taaaataaat  40800
tctcaataag ttctagtaaa tcttcttctg ttccctcaca aagacttact gtataaagta  40860
attcatcgta taatttatcc tttgcttctt gaatattcat tgatattcct cctttatcct  40920
atcctaagtg tatcataagt tttaggtaat gtaaagtatt ttattttaat cagtatctaa  40980
cttatccgct tcattaatcc aaccttaatt taatccctga tacttacctt ttatcataca  41040
tacctgtaat aattacttgt ctgcagaaaa ggtctaaagc tttcatattc aatatattgt  41100
agtaacaaaa catacttagc aacttgtaac ataactgtaa tattattata atgctgttgt  41160
aactaaattc tcatctaatt ctcataaaca tatgttataa tctaaacaac aagtaattag  41220
ttgttagtat tttaatacga ataacttatt acaggcgtta ccttgttgta gcgtagcgta  41280
aaacaacaag gtatacgctg ttttgttctt atctttttaa aaagataagt cgtacggtta  41340
gtacgaaata caaatatata aataagtaat aacaaatatt tatacataac taacagataa  41400
attattagat taactatgtt gaaacgggca tactatgctc aaattgatat acaattatta  41460
gccaagatta aatacagtat atttactcag aatgtaaata atgtataaaa aagaagcggt  41520
ttaataccgc ttctacttct tcgatatgat attgtaaata ctgtttatct tctttaacta  41580
gtttagttaa agcatactca ttctcaataa gaccataacc atactagata tcttgtaaca  41640
ttagtctagt tcctacaagt gttacggtat cacgttggtg tttattaatg tcagattctt  41700
cttcactagt atatttaatt atttaccaaa tctttcttta gcaatctttt tcatttgttc  41760
tttacgctcg ttacttacag gttttcttaa cgtaattaaa tcctcatcta atataacttt  41820
aacgagtaca ggtgtaccat tatctagttg ctctagtact tctaccttat ccggatattt  41880
tttcataata tcggtaatat aaggtttcct acttgcgtaa ataatccatt gcccttggtt  41940
ataattcata cttacttctt gttcttcaaa actatatcct ctacttacaa ctttagccat  42000
tctaataccc tcctttatat ttaagacctc taaactaggt acgttaaaat tctgtattaa  42060
acggtaatca ttttctagta gtatttatcc tataaaataa cttaatcttt aaaagcctaa  42120
taatctttaa tctgtacaca ctttaaaaaa ttcatatgct tttttaatct tgtccgcttc  42180
ttttccttca ttcatttcta aaccttttc taaaaacgct tctaaatttc cattccaaca  42240
tcctgcaaat acagtgtcta aactaggaat ataagttacc ttaccattaa aagttccaat  42300
attatctata gagtaaatat tcagtcctat aactcctgtt atacttgctc ggcttagatt  42360
agtaaacttt aaaatagcat tatctaaata agaaaatctc aaatcagcac tacttaaatc  42420
tgtagctgat aaaatagcat agcttaaatc agcgtatctt aaatcaacat attttaagct  42480
ggcgtgtgtt aaatccgcgt tacttaaatc aatatgactt aaaatagcac catccaaatc  42540
aacttctctt aagatagccc ctgttaagta agcatgactt aagtcagctt tacggagaat  42600
agctcttctt aaatcagcgc ctcttagatt aacacttctc aacatagtgc aacttaaatt  42660
tgctctagtc ccttctacgc catcactgtt caaccataat ttatgttctt ttaatacttt  42720
atctaattct tcttgtgtaa ttgttttcat aataaccaac tcctttaatc tttatatact  42780
aagtataaac catgctcata tacttgtcaa ctacttattt taaaaaaaga agcgggcaat  42840
agtccacttc taatagtatt tataataaat tagtgattaa cctaactgtt tctaaggtaa  42900
tagggttgct tttactgtct acataagaca gttcactatc gaaaccagag ccacttaaat  42960
```

```
agatttgatt actttccaca ttaaatacaa ttaatttagt agggtctact ttactaaaca  43020
ctactacata ttccttgtca ttggctaaag gaagaatagc tccgcctgtt actttttgaa  43080
tttttttgat tacaacagaa tcgtcttcca tcatagtttc ttctttgttc ataccttctt  43140
gtactatttt tctttttatt gttttcattg ttatttcccc ttatccataa atacagtaac  43200
tacaatgttt tgtaaacact taataatctt atctctttga gtaccagata cttcatacaa  43260
gtcttctgta ttatctaaga agcggttaaa ttcatcttga ttagtaaaat ctacaccttt  43320
attagtctca tctaaaaatt tctcaataac tctttctgct atttttttat tactactcat  43380
tatctattct ccttttattt tttagtaact gtataatact cgtcatcagt aagtttacta  43440
atatctatat cttgttcaga aaaatataaa tttttattat ctttacttaa ttgttctaat  43500
acactatcaa tgtatatagg tagtaccttc ccatcattaa aagtcacatc aacactatct  43560
cttaagtata tatgtttctc actcataatt gtataaatat tatagtcttc caataccta   43620
ctcccaatta acgctacttt tccgttactc atattaagca ctccttttat ataatatttg  43680
aagtggttat acttcattca tagggtattc cagataatac ttaattgttt gtaaaggttt  43740
atgtacatta gtgccataac cataggaata aattccataa gtatcagagt aaaatttctt  43800
tatatcaatt aactcaactt ccctatatac ttcaacctta tatggagata ctacaaactc  43860
ataatctcct cccataaaag tattatatag tacttgtttt aattcaagac cactagtgac  43920
tatatcttta tagaagaagt tgagataatt atctactgta ttaagaaagt cttttacacc  43980
tgtatactct ttataaatat taatccaacc taattctaat tcataatata ggttaccctc  44040
ttcatcaaaa cttagtttaa gtttaaccgt atcaatatct ttacgatgta tattaaaaga  44100
ttgctctaag aaacctacat cccatttatg cttaacaagg aaatactata ttatccgctt  44160
cctcaaacct agcaatgata tgactgtctt tatatacaag aatataaata aggctattac  44220
ctactctaca ccttacttta taacccctac ctaagtacat ctcataatct gtaatactct  44280
ccattatgcc agtaacttct ccatacttcc tacaaaactt agctaatttt gacatagtaa  44340
ccaactcctt ttttaccttt taaacttttc ttctagggaa aacctatcta attttaccta  44400
aatgtcaacc atagaatgcg ggttcaagcc ctatttttac ctttgactac ttttccctag  44460
agaaaaatct cttcttaaat agtatctaat tgtttatcaa acatagagta aatttcattt  44520
tgatgttctt tgtcttttag gtacttatca tattcatata gtagtatatc atacatactt  44580
tctattaaag tatctaaagt tgaaacatgt accttatcat ccttgtctag tacttttact  44640
ctatatgtat ctaaaccttc acaactaaca tcatatacaa caatatgaca agtaaaagat  44700
tctttttca tatgaaaact gtaaatatat ccgttactgg catgcttact ataatgagaa  44760
tacgtaaacg cttttatgcc taacctgttt tctaatacct tatttaatac ttgtagtttt  44820
tccatctata accctcctta tttaatcctt ctataaccct ccttatttaa tcctttttaa  44880
attacatacc taacatacgt agtactgaag cggatataag tatactcatt ataataaaaa  44940
ctacaatagc aaatatagct gagactatat ccctatcttt aatagatatc actaagataa  45000
cacctaaaat agtaagtaag aaaagttctg aaatacctag agcaacacat accaaaataa  45060
aacttaacat ttataatcct ccttacttaa tctcacttaa gctacatatt taacactttg  45120
gtagatataa gaataataac tataataaga gctacaatac ctagtgtagc tgagactata  45180
tccctatctt taatagaaaa aagtgtaata gtaactaaac aagcaagata tatgccgata  45240
ataaaccaac ttaaaattaa catctaaaaa ctcccttact taatatgccc tactctatat  45300
```

acctaaatac acctaacaat gtaacaaatt aactattaga taacctaaac tcaaaacaat 45360
agaaatagta ccaatacaaa tactcataaa taataaacca aacacacaag ctgattctaa 45420
atcactaaca ctatcataat tatcaagtac atgcttataa tacttcttac caaaccttat 45480
acttagtaca ataccaatag tagctaaaaa tatagcaacg atacttataa atatactcat 45540
aaactaatcc cctcctttta ttgaagcggt ttttatttcc attacttacc tcacaaaaac 45600
cgcttcctaa ataccaaata aagctaatat acttgatacc agtccaaccg tcataactgt 45660
aaatgatacg atattagtcc acttatcaaa cctatcatac ttaattgact gaaccatttc 45720
tactagcata aaggtataca taaacaaaac cattacagct actattgtaa gtaatattgt 45780
tagtcctatc atatttatct ctccttccta tcagacatat gatataagac agagagtata 45840
aaagcaagta caaaagtaat tacaaaacca ggttcaaaag gagctaaaca tgtaatagga 45900
attacctctt cccctatgat taaattccct acccacatac ctaaaattac tcctgctaaa 45960
caaaatatat aacgtaaaat aaactccaat gctttactca acttacttcc tcctttataa 46020
ttattctcaa gtataactta acaaaatact actttaataa cctttgttta aagaatctta 46080
ctacgtcttc accataatat acagataaaa atacattatc ccctgtaacc ctaaaaccac 46140
tatctataca tctattttcg atgtagtagt cattaacttt taatgtactt atatctccta 46200
aaacttctat gttatatcct aactgattta aatgtacata aatatctgat aaactcataa 46260
tacaactcct cgttactaag tctttattga agcggttatt taacccctct atatactagt 46320
actacacata ataatacaag tgctgtacat atataagtat actgaatatt actatatacc 46380
aaatcacaat acgttaccat ctttccatat agtaactaac tcattatcta caacagtact 46440
aacagacaat aaccatgtat ttttaccttc gacatagtag tcaataactt cattaatact 46500
acttctatac catactgagt ttaatacact gttaccttgc ttataagtaa ctactatact 46560
acttaactca gtagaagcat ctataaccac ttctacaata aacttagtgt cattaggtat 46620
agtaatagta atagatttat taggatacaa tgcattataa aacgatatat catcaacagt 46680
tataacaaca ataaactgac tatcagtaga atagtgtcga ccttttttta tatcaccttt 46740
ataatacata tacattaatt ctataaacga aacttctctt ttaatcttca taataaatca 46800
tctcctttaa ctttatatac ttagtataaa ccataagtaa tatactgtca acacatatgt 46860
gtaaaatagt taaaatttct ttattgttcg gaaattacta aatatattaa actttttactc 46920
tagggaaaat taagtcaata ctaccacaga aacaaactat atatatatat taaataagta 46980
atgttcagaa ttatagtata tcatatacac aatatctaat actaaatata cctttataca 47040
cagtaaatac tacttcagct tagtttaact acacattaga atagtttagc atataatcag 47100
catagtttaa tactacataa gcatagttca caatagttaa aactatataa aaatatatag 47160
ttaggtatct aatagttaga cacctaacta tatatacact atgaaggagg gaagcagaga 47220
aattcccatg tacctgttct tacttactac ttactactta ctacttacta cttactactt 47280
actacttagt atataggtat accatgtacc tgttttcttt taattactta ctagctatta 47340
cttatttatc tatctagaag atgtaaagaa attactaggt aactgttttt acctaagtga 47400
tagtggtaac tattttcttt tagctactta cctactactt aatatctatt acttactatt 47460
agaatattta ttaatactta agttacttaa taattctttc ttcttattca tatcttcaaa 47520
ctgttataca gtatttattt acttatctat ttagctatta cttatatact acctactacc 47580
tactacctac tgcttatcta tgtgctatca attattgttt ttttatctat tacttatttc 47640
cttgatatat aggtacttat aataccagtt gtttctttac gtgttactta tctgatttct 47700

```
ttatctactt atatatattg ttttctttta cctattactt atttatataa cttctaccta  47760
catcaatctc tatacctatt tgtttgtctg tttggttgtt tggttgttta ctcttctaca  47820
cttacctata tacatgtcta tatcttttaa ttacttcttt actatctata ttagagtatt  47880
taaatgttct ttgtaggtta cttaatatat gtttaaaggt agactttcta gcatcaatct  47940
ctatatattg tatactattt tctttacaat attctctctt ttctatgtct gataattttg  48000
ttttctggtg gttcatgtat ccactgactt cttggtaatg ttgaacattg tttagagcaa  48060
ggaagataag tctatatagc ttataacacc ttgttttgtt tttgaataat atatgtcttg  48120
ttctttccag tattccataa taagtgctcc tcttactctt tattgaacct gttctcctgt  48180
atcttgatta aacactttag catttgggtt atgtgtttca ccttcttgat actctgtacc  48240
ccataatctt ttacgttctt cactaacatc tttgtgttct ccattattct caggtacgta  48300
tgaagtatgg tcatctgcat cttcattatt ttgagattct tggttacttt gttctacttg  48360
ctcttggttt ttcaacacat tgattattgt tagtacaatt agtacggata aaactaaact  48420
taatattttt ttcatgatta atgtctcctc tataattatt taacttatat acttattata  48480
aaccttacac ttattcatgt caacacttat atatgaaaaa agtagggaat ttccctactt  48540
cttccttttt taaaatacca cagtattatt attcaatgtt tcctctacta tttcctttat  48600
atcaattgct ttttgcacat acctgttagt tagtagcata tcatctctat ataccttaac  48660
attagataca tcatcactta ctacaaattc gtatttactt gttttagtag cagtaatttt  48720
aaaataaggt ttaatatcta cctttaattt atacccatta atagttctta cttcttttac  48780
ccagtcatat aaatcaattc taacaaatct acagtaagct tcatacttat cacaaaaatc  48840
ttctagtgta ctaaagtctt gtacataacc attctttgta attttagcag ttaaatcatc  48900
ataaatatat attgtagtat aacctaacac atattcattc ctacgattaa gcaactcatt  48960
tttaaatgta tgcttagctg tgacaggtac tttattaagt atatctttta atttatttac  49020
ttcatcttgt tttaataaga tactcgactc atatgttaca ttattaataa tgtattggta  49080
ttttgtatta gaatcgtaga tgtattcata catatcttta tacactacct tttttaagta  49140
cttatcgtta acatgtaaga taattttgtc ttcattacta gaagagtcaa taattacagt  49200
agagacagta tactctttct ttatgttttc aattacctct tctactttag tttgaataat  49260
gtgttcagta ggtgttatat acttttcata gtactcagaa gccatgtctt tagtatattg  49320
actatagtta atatctgcgt cttctttacg tttttttgct tttcttaaat ctggtataac  49380
aataattagt acacttagca atataatacc taaacaaatt aaaaatgtaa tcaccatacc  49440
taccattacc cttcctcctc tatatctctt tttattgcat attcaattaa atcttctttg  49500
tcataaggta tcatgtacca actaccatag ctataaatca ttatacctag ttcagtaagt  49560
tcgtagtgtg ttctatgcga tacgcataaa aagtcagcac ctgactcacc atctacagta  49620
tctaaccagc aagtatatgg taatctatcc ataacattaa gtatatgttt atgttcgtct  49680
gaattaaatt ttatcaattt ctttcactcc tttaaagaaa tcgtaagcta atttaatttt  49740
ctttgagact tcttttattc tatcttcttc gtactcaagt gtaggttcta gtttaccaaa  49800
ctcttcaagg gtatattcat tataattact aataattcta tcataatcag gtaaataagt  49860
tacatgctca tcaaaatcaa gtacattact tatagtatat atacttattc caaatacgtc  49920
aagagtatta gcataatata atgttgtatt agttaggttt gtaccaccga aatctgcacc  49980
ttttaaatta gccatactta agttagcatt tttcatatta gcccacctag cgtctgcttc  50040
```

```
acttacatta gcttcagcta agcaggcatt ttctaagttt gcttttacta aattagccca  50100
ctctaagtta gtatgatgca actcaatatc cttcattcta gcatgtgtaa atatcgtaga  50160
tatacactca ttgtaactta agtcacaata acttaaatca caataactta ggttagcacc  50220
acttaaacta gacattacaa tagttgaata ttgaaggtca gcggaatgaa agtcaagatt  50280
tcttaaatct acacactgta aaaaaagctt ttctccttcc ttttcatttg tagctagcca  50340
ttgttcatgc ttttctatca atgaatctaa ttcaggttgt gttaccattt ttagttcttc  50400
cattactcca catcctttaa tgtaatttgc tctatattaa atctattaaa tccatataca  50460
taagctttta aatcgtcaat atcaatttta cttttaggta aacaaataac atcatagtct  50520
gcttcaataa ttactttagt acttgtaact gttataatta tttctttatc ttgatttata  50580
taatcttcaa ttaaatcttt taaacacatt attatcagtc ctttaatctt ttatgaatgt  50640
cttttaattc tacataatac ttatgtgctg ttttctttac accttctata ctatttaata  50700
gtaaagattt atttctttca agttcaacaa tatttttgtt aattatatct tttgtcttag  50760
ggtttcttgt tttaatcatg ctgatatgtg cttcatggat actaatatct attctatcta  50820
atttagtaaa tagaggtgta acagttcttt ttagcttacc tttaatatac gtatctattt  50880
gttctcttgc ttcttttata ccttcccaat tatcatcttc agtatctata actgtaataa  50940
tagttagatg cttatcaata acaattctat aatttttaaa tacatatact tcattaccgc  51000
ctttttgtgt atgttcaaaa gtagcttgca ttaaagcact agcaaaccac tgacaagcac  51060
gttctttact atcgttacta actcttaaag tataacgttc atacgcatgt ttagttaggt  51120
taatatgctt actctttatg ggttttcgtt gttctacaat gctcataatt aatcatcctt  51180
atatctattt acgttcattc atctctaatc ccttttctaa aaacgcttct aaatttccat  51240
tccaacatcc tgcaaataca gtgtctaaac taggaatata agttacctta ccattaaaag  51300
ttccaatatt atctatagag tatactttta gtcctttgat attttgagta cttgcttggg  51360
ataatttaac atctgttaaa tcggtatttg ttaagtctgc atattctaaa ttagcctcat  51420
ttaagttagc atctgttaaa ttagcataat ataaattagc ataatataaa tcagctcttg  51480
ttaagtccgc accttttaag ttagcacctc ttaaattagc atcttctaaa gaagaatatt  51540
ttaagctagc accttttaag ttagcgctca ttaacttagc atttattaat tctaatccat  51600
ttaagtctgt ataacttaag tctgctctct taccttcttg actattacta tctaaccata  51660
gcttatgttc tgctagaatt ttatttagtt cttcttgtgt tattgttttc atacttattc  51720
tcctgtatct tttattaatt ttattgtaat cctgcctcgg ctctttcttg ttgtgaacgt  51780
tgtaaccatt gttcaaaact ttcattagct cctgcatagt tccatgaggc tcctccgccc  51840
ccaccaccgc tagctttatc ctcctcagtt ctattctcta attctgcttg tgctcgttga  51900
gcttccctat attgattata cttgtctgca tattcagcat tagataaacc attatgttca  51960
cttctacttg cttcttgcat ttgttcgttc tgctgtgctt ggttaccttg tgtttggtta  52020
tcttgttggt tattttgaac agtgttgtct tctttaattt gtttattttc ttgttcttct  52080
actttagatg aatcatcttt cttattttct ttcttgtctt ccttataatt gtgcgtcggt  52140
gtatcttctt gtgagtagta agcacaacct cctaataata gtgtagtgct aaagaatact  52200
cctgttaaaa ttttatataa gtttttcata tttatcaatc tcctttttct ttgttaagtt  52260
aattatacaa cttgttattt agtaagtcaa catttatttt ttcttttttg tcattttatt  52320
ttgatactct tttaattgtg ttctttgttc tggcgttagc atgttataca tctcctttta  52380
aaattaattc tagatactta aataataaat ctaatgactc agtactttt aaacttttca  52440
```

```
tattagtaag ttctaaacct tttttagttc ttacatacac ttttctattt gtaaagtctt  52500
ttatactata atctacaaga ctaaccgatg tatttaagtt atgttgtgta tttagattat  52560
cactaatcaa ttccaacgtc aagcgttttt gtttatttaa atttttcatt tttactgtcc  52620
tctctgtaat ttataatacg tatacatatc tttacatact agtttagcaa aataatttat  52680
catgtattgt gctgtcgttt ttttaattct atcataatga aagtcaataa taggagttgc  52740
tacactaaac ctacctatat aattaccgtt atctctaact tcaaatacta atgtatcttc  52800
tttacacata aaaaatcacc tctaacgttt tgttaccctt agtataaagc aacatgttaa  52860
aggtgtcaac acttattttt gattttctaa atctttattt gattccgata ttgtaaactg  52920
taaacttttt gctaaatgac caagtgcaat acgttcaggc acttttaaac ctaccttatc  52980
aaaataggtg tatactaacc cttcttcaac aattaacata ataataccat ctacaacaca  53040
taagtactta ttttcttttg taactagttt tacttcttta tttaataaat tacttgctaa  53100
ttcttgaata ctaaccaaga tactatgtgt aatatggatt aaatttctat atttttctgt  53160
atacatacta accacccttt agaatataat atttgttatg cctttattat ataaatcttt  53220
agtaaacttg tcaagagcaa tacgtgctac ttttaattct tgcataaaac tttctacttc  53280
actagaattt acatatgtac atggtatttt taattccaag agtaactttt ctgtagtata  53340
ccctataatt tcaggggtat acttgtttac tgatttttta aaagatgata cttcatactt  53400
accttcatta tctatgacac aaatataata tcctctgcat tcattctcat atactacttc  53460
catttagtaa ccccctatca aatattttat cattatataa ctaagtataa aaggtactaa  53520
tactagagta gcccaaacta acgtaataat aacttgatga atcaaataag gtaataaacc  53580
tttaacccac tccttacgaa cataatactt aataactata tcagatatta aagaagttaa  53640
tttccagact tcccataagt accaaataaa tacacctaca taaaacaata aaataaaacc  53700
taacatgagt ttatctacta tatccattta tatcacctac ctatatcctt ttgtagcaag  53760
gtctacaatt ttatgttgca agaacttgta attatcttta aatattttta attcatcttt  53820
accaaatgta tgtttaattt ctttcttaac tgtccatata gttttaccct ctaatacttt  53880
acttagtaca tctaaaccaa ttggaattat acgctcatca ggtaaaacac cattcttaat  53940
acttacgacc acaatatgca aattatctaa atcacttttt ttcatcattt atcatctcct  54000
tatatttaaa ttataacata gcataaaaaa agagtcaagc ataaccttga ctcaatcctt  54060
gttaaataaa tagtatataa tagcaaaaca tactagtata attactactg tcatagacta  54120
tcataccttt actttttatt tagtactgct tcaaacctat acttatgtac tggattattg  54180
tcattatcct ccgtatacac acgaataagt ttaaagttta caccttctct aaatttacta  54240
gtcctataat atctcatatc aatactttta tcacttgttc ttcctggtaa ataggtaggt  54300
agtttttcca taaagtatgc tttgttgtct attactttct taagcgtgta gtctcctaca  54360
tactctacat ttttatcttt ttttaattta ccgtggtgtg ttaattggtc tgtaacttgt  54420
gatttggttt tttcatgata taaatatgag gacacgtaat aagtagatat agataaagct  54480
aacataacta agataattac ataagcaatt attgcttttt tactcatagc gcaccatcct  54540
ttactactta taatataata acttagtcta taactttaat acattttaac agtagaggac  54600
agtatatcat tctattgtct ccgacaagtt cttttagttt aagaaaatgt tttaaataat  54660
agtcaggatt ctttaactca taatacttta ataatgtttc ttctatacta ctatcaaagt  54720
aatacttatc aacaatttct aaatgtgtaa taagattatt tgacattaaa cttaatttat  54780
```

```
ctttaatctt tacatcacta atacttgtac ctactttaat atcattaatc atatcagcct  54840
gggtataatc tatatcagta ttttttatct taattagtgg ttgcataaca tgcgctttct  54900
catatacact tctaggaact tgacctatta aatggtcaaa agcagggtct tcagatacat  54960
acccaacatc tatacctata tactgaccac tttctacgtg gtcggagtta taatcttctg  55020
gtattgtaca taggtataaa ttactttcat taatctctct actagaagta tcaaaatcag  55080
gtactaagtc ttgtaaagat tctttgttaa ataaactatt ttctattcct tgtatagtta  55140
aattattatc aatgctcttt acattataca agtaatctac aattcgttct ttgcgcatat  55200
gacacctctt attctacctc gatagtatct tctaaggctt tctcttttaa atctgatttt  55260
ctttcaatat tatacaaatc taaaatataa tataaaccat tcttatgaat gttatacttt  55320
ttatagatac tttgtaaatc catatattga taatctttaa ttaaggcttg tactttattc  55380
ttatcattag taatatgttt tacacgtttt gctactctag atttcttatg tttcttaggt  55440
actttataga agtttaacac tgtataaatc aaacccatac ttactttagc ttccttagca  55500
atatcagtca caggtacacc tttattataa cttgtaacaa tatattcttc ttttggtgta  55560
ttgaactctt tattcttact taatggcgta tagttgcttt tattttctaa taatgctttc  55620
tcttcttcat ttaatgtaat aatcataatc aattgctcct tttattgttt gtaataaaag  55680
aataacacac ccatatgagt gtgtcaatca ttaattttta attttattaa gtttatcttc  55740
attatataaa gatgtttctc ctgaaagtgc atagaaataa ttacctttac tatctactaa  55800
aatatcttta accttagcta catctgattc ttgattatct cttacatatt ctacaattgt  55860
gttcttaggg aacttaactt ttgtagattc tacataatcg tcttctaaat aaacagcaaa  55920
agttagtaaa gaattaatag atacattata cagtacccaa taccttttat agaacatggt  55980
ttctttatct aagtctcttg acacttcagt aaacttatgt tttccagtac ttagtctaag  56040
taatatatct ccttggttct cttgtttaac tctaagtaca tcacctttat gtaggtgtgt  56100
tataatatct actatatctg taagtggttt aacatctttt attggaatta aactaatttc  56160
ttctgtcata tgtattacct cattatctat attgtatagc ctactctatc taatgtatct  56220
tttaactttc ttccttcttc atctaaatct aagtttttat agaactcttc ttgtaattgc  56280
tccattcttt gaagaacttc ttcatgttta tcttcaggaa taaactcaag cataacttct  56340
gtcatagcag tatcttgtgc ttgttgttta atcattagtt ctcttagtcc tatgaatgac  56400
atacctttta gttggttacc cgtaattcta tcttttgttt ccatagcttt aatcattaaa  56460
gcagggtcta atgtttctac aaagtttaaa cctttagcac ctttttgaat aatcatatct  56520
agtatttgaa tatcatcata tattgtttgt acattctgtg tagccagttc aaaaggtgta  56580
taattctcac tatctaattc tttcataggg ttttcttttt tctgtatttg agtagcgcta  56640
actttctttc ttttatcaat aagttctcct aaatcccatc cattttcaat agcttcttta  56700
cgtttactct tatatcttgt aatggcagat ttggataact ctaagtcata ctctttacat  56760
aggtctataa tatcatcata actaacatct tcatctatag cattatccac tttagacctt  56820
aatagtttat tattatatag tttagataga atactttcct tatctggaac tacctttata  56880
tcagattttt tatttcttaa attctttttt ctagccatta tatattccct tcttgtctca  56940
agtgtcttta catatgtgtg aactaaaata aggagtatgt gtattcacat aaccttatca  57000
aatcaactgt tttatacttt acactatata atatatcaca atttctgcat ctattttatt  57060
ttcataaagg atattctaat tttttacact atagtgtaac tattttaagc aatataaatc  57120
tttttctaa aaccctatac ctaaaaggta ttttaatgtt ttataaatat aattttaaaa  57180
```

taagaataat accttttaaa aattaactaa ctacttgaaa aaaatatgta taaaaaatcc 57240
cttatatacg tatatttata ccttagtata catatttaag ggagtattat actataagag 57300
aattgttagc tcatcattac caacaagatt aacaatcatt ttatagttat tatcactaac 57360
tttctctact ttactactaa caatatcttt atatctaact tttacatagg attgaccaca 57420
agcaataatt aagtctttat catcatctaa aaagaaaata ccggtctcat gtgtattata 57480
taaactataa tgatatttat ttgtatctag cttaacagag aacacacttc tattgattaa 57540
tttattacct ttgaataatg taagaacttt tagggtatct aatttgttta atgtaccttg 57600
gttacataat gtacctatga atgattgacc gtcatattgc ttatcagtta ctagtaagta 57660
tacaacatgt gtgtaatcat ttaaaggaga tacatcttcg atagtgtata atctaagttt 57720
taattcttta ttaatagtag tatcttggta cataatagta ggttcaataa aagttgatac 57780
aatgtctact ttctttgttg aagttaattc tgttccttta gataataagt ctgtcattaa 57840
tccagtattt tctaaccttt tatttaactg ttctgtttta acgtaaccta accctgattc 57900
acttatcata ttattcatac ctacaatggc aggttttaag ttctcagtaa cgattacttt 57960
attcgtaaat tctataccat cttctacttg tgatatgtcc tctaaataag gtactattgt 58020
tacaccacta gggaaataat cactatcata ggacactcct aatagtgtaa tatctttact 58080
ttgtagtttc ttaaataaag tacttacatt tgttttttta gcttttgttc ttaagtattt 58140
aaccattatt taccaccttt atatatcatt ttctttggtg ttcttttctt atctaatcta 58200
ctatttttgc gtacagatat tctatgtctg gtactaaaaa tatagattaa atgtgtacct 58260
ctaaatgtac gttgttcacg aatactacat ttacctatta atttcttacc tctataaaca 58320
taataaactc tatccgtatg taaaatagtt tgtgttaatt taccttttttg cttcattaca 58380
agatacttct tctttatatt cacagcttca ctaattaagt ctaacgcata cttcttttgt 58440
attttaatgt ctgtagcagt aacattatta aatcttttaa caaacaaagg tttgtattta 58500
acaacaatac tttcatctgg tatatctttt cttttttat taaaaaaaga agtacttcta 58560
cctgataagt tacccgtagg agcaaagtta acaggttgat gtttatatac gttatactta 58620
ggtttaaatg tatcaggttt cctctttgcc atataatacc ctcactccgt tctgtataac 58680
tttaaagaaa tcatcttcta atatctgcca tctattactg taaccataga taacacctct 58740
agtaaatatt ttataagagt tctctacacc taaataatga ataacttggt taataatagc 58800
tgactttttc attctcatac gttgtgttcc ttctgtataa ctaccctcat tattattatt 58860
tttaccgtgc tccctatagt tatatccagt taggtaagta ttataatctc ttaactgttt 58920
aagtatagtc attaaatgtt gcttccataa aatatttaat gtatgataag gacttcttag 58980
tggtgatggt gtagcttctt tatacttacc tactacagga ctacccttga agttaatata 59040
gctcataata cctacatgat ggtgtttata tctttttagt atttgctcta ctttaggtac 59100
atgcttatca tgacacatca cataaacata cttacatact agactataat agtataactg 59160
tttattaagt ctttgtgtag agtctcgttc tgtctttatc tctataccca taacagtacc 59220
atttctatca agaattaaac agtcagttct acatttacct tgacaaatag ctttttcatt 59280
aaatattcta atatcttgta tattacttgt tatctcatca tctttaaaca tgtgtctctt 59340
cgttctaatt aaatctttaa tatcctgctc atagaattta gttatctcag acatttattc 59400
tatccccttt aatacgttga taatattgta atatactatc taaaggtgta taagacttaa 59460
tccatttaac attagataaa catataaata ctcctgtata ctcaccatgt ataactttag 59520

```
tgccttcttt ttgtgtaata gttactctat ctttttctct ttcgaaaaac cctttaccta  59580
cagcacctgt agttgtatct gtacctaaag gtataatatt agctaaaaag ataggaggtt  59640
catatacctt tttatacttc ttattattag gtagcattga cttaattgta ttacttaata  59700
tcgtaccacc tctaatagtt ttacttactg tttctatttt atatttcttt tgtggtacct  59760
catcatcaac actatgtatg ttatatacta atacatactc agaagtttca tcttggacat  59820
gttctatgta gtaataagga acacctctaa aagagtaaac accttcactt actttgtct   59880
taataatttc attatcaaat ttaccaaaat ttaattgcaa caaaaatcac ctcatatcta  59940
atataccaca aataataaaa ggagtcaagt ataaactgga ctcccttctt tactattctt  60000
tattttttgt tacgaaactc aatactaata atactaacgc tgttaacaat acatctatta  60060
caataagcgc aataatagca aaaagaactt ctatccttgt tgtaatttta taaatcgaat  60120
ccccaaaata aacaacaata cctaagagga taataccaca taaattaggt aatagcacat  60180
tatagtactg ccaattgggt agagggttac ctcctttttt tactaaatca cgctcaccac  60240
gtaacatacc tacaaagttc attgtggtat taacaataat aatgataagc aatgttaagg  60300
ctataattga tagaatgtcc atattatctc tccctaatct aagaatacag ttttaatgtc  60360
aatgtcttta ttttttttat ttaaaaatag tagttgttgt gaaggcttcg ttctagataa  60420
gtgtagttct ttagcatagt tgttatatcc cataggacta cttgctacaa tatgcattct  60480
attgtaatct tcttgtgtta ctgaaaagtg atgtacatga cctgtaatta ataagtcaat  60540
atgtgtgttc tcaataaact taggtatatg cttaccttta cctttaagtc catctccatg  60600
gtttataata atatttaagt tacatactgt atctttaata gtgtatacat cttttctatt  60660
atcgataatc tcaatacctt ctaatacacc attttctttt aacaacagta aagaatctaa  60720
tacaatataa gctacactat cattgtatac tttttggttc ttattacctt gtacacggtc  60780
gtggttacct gctatcatac caaaacgtaa gttaccccat acatatggag ataattcggt  60840
taagaaatca attaatagtc tagttccttt tgctacttgc tcagccatag tgaactcagt  60900
atcaaaagct tggttaacat ctctcatgtt aatatgttct attaagtcac ctacaaagta  60960
tactgtaaca ttactaatac cacgtttact aatatcttta atagtttcct gtaatagctg  61020
atttaatctt ctttttagta cttcaaagtt atattcatta gttaaatctt ggaaggaaca  61080
tcctacgtga aaatctgata gtaagacaac caactcttct tcttcctcgg tagaagcata  61140
cctacttact ttatggtcta ataacttatc tcctttaagc tcattaacca tagtacgctt  61200
taattcatca aacaaaattg tagggtaggc agtttgtctg ttaatcttac gtagttctct  61260
tagcctagat agttcttttt cgtgtgctac tacataagat gacacctctt gatgatagtc  61320
attaccctca aatacttgtt tatcttctac atctcttaag tcttctaata acacttcacc  61380
tttaacagct ttattcttta gttggttaag gtactcatca cttctaatat tttctacaat  61440
gtcttttaac tcattacggt ttactctatc aataccaaaa cttgttagaa tcttattaaa  61500
tttagatgta actaccttac cttcatcttt aaataaaata cctacaataa ttgcttgtaa  61560
ctcttctatt gttttataat tacccataaa tacatccttc cgttattaaa tacttgttca  61620
tattctcacc taatacacta atatgactat caataaagat actaaatata ttagaatttt  61680
cattatagga tgctccaaac gttttagcaa cactactgac atcataacct tttacataga  61740
aagtaaggat atcactagta cctcttgttt gtgaacctat aacaacaata ccttttttctt 61800
tatccttaag acattcataa gctaaaggca atttatactc aggcgctact tcatatagta  61860
catacaaatc atttacgttg taaaacttgt cagtcataat aggtaatact atatctgcag  61920
```

```
ggtaacctac tagacccatt tcttttgctt cctcataagt agatttaaag ctaaacaact  61980
cagtatactt gtgagcaatg tcttttgtat aactactgaa attaatattt aaacctttgt  62040
catctagaac cacaagttgc tctaataagg ataggtactt taaatcatca cctactgtaa  62100
taaaatcttt gttatcaggt aagtttatat tagaaacaaa gtataatttt gtacctttta  62160
ataattcttt atattttaag taatcctcat cattgtatat aaaacctaaa aaaataacag  62220
aatcatacgt attatcacta gctaaatgta atgccgagtc aaaagatact acactttcaa  62280
cgtcgaacat atctatacct tcggataaat gttctgtgtg tgaagctact tcatttaaaa  62340
taaataacat caatcctcaa tcctttctaa taaataccct accatttcct tatccttatc  62400
attattagat aacccatact caacaatttt atacctatac atatgcacta ggtctttaat  62460
aacactaata accataacga cattgacctt acttactgat ttattatcat acgtaactgc  62520
aatatacttt tccttacttt ccattaattt tttaactttc aaatggtcgt tatctgaagt  62580
taagtatact gttttaatat ccatatagta cctcctttat taattcttgt ttaactatag  62640
catataaata aatataagtc aataaaaaaa agcccaacaa ttaagttgga ctttaattta  62700
ttatagctca ctatgtggtg ctgtcttaaa ttcaggtaca tctacctttt ctgattcacc  62760
agactcatta gagtatgcta ctttataagt tcctttagga tacgtagtat ctgctgttaa  62820
accactaata gaaatagttg ttttacctgt ttgttcagca gtcttagtac ctactacttc  62880
accatcttta tatactttta atgtttttc catttatttt tacctccgat tatgctgtaa  62940
tatcagctgt tgtttcttta gggtctacag ttacatttgt aggagcttca ggtactttat  63000
ctttaacaac tacagttaca gtatctgtat gattaccatc atcagttgta acagtgattg  63060
tagtctgacc ttttgcttta gcttctacta aacctttact tgatacactg gcaatatcat  63120
catgttctga agtaaatgta taagtagctt ttgttgcgtt actaggttca atcgtagcta  63180
ctaaattatg tgtttctcct acttttaagt ctagtgtttc tacatctaaa gtaacggata  63240
ctactttaat atctttagtc ttaaacgcag gaacatctac tttttctgat tctcctgatt  63300
cattagagaa agatacttta tatgtacctt gtggatagtc tgtgttagca gttaagttat  63360
caattgtaat tgatgtttta cctgcttgtt tctcttcact ttttaatagc tggtcacctt  63420
tgtataaatt taatttatcc aaactaagtc atcctttata tgtttattca gctgtaatat  63480
cagctgttgt ttctttagcg gttactgtta catttttagg tactgaaggt tctgaagtat  63540
ctccttgacc ttctcctgag tctactcctt taacgtcttt acgtagcgga ctagcaggaa  63600
actcagcgct cacgtcttca tgaggtttct cattactatc tactactttt ttagcatctt  63660
tactttcagc atcaactaaa gcaaaaacat ccttcttgtt attagcaagg aatacattgt  63720
atactccaaa gctgaaacgg tcttcaacga atgctaaaaa cgcttgaatt aattgtttac  63780
ctttatcttt acctttaata ttttcagttc taataaaagc atggttgtaa gggtctttaa  63840
cagtattaac tacaaaatga atttggtctc catctgtata agcaacagga gccttttca  63900
taattttaat atttcctcta ccatctgttt caatcgggta taagaataat tctcccttat  63960
tatctactac tttgtagtta tactgaccac ggtgtgtacg tgtataacca tcttgctcta  64020
cttgaacttg taaatactta tctgctacag tagcggtagc ttgttttaat acttcattaa  64080
tatttttctt agccataata attaagctcc aatcattatt ttttacatta taacatagaa  64140
aaaacctccc tatgttatta tttttttcac taataatata acaaaaggga ggcttattca  64200
ggttattccc acatatgatt ttgcttatct actttattat ctttgatata ccttttggca  64260
```

```
ttttgttcat gataagcatt aattttaaat ttaacataat ctttaagttc tgtaagctcc  64320
ttagctactt ctgaacgctc tacctccaac ctattagcta cagttgaaac aataaatgcg  64380
ttgtcttctt tatctgtatt aataaggagt tcttttagca gttcactttg tacttcagta  64440
aattgtgtat catcaaagac ataattaagt aattcatttt cttctaatcc cacatttaac  64500
tcctgtgtta aggactctac tgtataatct gttttaccta caagttcagt acgtttatat  64560
ttattgttct tcttaacata actgttctgt actcgtagtg ttagtttagt tttaatatac  64620
cctggaaaat ctactttact ttgtatatca tactccttaa ctaacttaat aaactgctca  64680
tctatgtatt cccgtagctc ttgtttctca aagtcatgac tcatacctct agagtatcta  64740
tgaaataatg accatctaag gttcttatac ctttttaaaa gcatatctaa gtctctacca  64800
aagtcagtag gaataccatc taagtctata atatatctat tcccattatt aactttcttc  64860
ataaggatgt gctccctcaa atacaatctt aatcctgtgt acatcatttg atacatagat  64920
atctgagtaa tgtattgttt taggtacttt gacttcagaa ccattataac gtactaaaga  64980
gtaacctcct gcccatcttg actctacatg ctcaatatac ataactgtag aatcagtgta  65040
aggaaagccc gactcttcta caatgatagg ctccttatta tctctagctt ttttaaaacg  65100
ttctgctatt tcaatataag gtaagggcaa tacatcattt gtattagccc tacctaatgc  65160
ttctttaaca ctattaatat ttctatctat tagattattc atttacatct tccttagtct  65220
ctttattagt agagctaagc tcttcgtagt aatcttgtaa tgctttaaac tcttctaatt  65280
gagtagtgtc tacttttgta ttgtttaaag gtgcatactt atgagggaaa ttctcgtggt  65340
aaactctact aaataattct aagtataatt catggttgtc cattaatgtc ggtacccaat  65400
ctttatcata ttttttaatt tcttcaccat ttaacgtaac ataattacgc catgttcctt  65460
tagtaattaa accacgctca acggcttctt tatagatagt atgataaggg tcaacaccgt  65520
ttaattgaat agtatcttca tcagaaccta cttcataacc tgataataaa tcaacttccg  65580
ctttttgacc aggtctagat agcttagact tcttagtttc aatacgcata acatgacctt  65640
tatacgtagg tttacctgtc atagcatcat tctgttttaa ttctgattct ttacctttag  65700
atactttaat acgtaaacta gcaccatgtt caaaagctct tcctcctgta gacttaatag  65760
ggtcatcata aggattactc atatttaaat tatcacgtgc ttggttaata acaattaatc  65820
ctgtatttgt atcattaagc ttaggtgaaa tagcatttac tactttttgt gtacttgtcg  65880
ctttcgttcc aagtttttta tggtctactc ctgcatcaat ttcatcttgt gtacgtgtag  65940
ctcctaggga atcccaaatg aacaaaatag gtacgcctgg tgctttctca ttaaatgtat  66000
caatccagta ttctaactct ttacctacgg tttctactga tagttcagta acatttttaa  66060
gtctaccttc acctgattgt actgagaata gtttagaaac atctacacct agttgttcca  66120
tacgttgatt atcagctgtt ccctcaatat caatccaaac tgtaataact cctaattgtg  66180
ttgctactct agataagtgt actgcaaagg tcgatttacc cgagccagtt aatccgtaaa  66240
cttctgtaag tcttcctaga ggaatacctc cacctaaaat tctatcatat tgtggaatca  66300
tagtaggaat gatattctta atatctgctc tattactatc tgatagtaaa gttaaaccta  66360
attctttacc taggtcaata gtatttaaat ttgtagtatc tacttcttta cctttttttg  66420
ctctagccat tgtatcatcc ttttatataa aatttaaata aaagagtgct aagatagcac  66480
tctataaagt tattataaat ctaaacctgc taatacatca tctacactct taggttgatt  66540
ttgtttagga ggttctggtg ttgattcatt tgtgttgaac ggaatttgag aatcatcgat  66600
gttgtttgca tcaaagttct caaatggatt actttgtgtt tgtggttctt gttgtgtcgg  66660
```

```
ttgttggggt gtctgttgta caggtgtgcc ttgaccaaac tgtgtatttt gttgtggggg  66720
aacttgtggt gttggttgtt gtacattatt aaagtttggt tgtgtgttat tttgtccacc  66780
taaattacta ggtaattgtt gctctacact ttgttgcgta ggagcttgtg tttgctcttg  66840
tgttgatgat tcttcaccta atgtgtttgt ttctctactg aatttaaaat tatcatgaga  66900
aacttctgtg ttattaacat tgttaatcaa ccagtttaca aagttagggt tattttcttc  66960
tgttggtgta gctaacttat ctaaatccga taactgctgt tcccaacctt gaggtaaggc  67020
acctaatttt actgtaggat aaacagttac attccatgat ttttcacctt ttttagcttt  67080
agcaatatta atagggaatg catcatcggc tgaaataaag ctgtgtgtag cagtaggtga  67140
tggtgataac attctatctt ttagtcggtc aatcaattga gacagacctg tattagatag  67200
ttccataggt tgaataataa cattaccttg ttcatctgtg ttaggaacta attgaccatt  67260
ttgattaaag tattcaataa catgaatata tgctcgtcgt gcaggtttat tagggaagtt  67320
actaaattgt acaccttgct ttaaccatgt atttacataa gggtctacaa cagatgagtt  67380
aactttctcg ggtaaagtaa gcatagagaa cttttgtgcc ccatcttttt taacatagtt  67440
aatacctaat gttctaaatt ccttaaagaa ctcattagaa cctgctacag gcggtagtac  67500
acgtacaagt gcagactctt tattaatttg attattgtta acgtccttaa tctttcctaa  67560
tcgcaaaacc ggattctttg gtttgtacgt ctctacctca ttgtcaaaac cacttgattg  67620
tagcttttct gattgctgat taataaattg attaaaatcc ataatatctt ttctcctttt  67680
attttaaaaa ttacttaatt agtataacat gttttctttt gtttgtcaat acctaatgtg  67740
taaatgggtt agtaacacca ccatttttat ttgtttgtct tagttccgca ctaatctgta  67800
ctaacatagt tgtacgtgtt tcaaaagctt ttacgatata atgtaattgt ttttctctat  67860
aattccatgc ttctacaacc tttgcttgct gttgatattc atcagaaaga aatacagcag  67920
actctacttg gtcttttgta ggtttctttc cctgttgttc gtactgagct ctaatttgta  67980
gattaagttg agctcctatt ttttctaact tacgttgctc tgcttcggta taattactca  68040
cacgttcttt taaggaagcc caccatgcaa atttagacga ctgttggtac atttcgtctt  68100
gaattgtata ctcactaagt tttagttcat catgaatatt aaacgtctga gtgtttccat  68160
tattatcttt taaggttagc tcattgaaat ctaatgtatc taaatgtatc tccataatac  68220
cctcctctat tttactgtac tatataactt taaaactgtc aatattattt ttaatatatt  68280
ccgtttttttg tttgtattgc tcctcagtta gtttatctga ttcatagtag tctttgattt  68340
gttgtaaggc taatttatac ttaatatatc ctttatacga attaaattgc tttattaact  68400
cttcgttgta ttctaccata tcattatatg ttaatcctat ctctatatct gcatctatag  68460
gatactgtct taactcacca ttaattttta tttttaagaa atcataagga aggttctcca  68520
ttacatggac aataacttta gccataatat taacttcttc aggaggtgag tctactacaa  68580
tactatcatg aacagtagct actaacttcg atttcatatt cttattttga ataaagtcgt  68640
caatataagt aatagccatg ttagtaaggt aaccacctgt accttgaata atcgtgttaa  68700
aggactgtct aagaccctca tttttaatct ttttatctct agattgtgct gagtgtatat  68760
atcttctgtg tccattcatt gtttctacat atccatgttt ttgaacaaac tcatgagttg  68820
catctataga cttcttaata gcaggtttat tagaataaaa cttattaaat atttcagtag  68880
cttcatcaac tgtcatatta tttttacctg caaacgaaaa ttccgattca ccataaatta  68940
aaccaaaggc tacagcttta ctggcttgtc tttcttctgc tgttacgtcc ttcatacttt  69000
```

-continued

```
taccatacat aatacttgcc gtatttttat gaatatcttg tcctgttaaa aacatctcta  69060
acatttcttt atcatctgta tatagtgccg taatacgcat ctctaaggca ctgtaatcgg  69120
cttgtaaaat tacaccatct ttaaatctag agataaaaga acgtttaata gggtggtgat  69180
aatcaaactt atttacatca gatgtatgag caggaagatt ctgaaggtta gggttgttac  69240
tagaaagcct gctagtatta tgatttacaa tattattagc tacaaatgaa tggctactag  69300
gaacatgtaa atcaaaaaat tccatatctt ttattttttc aattttcttt attttaccta  69360
ataaaacatt atcatataaa agaataccgt ttcttctgcc taatgccttt agattttctg  69420
atttatactt tactctatca cgcttaatac tttcaataaa ccctatttca tcgtaaaatt  69480
tatctaatgc atcataagtt atttgtatag aatagcattc attttgtact tttctattaa  69540
tatttttata aactttacct atagaatacc tacaatagat acccatattc attagcattg  69600
ttcttatttg taaagccatt ttattagata cagtattata gtacaaacta ggatactttt  69660
tcttttctgt tgcagtatct aaacttaaac ccttaagaaa tgcttgttgt acacttttag  69720
ggctatctaa tatttgttgt gggatttctt tatttaatgc tttactttgc atattaaaaa  69780
tatgttctaa ccatctacct aaaccaattg aagaaaattc aatagaatca cttctatctt  69840
tattactaat gtagtatggt gtaatatcaa ataaatcttt agttaggtta aagaatctat  69900
tcctaacttc aagattacta ttagttaatc ttatactgaa tgaaccgtta tttgtagaaa  69960
aagacccatc agctgtatac ataccgtacc attcagcaaa atcttcggat acataattag  70020
gtagtgtata gctttttgtg tttgtaatac tttttctttt actatatata aaatctttag  70080
tatctaaatc aatataacta ttattataaa gattagaatt ataagacatt tttatataat  70140
cacctatttt taaatcttca gctacaaccc aatcattatc taataaatgc ttagttgttt  70200
gttttgtttt atttagaacc ctaccagtat tactataata attatttcgt aataaggggt  70260
ggtttaaagt agtagttaat gtagtaccat cttctaaagt aatctttaat ccatttctta  70320
caccactata ataaaagtgt gaagcttttt ctaaatttcc ctgtctatta acaataccta  70380
catcaatact actaaatact ttttcttttc tattatttga taagtcttct attttttta  70440
tacctttatc agtaataact aaagaatcac ctgtaataca tgcagttcct gtactattat  70500
agttaccatg taaattatgt gtattcttat ttactctttt aggtaatttc ttagtaaaag  70560
aatttctttt agtttgcaaa gaggcataat aaataagtaa gtctagtagc tttttattat  70620
cttcattctc aaccaaagat aatgccatct ttatagactt agtatctgtt ttgtaatctt  70680
tccatgataa ctcatcttct ttagtaccat tactgaaagg tttatcctta actgtctctt  70740
tactataagg taactgtata cctaaaatgc tatacaatac ttcaccttta tggtcacctg  70800
agcttggttt aaacttccaa ccttcatctt taaatttagc tctatactca tgtatttctt  70860
tatttctatc agatggtttc ttctcatgtt ctgctaaggc taattggtat aaattatacc  70920
tagtctcctc aaattcttgg atagcccaat gttctctaat ttcttggtgg gttttttcca  70980
tctcattaat ataaaattca tcatttttat gcatgtattc taggtcacaa tgtaaaccat  71040
ttgattgtat tctagctaat gttctaatta atctagggta acttattgac attaagtcca  71100
atgctttagg tctattttgt tcttttaact tttcaataac atcacagtat attcttctac  71160
agacatcggt gtcaccactg gcataaggat gcataagctc taatggaatc caatcataat  71220
taaagtcacc tccatctacc tcattaataa ctttagtatt gtctttatac gtgttaatta  71280
aattaataga tgtacctaat acataatctt tagctttgtt agataaactc atatactcag  71340
gtgatgattc ggctacttct ttaaattcag aatccataag catattcttt gtaataacct  71400
```

```
caggtgttag ttttaactct aaatatcttt tttgctcttc tgtgatacca taatacttat  71460
cttcatctgt tagttctata tcaatgttat cgagtttatt tttcaaccaa gtatcatact  71520
catttgcttt tatgttatat tctttcttag caactttttt attttctttt ttaatatctt  71580
ttagtttatc tgataagaat cttagtagct tcaatacata ccactcttta aaatcttcaa  71640
ggggtttgtc atatcctcct acatctgtta cttcgtaagc aaggtctgat aatcttagag  71700
actctgcttg ttcttgtgtt acagctaaat accaacctac cttagtgtct tgattatttt  71760
caaagtctgt gaaaccttgt gttgtcatta gaaaatttat atcataagta gcattatgta  71820
gtaccttaat gtcttctttg ctagctatcc attcttttag taaggaaaga atttcatcaa  71880
tatcttgctg tccattctcc caagtaaagt ctgatttata taaaggtatt gtaacacctt  71940
gaccattctc ccaactcatt gatagtacta agggtttact tccttctcta tcaggactaa  72000
gtgagttagt ttctaaatcc catgcggtaa tgtctacacc gtcatgatta tcattcttta  72060
cttctttatt aaatatttct cttacacgct caatacttgt aacaagttca tacttaactt  72120
ctttaggttt aaatacgtct tcaccttgtt ctacaaactt acctaataac ttaaggtctg  72180
ctactacatg acgctcacta ttcttattaa cgtttgtgta ctctatacta taagtaggta  72240
atacccaaac atcatgtttt ttatcttcac tagtaatagt tactttatta ggtacacctc  72300
taactttacc aatagctgat acgtttaata aatatttaac gcctaactta cctaaaggaa  72360
taataaatatc atacttatta tttataatta tttgattcat tctttcatag tgaggtttaa  72420
cttcagataa cttaacgtct tggtacttaa ttgttttacc atacttattc ttaataggtg  72480
taggtacttt aggatataaa aaatcaatgt cataatcctt tgtactccta tctcgattaa  72540
taccagaaat attagacaat agttgtttta gtactctacc attaggtgta tttaatagta  72600
cattcttaac actaccatca gtactaactg aaaagtgctc ctctctaata tggtcatata  72660
aaattaaaac tttcatgctg ttaccaatcc cttctttaac ttaaatacag tataacatga  72720
ctattaataa tagtcaataa aaaaagagga atttaatcct gctactaaaa acatacttaa  72780
atatatattt agaaagtttc tctattcaac gaggttgatt gtattaacaa tcaggtctaa  72840
aaacctctcc cagagcgtta attccgatat agcctaccgt atttgtttag actttaagta  72900
agatactaat tcttagtaac ttctcttttt cttttataat agtattgtat attcttttgc  72960
ttgttttaag ttaatacttg cgtttatatc cctatcttct atcataccac aattatcaca  73020
tttgtaaatt cttttattta aaggcatttt ttgtctattt ccacattgat tgcatatttg  73080
acttgaaggg taaaatctat ctacttgtct tagttctata tcatattgat aacatttcca  73140
tttgagccat tcaataatgt agcctaatcc tatttgttgg aaactattag acaatctttt  73200
atttttcatc ataccttttaa tatttaaatt ttcaattgtg atagattgtg ggtttttcctg  73260
tactatttct agtattttct tttgtttaat atccttctta atgttgctta ttttacgata  73320
taatctttgt acttttaata attgtttaga ccagttattg gacttctttt gttttcgtga  73380
taattttctt tgttgtcgtt ttaaagactt atgtaattta actaattttt tatttttcct  73440
taaatctgta atcttaacgc ctgaaggtgt aaatagtgta tcttttaatc ctaggtctat  73500
accaatacct tcagtatgtg gttttttaag tatggtctta ggttcttcat ctactaacac  73560
tgacacataa tatctatcat tttctttaat aatagtagct gattttatat tgttttccgg  73620
tatatatcct ttttctttta acttaatcca ttttaaatta ggtagtcgta ttctatgacg  73680
ttctacatgt atagtaccta ttaaatagta agaaccgtta ctttgtgtct tcttaaactt  73740
```

```
aggaaaacct gatatattat taaagaatct tttatatgca tcctcagcat ttgccatagc  73800
ttgtttagtt gctttagtat ttacttcctt agtccatttt ttatctttat tattaggaat  73860
aaaatcatta ttataccaaa cactaaactt tctatggttt aaaaatttca acccgttatc  73920
ataacgaaat ttatttactt caataaattt attataaaca cttctacaag cattaattgt  73980
tttattaatc tcaattattt gttgtttatt tggttttact tctgttttat atgatttcat  74040
tgtatgtcac tattttcttt tactttcttt ttatattttc taagaccata taccctacat  74100
caggtaatgt atcattctta atacatacta caacaatatg taagttatct aaatctttca  74160
ttttcatatt caatcagctc cttatagtta aactataaca taacataaaa aaaaagagtc  74220
aagtataaac ttgactcaat ctctgttaaa taaatagtat ataatagcaa aacatatact  74280
accaactaaa tacatgaaga gtagatacta aatcttatgc tatataaaat atttaactgt  74340
tttcttcctc tttgtttaat acatctataa ctttatctaa ttcagacaaa ggtttaaact  74400
ttagtgcctt tctattaggt aaagtgaagt atgttttatt tagtccatcc catgcttttt  74460
taccettacg ctctactact tctatttgaa agtacttatg attctttacc ttatcgtaat  74520
cttcaagtag taattcagaa atagcttttg tttctgcttc tagtatctct tctacgtctt  74580
ggatataata ccctgtactc tcagatatct ttcttgctat atctcttcta tttgctgtac  74640
tcacaaaatc acctaaatct taatctttct ttgtcttttt aattcagtaa gtaggtcttc  74700
tattgtttca taatctttat tttctttact agcaagaata tagatataca ttttccacac  74760
ggacaaagaa acccttaatt tgtctgcaaa gtcaagcgta tacctaggtt ttagtttata  74820
agcttcttta taatacgtgt agtacttacc ttgtttagcg tctatagaac taatacgagg  74880
gaatgataga tgaacctcgt ctacattcgt tttaacatca tataaacttc taataatatc  74940
gtaaggattg acgtaaggaa atacaactga aatatcaata atgacttttg ttcccatgaa  75000
actcaaagct atattatcca tctctttgtt actaaactta ctacgcattc tatatacaac  75060
tgatgattta gggtgagctg ataaatcttt aagcacatag taaggaatta ctgaatcagt  75120
ataataggtt acttgtccac cgtgcttgca tattttttca atcaacttat cattgttata  75180
cttctcatta aatagcatgt aatgtttatc atctcttagt atatacctag ttgatttatt  75240
agctaagttg tccatatctt tttctatctc atcttcattt aaagttgtaa ctttaatagc  75300
tttagataat tcatctttgt tttttacatg tatattaaaa tatctatcac tattatatat  75360
agttaatgtt ttattttttg cgataactat tcatcctttc atgaaaaaac ctactacctt  75420
ttactaatat aagtatagca taagtagtag gtaattacaa attaaagtaa atctaattcc  75480
attaagtttt taggtgttac ttggtcttcg aacttcttag caagttctcc atctttataa  75540
ccaataagta caggtgtact cataatgtca aataacttga ccgctttttc tctatctaca  75600
tctttatcat ctaagttaat aacataaaca ggtttagtaa tatctccttc tgcttcgaaa  75660
agaggaatca cactttttaa aatttcacat ttagcacact catcttgtgt aaccatgaca  75720
ataacatcct gtttttgtct gattgttgta tttaactcta ataaactatt cactttttcc  75780
attttctgta tcatcctttt ctaatgtgtc aataatatct ttaaatgttt caatatcagc  75840
tacatgtgtt aactgctccg taccatcagc tttaaatagc tttaatgtac cttcatatat  75900
aagaatgtac acatatgtat tataaataaa ctctagctga aatttacttg atttactatc  75960
tgctttagta tcatcttccc tattaaacat cttaataggg tcttgtacat tacttacttg  76020
tgagaaaata tcatttgatt tgaatatatc ttcagttcta cttagtaatc caaacgcttc  76080
ttttttattc atttagtcac ctctttaggc ttcacaatta atacaaattt tagataaatt  76140
```

```
gaattgttgt gatgcatttg taccatgttg ataatacaat gacttaatac cattagacca  76200
tgcaaagaga taaagttcat ttaactcctc tgctgtaaca tgtttagggt taatcataat  76260
gtttatagat tgtccttggt caatatattt ttgtcttgta gaagcttggt ctaatatatt  76320
atattgatta atttcaccat atgttttaaa tacttccttt tcataatcac ttaagaaagt  76380
taggtgttga acggaaccat cattatccct gatactctca ataacttttt tattgtcctt  76440
tcctttttct tttaatagtc ttttaaggta aggattaatc atagttttct ttactttagc  76500
agtgtctaca acgtaataat tactcataaa aggttcaatt gatttagaaa cttgacctag  76560
gataaatgag ctcgaagtcg taggagctac cgccatcaaa catgaatttc ttctaccata  76620
accttttaaa atagaaggct ctccataaag tttagctaac tgctcactag ctttataagt  76680
tttttctttt aataatttaa atatctcttc attaatttga ctagctttaa tactttcaaa  76740
aggtatgagt tttgattgta ggtatgaatg gtaaccaaga acgcctattc ctaaggctct  76800
gttctcaaca gaaaagttat aagctctctc cataaattta aatgcttctt gtttatcttt  76860
ttcatctgag tctcttagat attctaagtc tctaataaac tcagacataa cagcatctaa  76920
aaagtaaaca agtgtctcta cagcatccgt gtgtttccat tcatcatact taacaaggtt  76980
catactagat aggtcacata caaatgacca atcttcttta ttaggtaaca ttatttcact  77040
cctacatgtt caatagtggt cgttaatcac taccagttct ctaattaaca atatttatag  77100
ttagggaatt tttcagaatt acatcttctg gttaatgtat ttctgtttat tcctagctct  77160
tcagagcata tacccatatt tttataaact acgccatcaa caataacttt tttagcatta  77220
gcgctttctt taccatacat cggattgttt tttcctcgtc tatccattat attccaccca  77280
aaacctatct ccatattata accttttttt acagattcgt acatgtctat aaaaatttgc  77340
tctaccatgt aagcaaactt tttatcctct gtactaaaag tgtataattc ttctacataa  77400
aaattctctt caccatgttt catcattgat cggtgtaaat tagttgttga gcctatctta  77460
gcttttctaa tatgattttt aaatctatgt tgaactgttt ttgatgtaat tccgatgtat  77520
attttattat tgtttttgtt tgtaatttta taaatatggt actccatttt cgaccctctt  77580
aattattatt gttaatatga acttctatat gtttccatat agagcagact atatcatctt  77640
ccttaataag gaagtccacc atttcgattt aaataagatt tacttgatta ttactcaata  77700
cttataccac ttggctctaa ccttatccct tcacttatgt gaataggtta cagatagtcg  77760
ttaggcattt acagatttat aatctgattt agcacggtgt tgtcatatat tttaacttag  77820
atattcaccg tttagatgga tttttcgata gtaattactt actaaaggtg caaattttta  77880
cacaaatttg agttattaat agttaaccct ttgtctttat atacatctac tgtattacta  77940
tttgcattat catgaaagaa gatataaggg tatcctattt gtgttcttct tgttaatact  78000
ttagcccatg tttttctttt ttctttatcc ccattaatca tgtctaataa ccagtcatca  78060
gtaactgtta ctgcatgtgt taagttttga attggattac cttcggtacc aatctctaaa  78120
aactcatcaa tatcctcatg ttctataggt aaataaggac taaaacgccc tctacgtgta  78180
gaattaccac aaactaatgt atgccctttc cttcttacaa caagtttatg agtaggtact  78240
tcaacacaat atactttacc tttatattgt accgtttcca cagtaacatt tgagcctcca  78300
aataattgac cttcagatag atatatttta tacatagtgg ctttattagg ttctctttcc  78360
cttaaatcaa ctgatttacg agatttataa cctaccatag aagctatggc ttgaacaatg  78420
tctacattat gttcaaccac actcatgtag ataaatgatt tatccgttct tctactagca  78480
```

```
tcccaatgag acaactcgtc aataaaatca taagcccatt gttgtgtgac attttgtaaa  78540
tttacccatt tactaaattc tttaggtaat tcttcaccca tattaacata aatattatga  78600
ttattgtctt tgtctacatt atatgtgtat tcaactccta gaccatctaa tatccataat  78660
agtctatctt ttttacgttc tttactaaat ctaaacttca aagatttagg gtattttttta  78720
ataatactac catctgcttg caaggctacc aaaagacgtt ctttaaatgt gagtcctctg  78780
ccttctttag caaatgaaga atgtgctaaa taaacgtctc tatgtaatgg catatcttct  78840
gctaatctat ttctatactc aggtactaaa acactttctc tttttcctgt ttctttatta  78900
gtccttttag ttctgtattt aaaaaccata ttatggttct tagtcactaa taagtcaata  78960
tttttactat ctttaaaatg aactaattca ttatcttcag gtacaaattc catataacct  79020
gtaggctcta caaactctat ttcatcatta tctgttacct gtgcaacttt tgttccatct  79080
tttctactaa ctacattaga taataattca tacccattct ctgtgagtat ttcagtttta  79140
tcatcataac atccttggct tatcgtatct gtcatttgct caaatagctt cataaaatga  79200
acggaaccac ttgtcagtcc attatcagtg atttctgagc ctctaggtct gatgttaccg  79260
aagtaaccac ttgtaccacc accgtattta ctcatcatac ctacttcact agcagtatta  79320
agtatcgatg gtatagtatc atctacccaa ctaccaaaac aactaatact aaatcctcta  79380
tctttcccga aattagacca tataggactg gataaggaat aataaccttt actcatataa  79440
tcataaaact tgtcagaaaa cccatcaata cctaaaatat cttcagcata atctgcaata  79500
tctttaattc tttgttctgg tgtttcacca tcacttaaat aaccacgttc tagaaaaact  79560
ctagaatcat tatttaacca ttcaaaatta ctcatctata tacactgcct ttatatcatt  79620
tttagtctta aaatagcgtt tactttatct ttagtaactc gtttaccagt attttcaaaa  79680
tcagattccg ttgaaaaaat agtatcttcc gttacagaat tactaaattt tgtatagttt  79740
acagaacgtt tagataaaaa gtccgttaac ttagtactaa taacttcatc atcaaaccat  79800
gacacttcac ttagtaactc ttcatcaaca tcaaaaagtt tagtataccc aacagctact  79860
agagagttat taagcctatt tttaataaat tcttgtacta ctttcttagg taagaactct  79920
agttccccat cttcatacat ccaatcaagt aaccgtgttt ctgattcata agatttttta  79980
caggctgtgt aaactgcatc ttccatttct ttgttgaacc actcaggtct ttcttctcta  80040
agaatattaa tgatttctgt tccaaataat ccatggattt gctcttcttt agatgtagct  80100
tcaatagcat ttgataaacc tctaaataag tttttatatt tattaaaact catcataatt  80160
aaaaattgac taaataaaga tacatgttca ataaatatag aaaataataa aacagatagt  80220
acgtaatctc tatcatcctc actcttactt agttttacat gcatcgctaa ctcatcaaca  80280
cgttctttaa gagcaggaat atcgtcaatt gttttaaact cctcattcaa acctaaaatc  80340
tctaataaat gtgaataagc gtcggcatga cgtgcttcac tctcactaaa agttgcaccc  80400
acagctccag tttcccattt aggcattcta tgatataggt caccccagaa agtctttact  80460
gctacttcta cttgggcaat tgctagcata gctttttttaa tggtcatttg ctcattgtat  80520
ttaacgttat tcttatagtc ttgaatatct gatgtatagt taaactcagt gtgtacccag  80580
taactttggc gtatagcatc tttatattct aataattcag ggtattcata gggttttaat  80640
tcttttcttg gtttgaataa gtctctttta cgctctcttt tctttttatc cctatataaa  80700
ataaaagctt tagcagtatc tttatacata ctactaaata aaacttcttc tactatatct  80760
tgtattaatt ctacagtaat gatagtgtct tgttcttcta gtaaagagtc tacgtcatct  80820
acaagagaat caataacatc ttcaatatat tcttctgttt ctgagttggc tcttaaaata  80880
```

```
gcattagtaa ctttacttaa atcataatct acaacggaac catcacgttt ttttatttgt  80940
gtaatcaact agtatccctt ccttatatac catcaagtaa accatcaatc aacttatctt  81000
ctttttttact aactttagat attttagact tgacaactct atatggttta atctcttttt  81060
tgttgtagca agatataata taagaaggtg ttaagttagt caacccatct atcgtagtta  81120
taagaacatc ataaaaatgt ttatcttttc taacattttc tacaataaaa tccgttctca  81180
taatagggta ttcttcatct cttaacttaa catatacatc ttctatataa ggtaatgcta  81240
catatgactg tgctctattt cttgtaaata ttaaacaagg agttttatta acttgcaaac  81300
tatctcctat aacttgttcc caccatgtat gaggttcttt attattaagt agaacattat  81360
ccataatcca attttctcta tgtttacact ctacaactaa tggaaaatta gattctaaag  81420
gtgctacaat gtcaccgaca gcattattgt tagctcccca tgatgcacct cctgattgtg  81480
gagacctact aaaaggataa ccccaccaat cagaaagttc tttggcaatc tttctttcga  81540
atacatcacc ttttttttta ctatttgtca tgtttcttca actgcactac tttttcatta  81600
tcttcttttg ctttatgctc ttcttgtttt tttcttactt cttcttgttt ttcttctaaa  81660
tacttttcac gtttttcttt taatttaagt tgcgccttct ctacttgctc agtagttaca  81720
tctaggttat cttccataac aatcattaac aaatcaatag cattaaaagc atcattaaag  81780
gcagatgcat actcttgaac tgtaacggca ttaattgctc gtgcaattct agtagcctca  81840
tctaatgata cactacgtgc tccaatacga tgtaattgct tagcagtttc ctcagttaat  81900
tccttgcctt ctactgttcc ttgtgtaata gcttctaacc acatgtccat atctttttgt  81960
gaaatacctt ttgtatgtgt actaatattt ttttccatta ttcttcatcc ttttcttttg  82020
attcttcaat tgcttcctca atatatttta atacgtcatc gttaactaac tcagctttgt  82080
ataaagcatc aattagaatg tttaagttta actctgtatt ttgctctagg tcaaccattt  82140
gtttattaac acctaacaat aagttagtaa tagctttcat aacatctgtt aaagttgctg  82200
tttgttcttt acctaactct tctaattggt gcatacgctg ttcattacct acacgtaatg  82260
ctgtaacata ctcatctaca aaatgtagaa tatctttctc ttccaaaata acacttcctt  82320
tatttttata tatgtattgt aacatactat acattataat gcaagattaa agttttaact  82380
tttgttgtaa cttgtaactt tgaatacttt caggtgtaac taaaaatcta ttgtgtttca  82440
aagtactaaa agctttttcc atacccatat cattagcatc ttcattacca tgaggtacta  82500
aatatactac attaaaatgc ataataagtt tactagctaa attaatacta aagtctgtag  82560
cgtccgtatc taacataata tatataggtg tttctttagg aatacttgaa atgaggttat  82620
taacttgtat ctttgaaact tgtttaccaa acgtagctat accatactta tcaaatgtaa  82680
gtgcgtcaaa aacaccttca gttataacaa caatcttttg tctactagct atatttaaat  82740
taaatataac atcgctttta ccatactcat taggtttaga aggtgcattt atagatttaa  82800
tatatggatt tgtttcaata cttcttgtat tccagtatat atacttacct tcattgtcat  82860
aagtaaaaaa tataacacta tttctaagta ctattttctt tttctcatta ttaataccat  82920
aagaatagca ataaccattt ataatatacc ctatactata gtctaggatt tgctgtagtg  82980
taatacctct attcttgaga tatcttaaat agggtactac ttctttatta tttaagttat  83040
ctttaatcaa tttaaaccct ataggtagtt caggtgcttt tgattttata ctactattat  83100
cttttgtata tccattaagc cttagtaata atttctcact ttcagttaaa tctgtgttat  83160
atatttctaa tgttggtgag aattgtatat caatattctt tgtttctaat aactcaaaag  83220
```

```
cttgtctacc tgtaatacta taataagatt tcataaaagt aataggatta ccatgttctc  83280
cacacttctt acaatgatac ataccattag tagagtctaa agactgttta acataaaact  83340
tgtatttctg ttccccacaa aaaggacaac aatatcttaa ttcccctaca gtattctctt  83400
tgggtgttcc aatctcttga cttaaaaagt cttcaaacct cattttcagt cacttcctat  83460
atagaaacaa ttttcttcat taatagtaac atattataga tttgacttaa atcactataa  83520
gtatcatcta ccagtgttgt actgtacttg agtacttcat ttaattgata atcctctgat  83580
ttcttactaa aggtgttaat ctcttcaatt gttttatctt ttaagtactc gtttgtactg  83640
attgttttta gcgtttggaa aataacacct aagtcactaa atccttgctt tacatcttta  83700
cttgtgaagg gttcatctat agtaggtaaa ccgtacaact tagctttctc aataattttc  83760
tcattatctt cttttatttt ttcattatac cataatccta gtttacattt aacagtttca  83820
cctttatata aagttcggtg tgttaatcca taagacatag gtaaactaga gcgtaatctt  83880
tttaactcaa tatatccaaa gtcattacta gctttatact cgtatgcatt acttaaaggg  83940
taccagtcta ctaaagtaga aacaggaata ctatctatat gtaactttgc attgtttgta  84000
taacttactg ttaaagatgc aaactgatta tcattaattt ttagtttcat tgtttaaatc  84060
ctttcttagt gtagctacac cattctcttt tactaccgta attgtgttct caaacaaagg  84120
tgctaaactc ttattgtgtg taataacaaa gatagtacct actgttttta gtctatcctt  84180
aagtagttta acaacgttct cacaaccaat agtgtctagt ccgtcaaagc attcatcata  84240
taacgctatg tttgtagata tatcttcttt actcataatt aagtcttgga tagcaaaact  84300
aatagctaaa tcaatacgct tttgttctcc tgctgaatta gatttgtaag attctccacc  84360
attgttattc ttaacaataa catcgaactt gtctttgagt tctcctttag catttttctac  84420
ttgcgtttgg aattcaattt cgatatctga gcctgctaat atttgtaagt actcgttagc  84480
tttttcattt aagaatggtg taataaagtc taatattaca gaacgtaatc ctttattact  84540
aaatgcgtct acagcttgtt tatattttgt tttcttactt tctaattgta ctatactttc  84600
cttatgtttg tcaatagcat tatcaatatc ttttagttct ttattgtgta attcttcatt  84660
aggttcttct atataagagt aatcatttaa tgttggttct tttaaattag ctttagtgtt  84720
ttctaattgg ctaatttcat catatacttc ttgctgttct ctatattgcc gttgaatatc  84780
atcatcatgt tttttctttt ctatatcttc ttgctgtata aattgttgta gttccttaga  84840
tttagttagt agctcttctt tcttattaat tatagcctgc tcattatgtt cgtactgaga  84900
tattttagct tgttcttctt taatttgtaa ttctaagttt tctttttctt ttattttgtg  84960
tgtattatct ataggagaac cacaaacagg acaatggtca tttgtatcta gtttattaat  85020
agattgtttt aattgattaa ttatatttag agttgtattc ttatttgttg tttcttgact  85080
caataatggc aataatttat cattaatatt tgtgttaatc ttttcaatac cttggttagc  85140
ttttgtataa ttttcactaa atacaaattc aaagtcttca actttaggaa tactaccttt  85200
acatacacca atctgattgt ctaaatcttt taatttattc tcgtactctt gtttcttttg  85260
attaaactgt tcctcttctt gcttcttacg ctctaataag ttattatatt tatttacttc  85320
attattatat tgttcttgtt ttaggtttct tttatattct agtttttcta tttcttgttg  85380
ttctttactt tgtttctctt ctacttcttt aacctttttct ttagctactt cttgggcttg  85440
cttataaata tcagtcttag taatagattc tagtatttct tttttacctt tgtcggtagc  85500
ttgtgaaaac attggaatgt ctccttgacc atatataata gcatttacat atgtattaaa  85560
aggaatacca aacaattctt gaatttggtt atctgtaaca tcatttgtag agcctgttat  85620
```

```
ctctttgtta ttacagaaca gcttaacctt gttcttgtgt tctttatgtt tacggtatct  85680
ttcgattaaa tactcgtctt tacctatgtt gaaagaaagc ttaacgtagg tgtctttctt  85740
cttatactta ttaacgacat catctgcctt taaacctttc tcagtttttc caaacagtgc  85800
ataggtaata gaagatatca tgctcgtttt acttgttcca ttactttcaa aactatcatt  85860
tgttttatta ataccctcaa taagtacaag accttgctta tccagattta gcttgatatg  85920
ctcaatagct aaaaagttat tcatctctac ataattaaac ttaaccattt gtaccacctt  85980
cttttaacaa tttaaagaaa cattgatgtg aaccataatc tagaatataa caatcttctt  86040
gttcaataac cctcgtataa taatgagcat agttagcttc ctctaatact tttttaataa  86100
ggtacatcgc atcatcaata tttttaacat tacatacatc atatgttctt ttattatgta  86160
agaactgtaa aataggttta gatttatata tacttggttt aatattcttt ataataatat  86220
ctatcatact acagcaccgc ctttaaacac tctagaatct catcttttgc ttctggatag  86280
tatttgtctg cataactaga agtaatcgtt atagggctgt cagacacgtc agcgtcgact  86340
ctcttttcta ccgtgtattc tttcttcatt tgtacttgta cattagattc atcttctgtt  86400
ttatctaatt caattacttt agcttgttct ggagtaccaa taaacctaat aaagtgacct  86460
tggtttacta aatcattcat gttatctggt acattgtcac cttgtactgt aataaacttt  86520
ctagtatcta atgaaatgaa cgttgatgtt agcttgtctg tgtctattaa gtgtacgcca  86580
ttagcttctt gttcatctga aaaggattgt tgcattagag aaccaccata catatgatta  86640
gggttattgt ttaaatattg tcttctatga tagtgaccaa gaagaataaa atcatattgt  86700
tctggtaata ggtcttggta accaaatgcg ccttctaatc tatgggagcc tttacctgtt  86760
aaactattct ctacgcctaa atgtgctact agtatattta ctttatcttt ttggtaagat  86820
tttttaatat actccttaat ttcttctgtt tcatctccat aagcacacat agttaattgt  86880
actttactag aaagtgagtc actacgtaaa tctttagtta cttccacatt aggtaatgtt  86940
tcaaagatat caatactaga ttccgtatat aaagaattag acacagcatc atgatttcct  87000
ctaaccatat atactttaac atcttgattc ttagcaaagg tttcaaatac cttattatat  87060
actctagtat ctaccgcatt tctcttatgg aataaatctc ccccaaatat aactttagct  87120
ttattttctc tagctaaatc aaatactttt tgtagtgtct caatttgttc tttaaatcta  87180
tcattaccgt attcttcatc aggtttacta taattcgtaa acatatgaaa atggctatct  87240
gtaaaaaata taaatttcat tagtgccctc ctttagtacg ttatgataaa agtataaccc  87300
ttaacaaaca tgttgtcaag ggttttgttt taatttgtat tatttagtaa tctatcttgt  87360
gccatactga agtattcttc tgataattca caaccaataa aattcctatt taacttttta  87420
catgcgacac ctgttgttcc gcttcccatg aagcagtcta gaacaatgtc tctttcatta  87480
gttaagcgct ctaacaacca ttccatagca tataaaggtt tctgtgttgg gtgtcctttg  87540
ccctgctttt cacttctagg tgttacacta cgtataacat ctttaaattc acagcctaat  87600
gcttccatag tatcaataat aggtgtaaat tgtctcatat cacaaaacac aacgatatta  87660
ccaccttttt taacttttgg tatagcttta ttaatccata aagtagattc aaaattttta  87720
tcccactctc caaaatcaat accagctcta cccatagttg taaatctgtt ttcttttgca  87780
atgttatatg gagggtctgt tacaatagca tcgatactat tatcttcaat tgtatctaat  87840
aactctaagc aatccccctg taataatttt atcattattt tactccctct tcactaattt  87900
ctatagcatc atgattagca aactcctgta atttaaacat atgattgtca ttaatctcat  87960
```

```
ttagtagctt acttgaataa aaatgtatca attcacatac ctcatctgtg taaggctctc  88020
ctcttaatat atcttcaagg atatccattg cttcttccgt atctaccttt acatgtctta  88080
aaaattcagt cttatcttgt agttcctgta ttgtcatttt cattgtttag tatctcctta  88140
tgtttttcta ttctttcact ggctaaatta tagtattctt cgtctaattc aaaaccaatg  88200
taattgcggt tagtactcat acaagcaata gcagtagtgc cactaccaat aaacccgtct  88260
aaaaccacat ctcctttatt actatgcttc ataatacatt gttttattaa atctaatggt  88320
ttttcatttt ggtgtaattg ttttttacca cttaccctat caaattccca tacatcagtt  88380
aatcttctcc cattaaaatg ttttttgccc tttactacta aaaataagat ttcgtatttt  88440
ctaccaaaag aaccttttaa atctcctgct gtatgattgt tttttaccca tataatcata  88500
ttttttattt taaatttctt ctctaattgt tgtttaaaaa aatctacttt gtctgatgag  88560
caaaacatat acatggcact attgtttttt agtaacctgt aacactcatt tatataatct  88620
ataataagtt gttcgttatt atcgtttaaa ataacttttc caaatctatg ttctttattt  88680
tttctccact tggttctata attaattaaa tagaggggtc tgtaacaatt aagtctacac  88740
tattgtcagg tatcttcttc ataccttcta aacaatcttc gttatagatt ttatttaatt  88800
ctaattccat gttaataccc tactttctta aatgtttaat tttattgttt gttagttcta  88860
attctataat acttctttta ggtctaatgt taaataattt acagtcatac ttatctaata  88920
cgtaattatc taatgtatta aataagtcaa ttgaaacatc ttctaattcc ttttcagaat  88980
actttgtgtc tgtagtttct ataaatccgt gtttattgat aacttgaaag ttttctagtt  89040
ttacttttgc ttcatttaag ttcaaatctt accacctctt tattgtttat aataaaagta  89100
taagccttga caaatacatt gtcaaggctt tttctcaatt ttttaactta tattcaattg  89160
ctttaattac ttcttgatgt gtattgcaag gtatagcagg tactttatta gacataacgt  89220
tatacttata tcctgttgta ttattccttg ctatagagtc tagtaatgta acacatacat  89280
tagttccttt taattggaag gttcttaacc ctgtatttgt ataatcccat tctgctttat  89340
tgcgtgtaaa tgttctacgt actttttat aaagcctagt aaagtcatcc attaaaaact  89400
cagccctcca aaagaattat taatagcttc agctttatta ggtttttctt taaatctact  89460
tttatcttca ccattaaatt ccgctagtat ttgcttatgt tcttctgcct cttctggtgt  89520
ttcatctcta acaaccattt tagtaggctc tactttaaga ttaacaaatc tctcacctgt  89580
gtttgaactg tttcttactt tatctaggta caatcttaag aaaccatttt taaattcttc  89640
atctttttgg ttaacggcaa aagcaacctc tacagcattg acaatctttc tgcttccctc  89700
aacatgctca cttgtaataa tttctgaacc gtaagctgtt ctgtttgttt gtgctaatgt  89760
ccaacaaaca aaattgtatt cttgtgataa ttttcgaata tcttcaaaga tacgaccacc  89820
agcatctgat tcactttgat acttaaggta agggttacgc ataagtttag gataatcaat  89880
aataacaaca tctatatgct tatctttctt aattgttgta ttaactataa tttgttctaa  89940
ttggtttggt gttacctcac caggcatatg tttaacgata taaaagttac ctagcagttg  90000
tctattcttt ttatagtgtt cttgtatctt attataagca tctgtgttta aagataagtc  90060
accattaagt aattgattct tttgtacacc taccatttgt tgttccgctc ttaataccat  90120
tctatccatc ttttcctcta gggcaatata taaaacattt aaaccttgtt taacatagtt  90180
cttacctaaa ttacttgcca taagagactt acctctacct gtaggtgcaa taactaatcc  90240
tacttcccct ctacctatac caccttcaat ttgctggtct atagaatgga aacctgtaga  90300
atacttatta atacttaagt tgtttaatag ttctctcttt ttatctacgt cttcaaagaa  90360
```

```
atcaataaat tcaccatcag taccattaat gtcactaact tctatttgtt ttaatttctc  90420
tactaattca ggtaagttat ctgagtcctc ttgcttattc tcagctatga acttaactaa  90480
tacttcttta gacatttctg ttttaatata cttttctact tcatagttta cagaatcgtc  90540
tttattattc atgtctactg tatataaact atctaaatat tttaatgttt gtgttacttt  90600
ttcatcatct tgtttatcac tacccattaa ttgctctact ttaatagcta aagattcatt  90660
tgacatttta tcagcaatgt gtgctgttct ttttatagct gtgaataagt aacccatgtc  90720
ttccgattct gtagcaaata gacttttagg taacttatct agtacttctc ttgcaaaatg  90780
tatatccttc atagacttat gtaggataat ctccttaatt cgtttactca tatgtgtcat  90840
cctttactat atcaataacc ttattatagt tcaacatacc ttcttttgtc aatggtattt  90900
tatcaattaa attatatttt tcaattatag acttaacttc ttttaaatta acctcataac  90960
ctaagtaatt actatacatt tgtaaaatat atgatgttga agtaaatctt ctcatatgta  91020
gataattcat tgttgtttgt tctatattta caatatcttg tttacttaag tctgtagtgt  91080
ttactaaact tatacctatt aagtctcttc tatctatacc gccatttaat tctgcgatat  91140
ttgctttata ctctttttgc attaaaaaca tagatagtct agcattatta ggtattgtag  91200
taggtgaata ctcatttaca atacattgtt taataaattt atttaataag tttttatgtt  91260
tactaggtaa tttttctatt agatgttcta tatatttatt atatgataaa agtataaatat  91320
gtttcatgcc attaaatata ccataaatag tatcttctat atctaaagct gttttaaaca  91380
ttgtatcaat atcatgtatc tcttcattta aaggtgttgt atatagttga tgtaattgtg  91440
ctacagcagg atttaataag taatcagatg acttaattaa agactctact tccccaattt  91500
gtctatttgt tttatttaca cctcgtttaa taccttttac ataattttca taattagtta  91560
agtatttatc ggaactaaaa aaatttggtg caggtatagg gtaaggttgt gttttattct  91620
caaacccaaa tgtggtattc ttaaaaacat tttgcatgta tttaaaaaca ttaatgttct  91680
tatcttttat ctttaagtaa aagttgtaga atgtattaaa tgtcttacta ccaaagaagt  91740
ctttacaaat actatctcgt gataaattct gtaacatttt ctttctgtag tactcagata  91800
aatgcttatg tctatctacg tcttcattac catttgataa tgttaaatgt tgtatatatt  91860
tagcattcat gtgtgctata gcatattggt catataactt acataaatata taagctttat  91920
aaaaaccctc agggtcataa gacatattaa aaatatcttt agtagggtaa ggtaagctac  91980
tactataaaa attcatattt gatattattt tcctgttttt atctttaata gcattatatt  92040
gaaccatttc tagttttgtt ctacgtttat tttcttttct ttcatatacg taactaggaa  92100
aaaatctatt tcgtaattca gtagcgtatt ctagattaga agtaataaca ttatcatctg  92160
tagcattaaa atgtaagaga ctatctgtat cataatctct tactagtgat ataacaatac  92220
cacctttatt tcctctttta gaaacaacat taattttgtt atcctgttct aatcttttaa  92280
ggtttttaga taaagtagag actgagacat ctagctcttc tgctaactct tttttagtag  92340
ctatttgata agtattattt tttgattttt tttcaatgta atcatataat cttctttctg  92400
tcttagtcac tacccatacc tactttccta attctttaat ttcaaatttt tcttcttcat  92460
atatttttct acgctcatta gaatgtttat ataaaaactt atgtgtcata tcattaaaat  92520
caaatatctg tgttgtatta tcttctttct ttttacgtaa cgcacgacct acacgttgta  92580
gtgtttgtcg taaagattta ccacctgcac ctaggattaa tgaacgaata ccactgatat  92640
caacaccctc atcaataagg cttgtagcaa tcataacttt aagtttacca ttacgcattt  92700
```

-continued

```
catctaactt ttgtttacgc atatctgact ctatttcacc atgtaaaaag aaattctcta  92760
cacccatttc attcaacata gtggatagta tctcaccatg ttcaacaaaa ttaataataa  92820
taagcgtagc tttatcttga ttataccatt tagctgttag ttttgcaata agtttatttc  92880
taaactcgtt atgtacaata cctttattat atgcatccct gtaatcctta atattatcta  92940
tatcatcagg gttagcaata gggataatat ttattgtagg tctagctgaa tagccattct  93000
cgattaaaaa ctcattagat gttcttacaa taatatctcc gaataatgct tgcatacgca  93060
tccatagtag ctcatctttc atgtctatgg agcctgttaa tgctatcctg tataatgcat  93120
tctcacagga cattaaactt gtataccatg aatctgattt actgtgatgt gcttcatcaa  93180
ctatcattac agctatagag tctaggaact cacgcatttt atgatattta tcatagctct  93240
tttgattttt ctttcttact tctttttgga aaataacatt atgattgttt aatgccatta  93300
atacttcagc atccgtcttt gaattatgat aaatatcttg aagtatatca agcacattct  93360
gctctacttt agttttaggt gttgtacttt ctaataataa cttaagtaac ctttttttgat  93420
ttttaccacc ttcaaattta ggaagtatct ctttagctat ctttttactt aagtttactt  93480
tagcagatac ttttactcct tctgtagggt cttttaagtt agagttaaca gtaggaatca  93540
taactacagt tacttgttta acatcaaact taccagaacc tactttacct actggtatat  93600
tcaatcgttc acttaaacgg tcagcagatt gattaaaaat ctcggtagag cttgtaaaga  93660
aagctacacg ctctcctttt tctagttgtg gtaatagttg gtctatgata ccgctagcaa  93720
cctctgtttt caattatgtt acgattaggt tcgttactcc taaccttctt gtagtctcct  93780
acaaagttca gactatatct taaccatatc taatgagact taggttctcc ccgtttccat  93840
ccacttggat gtacataata gtcgttgcac cttcctattt ataggcttgg ctcatgattg  93900
tctcaaatga gagagttccc atgaattaaa ggagtcacac ttataatatt tctactataa  93960
ggggcaaaat ttacctgcat tagtagcttg cttacatata ccattataat tgactagact  94020
attaaataca gcttcgtact gatagtcacg taatgtaatc ttacctacgt tattatctag  94080
tagttgtatt tcatcatcaa tatcttcttc agctaaaaag ctttcagatt tttcatcaat  94140
aatttcgtat tgaaagttat gtcttgattg taactcacct agtaatgtta tcatcttagg  94200
taacaaccca ctggggaatt tgttctcaga ataatcatag aaatctacat aaccatccca  94260
cacacctcgt ttaaaagcta agctatgttg ataaccatct tttttagctc ctaatgtttt  94320
atgaacacgc ttaagtatga tatctttaat atacccatca ctttcgtcaa aatctacata  94380
tgtatatata ttctgttgtc ttaactgcat atattctcct ttctttttag tcctttatta  94440
tcttaccata tttattaaag ttagtcaaga aaaaaagact aggaattatc ctagtctatg  94500
gtaaagagat acctacaaca cgtgtaacat attggtcttt attattattt actgcactat  94560
ctttaattgt ccaagtatca ccactaatag atagtgttac tctataatac tctactccaa  94620
tattagagtc tcctgataca taagctcctg aacatgtgta aataccgtct ccgtctatat  94680
agaacttatg acatagtgta cctgttttat cagtaccttt tgtattttgt agagctctat  94740
atcttgtgta tacttctaca tactggtagt tagatataga atcagacatg gtttcttttt  94800
tatttgtatc tttaaagtta tgtgcaccat tccacagctc tttaaatcct ggtagtgttt  94860
ttgttgtgtt ccacacatta ccatttacag aaccattaat agttcttcca tcagtaccta  94920
tagcagtata aacaccatat agattagtaa agttagttga atctgatatg aatacacctc  94980
tacaactaac cgaggacgga gaccctacaa cacctccttg tatataaaaa gtaaaaacag  95040
ttttacttgt ttcttcaata tgtttagcta ttgcctgttg aaatgttatg ttgtctgtag  95100
```

```
tatatacaga taaagagtag ttattacttt cagcatcacc atctacatta gataacaaat  95160
acttacttat tttttgtaca tctaaatcag ttttccatgt gccccagcta ccatacgatt  95220
ttttaacatt aagatattct tttcctgtgc taatatccgt taatcttaac attctatttt  95280
cattattgtc tataataacc tgtaaaaacc cttcatatac accatttggc atatccgaca  95340
tactagacac ataatatata ccttgtgtgt taatatcaaa aggacttcca cctatttgag  95400
atgtgtattt attatttggt agactttgta ctacttgcca ttgtgatgtt tgataattgt  95460
taacaaacct atatagtact tttactttag aatcagcggt agataatgta tgtaatatct  95520
gtactactct atcctcagta tctaaggtta gtacttgaag tagtacatcc atgttttcca  95580
tatcaggttt atcatacata gtagctaatg tacgagctcc tatataatat agacctacct  95640
ttctaatatc tcttaagtaa ttagtataat caatatcttt agctaaccct ctatctgttg  95700
ttaacttaac tttttgtgtt ctacttacat ctgcttgtaa gtctgttgtt acttcaaaga  95760
catttctgtc ctcagttagt acaccaccta tattattaac ttgttttgtt aaatctgcta  95820
ttgtactatt ttctgtaata ggtgtaaaat ttagtgccat attatttatc ctttcttaga  95880
taacaattct tgtagcattc tttttaattc ttctacttca ctttctagct ttttataatc  95940
ttctttagga acatactctt taggtggttg gtaatcagca tcttcaatac tcttagcatt  96000
atccttaaaa tttttgttat atattacttc gttagtattc ttatagtata catacttagt  96060
actaacaaac tcagtaaaaa acccgtcagg aagaattgac ctagaaattt ttacgtcacc  96120
gttgttctca tcatatcctc caacaatagt gtaacccatg atatacttac tatcttctaa  96180
atgtaacaca atttcatctt tactaatatc atattttatc atttacaaaa ctccttatta  96240
aatatacgtt agtcctacaa ctcttaatac ttcaatatga ccagtttgat taaactgagc  96300
aacagacata gtatttctat tcccatctat tttatttgtt tttgacattt tagcagtaac  96360
attcactcta tctgtaatgt cacaataccc ttcaaaaaag tctacactag cattagaacc  96420
atcatttact aagttaaaat ctctaattac aatactagat gtacttgctg ggtacctttt  96480
agttgtatta tgtccagaac ttctagtcca gtatactact tcaataaaat cataattatc  96540
taatgaatcg gataagttta ctgtattacc tgaagctagg tcaagagtac cttcccaaag  96600
actattacta gacatttgaa ctttcatatc ttgccaacca ttagtatctt tattatatgt  96660
taaagaatat cttttacctt tagggtcact aaaatccatt tgtattattt tatttgtagt  96720
atttatatta ttattcttat atgctacttg tatcgtacct tgtatagttt tattgttagg  96780
tgttccactt atagagctat cacaataaaa agtataaaaa ccttgaggta cagacattgc  96840
taattgttgt aaacttctac cgtttgcgtt ttgataattc catacatatt tgtagtagtc  96900
attgttgtac gtatctacag cactatgtgt ttgaagttca tccttgcttg ttgtctctat  96960
ccaattgctc catatctcat catattttct tttatcataa gtatttgtaa taaatggagt  97020
taccgagtac gatttttcta attttggtag tgcataatat acaatagcac cattattttt  97080
agagttagaa cagttaaatc ttaataatgc tgatatataa ttaacagtgt cattgctagc  97140
ctcttggtta taatactgca atgtaaaagt aaatgagaat tttttccatt ctgtagataa  97200
ctcatagtaa ttaacttctc tccttcctcc tgtgtaaggg ttatttgttt gagatacatt  97260
atcataaccc gctatttcaa agtaagggaa gttaccattt aataaactag tgtcatttac  97320
tttaaggtat acagacattg taactgtatc acctacatat aaataattcc ctaatctaaa  97380
acgtttagat ataacagtag gatatgattc ccccccatca tctaattgaa tagtattttc  97440
```

-continued

```
acccatatat ctaactgttg aggtagatgc attattagta aaaccccaaa aagatgtatt  97500
atctatataa tccgttctta tattagctac atccgtcatt ggtaatgtga ataaactatc  97560
ccttaacaag ttaggttgtt ggtcttggtg tggtaacttt ctaatcattt taaatgttga  97620
agtagaatta ataggattaa actcagctaa agctgaggta ccatttttac tttccttata  97680
atttatccat cctgtgttta aattactttt aggaggattt atgagtgttg caaattgagt  97740
tgtagactct gttaaatctt ttacattaat tgtatttcct gaatcgtata gtgtaccttc  97800
atctagttta aaactaaccc aatcatagac agtaccatta taataagttt tcacaaacaa  97860
tttatttgtg ttagatgggg cataatataa cttataataa gtactaccct ttttatctaa  97920
gtgtaaaaac cccgtagtac ttacaccttg tggggtgttt ctggcttgtg ttacaaagta  97980
gtcacctgag tcttgtatga aatttagaac attatttaag tcaggataac taatcgtttt  98040
taaatcagat aagttaactt cttcttttaa gtatttaccc atttcattta ctttagggta  98100
catatccttt aatctttgtg attctgttag aggtgtgtag ttaaacgtca tgtgtgtaat  98160
cacctttcaa tttttaagc tcatcaataa gctcattaac ttcttgtagt ttatctttat  98220
atgtttgttc catttctttt atagcttttt cttctacagt aggaataaag agtttagctt  98280
gtgagtaagg gtctctatat tctgtaggca taatatcact tccttagtta aataaaaaga  98340
gggtatgaaa ccctctttaa acttactcat ctcttgttgt aaccataagt ctacgtacac  98400
gaggtcttaa gaaactattt tcagttgata agtctaatct tacttgtaat ttgttattct  98460
tagtagattg atttactttc tcatcaataa catatctatt aaagtctcta ttagccttaa  98520
ctacctgagc agacttagta aatgctttcc aagttttacc atcatcgtct gaatatttag  98580
gaataacatt agtgccctta ggtaagaatg cttcataact aaatcttatt gtgttatatg  98640
gagcttctgt catatcaata gctctaccga tataggaacc ttttaactca gttaagaatg  98700
tagtaaacgt taagtcatta gaacttaata aaggtgaaat atatttatta gactcaaatg  98760
tagcttttaa tttaacttgt ttagctaaac ctaatacctc taaatcttgg tagttaccaa  98820
taggttccca ttttaattgg tcaaatgtag tagatgtagc catgtcatct aaaatcattt  98880
taatttccca agtacaacct gttctttcag gggttaagta cgtagacatt aaaactaatc  98940
tatctgctga tacattctta ataggttcaa attcaattgt agctgtttca ttaaacttag  99000
aagtatatac accaaatttt aaatctgaat tttggtgtgg agtccaagta ctagcgttag  99060
atgaactaaa tagaacgcct tgtacatatg gattaccact aataacttca ctaggtttat  99120
caatcttagg ttttgttctt gttccgaccc acatagtata atcactattt tctgtaataa  99180
tgacaatagc atactcttta cctgcttcag ccatcatagg gtcatcaaag tatactctag  99240
tttcagcact agcattatta gatactttaa tatcatctga gttgattact gtttcagcat  99300
ataccgtctt gttagggtaa cctgtatctc ccataccacg aatttgtaca gttacattac  99360
tagacttatc tcctttacta gcaaagtata aacctaaaga actaatagtt ctactttcat  99420
catattggaa tgattgtgct aatgggtcta ctaagtttac tgtaacacgt gttttgataa  99480
taacatcttg tacagtcttc ttacgtcctt gagctgtata tgttgtagca cttgtagagt  99540
tagcattttt caatgttact tctctattac cgcaacgaat acctgctgga attgtaaatg  99600
tacctttagc tgtgccttta gcatcagaca taattgtacc atcttcagaa ccttttctat  99660
aacctgttgc tggtgtaata gcacaacgaa caccatcaaa taaaatatac aaattattat  99720
cattaggatt taaaccatta acttcgaaag atacgtcacg aacacgaata aattcaatca  99780
tttcttcaag tgtacgctgt cctccagcct ctaatagagt acctgttcta ccatgttctc  99840
```

```
tatcatatgc atatgactta cctttccact cttgtccttt atctaactgt aagttagaat  99900
ataagtaatg ttctgtttct ccataataac tttcattatg tctccagaat cttttcattg  99960
ttactttttt agtttctgt tctgtgattg ttacattctg agtatctatc cagttatctt 100020
cactaggagt taattttaac acaccttgtt tatttggtat attataaggg tttacattta 100080
aagtttctga tgcttgtcct tggtaaattg tacgttcttc tgtaaatggt gcagaaatta 100140
atcgacccca tacatgagct gtagtgtctc cttgaataat cttaggttgg ttcacagctt 100200
ctttatacgc tagagtagcc tctgcatcat caaaactaaa cacaatacca aagtcagggt 100260
gtgtaatatc agctttatct aaagatataa aaccttcact aaatacagaa cgtaatgtta 100320
atgggttttg tttttccatt gcgccatcat ccaaagcatt aacagcttgg ttatactcta 100380
aattatctac tctagttttt actttttgta agtcttccat agataatcta gtaatagcat 100440
atgaaataca tactgcttcg ttagaatcag gtaatactgt tacagtacct aattgtaagt 100500
tctcagggtc tgtatttaaa ggtggtgtta ctaatctcat aatattaggt tcacctttaa 100560
gaatagcaat atcaccaaac ttattaataa aaacagcatc tttacgagct aagtagtaag 100620
tatagtctac aagtacaaca ctttggtcaa taggcttagt accattaaca ggtgtgaaat 100680
taatagacca acgtttacct actccctcac ctactgtaga tacttcataa tctttaccta 100740
cttccatctt tctgttgtac ttatacgaaa cataataaga tgtacctcca ttaggttctt 100800
gacctgaagg agaccagtct attgtttgac catcagtaag tctatagtct tctccttgtt 100860
tgtattcttt tgttgtctga cctggacttg tttctgtcca tactctaact acttcaaaag 100920
ctgttttatt agataaatag tcttgagaat ctcctgttga acttcttgta acacgctctt 100980
tatctactaa tacttgcgct gttacacgtt gaacatcttt tacaggggta ttagctaaag 101040
taatattatt tgatgattta ttaaatacag tactttcatt ttctgcttta cctagttccc 101100
ttgacttctc tacactaatt ctagtagaaa ctggtttatc tactttataa ccttttacat 101160
atgccttacc agcatctaca acaacagata catgattatc atcttcggcg tttccttctg 101220
aaaatagctc aaatccacta actttatatg aacccgactc atcataagta cgctctgcta 101280
atactttgtt gattttatcc atctcagcat tagtagattg gatatagagg tctccatcca 101340
taaaagtata aatagtagca gaagtagggt cattgactgt taaagataac ttctcttcta 101400
gacggtctgc acccttagaa aaataactag gaactccgct tgtttggtct aataagctat 101460
tatcttcatc aggtgtaata attctttctg ttagtttaat acctactgtt tctttaccta 101520
cacccgtaat tttaacagtg tcttcactac tatagtaacg tatcttacca tttatataca 101580
cataacctgg gttaacttgt agtacattat ctttagttaa tgtaaaacct aatcctgatt 101640
gtttatcccc atctttaaaa atagaatccc ctaaattttt taagtaatat tgttcaatag 101700
actgcatttc atttagttct gattgttgta gtggtctatc tggattaaat agtactcttg 101760
ttctatcttt tgtagggtca aatctatcta agtatggaga acttttaaaa ttaattgcca 101820
tatattcaat tctccttttt aaacttcaat gataaagcgc tcttttacag ttgtttgttc 101880
acttctattt tggaattgtt tattatcata aaataataaa gttcctgtag attgcacttc 101940
actgggtagt aagttaaatt tagaaatact atctttagct aacaaatcca taacaaatcc 102000
tacttgtcta tatgtaccta agggtaattc atccccaaca atactacttt ctaagtacac 102060
ccacttagca ccttcagcaa ctgcattagc tgagtcgatt tctacccatc gtttattacc 102120
atatgtaatt tctttttac tttcatcacc tgttgttttt gcaggtctaa ctaatgctac 102180
```

cttagttgct tttttatatc cgataacttc ttgtaatgat gttgctgttt cttcaggttg 102240
aggtgggctt gtttcattag cccacgctgt acttttacca attgttaaat aaatagaatc 102300
agccttactt acaatgtatt tagctaattc tacatgtgaa gcatttgttg ctatagccat 102360
atttttattt cctttcatgt ctagtattct gtattaatat aacaaggtat actataatac 102420
gcatacctta ctatatcata ttaatacttt attgtcaata tatttactgt acttctgtgt 102480
acgtatctat tactttaatt ttattatcta ctgtgaatgt atcacttgat agtaacatat 102540
cccgtaagtc ataaataaat ctatttgaac ctaatgtaat attctcgtta tatagagtag 102600
tagacgttag caatctatct acatcagtat atccttggta tatcttaggt gctaatttta 102660
ttacctgtcc tgttgaacta tcaaatacat taccttcact atcagtaagt atgctcatgc 102720
tacttaatgt agtgttatat atcatatcta cctcttgcca cacagcattg aaatagttat 102780
tactcatgtt agaaatacta ccttttttat ttgttaaatt attcaagtta gcattccata 102840
tagttttaag tataacccta gagaaaggtg taatacttga ataatctatt gtttctaagc 102900
catataaatc tactaggtta ttaggtgtta ttgtttcacc ttgacttaaa ttacttattg 102960
tttttaggtt tgtccaatta tccccatagt aagaataact tagctcaata tttttaagag 103020
gtgttgttgt atttattcct attgtttgta tatctgttaa tatgttatca aacacaatag 103080
ctttgtctat aacattagtt acatcttcag gtgctaccgt gtagtccttc ttagtagctc 103140
cttcttttag ttgaaggttt gttactttta ccgtattaga agcaataggt gttttagagg 103200
cagtaccatc tgctgtatat ctacctgtgt aaacaacaag tctatggtct gtaattgtag 103260
gtgctgtaaa tgtgatagat acctcaatct tattacctat ctttctttgc atgcttttaa 103320
caccattagc aacaatacct ttagtactac tatataaata tataccatga ttgtcagaat 103380
atgtttttaa gtccatatta gcatctgtga tttccatctc gaatgacaaa gtatataatt 103440
tttgtggttc tagtacttta gataaatacg ttgaattata taaggtgtca gcccatgatg 103500
agatataaaa ctcttttgtg cttacaacac ccttgaatat attactatca cctttatatg 103560
attgcaataa gtttctatta gttgtatttt tatataaatc tataggtgta ttattttgta 103620
cctcattatt gctgttttta cctgtaatac ttacaatagg tttagttgaa tcataagtag 103680
catgtaacct taaatatttt atgggttgat atccattttt attaattatg tctccattta 103740
ataatgatgc tactttaaag ccttcaatat aagtatcttt agtcaaatct atgtagtttt 103800
caactagtgc cttaaaaggt ttgatagtat acacatcttt tttataatta taaaaatgta 103860
aatccatgta gttaatactt atatcttttt gctcatcttt acctatatta acctctaatc 103920
ttgtaaataa attaaggtca tcatttaagt aatctcttat ataacctatg tttacaccta 103980
tgtttttctc gtaaaaagat agttctgttt ctgatacagt taaccattca ttagtacgaa 104040
aatcaaatat ttgtaactta atgggtaatg attcatcagg tgaaactaaa gcttttgcaa 104100
agaaatcaat tgttagttct cctataaaat cggatatttg ttttttagca ttatctctag 104160
ttatatctat attaggtttg tatctactga taaactcccc tacattaaag ttattgtata 104220
aataagatac accgtaagca gtttccattg atatatttat atcattagta ttctttaagg 104280
atgtatataa gtaataatct aaaggtggtt cttttccttt atcatttaaa gaagctatat 104340
gtgtgacggc tgatgtacta gtaggttcat atgcatatgt cgtaacataa gcataattta 104400
taaatctacg tccaatatta gaagagcctg atagaatatc ttcactattt aatgtactct 104460
tatttgttct gaaccttgtt ttatcagatt gttcagctgt tgcttcactc atgtttaaat 104520
gtccatagaa agtttcatca taacctaata atctatctaa atccgtatat gtttcaattt 104580
taggtagatt tttaagccat ttaacaacac catcaccctt tatggtagta gcaccatcat 104640
aagttaaata taacttaaca cctgcgggtt taaattcatt tattacatct ataatctcta 104700
aaggaaagta accatcaaca gaaacattta tcacagcaaa tctataataa taacccatta 104760
aataatcttc accatttaat tttgatttat tggtataaaa tatattttta aaaggttcat 104820
atacactaac atttatattc tcattatcta agtagtcttt aatagcacta atgatagcat 104880
tattagtacc tcttttcaat aataagtatt ttataattct ttttctatag ctgtcatcat 104940
tctcatttat tcttctgtat acaccaaacc aatccccaaa cttatctaag taatctcctg 105000
tggcagtttt taatgatgat tgaagtttgc ttttaatggt gtctaactct atattgttca 105060
tctcatcatt aagtgctgtt attaaagcat agttagggtc ttggttatct ttattattct 105120
tatttcttct taataaaggg tgtaagtttc ttaaaaaatt agccattgtt taccccctat 105180
attaattcta ccttaatatc ccctgctcta ataatacctt tcgaagatac ttctatattt 105240
gtagataaat tcttaaatgc tacatcataa attaaattat catctatatt cataatagct 105300
tgaattaaat cgttaataat taagtcatca gaagtagtca gactatttat gtatcctcta 105360
ataacacttt caatatgtct ttgtaatgtg tcacctatcc tagctttatt agatattgtt 105420
actactgcag acacatctat ttcctctttc tctacaccta caacatctaa ttttatacca 105480
ctaggtctgt aatcttctaa tgccgttatt atgtcatttt ttagagtagc agataaattt 105540
ccgtttttat catgcgcata tacagtaaca tgacctactt cttcataaac ataaacacca 105600
tcaacatcag gtacttgtaa tgtaccatat ctaatagatt tattagtagc tcttcctctc 105660
gattctacaa acatatggaa cctacgttta aaatcctctt gagattcttc ttttgttcct 105720
gtattaaagg aagtcgggtt tgtaattgta cgaattaaac tagagcctga ggctattgta 105780
ttaatgatat cttcaggtat attacctaca ataccaactt ctttacagta aacttctact 105840
gtaatttcag tggttccttc ttcagcatag taatcaacta atgtttcaaa ctgttgaggg 105900
tattcttgcc tagtagatga gaatgtagta cctgcaggta tatacattct catgtctaaa 105960
ggttggtaaa attgaatgtt tacattacca taagcacgct tagcttttct tttttgaaaa 106020
tcaaaagctt caataatccc ttcttgaatg ccccaattaa tgttttctct tgttaatata 106080
taatactgtt ctatttctaa agctactgct tctaaaagag agcgtacagc tgaaccaggt 106140
gtaaagtctg ttattttgct tgtaccttgt atcgtcttat ccattaacct agataatatc 106200
tgtgttaact ttcttgttct catataaatt tcctttctta gtcaaataaa gcaaagacac 106260
ctgaatcatc ttgacctaat acaaagtcta tagattcttc tacggacttg atttctacat 106320
taaatgaccc atagtattca ttacctttta tctcccaacc ttttaagtta gctgatttaa 106380
ctctactatc tgatgttaga gtctttaata catctacttc aattaacgta gcttgttcag 106440
gtatatttaa accaaataaa ttatgaatgt tagaaccata ttcaggatgt aataataaag 106500
aacctttagg tgtcaatagt ctagctctta aagattgctt aatattatct atgcctttaa 106560
ctatatcaag gtctcctcta ccatctgaag atagggctaa tatttcatca tctgttccat 106620
gagcgtctat atactcttta ttatccgtca tatttaggtc tctacctaaa gctaattcta 106680
ctaatacatc tttatctctt gatgttattt ctttagaaac cgagtctgtt aactcagcat 106740
ctaaaggtat aataataata tcacccttag ttattaagtg ttcagggttc cttttctttt 106800
cttcatctgt atctacaata taaggatatt gtaagttgtt atgttctatt aaatctaacc 106860
aataactaac atcaccataa tacctttgtg atatagcttg taaggtttct tctggttgga 106920
cttcatgctt tctaaatctc attataccac ctcactctta attagtggta gttgtaattc 106980
caaagagcca aaacataagt ctaagtctct taaatcgaga acaatactat tgtattcttc 107040
ataatcactt aagtagtcag ctacgtagtt aacattactt cttactatag atacatcttt 107100
ttctgttaaa tattttaagt attcaggact ttctacaaag cagtttacaa tagcgtaagc 107160
ttccattacg atagattgca taattaaata cattctaggt gattgtaact ttaaacttgt 107220
ttgttctact ttattaacta ttgtattgtt gttaaatgtt ctttctaaag tagggatatc 107280
agtagactta atctctttta attttattct tgcaagttca cttagttgta tttgtggtgt 107340
ataaaattta gaaacaaaag gtacttcctc atctaataag ttcatatgtg tgtaagacat 107400
gtctaactct aatccattta aaaaccttaa tagtccttgt ggttgaggta tataattatt 107460
cattacctag atacacctcc atcaccgtat cctattttaa gtgccatatc atcaacagta 107520
ctactaagac cgttagtatt ctgtctaggg ttatatatcc ctatattact cataccgtct 107580
ctattacctt cagaaccacc tgttcttatg ccactacctc ctcttaatgt tcctgccgtt 107640
ccatatcgtg aaccactact actagaatta gaagagcttt tactactttt attttcaaat 107700
tgtgatacta tttgattatt cttgtttctt gtttttcgtg cgttactatc taaatcatta 107760
acaccctcat caactctttg tttagcatta ggttttacat taccaaactc agcagatgtt 107820
acggaacctc tatctgcttc agcaaggtta cctatcacaa ctaaagttat ttcatatcta 107880
tataacaagg attcatcttt agaccttgtt atttttaaac cttgcggtgc tagatgtact 107940
ttgtaatatt tatcatcagt aaagttatag aactctatat aagctcctgc tacgctacca 108000
tctccaccct gcttagcata tgcttctact tgttcttgta gttcctctat tttttgtttt 108060
cctgttttag taccatctac ttcttttaca ggtctaaatc cagtagtacc agaaaaagtt 108120
attgtctcta tatctttacc gtaatcttca acaataatgt ctgatttagt tttagttata 108180
gatgttcttt gtggtgcatc tatttcataa ctttcagggt ttactttgaa acggtacata 108240
ttatatttac cgcttgcggt tggaaaacgt aatgcaatac gtcttattgt attctttcca 108300
tctgattgag gcataactta ccacctttct atatcgtatt atatcatata taggatttaa 108360
atacaactac tttctcaagt ttaatataac atgacatata taaaaaagcc ctattaatag 108420
gacttttaaa ctttttaaa ctctaatatt ttatttgttt ctacaccatc tataccatat 108480
aaaataagct tatttataat atcacttgtc atatcaccac tagaatatat agataggtta 108540
ttattatgtg ctgtatttac tgtatcttga gtgatgctag tatatggtag tagtactcca 108600
tatatatttg tatatatacc tttgttaata tctgtatttg ttagatagga agtattatat 108660
aatactggta agttagaaaa attatttaat acttcttgtg tgattgttaa atctttaact 108720
ttcaaataca cttgattcct aggtgctctt ataccaatta aattatattt tttcagtagt 108780
tctactatgt ttgcagtagt tggtaaatta atactatatc taatagaatt tttatattta 108840
gctaatacat cttctaaaga taaaatactc tcaccgttct tagctgaaaa tgactttatt 108900
tgttgtagag tatagtcaga tacattacct ttacctgttg ttatattgtc taatttggaa 108960
tcattaagac agactaattg attgtcttta gtaacttgtg ttgtcaaact caataaatca 109020
acattagaat ttacaagtgt ttgtagttgc ttatctgttt gttcggatac tgtacctaat 109080
aactcagtgt tagtaggtgc taaagtagtt tctaatactt ctatactaaa cattgtatta 109140
tcttgtagta atgtaaggtt aatatcatta tcttgttgta cttctactgt gaatgtatct 109200
ccttgtttaa caggtataac atttgtaatt atattatcgt gtgtattacc attagttata 109260
gttttgtatg tattactatt cttcttgact gtaatagttt ttactttatc ttgtaatata 109320
tcccatttaa gattaataga aactttaact ttagatacac ctaacggaat aacaaaagca 109380
tccttagtct tatttacaaa ctcagaatta ttaaaaacta tcttattcca tgtaatacgt 109440
gtaggtgtgt atggataaat agtaaggtta ctatctagtt gcagtaatga acctagataa 109500
ttactactaa aactttgaga actattatta acataggtct tacttgattt ctctaataag 109560
gtattattaa tgttaggtaa tgtaattgta tctagagtat tcaatctact ttttaactca 109620
ggtatttctt ggttgtattt atttatcata gtagaagcat cttcatataa gcctttaaat 109680
gttttgtctc tgaactcttg aaactgtgta ataatacctt cagctctact acttacatta 109740
gatatttgag atttcatagt cgtaacatca ctacttgctt tactagaaac ttctatagat 109800
tttttagtct cttggattaa ctcctctaag ttttccttac ctacaccctc aagtaagtag 109860
ttaatgtcat ctaattcttt ctgtacttcc ttaagcctat ctatagactc ggtaatgcta 109920
gcatctaacg tatctaaaat tggcttatca tctaaatata tacctttatc attaaattca 109980
aacatatgct tagggttttt tatataaaac acattattat catttatacc aaactctacc 110040
catacttgcg ctgagtctaa taataggtca tcatcttgct ttataactct ataagaacca 110100
tcgtgagaca tctcttgtgt tgttcttttt tgtgtgcttt tgtctaatac tgaagctctt 110160
acatcacctt tttcggaaat aaataaagtt gtaacatgat tatcttcgga accatcatca 110220
aagtatagac cctggtgttt aagtaacatg ttaggtgcct tttgtattct aggttctatt 110280
aaatttttgt tactatagta tgatggaaat aagtcttggt attcagtacc tgtataaaag 110340
tctgaagata aaggtttttc tttatcacct gaagtaatgg ataagaaaga tttaccattg 110400
aatgttttta tagatgtacc ttcaccatct ttatatgtat aagttaggtc aggtaatata 110460
gagtataaag cactgctgta tttataaaca tcatcattac tcattttacc accctctaaa 110520
ggattcgtat ttatgagttg gtttgcttct gtattaccgt agatagctag tataataggg 110580
taattaatgt catcattaat aaaccctaac agtacagtag ttccttccgt tattaaagta 110640
ttactgccat acatactacc ttcaggtgtt cttcctacat aatctttagg ataaggaaca 110700
gctaacttac catcatcact agggttatgt cctaatgtta aactatttat tttaacttct 110760
acagtttggt acttataatt tattttgctt actgtaccta ataatagacc tttaacatta 110820
agttcttctg agtctatctt ttttaaactt ctacctaaag aagattgtaa tcttaccacc 110880
atgctatatc atcctcatca aacctcataa ccctaccatt aaagtcatcc caataatcgt 110940
ctaactcata ggtactaata gaggtgttat ctttaggaaa tgtacctata agagaaataa 111000
acttcttatc tcctatgtat atccctatat tatcatcact acgtccaaag aatagtatat 111060
cacctatttt gaatttgtca atatcaactt tatatttgtg tcccttacca aatatagtat 111120
agaagctttt acctgtgaag aagtagttaa ctgttaatgg atttttaagc tctacatttc 111180
tctttttata catccaatat aataagttgt atgtatctaa aggtactata tccttacttt 111240
caaaagggtt tttatccgta ttccctttaa acatatactg tatatgttta taattattta 111300
aattctcttt caagtctaat gttactaatg tactaactgg aacatcttca tcaaatatat 111360
gctcattctc catgtagcta ccatacagta tgttctgtaa ctcatcaaag taatctataa 111420
caagtacacc atttctttct accatatgca ccatacaagt tgataatgca tcagtaggta 111480
ctgtgagatt atcagtagta taacttattt ttctaaatgt gagtttagct tctatatctg 111540
taccattatt agtaaaacta tcatatgtta cttgtctagg tgttacactt tgtataacac 111600
ctacatatgg tctaatataa acaactttat tgtatacgtc ttctgtagtt atctttttaa 111660

```
cttccttatc tttttcttca accttttctt tggttaatac ttcaaaattg aaaagattat 111720
ctataaattt atctataaca tctttaactt gtttatccgt tgccatatca attatccttt 111780
atcatatata aattgagcac ctttacctat tgctgaactc atatctattg ttcttgtacc 111840
gtaaccgtta ggagttgcaa agttatgttc tgatataaat atactggctc caccgtctaa 111900
tactttttct acaaaagcaa catgtccata ctgcgggctt ccgccaggag cgcctctctg 111960
ccatatgaca caagctcctt gtttaggtgt tctacctaca ctataaccag cacttttagc 112020
accaccaatc caatccgccg cgtctcccca taacggaaca ggaataccta actcaccacg 112080
tctattatag gcataccatg tacattgata cttataatgc ctattgcctg gttgaacaaa 112140
gttagggtca tgtttaggta atttaccatt atatttttct aatgaagcta aagtgcctcc 112200
atcttgtgca ccaccttcgg agtctccatc tttatttcct tttgttttct tctcggctac 112260
accttttctt tttaattctt tagatgtctc ttcacccata agaccaccca taaagtcaga 112320
tgactgattc catagtcctt taaacctatg tttgcttcct tcaccatctt ttataatagc 112380
atcttttagt cctcttgtta ctcctattgt agtaaagtat ccttgtttat aatcaaactt 112440
atgttctacg gactctatgt aaaactccca tatatcccct cgttgtttat cttttataaa 112500
taaccgttta cctaggtcat acttagggtc acctaataca acaatattac ctgcataaaa 112560
attagggttt gagtgatacc aattaaatag cattttagta aatataatta aagagtcatc 112620
acttgcgtca gaacctgtat ctctagcaac attagctact ccttctacgg ctttaagata 112680
cttatcataa atatcacctg tggtacttgt cggtgggttg cctttaaatc tagtgtaatc 112740
ctctagtagt ttcttagcat gtgtaggatt accatactta taattctttg taatatcatc 112800
tattacagct tttgttgttt tcttatttaa atctttatca tcaaaagttt ctttcttatt 112860
aaacttttcc gctaatatag actttaattt ttcttttgtt agttttggtc tagtatcaga 112920
tactgactct cttgaagtat tgttctttgt tattttttca tattcttctt tacttagatt 112980
accttttttt atataagatt ctaaaatact ctttacttca ggtttagtaa tattgttgta 113040
ttttgatgat atcttactgg agtatttatc taatccttta gatatagact ctctaccata 113100
gttatttaaa tctttaagta gtctgtcata agttactcgt tcgtgtccat tatctccacc 113160
tgtagtttca ctatcttctg tagcactacc acttttagtt cctatatata ggttttctgt 113220
ttcatattta gaatacccgt atctatctac taattcttgg tggaattgtg gtttagagaa 113280
tacatcccct gttaattctt ttaacatacc tgctggtttt actgtaaaga tagagtaggt 113340
ttctacatca ctcttaccta catcctcctc tataaaatca tcagttggta caactatata 113400
ttctaatgct ttccattcag ttggattaaa aggagttttt cttaatacta gctgtgcttt 113460
acctttatgt ttatctgaat ttctaaagaa taactcatta aaaggtctag cagttactaa 113520
gtccattagc tgttttaatg taccatcaaa gttagtaaaa gcggaaactt cagttaactt 113580
ttcatactca tcccaactag ataaatcatc ataatctaag taactctcta atgtgttgta 113640
tgttttatcc gtataattgt acttcatgta aggaataaat cgttgtataa taccttgcat 113700
tacatcttta gcggaactac ctgtaaattt aacctgattc tctccatcgc catcaactaa 113760
ccaaccaaca gttggtaata cagcttgtac ttcttgtata acacctaaac caaacttcat 113820
aaaaggtttt acaaatgatt gacctgttat tctaaattgt acttggtcat tgccataact 113880
acctacttta gatacttgag ataccatacc cacttgtata agtttctctt ggtttccctc 113940
tttatcttta gggtcattat taggcgtaat atatatctta ataatatcat ttgccattac 114000
tagcttatcc caatacgtat cccctgacat agttatttgg aatacagcac tatcatcttc 114060
```

```
catagcattc ttagtttgaa aactaagtaa ctttgaagca aattgattgc cgttgtaatc 114120
tttagtgtct tcaaacttta atgtaaatgt attatcatct gttactattt ctattcgtat 114180
cttaggtcgt ctaattctat acatatatgt acttccttta tttttatata aagggtagta 114240
cttaataata ctaccctaat aattacgttt atacgtgttt gagaagatgt ctaaatcgtc 114300
accaaaggta gacttaatac ctttgcttat gccttccgca tcttctttat cgtttactcc 114360
tgtgatgtta acactcacag aaacattgtt ttgagattta ctacttccag atgtactact 114420
aagtatagga tttctcatga ctgaagtata tgacgatggt ataactccgc caccgccacc 114480
acctgactta ccgtatttac taacatagct tttggcattg ttaactctgg tactcatcat 114540
agcttctcca gcacccatac gctcaaaacc ttgtgcaaaa gcttttgtat ttttttctaa 114600
gcttccactt ttactccatc ctgcattttt aagcatatca ctgttttgac cagaactcat 114660
ttctttccat aagaaatcta attgtgcgtc taggtcatta gacttcttac ctttagattt 114720
agcaaagcta tcaaggtctg atttcctact acctaaccat tgtgcaatac caaaagcacc 114780
gctagaggcg ttctttgcat tagggtcaag ccctgattct tgcttaaggt tacccataac 114840
ggcacctact tggttatcgg ataaaccttt acctttaagg aatttgtaaa tcttacccgc 114900
accttctcca tctacatcgg aagctgaacc tcctgaatca gaactactgt ctgaacctcc 114960
tgagtctagc gctttagcat cttctataat ttgttgtgcc ctatctaata ggttactgta 115020
agtttttaag tttttagttt ctgatttatt attcttttct cttagttgtt ctgtagacat 115080
tttctgtttt ttattgtttg taccctttgt taaagtatat aaatattata attgtattct 115140
aaaaattaga ttctaataat tgttttaatt ttctacctat tgctttccct gtttcattag 115200
ggtttttact tttaggtact tctatgttat atttaagatt ctttggttga tggtcatttt 115260
ttagagcatg tctaggcata acatcactgc ctccacctcc accacctatg aacttgtctg 115320
aacctttcat aatactggca atcatagtat cccaattacc tgctgttgca tactcatgaa 115380
caccattgtt atgtctcata tcatgtaagt tcttttgtcc tttgttgtag aagttatctc 115440
taatccattt agcaccacca acaataccta atccatagtt aaaaccatta ttaggattgt 115500
tatcaaaagc acctataccg aaccaattac ctttgttagg gtctccacct ttggaaaggt 115560
tcgaggttcc ccagcctgtc tcaacagcac tatgtgccac taagtacctt gggtcaagtc 115620
ctgactcttt acctgctttc atataaagct cacctaaacc acgcatttta gaattactag 115680
gtgcttgaga ctcaatccat ttatttaaca tttcggcatt tacaccttta gcagttttac 115740
ctaagtcatg cttagttacg tctttatctg taaagttctt accatcaaga tagtcaagtg 115800
ttcctcctga tgaactattg tcggaactac tgcctttatt tgttagattg tctgctaaat 115860
ggtctaagaa atgtgagtat actgttacat ttccttctct agaatcatta ttcttttctc 115920
tttttt cttc tgctttttgc ctgtctttac tttgtgattt atcattaata ccataagtta 115980
aaacatataa acaatagtat actttcatat ataacctatc gtattagtta tgtatattta 116040
tttaataaca agtttacctt acaaaataag aaaggtttat atgcagaagt agaatacaaa 116100
ttttaattat ttatatattt taacaatgtt taaatataca cgctactgta tattctctag 116160
ttatttctag acactaggtt tccctacgtg tgcagactat ttgttatccc tagtttatag 116220
ggtgagtatt tttcttccac caatagcttg tggttttact tccgtcacct atacggaata 116280
gtcgttgaac gttctccatg ttaaaggagt ttcgatgcta tacacccatt gtacttctcc 116340
ttaggattta accttagagt atctaactaa tttttctga tttctcaaca ttcaagctta 116400
```

gtctttcgac ttactttgta gtttagttag ctttagtagt ttcatagcag ttaacactcg 116460
gtacttacag attgctctat aagcaaggca attagtatat aactaattat gttacctttt 116520
ttatttttca ctgtttcatc taatttagaa gggtcatctg gtgtgaagaa atctgttatg 116580
ccaccccata gtttacctac aggtgagtct tggaatttat tcttaccatc tttatctcca 116640
ttagcccata atttccaacc atcacctgtc gaagcgcctt ctgctgtttt cgtagcatag 116700
tctcttaatc cgtctccata acctaggttt aatgggtcta tgacacttcc tatagtatta 116760
ccaaatttag aagaagcttc tttagtatct ccttgtatta aagaactacc tatatcaaac 116820
gccgatagac ctgcaccaat ccaacctagc ttacttgtaa gaccacctag tttaccaaga 116880
ccacctgcgt tagcagtagg tgcttgtgac ataaaaccta aattggaacc tttaccacta 116940
aatttacctt taactttacc aaaagctcct ttacctttgt tccatgcacc tttacctaag 117000
tctttggttc ttcccatata ttcaccaaat gtaaagtctc tttttccgaa ggtatcaaat 117060
agggttttac ccatacettt agcagtttgt cctgcacctt ttacttggtc tttaaatggt 117120
cggtctccac ctttaagatt atctcctagt atagtgtcag ctaagttttt aagtccacca 117180
aaacgcccac caccgttagg attaccacca gtcttaccta ttgaaccacc tttacggtta 117240
ttaaaccaat cttttagtcc tttttgacct ttacctaata aagagccacc agccatcatg 117300
gcagtagatt tagctaaaga tgctacaaag gcaagtactg ctcctgaagc taggtataaa 117360
ggagctggca agcttgccat agcactatga acatctctaa taggttgagc taagtcataa 117420
atatcctcgg ctttatcatc tgtcttagct ttgttctggt cattcctacc tgctttagat 117480
tcggaatact tatccctatt cttatctcct gctttggaac cttcttgctc catcttttta 117540
gctttactag ctaactcttc tttagatagt ttacctgagg cgtaaagatt atacaactca 117600
tctgtttgct cttgtgttaa attagctccc atgctttcaa agcctttttt agctatggct 117660
tgtttttctt ttgttgtact tcctatatta ttagcttggt caaatatatt aactaaatta 117720
ttagggtctg atataccttt atccatttgt gcttgtaagt catgcatacc ttctaatcct 117780
tggtacttag taccccatcc cattgctagt ctagtgtaag aattacccat accattttta 117840
ataccttggt caatactact taacgcttga gccccttgag ctccttgtaa acctttacta 117900
cctgtacccg ctacttgagc ttgtaaagaa gtaagattag acatgtctcc tttagataat 117960
gttctacctt gtcctgactg ctcggcaata gtacttaaag cttttaattg ctcatcttgt 118020
ctaccaacca tatcagattc acgtatacca cctaagaaag catcttgcat agctttcata 118080
ttatctgaat ttacgccacc tgtatgcata agttgtgaca tagactgttg gtacatttct 118140
tggtcttgta tacctaatga gcgtccacct acagctaact gtttagctcc tttgtatgta 118200
tctgcatcac ttttatgacc tatagaactt tcatatgatg tagccatttt taacacgtca 118260
gttgaattgt aaccaagctt attatctatg gataaatcac cataagtatt tcttactgca 118320
tctatgtcca tattatctga attctgtcct aatgatgtta ccataggtct atttgcttca 118380
gatagggaag caccacgcat atacataccg cctgcaagag cagttactgc catagtagca 118440
tgtgcaccaa tagaaggtaa cctatcttga aacaatttac ccattgttcc tctttgctgt 118500
tctatctcac gctgagcaaa ctgtttttta gcactatttt tatagtagtt gattgacttg 118560
tctaattcag cacctgtttt tctatagact tcagaaagct tttcactttc atcaatcatc 118620
attttaatag atgctgattg ttttttatag tcttcagaac tgatttcacc acgagctctt 118680
ttacctacta aatcttgttg ttgctgtcta taacctctat atctatcttg gttttctttt 118740
attcttctat tgttagcttc tcgttgcttt tcaaaagtgt ctactttacc taattcagaa 118800

```
cgtactctag caccttggtc ataggacatt ctattagagc cttcagacct agatatatga 118860
cccctaacca tattacgatt agctcttagt tgctttgtgt actccttagc tgaactggca 118920
tcttttacta atttattata ctcttctgta acttggttca gtgttttcat ttcttttatt 118980
ctgtttgtta catctgagtc tgaaccaatc ttttgagatg ctactttctc tagttctgtt 119040
tgtgtattgt ttagtgtctt attaagttta ctatatactt tctctacttc agggtcagga 119100
gctataccct ttgtaatatt atctgtttgt atgtcattta aagctctctt taggtcattt 119160
atgttcttag ttacattctg tgtagaacta atagcctcgt ccatagcttt tggtgatatt 119220
aaagatttat cactttgctt gtccataata ttttgtacag attttacttc ttttgctatt 119280
acttttagtt tctctaagaa gtttgttaat ggtgcatcta tgttcttaga ctctaacgca 119340
tccatataca tctctatagc ttttaaactt tgttctaaac tagaactatc accggtcaag 119400
accaacctat aatcgtcatt cattgccaaa cagtattcac cacctaatca aaaaataagg 119460
gtattggtat tataccatta ccctacatgt accaatcatc tacatttttt attgctttgt 119520
ttatatcttc ttgtgttatt tctttactgt caatacctaa actttcatca agctcttttt 119580
gtttttgtct tatgtgttcc atcatagcca aatgttgagt tgttaatcct tcagtttcat 119640
cttctaactc agcttcaact cgtctatctc tttctatctt ttctttctca cttaaacttt 119700
tatctacttg tgtatttaaa tcatctaagt ctaagaaatc aggaacaaca tcaaattcat 119760
ctgtcggcgc ttcgaaccat gatgtgtcta cgtcttccgc tttcatatca tagtttttac 119820
cgtctctagc ttccatcatt tcttttgtat caagattcat gttagctata ataaactcta 119880
tttggtaatc atctaaatct ttaaaacgtt gttcagtagg taatacatta aactcacgca 119940
taatagccca taggtttctt gatagaggct ctttagctat atgtgaaatt ccacctaacc 120000
gttctatatc ttcatttaac tgctttacgt tactagtaac gaaaggacgt cataaagtct 120060
aaccaatcat cccacataat agcaagcgga gttagattat aaatctcctc agggtctcta 120120
aattctttag gtacttctac ccctacttct tgtaaagtag ctaacatctg ataagcatta 120180
ataacttggt cagattggta agcatccatt ccacctaagt atgcagaacg taaagccata 120240
atattacctt gttctctagc attaggtaat ctaattttta ctttgaattt taaatctaat 120300
tcttcaaagt tgtattcttt ctcccataca tcattaacac ctttaattac tttgttaata 120360
acacgctctt tatcttttcg ttgctgatat tttaactcat caatttcttc aggtgtcata 120420
tctttaatat ctttttgttc tttttccaat tctttatcca tcctttatta tgtattcatc 120480
attaatataa cagctaactt atgtttttta tacacataca gtataacata atgtggttat 120540
aactccaaat tacttaacat attcagctac tctttttttca atttcttgta atctttgttc 120600
aattgtttca ctatttttaa gtaagtaaat atagtaatct tgaagtgagt cataatattc 120660
aaaatcaatc gtcaaaatct cttgaccctc aaaatacttt ttagtgattt tacctgcttg 120720
ttccgttaag gttttaaact tgtcaagaat ttgattgatt gcgatagcag ttgtcttact 120780
tgttaaatct acattctgtg ggaatttatg taactcaatt ttcatttctt catgaatagc 120840
tcttaattta tttgtcattt ttttattctc ctctttatta atgtaacctt agtatatatt 120900
atgtatttac ttatgtcaat actttatttt taaattttta tcataataat catttaaatt 120960
taatgttttg tggttatctg taactctgtt ataatacata gttacaactt cacctgtttc 121020
tatctctata actagatatt gataagataa tttattatct acttttacta cataaggatg 121080
tctaacaact accctacgtt gtattttgtt attatataat gtttcattat attctataat 121140
```

```
atctaagttc ttattatgta tgtaatgaac aaacgcttta aaatttactg gtttcttaca 121200
tttacctttg aagtgatttg ttaacttaaa gtaattgttt ttattgtaag cctcttttaa 121260
taagttccta catataatta tttcttggtt agtcatttgt ttataatgct tctttacttg 121320
cctgttttta cttgttgttc ttctgcctga atagaaagtt ttcacagttc atcatctcct 121380
tatataacta tagtattaca gttatttata attgtcaata cctttatgct tattttttct 121440
agaatatttt gttttatctt ttttaattct tgttgttggt ttaattttcc atgttgccct 121500
tgaattactt actttaccta ttgttttcct gtttgtcatt tagttcacct ctttttattt 121560
ttaattataa tacagtactt ctaataaaac aagtataaaa aaagacctaa cttttattgt 121620
taggtcttaa tacgaaattt aagttctagc cttatctgat gctgtcctct ataccctatc 121680
tttcgatata ttttaaaggg agtagactat accataatct taatgtgtaa ctaagactca 121740
cttattatag tcgttgaagc ttcccactct cgtaggcttg cctgcgtatc atctatttta 121800
ctgtacttag ggtttaacct tatactatac tagatatttt ttctgatttc tcaacattca 121860
agcttaccct ttcaggttac tttgtagtta tctagtcttt aagactttca cgcaatttaa 121920
agtgtttttct atgcttgtca ccaaacatag cctctattag ttaaaggtag ctaaactcaa 121980
tttcttctgt tacaatttca tttgtctgcc aagtctcgtt gtagttgttt gctgaaccgt 122040
ttataccccta tctttcgata tattttaagg ggctagacta tgccataatc ttaatatgta 122100
actaagactt acctattata gtcgttgaac cttctccatt ttacaggagc ttggatgcta 122160
attaccaatt atgtagtact taggatttaa ccttatacca tctaactaat tttttctgat 122220
ttctcaacat tcaagcttag tctttcgact tactttgtag tttagttagc tttacggtgt 122280
tctagcaatt taaggtatta ttcaatgcac atcactgtac aaggggtctg tttaattaaa 122340
ccatgatatg aaataataac ttgtttcgtt aagttatcta ctactaagat atcaataata 122400
tctttcttaa gaatctcttc accaagtgaa gcatatccta aatctgcgaa gttttctttt 122460
ttcatacgta aacgttctag tgtaattgta ccagcatatt ttaagtaaac atgctcttgt 122520
ggcataatac taccaatttc gtatacacca gtagttccgt attcacgttg acctttagca 122580
gattgtgctc ttccaactgg tttacctttt accattagca taacggtatt accagtatgg 122640
acagactgct tagcctctga agccatatta attcactctc ctattaaatt taataggagt 122700
acctaaacta ggtactcctt gtcctagttt aggctcttaa tgtttgttgt tggtatacca 122760
agctaacaga aattttcttg aagcttctga tagggtatac aaccattgag attctagctt 122820
cattaccctc gacaataact tgtacgtctt caggtgggaa gtcttgaatt tcgttatctc 122880
gtttcttgcg tcctaagaat gactgtacaa agtctttgat aattgaagca cttgtattga 122940
tagtacgagt accaataaag ttattttcaa gctcaagttt taactcagaa cataagaagt 123000
catttgcttc cccaacagcc atttctgact taacagggtc atttttatca ttaaatgtcg 123060
taacatcgtc tgttaatcta aagaatgtat tagctctatt acgaacatat tgtacggtga 123120
taataccgtt ttcatttaac tcatctaagt ctaatgattc atataattgg tctacattat 123180
taatacgtag ttgcttaaag gtaatagact cacctatagc taaaccactt accaaacctc 123240
cgatagcaga agctaccata taagctggta catgtaactt acgaccattg tccattgtga 123300
atatacctga gttagctact aaagcaactc gtgggctaga taatgatgat tgacgaccaa 123360
acaactgttc tttcgtttca ttaaatcctc cacctagaat agcacgcata ggttcacctg 123420
catcagaacg ttctttaaca aaagaagcta cttctgcatg aacagattgt ttagatgata 123480
gaggtaccat gtagtatccg ccttcatgtg caaatttttc aattttatct gcccatgtag 123540
```

```
ctggtggttc accatttgta ccgccagaaa gttttgttaa ttcaaaaggt gtgatttctt 123600
gaattggtga tacagctgtt acagtggcag actcttcgtg tgcgtctact tctacgtttt 123660
taggtgcttg ttcagatact aatcgttcaa atgaaacaag tccgttatag gctgtttgtt 123720
tctctaagtc accaaatact gcttttacat actcagcttt atccttaata tcaacatctg 123780
tcatagggtc taataagtaa gactctaagt tcttgtctcc aaaaggtgat aacttagctt 123840
caaaatcagg taattggtta atatcgttga tgatggcatt agtagtagcg taagctcctc 123900
ctgttaagtc ataagactta acttctgtgc tattagcttt taatactaat ctttttgctt 123960
tttgtgtttc tttatcatgc tctacagaaa aagtagctgt actttcacta cctttatatt 124020
tgatagtgaa gatattacca atattatcat atgtttcatt aaatctatca tcttggaaga 124080
ttaaatgtaa acgtaatgaa ttactgattg tatttttttc taatcctact tgaatgttgt 124140
tagctacgtt accataaatc tgtgaagtaa ctttcaatcc gcctacttca gctgtagctg 124200
gtttagcatc atctacacgc atagcaaaaa tcttacctgc tgtgtattgt ggattagaac 124260
cccaagctaa ttcaattgca tcaagtaatt cacctgagcg gaatagtctt ttagcttgtg 124320
cgtagtttct taattcatat acggtatcag gtttaccacc ttcagcttgt ccaattaaac 124380
ataaaatctt ttcactggag ctagctgatt taccgatacc tgtactgtct acattaatga 124440
ctgcatgtgg acgagtgaca ggtcttcttg gaaacggttc aactgccatg tataattctc 124500
ctatctctat attaaatttc taattctcta cctaaatact tttctaaaaa tggaataaag 124560
tctttttcat tgaataggta atgtttacct tccatatagg ctttaaaacc tgcaacttgt 124620
gactctttca tattaaacaa ggtctgtgct gtttttaaaa atgtatctat atgtacataa 124680
cctgtaaagg ttttaccttt aggtgttttc ttagccatta tctttttgct cctttattct 124740
tgaaagtaat cttattaata tcttgtgtta ttgtataatc taaatctaat gaacttgtgt 124800
atttaattat agtaggtcta ccaaagatag atgactcacc gtcttggaat ataggtgcga 124860
tatctccaaa tgcaagattt tgtagctgga atgtttgttg ttcttctata ctgtctctca 124920
tagatatcaa tatcattttt aatacggcat ctaaacatct agcaacatct acattatacg 124980
acatacccac aattgttact tgttcttcta tggtaatacc ttttactaac cctttactat 125040
catttgtttt ttctacatat acaatatttg cgttgtagcc ttcataagtc tcattgttag 125100
tataattaaa agatacagtg ttatccgata ctttaacatc atcgtaagaa tcaaacgcta 125160
tgtcttctac tcttattaca ttagaaatag gtttagatac atgaaatact aaacgattac 125220
cttctctttt agctactgat tgttcactat atgtgttacc cgaagcttct agataagacc 125280
cttgtatact acctaaagag tttttaacct cttgaccttg tcctagttgt attaggtaat 125340
gagcttcgta gttgttttta aagctaggga aattgaaccc taccgttact tcgtgctttg 125400
cgttcttacc gcaaaaagcc tctttgaaca tttccctagt ttgataatca aagtctttta 125460
aaacttcatc tataatataa caattactta gtactgtatg taatctgggt tttatttgct 125520
ctaataaata tgagtctact gatgttattg ccatcctact tccataacct ttctacatta 125580
aatttttaat tttccaattc attaaattcc taacatattt taatgttgtt ttagagaaat 125640
tattctcgtt aactttgtct ctatttaata tccatgaact tgcaggtgac ttactagaaa 125700
ctgttctaaa cataaaataa ctagattttt taccatttct tacttttgtt attctgccat 125760
tactgctagg tacttttaaa gaaggatggc ttatgttatt acgtctacct tctagataat 125820
cagtaagagt agatactgaa ttacttgaac tgcctatttt taaagacctt aaatcttggt 125880
```

```
atgttttatt attcatttta cttgttttta ttctaattgg aaccgttaga taccaaccac 125940
catcttttgc tctttttttc ttagatgaac gtgcaaaagc ttttttaagg tctattacac 126000
ctttcttctc tagtttctgc tcagttattt gtaagtaggt aggcatacgt ttgacactca 126060
cattatctac ttgtaatgct gtagcttgta atctatctaa aatatcagaa cgcatagcat 126120
ctactgttct cttacctaca tttttatagc tcttgtctct aaataactta ggtctagttg 126180
cttttatagg cattatagca ttcccccaaa gaaaccacct gaatgattat ctttagattc 126240
tttttagggg tcttctacct gtatctctaa gtcctcttct ataccatcat taactttaaa 126300
tggctcaggt agtacaataa cgtcttccct ttttaataat aacttctgag gtaaattttc 126360
aaactttgta ttaggttgat taaatttagt atattggtat cgactttctt ttaatatatc 126420
tgatactaca tatctaagta ccattaaaat atttaaggat atagttttgt tttcaaactt 126480
agcgtccatg aataatctat tgttctctat attatagtca tcttcataaa cattaccatc 126540
gttagatgta ataaaggtta cttctttgac atcatagtat agaggtatac ctttttgtat 126600
acgctcttta gtaacatggt atataagttg ttgtggcatc aatacttcag gaacagtaaa 126660
cctgtctcta taagatactc gtttttctaa ttgtgtagtt cctatagctg taccagtatc 126720
taaaattcct atatctaaat tgttagttcc tttttcttga gattggatag ccattattgt 126780
ctctttagga ggtaaatagg caataccttt accgtgacac ctaggacaat ctactctagg 126840
atgtcctgtg tcagggttaa ggcaaggaca aaagtaagcc ctttcccaca gtacctttat 126900
acctctatca ttgacaaatc ttctcatatc cttagtgtca aactctagtc tagctgtaga 126960
taacttttgt tcttgttcat ctgcttgtgt tgtagatgta tacatagtag acttattaat 127020
tatattagaa gtattattat tagtacctat cataaaaggt ttttgcattt aatatctcct 127080
tcctactata tgcctatcat attggagcca aagtaagatt ttaacccagc taatagctct 127140
tttatatctt cattaatttg tagtatctga gcacttgctc caccatacat agcagattgt 127200
gtagtaccta ttgtttctgt aataccatct acatctagag ttttgtttgc tattcctgca 127260
ccgataatga gattaccata tgttaattaa attaacttcc tttgtaaaat aaaaggcatt 127320
atacattcgg gttatggaac cctactaaaa gcaaacatat tattggtttt gttcttttaa 127380
ccattgggaa ttatggtaat tttttaaatt aatacttgca tttatatccc tatcttcttc 127440
atatccacaa gcattacatt taaagacttt atcacctaac tgtaatttta aagcatttct 127500
ttttctttct ccgcaattac tgcatatttg tgatgatgga taataagtac tagctactgt 127560
aaattttata cctctatctt cacatttata ttgtaattgc tgtctaatca tatagaaatt 127620
agaaaactgt atttgttttc ttttttgtcc tgtatatcct ttgtctttta ttaaatcacg 127680
aactcttata tcctctacaa taatctcttt aggatacttt tcaacaattt cttttgttat 127740
ttcatgtaca tgatttttac ggatatttga catttttcta taaactttag ctatcttatt 127800
ttctagcttt aaaacattat ttgttttggt gtgattaata tcatatttat tacttaatct 127860
tttctgtagg tcagataatt ttttttctaa ccttttcatt ttcttggaat aaataatatt 127920
accatatatt tttctgttag aacaaattac gtgtttttta ccactaccta agtctatacc 127980
tatgacttcg ttagtattat ccttttcttt cttgtattga ttatctactt caattgaaaa 128040
agatatatac caatatttac catcatagta acatttaggg tttaaaggtt taatgctttc 128100
attctctagt actgatttat tatttttata tgtaccatta gaaattctta agtaacctaa 128160
tttttcaact ttaacatgtt tttctttgtt aaagtgcatt cggtcatatc taataggaaa 128220
cctcttagat tccctttttct tagacttaaa tttaggtttt ctaatttcat gattatgata 128280
```

```
ttttattaat gtttctctta agtcatctat tttaccaact aaggtttttc tagatacttc 128340
atttaagaaa ctatacttat catcattctt tatttctttt aatatagaaa tcatattttt 128400
atggtctata tatttaccgt tatcgagagc tttccaatat ctttctaaca tataattata 128460
aataaatcta gaatggttta catgtttcca cattaactct tcttgttctt gggtagggtt 128520
tacttttagt gttatacctc tataaaattt attttccgtt tttttcattt actttcacca 128580
ccttatatat tatatctata atataacata tacttggggt aatttcaata ggaagttttc 128640
atttaattaa cattgtttcc ttacttacgc tactaaataa gtctaggtca attcctagca 128700
ctccttttca agacgtgtgc agactatttg ttatccctaa gactagggta aagatttttc 128760
ttctcccaat cacttggagc tttacttctg tcgtctatac agaatagtcg ttgaacgtat 128820
tccttatcta ttgacttagg actttcgatg ctaaacttcc attgctcttc tctttaggat 128880
ttaaccttag agtatctaac taatttttc tgatttctca acattcaagc ctatcctttc 128940
agattacttt gtagtttagt tagctttagg atttcttagc agttaacctt tgaaaatgtg 129000
caacttacgc tacacacagg gtaatatcat cgtaacccca tatttggtaa atctctttta 129060
gtgcatactt aataactaat tgctctaatt ctggtggtac ttcccatggt ttagttctac 129120
ctgctctttg tctaggtaac ataccactaa tataatctaa tgtaatcatt tgaggtgcaa 129180
aagttgctcc acttggtggg tacattcctg ctaattgagg atatccactg aatacagcat 129240
cgtaagacat agattgaccc gtctgcatta aagctgtagg gaataactgt acgtgacctg 129300
ctaaatgctc cactttccac cagttagctg gataatcata cataggtcta ccattaaatt 129360
gtagttgtaa attttctacc tgtaatatag gtttttata tgcgtgtaca aacatataac 129420
tattaaattc tgtttcgtag taatctctca tttcatgttg taagtcaggt aaaatagata 129480
tatctaaagc tctttccgct ttacctatag ctctttctaa tatatgatta taaaaatcat 129540
cacccatagg ttgtcctgta tcggggtttt gtactgttat accaaacata taggctttca 129600
cagcatctgc tgaccaacca taatcagcta gagtaatact atctaattct cttttatcta 129660
tatgttttgg gtttccagat gggtgataag gatactcata tgataaagag ctttcgtaag 129720
ggtctaaact accaccaaac atactgttta ccattttatc aacctactta tcttcttttt 129780
tagttgtttt tttagttggt ttcttctctt ctttttcttc cttaggcttt acttctttct 129840
ttgttgtttt cttgtcttcc atatgtgtaa aacctggtaa attagcaaaa tctttttctt 129900
gtttagcagt tagtccttta actacgcctt tatcatctac ttctacttga ccatgtacag 129960
tagccatttt aatattttt aatttataag ttaacattga tttttagatt cctttcttgt 130020
atactataag tagtaataaa aaaggagcaa ccccttaggta tactccttat tctattgtat 130080
tcaattttta attgtattta ctattttaat gcaaggtaac ttacgttttt aatacgagcc 130140
cattttttag gagcacgtaa cgctaaagca ccataccata atactgcaaa tgtaatacta 130200
gcattaattt gagctaatgg taatttcatc attggtaata actcgaacaa gtgtaatact 130260
tgtggtgaca tttcaccaac gaatacgtct gctgtttcag gtaatgtttc gtttttatca 130320
acgaatacta aagaaccatc ttcttgtgca tctttaagtg ctacacgttt aattaagtag 130380
tacatacctg tttctttacc ttgacggtaa atagatacga attgtgggct ttgttggtac 130440
atagagttaa cagtaatctt taattctact ccatctgtag catttgttac tgtagcaact 130500
tgtgcttctg atggtgctga ttcagcttca tcagagtgaa caactacttt ataagataaa 130560
cctgcacggt cttcttcttt agtaaattta cctttttggt ctgtttttac agtagcagtt 130620
```

actgtagctg gttgtggtgc atttggttgt gggattaaag tttcatctag gattaattca 130680
ttttccatta cagtagaacc atgtaatcta atgaatccac gagatgaata gaatccgtta 130740
acactgaaac cagtatttac attaccacta ttgtcttgca ttaattgcat ttgtcgacct 130800
aaaatattag taacaaagtc agaatgtaca ccgataggca tataagcatc tgtagctgta 130860
ccaaaacctt taccgatttt aactgaagct aagtttaata atttctcatc taagtgagca 130920
cctttagcgt cgataacgtt atcagcatca attaatttag ctaatccatc gaactctaaa 130980
ccttctccac caacttcaga agttaagctt gcgtcaccat agaatgaagc ccattcaatt 131040
gttttagcaa caactgagat agcatcttca gtcaagattt gacctgggtc agcaatgttg 131100
tttactaaac tagatgccaa tgacatattt ttagtatcag aaatatattt cattgtaacg 131160
gtcttttgac ggatattagg gtctgaaact gacgctactc cgatttcacg tacaaaacga 131220
gaatggccta ctttaccatg acgtaagaaa acatcatatt taattactgt tgattcagct 131280
ggtctacgag caacatcacg atagaatact aaatcattat ttccccatgt aagcatagtg 131340
atttggtcgt ctaaaatttc acgacgtaaa gcacctgcat ctacttgtgt ttcaggagtg 131400
atgccatatc cagtttggaa ggatttcgat aatttttctt gtaattcatc agcaactgca 131460
tgttgctttt ttgaaagttc attttggttc atttatatat atcacctttc atatatgctc 131520 ttttttatt gttttatttt acacactata atataacaca actttgtttc ttaattaaag 131580
attagcaaat tcttttacaa tattaaagtc tttttcactt gcttgctctg gattgttgcg 131640
gatatttaag taagcttgat aagcattcaa tacttctgaa cgattcgtat gtgggttttg 131700
agatttttct ttataggtac tcatgaattt ttcacggtct tctacagata agtctctact 131760
ttcttcttta acttctactt cttgttcttc tttatcttct gtagtttctg cttgttcttc 131820
tgtttgtact gatttagcta cataaccaac tacatcttgt tcattcgaag tgttattagt 131880
cgttacggat ttttctactg cttcttcttt atcttcttgg ttgctctcaa ctgatttaga 131940
aacttcttca ttagaattaa ttttatcagt taaatcttga atagatttag ttacttcttc 132000
taaatctgat ttagtcacat attgttcatt ttcttttta atgtcttgga atgatttcaa 132060
gatagtacgg aaaccatcta caatatcttt atcagaaata gatttagatg ttttctcttc 132120
ctcttcttca tctttttctt ctttttgtc ttttttattt tttcgtttct cgttgtcttt 132180
gtcttctgtt ttagtatctt ttttatctac agggtctttc gactccttag ctgacttaga 132240
tacttcttct tctagatttt cttcttgttc atgtgcttct ttagcatctt ctttagcatc 132300
ttcttcagta acctttgcag gttcttgtgg ttcttcttta gcttctgcta cttgctcttc 132360
tgtagcttct acttcatttt taatttcttc tttttcttct gttttagtgt cttctgtttt 132420
atcttctttt acttcttctt tagactcttc tacagatttt gatacttctt ctttgtctaa 132480
gttatcatat tcttgtagaa tattttgtaa ttccgtaggc atataatata atcccctatt 132540
ctaaattttt tttattaata ctcataactg ctatctcagc atcttttctt gatagtcctt 132600
tggctaattg taatgtaata actgattctt cataacccat attattagat ttagttaagt 132660
cctctactac attattccaa atatcattat actctttaac atctttaatt tttgttacat 132720
aggttaaatt agtaatagag cttgctaatg actctttacg taaggctcct gcatctactt 132780
gtgtgtctgg tgttgtttcc gttccagtaa ggaatgattt aacaaaactc tcccatgtag 132840
cttcaggatt agctgggttt tttactagtg ctacccctgt aatcataagt tcatcaacaa 132900
ttctattgtc atttatgtta cgtttcttaa cagcgccttc tatagaaaac cctaaacgtc 132960
taccactacc tgacttttct agtttctcag ctaggtctaa catttttata acattttcat 133020
catctttcca tagtttagct tctataaata aacctttttc taaatcaaca taacagttat 133080
ctgtaggtat acctactaca ttatcttgtt gatgttcgta gttaatatat ccattttttt 133140
taaagtattc tatatcaata ccttttggat ttataatgtc attctgcaaa tcaacagctg 133200
gtgtggaagc ccaaccagat acgatagaat atttatttgt atcatcttcc gtatctatgg 133260
atttctttaa gtccatagga acaaaagcat taaatttcat ttcttccaaa gtgattatac 133320
acctcactta attgttattt tatatgtaca tacataatat aacaaaaagt atatcatcaa 133380
cattattcat tactacacac atagtataac atagtataaa tgtagctcca aattaaaaaa 133440
taacaaccta agtattaatt aggttgctaa tattatctac ataaagtcgg aagatttctc 133500
accttttctt ccttgtcctt tatttgatgt ttgtgttcta tatacgttat catcaccttt 133560
taactgatta tctgttccta catcttgatt agttgtttct tgtttactat catcagtagg 133620
ctcatcagtt tgtggttgtg tataactcat aagtaattga agtctttctt tttgtttagt 133680
atctaaatat tggtcttttt gtatttcttg tgctgtactt tgtaaaaatg ctgaatcaag 133740
aattacatct ccaccatcta tcggttttaa tccttgttct tctcttgctt catttacagt 133800
tttatatact tgtacttctt tttgtaagat actaagctta tctaattcag acttagtatc 133860
tcctccaaca aattggaaag tatacttatc accaaattca gatataatgt gtctgttaat 133920
taattcttct ataaatctta atagaggttg taaaccttta ttcatagatt gttgttgctt 133980
cttagcaggg tctgactcat tcaatgtaga accgcctttt gaccctgtag ctcctcctcc 134040
tctattaggg aatcctattt cagaagggtc tataccatac aaagcagaaa taatattgat 134100
taaaaagttt aaccatttct caaattgcat atcatttgct gttggtgtca tattaacaaa 134160
cttaacatca tcagccatca tcacggggac ttgccagcta ccgtttatac ctgaaaaact 134220
agatttccat tctcttttaa aattttctaa cgcatgttga gattgctgtt ggtctgctct 134280
aatctgtaag atgcctctag ttgttccacc atgactgaag aatctatcgt taaaactttc 134340
agtattatta taagctataa attctttcat tgcaatctct acttctgaca atccataccc 134400
actagagttt aagtctgacc tagggttcct aatacccatg acaagttctc tgcttgtaaa 134460
actagctact acttgcttat ctatgacctg tacaaaacga ttgctacctt taattatctt 134520
accgttttta tcagtagcat aaaaaatggt gctggggtct actgcaataa acttctccat 134580
cttagttttg tttttaggac taaaaacttt ttcgaagtta acttggtcgt acgtgtaagt 134640
atctcttact atttttttac aaaactcttg gaatgaatcc ctgtctatat ctttatctgt 134700
acctgtatta agaataaatt cttcaatacg tttcatctgc tctttttctt taataccagg 134760
tgtagcgtct aagtctttta atttaacttc aaaaccgact cctctttctg aatacctagc 134820
aggtttacag tatgtagata cttgattagc tcttgtaata attatagcat ttagtataga 134880
gttattacca aatttcttta acacttcatg taagttatga gcattcctca tatagctctt 134940
cttatctcta taatcaggat ttgtatccat catttctaaa aatggttctg cataagcttg 135000
ctgtttacca tatagagatt tagtaatttc ttgcatctct tttgtatctt gttctatttg 135060
tctaatgtta gcttgtattc cgtcatctac aggaaccata aggtcttcag tatcttcttt 135120
atacatacta cctaacctta gacttttaaa taaatcaggc aactttttat ttacctcctc 135180
gaatagtagt tagtataaca gtgttattat aggtaatgtc ttggatatgt ttaggaatat 135240
ttatctttac ttcgaatggt tcttctatat aataaaacat tttcttactt tccataacaa 135300
tatcataatc ctctaacaca atattattat ccttatctac caatattact ttattatcct 135360
ttgtagcttc tagtaccata tatttaactt tatcaatagc aataaacata gctacatgtt 135420
taccacctat ctgtctataa taatccacta cttctatcca attatctgct aatccttgac 135480
cttttataaa gtcttttgct tcatcccatt tatcgtcttt tgaaaatagc aaatgcttca 135540
atcctttaat tttttatttt ttaaattcct agtatttaca atcttcataa ctaaaaacca 135600
aaaactgcct attacagctc caaagaaact tataccaaaa acaattaaag ggttattaaa 135660
ccctacatac tgctctgtat tctcaataga gtctataaca tcattttta taatgattga 135720 cgtggcttga aacattgtta atactacata agaacctata gaaattatag catatatcaa 135780
gtatagaacc aacttactac ttttttcagt tttaatatac gcaaatacca ttagtgctag 135840
tagacttaca caagcaaaaa ctacggatat agctgtaagt acgtttaatc ctaccaaaaa 135900
atcaccaact ataatgttta ttttattact cttttaatat agcaaaaaaa ggagaggtta 135960
tccctctcca ttagtatcat tactttcatc tacaggtgtg ctaggttcca atggaactaa 136020
aggtatcgta gtatctgagc taggtttttc aggttctata ggtttttcag gttctatagg 136080
tttttcaggt tctataggtt tttcaggttc tataggtttt tcaggttcta taggtttttc 136140
aggttctata gggggt 136156

<210> SEQ ID NO 4
<211> LENGTH: 17629
<212> TYPE: DNA
<213> ORGANISM: Artificial Sequence
<220> FEATURE:
<223> OTHER INFORMATION: PN1957

<400> SEQUENCE: 4
aatccactta tcatttcttt actaaactta taaaaactgt gcaacttcta ttccaactta 60
tctaacctat tacatattaa tcaaatacat ttattataca tctattgact tttatcaaaa 120
tttatgattg gaacataaaa tctaatttct tctattaaat agtagtttta aattatttaa 180 actttttaa gaaaaactgt tgacaaaact tttaaacgtt tgctatacta attatgtaat 240
caaaacaagg aggtaacaaa aatggttaat gttgataatg caccagaaga aaaaggacaa 300
gcctatactg aaatgttgca actattcaat aaactgattc aatggaatcc agcttataca 360
tttgacaatg caattaactt agtagcagct tgccaacaac tattattaaa ctataacagt 420
tctgttgttc aattcttaaa agatgaacta aacaatgaaa ttaaaccaga atcaatatta 480
tcttacattg ctggtgatga ccctatagaa caatggaaca tgcacaaagg attttatgaa 540
acgtataaca tttacgtttt ttagaaaagg aatgatataa taatgaaagc tgatgacatt 600
gttgttttac gtgttaaagg ttatatactt cattacttag atgatgataa tgaatatatt 660
gaggaatttg ttccacttca cgagtatcat ttaactaaaa cgcaagcaaa agagttatta 720
ccagaatcat gtacactatt atccactaca cgtacaacga aaacaattca tgtttattac 780
aatgatttac tacaaatcgc aattgcagaa agcaaataat ttaaataaga ggagaaatta 840
aaatgacaaa cgtaaaagat attttatcaa gacaccaaaa aacattagcg agatttgaat 900
ttgaggaaaa agaaagagta tttatcaaac tatcagaatt agtagaaaaa tacggtatga 960
aaaaagagta tatcgttaga gcattattca taaacacaga atcccaattc ggtgaacagg 1020
gtgttattgt cactgacgac tataatgtaa acttaccgaa ccacttaaca gagttaatta 1080
aagaaatgag agcagacgag gacattgttg acattatcaa cgctggtgaa gttcaattca 1140
caatttatga atatgaaaat aaaaaaggtc aaaaaggtta ttcaatcaat tttggtcaag 1200
tatcatttta atacaatttc atagggata tttatcccct atttttatga ggtgctaaac 1260

```
aatggaaaaa atatacactg ccgtattatt atacaatgta tcaattaatg aaacatatga   1320
acatgaaatt gaacaattcg aaaaaataaa taaagttaag gtaatatata gttattttga   1380
cgcaaacttt tacaaaaaag gtgcatataa tctttgtgta aaatatatta aggagctata   1440
aaatgaaaat tacaacaaca ttaaacacaa acaaattaat taattacatt ttaactaata   1500
gagagtgttt tataaataaa ataacaaaat ttacatcact aagtgataaa tgtgtcgttt   1560
ttgttagata cggtgatatt tctattgaat actatgatag tgatacaaaa aacaataatg   1620
atttatttac tttagacatt gacgttgata ttaataaaca tgtttttaat tttcttgtgg   1680
ttttttatcg agaacattta aacccactat ataaaaaaga agttttcacg ggatgtacta   1740
ttgatgatgt attagaacat tttgagaaac cattagaaag ttatattact attatatacc   1800
aaaaaaaagt catatacggt aatgggaaag tgattgaaca tgaataacct attaaacata   1860
gccattgtat tccttttagc atttttaatt acactgatta tacttatgac actgcatata   1920
cgcgtgtcat ttggtgtttt attcactaca ttgattatat tctatattat ctttttaatg   1980
gttatttacg ctttatatgg aggttgatat taatgccaag acatacgtct gaaatggata   2040
aatggaaaaa agaaagagaa gctagaaaag agcaagaaaa agatttattt ttaaacgatt   2100
ttagtactgt taattttaaa tttgatgata aagatttaca agaggcgtat atagacgcat   2160
ggaaacattt cgcacatctt ccctattttc caaaagaaag atacgtatca tatgcaaatg   2220
ctgtatcatt ggtaagaggt aaaagacatg acaaattaaa tcatatactt gaaatatata   2280
accgtaaaga tgaatctaat aataaaaacg ctaaaaagca taaatacgct ttatatgatt   2340
tacaagctaa aaataataat tcttcaatgt ataaatatat taaagaaatt gatactttat   2400
ataaagaaat tggtaaatct gatagaccag tgacaactat cgatgatgaa gatgtgaggt   2460
ataacttttt atattatgca acatttgact aataaattta atactgtaaa cgatatcata   2520
aactattaca aggagcaaaa acatggtaaa acaaaaccgt ttagacatgg taagagatta   2580
tcaaaatgct gtcaatcatg tcagaaaaaa aataccagat aactataatc aaatagaatt   2640
agttgatgaa ctcatgaatg atgatataga ctattatata tctatttcaa accgttctga   2700
cggaaaatca ttcaactatg tttcattttt tatttattta gctattaaac ttgatataaa   2760
atttacttta ttatcacgtc attatacatt acgtgacgct taccgtgatt ttattgagga   2820
aatcatagat aaaaacccac tattcaaatc taagcgtgtc acgttcagaa gtgctaggga   2880
ctatttagct attatctatc aagataaaga aattggtgtg attacagatt tgaatagtgc   2940
cactgattta aaatatcact ctaacttttt aaaacactac cctattatta tatatgatga   3000
atttttagca cttgaagatg actatttaat tgatgagtgg gataagttaa aacaatttta   3060
tgaatcaatc gaccgtaacc atggtaatgt tgattatatt ggttttccta aaatgttttt   3120
actaggtaat gctgtcaact tttcaagtcc tatattatct aatttaaata tatacaattt   3180
attacaaaag cataaaatga atacatcaag actttacaaa aacatttttt tagaaatgcg   3240
acgaaacgat tacgttaatg aaaaacgtaa tacacgtgct tttaattcta atgatgacgc   3300
tatgacaact ggagaatttg aatttaacga atataatttg gcagatgata atttaagaaa   3360
tcatatcaac caaaacggtg attttttcta tattaaaact gacgataaat atataaaaat   3420
tatgtataac gttgatactt ttaatgctaa tattattgtt ataccttata caaaacaata   3480
tgaattttgt actaaaatca aagatataga tgacaatgtt atttatttaa gagaagatat   3540
gttttataaa gaaaacatgg agcgttatta ttacaatcca agcaatttac attttgataa   3600
```

```
cgcttactca aaaaattacg ttgttgataa tgatagatat ttatatttag atatgaataa   3660
aattataaaa tttcatataa aaaatgaaat gaagaaaaat atgagtgaat ttgaaagaaa   3720
agaaaaaata tatgaagata actatataga gaatacaaaa aaatatctta tgagacaata   3780
tgaattataa aggtgtgtac gattatgggg ttactagaat gcatgcaata tcataaacat   3840
gaacgtcgaa tgattttata ctgggatata gaaacattag cgtacaataa agttaacgga   3900
cgaaaaaaac caaccaaata taaaaacgta acgtattcag tagcaattgg ttggtttaat   3960
ggttatgaga ttgatgtaga agtatttcct agttttgaat cgttttatga cgcattttat   4020
acgtatgtga aacgacgtga tacaatcact aagtcaaaaa caaatattat catgattgca   4080
cataactgta ataagtatga caaccatttt ttacttaaag ataccatgcg ttattttgat   4140
aatatcacac gtgaaaatat atatttaaaa tctgcagaag aaaacgaaca cacactaaaa   4200
atgcaagagg ctactatttt agctaaaaat caaaatgtga ttttagaaaa acgtgtgaaa   4260
tcgtctatta atttagactt aaccatgttt ttaaatggat ttaaatttaa tattattgat   4320
aactttatga aaaccaatac atcaattgca acattaggta aaaagttgct tgacggtggt   4380
tatttaacag acgaccaact taaaacagat tttaattaca cgatatttga taaagataac   4440
gatatgaatg atagtgaagc atacgactat gcagcgaaat gtttttcaaa actcacacct   4500
gaacaactta catacattca taatgacgtg attatattag gtatgtgcca tattcattat   4560
agtgatatat ttccaaattt tgactataac aaattaacat tttcattgaa tattatggaa   4620
tcgtatttaa ataatcaaat gacacggttt cagttactca atcaatataa agatattaaa   4680
atatcatata cacattatca tttccatgat atgaattttt atgactatat caaatcattt   4740
tatcgtggtg gtttaaatat gtataacact aaatacataa acaaacttat tgatgagcct   4800
tgtttttcta ttgatatcaa ttccagttat ccttatgtga tgtatcatga gaaaattcca   4860
acatggttat acttttacga acattattca gaaccaacgt taatccctac ttttttagat   4920
gatgacaatt atttttcatt atataagatt gataaagatg tatttaacaa tgatttatta   4980
attaaaatca aatcacgtgt attacgtcaa atgattgtta aatactataa caatgataat   5040
gattacgtta atatcaatac aaatacatta agaatgattc aagacattac gggtattgat   5100
tgtacgcata tacgtgttaa ttcgtttgtg atatatgaat gtgaatattt tcatgctcgt   5160
gatattattt ttgaaaacta ttttataaaa acacaaggta aattaaaaaa taagattata   5220
atgacatcac catatgatta taaaattact gatgatatca acgaacaccc atactcaaat   5280
gaggaggtta tgttatctaa aatcgtttta aatggattat atggcatacc tgcattacgt   5340
tcaaatttta acttattccg tttagatgat aacaatgaac tatacaatat cattaacggt   5400
tacaaaaaca ctgaacgtaa tatattattc tctacatttg tcacatcacg ttcattgtat   5460
aacttattgg ttcctttcca atacttaacg gaaagtgaaa ttgacgacaa ttttatttat   5520
tgcgatactg atagtttgta tatgaaatcc gttgttaaac ccttattgaa ccccgattta   5580
ttcgacccga ttgccttagg taaatgggat attgaaaacg aacagataga taagatgttt   5640
gtactgaatc ataagaaata tgcatatgaa gtgaatggaa agattaaaat agcttctgct   5700
ggtataccga aaaacgcctt tgatacaagc gtcgattttg aaacctttgt acgtgaacaa   5760
ttctttgacg gtgccattat tgaaaacaat aaaagtatct ataatgagca aggtacaata   5820
tcgatatatc cttctaaaac tgaaattgta tgtggtaatg tatatgatga atattttact   5880
gatgaactta atatgaaacg tgaatttata ttaaaagacg ctagagaaaa tttcgaccat   5940
agtcaattta atgatattct ttatattgaa agtgacatcg gttcattctc acttaatgac   6000
```

```
ttatttccag ttgaacgttc agtgcataat aaatctgatt tgcatatatt aaaacgtgaa   6060
catgatgaat taaaaaaagg caactgttaa aataacagtc gcctttttcg tttgagataa   6120
catgaaaaat gtgtacgaaa attgattatg ttttgtattt tatttactag cattactagc   6180
atgttttcat tataccacag ttaattaagc tataccacta aagaatacaa tattatcacc   6240
tgcattatgt ggtacaccat taatgagtgt atataatact acacgtgacg gtgcaacgta   6300
cggcggtaca ttatagttag cgactaagaa tgacccatca tcaaatactg ccacgacaac   6360
accagtgtga ccaataccat aagcagttgc ttgtaagtag ggtggtttac tagagaaacc   6420
atatccaaca gttggattat gtgttgtttt tgctcctaac tttttataga cgtaccatac   6480
acgttgaccg tttgtcactt gaccgtcgtc tgtcggttgt cttttaccat gtaattgtga   6540
catatacgcc catgttaatt ctgtacactg acctgcatta cccgtttgag gaaatatgtt   6600
acctgatttg tataaatatt ctttttgaa taaaggtaca ccaattgctt ttttatattt    6660
ttctggtaac tgtgcgtacg tccagttacc accaatcaca cgaccacttt ttccatttgg   6720
tttgactgat ttaccactaa ttggtttatg gtcaccgtca tcatcagtag gattagaact   6780
actaccccca ctatctactt gcacgctatc aatcagtttt tttaatgaat cgagtagacc   6840
aatcgtcatt ttaatatgat atgtgttgtt aaatgttttt tgtaatgtaa aataatcatt   6900
actaaaaaat ttgtcactac ctatactgtg tacatcccat tgtaatgcgt cttgtacttt   6960
ttttaataat tcttgcatag cttgttttgc taaagcgagc agtgaactac cactgtcacc   7020
attactacca ctgtcagacg aatcactagg tgaaccacct ttaccgtcta atttaccacc   7080
ccatgctaaa atagtatttg caccgtctaa aaaaggatta ccatagtttt gtactttatt   7140
atatgacgct ttcaaaccta gggggtaata tgccgcccaa gtagccgctg ctgttaatgg   7200
aatatacgca cgtccgattg tacctgcttt catattttta gcaaaatctg cattaccttt   7260
tctttgtacg tcttgaggta caaagtgaac gatgttacct gcgtcatacc aagacggttg   7320
tcctgcttgt tttgattgtg atactaattt tcttgcaatg aatttagcgt ctgttaaata   7380
gtcacctcgt gcagatgtat ggttcaacca acctaaacca gcgctatacc cttcattttt   7440
ttcatataca gcaaaaagag taggcgacac acctatctct tttactgctt ttaatacttg   7500
tcttatttta ctttcattac caccaagcca tacattaaag cgtccatacc cttttacttt   7560
agggactaac tggtcaatgg ttaaaccgaa atcgtcatta atataggaat gtgtaaattt   7620
atctatcttc tcttggtcgt tcatttttat cactcttttc agaatcattt ttaattactc   7680
ttaatttatc tttaatttgt tctggcacta atacgtccat ttcagcgcaa ttttccacga   7740
tagatagccc ctcatttgcg atataataga aaatcgtaat catgagtaaa ccacctttta   7800
attgtaaaat ttggtcgatg atgttagcta aaatgataat gcagaatatg agtaattttt   7860
tagcgaaacc tttcattgat tttttagacc atagattatt atttttaatt gctttagcaa   7920
aaccagttac aacatcaaca atcatcaaaa caaataaaaa atatagtaac tttaaatctc   7980
ctgcatatat gaacatatga aatgcttctg tgtccgtaaa tcttaatttt acctcattca   8040
tttttataca cctgctctaa atttattatt taacgggttc tgtaacattg gattacctga   8100
accgtcatta tgccaaaatc tcacgccaga ttccaaaatt gcttttaatt gctccattaa   8160
catcgggtcg atgtcacgta tagtatacgt acctgtacat tttaaatagt tgcaaacggt   8220
catactgtta attggttcaa taaatgcgtt atagtcattg acttcaaaac caaataacat   8280
ataatatttt tgtaagaatg tgatttcttt tggtgacggt acactaatct tcatcgttaa   8340
```

```
accattaata ctatttgcga tttggaatgc gttgcccatt tctgattctg tcactgatgg   8400
aggttgtaag gctaaatctt tatattctgc ttgttgttgt ttgtagaaat tatattcttc   8460
attaaactta ccaaataaag cagtaggact taaattactt gctacactca cagcgtcata   8520
aaatcgtgat ttcgggtcac tgccatttaa tacattatca atacgatttg taattaattg   8580
actttctgca ttcttctgtc tatttgcttg ttgtgattgt cctaagatac cattattgat   8640
taatattggc acttgtgcaa aactattaaa tgtgatattt gtgtttaaga atgaacctgt   8700
atcaatcaat atatctttat tttttgcaag tatcggtcta tcattttctg cactgttata   8760
atctactgga tatacacgta cttcattatg ataaccaatg attgactttg tacgtaactt   8820
aacacctgtt ttttgtgata ttttaccagc gtcaagcaac attgtatttc cattccaatc   8880
ataaaattca atggtcatgt actcattacg tatcatatgc ttaaattcat cttttttaga   8940
caacatcatt tcttgaagct ttgtgaaact taatgataaa tcgtttaaac tccattcttt   9000
tgattttcca ccttgtttta acgtctttaa tccagtaatt ttttcacttg ttttaacgtc   9060
ctctaaatct tttgtattaa taaagtcttt aggtaacatt tgaacctttt gaaagttttg   9120
tgtaatccac ggataagcac tcattttatc cataaaattg ataaaatccc cgtattccat   9180
gacgtataag ttaactggtg atgtgatatt gtcatatatc gtacccttag acgtatccaa   9240
gttcggttct ttttttgtac caaatttctt tgataaatca gcactggatt gaaataaaac   9300
taaattttct aaatactgtt gcatttggtt atacacatag tttttattcg atacttttaa   9360
cacatcatca ttgttacgta acattggtaa catatagtta tacgtgcgtt ttgataaatg   9420
ttggcgttcg atattaacgt ttgtgagttg ctctaataca ttgccttgtg tatacgtcat   9480
aatagtatca ataacaaaat atattttaac cacaacgtca ttcacgtatt cgatttggtt   9540
cacaaatgcg taataacgtc tgtcctcaaa atctgataaa aacgtcatat agttaatccc   9600
ttgtgcgtca tgccactgca tatcaacatt gatttccatt ctatcacgta taaaattata   9660
cggttgtttt gaatagtcta acgatttaaa atgacgacca tttaaaaaat aatcatcacg   9720
ttctttatta ctattaaaat gaatcgtatt ttgatagtct gtaaacggtg tgttatagaa   9780
aaacttaaaa ttcgttaact ttctcatatt ttcctcctaa taaaaaatag tcgtataaat   9840
aatttatacg actattatat catttttatt caatgatttg tgtatctatt gcaaaacgtt   9900
tatcaccatt tgttaaatca ctatcactat aatttgatgt aacaaaatgt aattcattat   9960
taaagtttaa atataatctt gtattaatca ttttattatc aatcgcacat tgtgtgtagt  10020
gatgtgttga ttttaaatta gcattaatcg tacctaattt aatatcaccg tttttcttaa  10080
tcccttttaa taccccttt aattgtatgg ttttaacacc attaattgtg acaatacgat  10140
attgcggtgc cggataacca ccgttgctat cacttgcaac tataccactt tctagcgata  10200
tatcttgcca acctgtatcg ttaaattgta attttgcact gttaattttt tgatcaaaat  10260
tttgttcaat ttctgtttta gattgtgcaa tttttgtatc aatatttaag ttatccactt  10320
ttgttgataa actgttaata tttgattcat ttttagatgt tttttgtttt aaatcactaa  10380
tatcattatc gtatttagat aagtcaatat gaccgtttcc gtcaacaact ggtctatctt  10440
ttaattcttg aatatctttt tcaatttttg atattttatc attatttgtt tttaaagtag  10500
cgatgtcaga tttaatagaa ttaatatcct gtgtataatc tttttggtta atgttattaa  10560
tttttgtttc taattctcta attttatcaa ggttagcatt tgttttaata tcattaatgg  10620
attgttctaa cgcttcaagt ttcccagcac ttgaattttg ttttaactga ttaatatcct  10680
gttgcatttc ttgtatagta ttgtcgtttg ttggttttga ttttaatgat tcgatttgtt  10740
```

```
gttcaatatc ttttatttta tcaaggttga cactcttttt aacctcagct aattctcttt  10800
ttaacgcgtc aatgttttca gcaccagtat ttgctttaat taaattaatt tcatctgtgt  10860
tacgccctac actatcttta gtagcgttta atgattgtgt aattgtatga tatttctcat  10920
catactgtaa cattgatttt tcaaattcat ttaattgtgt ttgatgttgt tctaaacttt  10980
cacttaatat gatatctttt tcttttaatg cgtcaatgtc atttttatta ctatcaatca  11040
ttggttggaa tttttttatc ttctctaaaa atgttgatat tttctctttg ttatcattaa  11100
ttgcaatatc atgtttatct atttgaccac tgtatttatc aatcaatgtt tttaaatcat  11160
tataaaatgt caatttataa taacttgaat cagtacggac ataaatatgc ccgtctgatg  11220
tactgattaa gtcattttct tctgttaaaa aatctgctaa acggtctata tcttcgacac  11280
gtcttaaact tcttacgatt ctatcagcca ttgtttacac ctcttattta tatcgtttcc  11340
aactaaactc aaagaaaaaa cctaaaatac ccattatgag aacacccccc acggaatatc  11400
aacactgtaa ctattacctg ttttaccatt ccattgcctt actggtaaat aataacgtgt  11460
accttgccag ttgtaaccaa tccaaactaa cccatctgat aaacatactt cgtcatatgg  11520
tgtatatcca ccaggttgaa accagtagcc gttaggttct gataatttag gactaccaac  11580
atgtgcaaat attggtaaaa agccacatgt aaatgttgca ttttcatttc tgtaatatgt  11640
gccgtattga ttttgtttcc agttgttagt tttttgaata tttttttcta atactttact  11700
atcactattt gaaaattttg gacgaataaa gtgtgttaca ccgtcataat aatgtgttct  11760
tattgttgct ttttcccatc cgtcaaaacc tccacctaac cagttttgtt ctaaacatgt  11820
gtaataatct aaattgccac ttgttacgca ttgaatatga ccatattgag aattagtgta  11880
tactgcaatg tcacataatt gaggtttaaa gcttggtgta ttttcataca cctttgctaa  11940
acctttaaag tcattattaa tcgcgtcttt ggcattaccc cacatacgaa ctttaccgtc  12000
tgtaatgtaa taaacataag caactgctaa gtccatacat tgaaaaccat atgcaccatc  12060
aaagtcaaca cctacaccct catgattata tatccattct tttgcttgtt gttgtgattt  12120
catttatatc actcctattt tttatgtttt gctacccaac catactcacg atgtttggtt  12180
tcagcattaa cattactaaa aaattcttta tattcggaaa catttgcctc taatgtttgt  12240
cttacttcac ctacagcgtt accactcgac acgcgtaacc atgcacctac ttttttaatt  12300
tcttctggtg cgtctctaaa caattccatt tggtttccag taatataata ttcacctggt  12360
gctgtaacgt aagcaatcca attattgtac tgacttgcct ccaaatattc ttggtatggt  12420
gcgtctgttt tgatggttgt ccataaacca taatcccatt ttagcgtgaa cacgtctaac  12480
gtcataccac gcaccatttt aaccatttta cgacctgttg aaaaacgcgt taattcttgt  12540
actgtaccta atgtttgtgt tgtagggtat acattgatga aacaaccagc gtctataatt  12600
tttttactac cattcattgg catattttta agtttactag ctgtaccacc gtcaatataa  12660
tagaaccctg cttgtgttaa gtcatttaag tcgtcgatat ggtctggaat agataacgca  12720
cgtccatcgt cttttgttaa tttatagttt tgtgaacctc ttgcgcgtaa tgcttcaaaa  12780
tgttcatatt ctccaagttg gaaaaaacca tataaattat tgaatcgttt tccgccgccg  12840
ccatttgtca tagcaagtaa taaagattta cgttttgttt ttgggttagt ataaatacaa  12900
ataccctcag gctctttaaa gttatcacgt ggaaaattaa ttccgtcttg atatgataat  12960
ttaaacggat aatcataaat ctttttacct gttgttaatg aatatttacc tatttgaacg  13020
tgtgaattaa ctgaactgtt accacttagc cagtacaaat catctccgtc aactgcaatc  13080
```

```
ccttgcatcc aacggtcatc gttattctca gaattgtcaa ttgtcatttc tttttctaca  13140
ttatcaatgt gatttttttac gtctgctctt gaacgtacct gtattgtccc gtcaccgaat  13200
cttaaaacga ttttgtcatt tgcttcatca attaacggtg taaatgtatg tttgtttaaa  13260
agtgactgtg gtgtataatc tgttaaacct ttagcctctt ctaaatctaa aacataatta  13320
tctttatatg caacttgtaa caattttgat acaccgtcat gatgtaacca tattttcatt  13380
tctccattag attgacgttc taatccgatt gttgtaccat gaccaccctg tacaatacgc  13440
atgctagaaa ttaagtcacc actaggcgtt aatttattta tccaaaatcc ttctggtttt  13500
tgtgagtcgg attgtgtaga gtacatgtga ttagtctctt tatcaatatt aatagattgg  13560
ttaacagcat tacgaatacc accaaagccc ataacaaact ttggttcaag ctcatttaat  13620
tcaaaaccat taacgaaacg gtcaatatct tttattaagt ctttcacttc ttctttaaag  13680
tcattcattt gtttcatttc tgcaacttta aataaagcaa atgcagatgt taaaccagca  13740
ctatattttt taaactcatc atgaataata ctgtcaatcg taccgtcgtt taaccaacct  13800
ctgaataagt ctttcgcttg ctctggaaat gctttcatta agtcgtccca gtttctaaaa  13860
cgttttttta actcaccgtc atagtcccaa atacgacgtg ctaatacttc aatgagtttt  13920
gataatcttg aaatataatc ataatacgat tttgaatttg tattataatc tgctctatca  13980
tcgtaaaacg gtgtataacg ttctctcgtt ttataaattt cgtctaaaaa tggacgaatg  14040
tcatcaaaat atttaaaatc gttttcatta tataccataa ttttccacct ttaccaaatt  14100
tgtaaaaaac attttttatc aaattcattt aaaattttct ttcttaaatc gtatacttta  14160
tcaatattat caattaaata ctgttttgaa aattgtgtac ctttcgcatt accttttttga  14220
ttttgattac gttttgcgtt ttgattactt tcgttacttg atttattgac ggatttaccg  14280
ttatcaatag tgttattgtc tgcaaattgt aacgttgttt tatctacatc aatgttaacc  14340
tcgctttgtg gtaatgacgc ataagcattt ctgtttgctg tcatacctgt tgaattgtct  14400
aatgaagtag cattttgatt tgacgtttca tcagtgttgc ttgttgtatc ttcattgtgt  14460
tctgtaaagc cttgtgattg tagatatttt tcaacttcgc ttgatgaata aaccacattc  14520
aaataatcct catgtgtgat acatacagta atcacttgca tgccaaaagc ttcaactgtt  14580
tgtctgttga tttctctatc taaaaagtgt attgtaaatg attttttaaa aagtaagtca  14640
gataagtcat ctttaagttt aaaaccttta aacacttttt cattaacgat ggctaaaacg  14700
tctttgtcaa acttcaacat tttttgcatg aattgaaatt catcatcata aaacgttaat  14760
ttatcattat ttacaaattc attaaaacct tttttaatta attctgattt aataaaatca  14820
aataaagtca ttgtatatct agccattgta ttcactactt tcatcattag acaatgtatc  14880
tatcattgtg atttctgaag taacttcatc gtcgtaatac ggtttaatat ctaaaccata  14940
acgttttgat aagaatgtaa tcggttcacg accttttaaa taaatattac tatttgatgt  15000
ggtaaaacct cggttgcttt ttgcctcttc gtccgaaacg ccgctttcct tatccactgc  15060
tagtgaatta atacctaaat agttacttaa ttcactaatt ttattttggt attcgcgttt  15120
catctcagtt agtgctggaa tcacactatt actggttaaa tctataatat catcatcggc  15180
gttaaacata ggtgacattt taacaaatgg tgcaccgtta tatatttccg atacaagttg  15240
attaactgac tcatcattaa tgtctgattt aaatattttg ctaaattttg cttgcataat  15300
taatgaaaat cgagataaaa caacctcaga taattcatca gtataatgtt ctatgatttc  15360
tatatcacta ttatattgaa ttggtttatt ttgcataaca acaaagttac cactcataca  15420
gttatcatat attttatgaa tctgtaagca ttcatctggt attaaatagt ctgggacaat  15480
```

```
gaaataaata tcatcttttg ttaatcgttt ttgaaattga aagttaaagt ttgatgaaaa  15540
atttggtgct tgattaaagt aagtattatt tacgtaacca agaatcataa tttgttcatt  15600
tcttgctttg ccaaccacta cattgatgtt ttgtcttaat gctgattcta attgaataaa  15660
atctatacca accgtatcac gattggtata gttgatgagt agtggtaaaa attccaaata  15720
acgattaaac ataagacgtt taaatctgtt gcgatgttca acaactcttt tgttgatttc  15780
ttttgataat tcaacctgta cgcctttatt atgtttagtc atttatagca cctctattat  15840
tctgttcttg atgttacatc ttggtcagta attaaaattt tattaaagaa tgggctaatg  15900
gctttaaatg aatagtaatg aatccagtgt gtgacttcat caaattcacc attatagaat  15960
ggttgtttta acataccttt tgtgtaacgt ttatatttaa ttgaattaat atccaaaata  16020
aacgcgtata aatctgattt tggtttaatt tcttcaacac tatctttaaa ctctgatagt  16080
tttgacacat cataagtgaa tactgaacca actggaattg tatcaccttt atgagtttga  16140
taatcaccat aagcacgcaa gaaagctact gaatcatcac ttgaaacgac aatgtcttta  16200
gtaactttaa acacaccacc taaatcatca aaactaatga cgtggtctgt gaaatcaatt  16260
ccagcaattt ggaaggtatt cgcaatcttt gtatctaaaa gataagattt taatgaatct  16320
gttgttaaaa tcacaatatc ttttaatttt gagactgttg tatattgtcc aatagcacca  16380
cctgaagcac gatgaacttc attatattta gcactgttgt tttgtaagtt aagaatagct  16440
tcaaaaactt tacttgctaa atcctctttt gatgttgctt tacgtacatt tgattcagat  16500
aattgattca atgagtaatc aactaacatt gcacgcattt ctttttcttc taatacgtta  16560
atatcagaaa ttttcttttt atagacacct aatgcataat tagttgcgtc tgctaatgtt  16620
tggaaattga aacgtgtatc attgttattt aatgtgaatt tttgtttctt cacaatacca  16680
ctaccatata acttagttgc catacgtgga taattacgtt ttaacattaa ttcttcattt  16740
ttagataaat ccatgttaat aggtactgta tccataatta catattcttc actgtattga  16800
cctataaagt cctgctcttt agctaaccaa ttaaaacgat tacctaatgc aatatcgatt  16860
aataacgttt cattaatctt agggaataaa aatttattta caaatgtttc aaacattgta  16920
ttagaattat cccacttatc gccaaacgtc catgattttg aataagtatg attaaagtct  16980
tgtaatgcag atttagctga ctgtgcaact aatagtgctg tttcgttttt tgtactcttt  17040
tctgccatga tttattattc ctcctctaca tcgccagtaa atgactgttt tgaaagtgaa  17100
tgaatttgta caccataact atcttcactt ttatttgtat caattgacat attttcattt  17160
aattctgttc gtttatttaa tcttgaatct tcatatgatg tacccatcat agaacgcata  17220
ttgttaccct catacatgtt taaattcctc ctaatctaaa tctaacttat cgactaattc  17280
ttcatctgaa tagtctttat cattatcatc tggttcagta acatctggtt gtgtttgttg  17340
tacttgttgc gattgttgca tttgtgaaga taaaaaagta gtcacttgtt gttctaatga  17400
agcaatacgt tgttctaata caacagggtc aaatttcgaa ctatcttcat ctgttgtagt  17460
aggttctaat ttgttttcat tttcttcttc gattgtttct actgttttat cttcagttga  17520
ttcttcagtt gattcttcag ttgattcttc agttgattct tcagttgatt cttcagttga  17580
ttctttgtcg tctggtttta cgatttcatc aaattctgtc atttagaca              17629
```

ANTI-BACTERIAL COMPOSITIONS AND USES THEREOF

CROSS-REFERENCE TO RELATED APPLICATION

This application is the U.S. national stage application of International Patent Application No. PCT/EP2018/055629, filed Mar. 7, 2018.

The Sequence Listing for this application is labeled "Seq-List.txt" which was created on Aug. 21, 2019 and is 389 KB. The entire content of the sequence listing is incorporated herein by reference in its entirety.

The present invention relates to novel bacteriophage compositions, their manufacture and the uses thereof. The invention is particularly suited for the treatment of an infection in human and animals.

BACKGROUND OF THE INVENTION

Bacteriophages (or phages) are small viruses displaying the ability to infect and kill bacteria while they do not affect cells from other organisms. Initially described a century ago by William Twort, and independently discovered shortly thereafter by Félix d'Herelle, more than 6000 different bacteriophages have been exposed so far and described morphologically, including bacterial and archeal viruses. The vast majority of these viruses are tailed, while a small proportion is polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic and pseudo-lysogenic (Weinbauer, 2004; Drulis-Kawa, 2012). Lytic phages cause lysis of the host bacterial cell as a normal part of their life cycles. Lysogenic phages (also termed temperate phages) can either replicate by means of the lytic life cycle and cause lysis of the host bacterium, or they can incorporate their DNA into the host bacterial DNA and become noninfectious prophages. Pseudolysogeny can be defined as the stage of stalled development of a bacteriophage in a host cell without multiplication or replication (M Łoś, 2012). Whatever the type of phage cycle, the first step is the attachment to receptors of the bacterial cell wall before phage genetic material may enter into the bacteria. This specific process defines the spectrum of bacteria that a phage interacts with.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infections was, however, highly controversial from the very beginning and not widely accepted by the public or medical community. Early studies were widely criticized for lacking appropriate controls and inconsistent results. The lack of reproducibility and many conflicting results obtained in various published studies led the Council on Pharmacy and Chemistry of the American Medical Association to conclude that the evidence for the therapeutic value of lytic filtrates was for the most part contradictory, unconvincing, and recommended additional research to confirm its purported benefits.

Since the introduction of antibiotics in the 1940s, little attention was paid to this field of therapeutics, especially in the Western world. But the extensive use of antibiotics has led to the widespread emergence of antibiotic-resistant bacteria around the world, causing increasingly serious problems. It has therefore become a major challenge to overcome the remaining limited therapeutic options, which are still available to treat major multi-drug resistant microbes.

*Staphylococcus aureus* (*S. aureus*) is a gram-positive cocci bacterium which is frequently found in the nose, respiratory tract, and on the skin. *S. aureus* distinguishes from other staphylococcal species on the basis of the gold colonies pigmentation and positive results of coagulase, mannitol-fermentation, and deoxyribonuclease test. *S. aureus* is one of the most important pathogens worldwide and has emerged as a prominent organism infecting critically ill persons.

*S. aureus* can be a commensal but also a dangerous pathogen. Approximately 30% of the human population is colonized with *S. aureus*. *S. aureus* infection is a major cause of skin, soft-tissue, respiratory, bone, joint and endovascular disease like for example skin abscesses, wound infections, endocarditis, osteomyelitis, pneumonia, and toxic shock syndrome. *S. aureus* is particularly adept at infecting foreign bodies within the human host. In those cases, *S. aureus* typically forms a biofilm on the surface of a foreign device (such as implantable cardiac devices, intravascular catheter, prostheses, stents), making eradication of the infection without surgical removal of the device all but impossible. *S. aureus* can acclimatize to live inside cells, where it finds protection from host defense mechanisms and from most antibiotics.

The number of staphylococcal infections continues to increase while the treatment of these infections becomes even more difficult because of the emergence of staphylococcal strains resistant to multiple antibiotics, including methicillin or vancomycin. In the United States and United Kingdom, 40% to 60% of nosocomial *S. aureus* strains are multidrug resistant.

Therefore, there is a great need for new antibacterial agents or compositions that can be used to destroy or control *S. aureus* strains, suitable for use in human or animal therapy as well as for decontaminating materials.

Experimental phage therapy against *S. aureus* has been tested in mice (Capparelli et al., 2007), without development for human use. Therefore, in view of the high resistance-acquisition potency of *S. aureus*, there is a need for new antibacterial agents or compositions that can be used to kill *S. aureus* strains including the troublesome methicillin-resistant strains (MRSA).

SUMMARY OF THE INVENTION

The inventors have isolated and characterized new bacteriophages presenting strong lytic activity against *Staphylococcus aureus* (*S. aureus*) strains. These bacteriophages, alone or in combinations, provide very potent antibacterial effect and can be used as active agents in pharmaceutical or veterinary preparations, particularly to treat *S. aureus* bacterial infections.

An object of the invention is to provide antibacterial compositions comprising at least one bacteriophage having lytic activity against at least one *Staphylococcus aureus* (*S. aureus*) strain, said at least one bacteriophage being selected from the bacteriophages having a genome comprising a nucleotide sequence of anyone of SEQ ID NOs: 1 to 4 or a sequence having at least 90% identity thereto.

A further object of the invention relates to a bacteriophage having lytic activity to a *S. aureus* strain and having a genome comprising a nucleotide sequence selected from anyone of SEQ ID NOs: 1 to 4 or a sequence having at least 95% identity thereto.

The invention further concerns an isolated nucleic acid molecule contained in a bacteriophage of the invention, preferably an isolated nucleic acid molecule comprising a nucleotide sequence selected from anyone of SEQ ID NOs: 1 to 4 or a sequence having at least 95% identity thereto, as well as an isolated polypeptide encoded by said nucleic acid.

Another object of the invention is a composition comprising a nucleic acid or polypeptide as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in humans and animals, for modifying the microbial flora of the human or animal, for decontaminating a material, for killing or controlling a *S. aureus* bacterium, and/or for compromising the integrity of a bacterial bio film generated by a *S. aureus* bacterium, and/or for decontaminating food and beverage.

The invention also relates to a bacteriophage, nucleic acid, polypeptide or composition as defined above, for use to improve a subject condition by modifying the microbial flora in said subject. The microbial flora may be modified by correcting, adapting or restoring a proper balance of microorganisms in said flora.

The invention also relates to a method for treating an infection in humans or animals, comprising the administration to said humans or animals of at least one bacteriophage, nucleic acid, polypeptide or composition as defined above.

The invention also relates to a method for treating a surface or material suspected of being contaminated with a *S. aureus* bacterium, comprising applying to said surface or material at least one bacteriophage, nucleic acid, polypeptide or composition as defined above. The surface or material may be a surface of any device, vessel, laboratory material, clothing, footwear, military equipment, air cooling systems, housings, etc.

A further object of the invention relates to a kit comprising a composition as defined above and a mean for applying the same to a subject or a surface.

The invention may be used on and in any human or animal, preferably human beings, or to treat any material, including laboratory materials or medical devices inside or outside human or animals.

Another object of the invention relates to a method for determining a cocktail of bacteriophages effective against a *S. aureus* strain target, comprising:

a) separately contacting a targeted *S. aureus* strain, or a sample containing said strain, with (i) a bacteriophage having a genome comprising a nucleotide sequence of SEQ ID NO: 1 or a sequence having at least 90% identity thereto, and/or (ii) a bacteriophage having a genome comprising a nucleotide sequence of SEQ ID NO: 2 or a sequence having at least 90% identity thereto, and/or (iii) a bacteriophage having a genome comprising a nucleotide sequence of SEQ ID NO: 3 or a sequence having at least 90% identity thereto, and/or (iv) a bacteriophage having a genome comprising a nucleotide sequence of SEQ ID NO: 4 or a sequence having at least 90% identity thereto, and (v) one or more combinations thereof;

b) selecting bacteriophage(s) which exhibit(s) lytic activity on the strain, c) optionally further selecting active bacteriophages which, when combined together, exhibit synergistic activity on the strain; and/or d) optionally further selecting active bacteriophages which, when combined together, exhibit no antagonism; and/or e) optionally selecting active bacteriophages which belong to different genus; and f) combining said selected bacteriophages.

DETAILED DESCRIPTION OF THE INVENTION

The present invention relates to novel bacteriophages, components thereof, compositions comprising the same, their manufacture, and the uses thereof as antibacterial agents, particularly for the treatment of an infection in humans or animals or for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the part and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on *S. aureus* strains according to techniques known per se in the art (see also experimental section).

The term "variant" of a reference bacteriophage designates a bacteriophage having variation(s) in the genomic sequence and/or polypeptide(s) encoded thereby as compared to said reference bacteriophage. Said variants may have different phenotypic characteristics such as a different bacterial host range compared to the reference bacteriophage. In a particular aspect, a variant may be obtained by directed evolution (also called phage training) which allows the variant to acquire a lytic activity on one or several bacterial strains. Variants typically exhibit the same morphology compared to the reference bacteriophage. Typically, the reference bacteriophage has a nucleic acid sequence comprising a sequence selected from anyone of SEQ ID NOs: 1-4. Variants typically comprise e.g., silent mutations, conservative mutations, minor deletions, and/or minor replications of genetic material. In a preferred embodiment, variants according to the invention retain any observable characteristic or property that is dependent upon the genome of the bacteriophage of the invention, e.g., phenotypic characteristics of said bacteriophage and/or lytic activity against the *S. aureus* strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The term "specific" or "specificity" in relation to a bacteriophage refers to the type of host that said bacteriophage is able to infect. A bacteriophage "specific" for *S. aureus* more preferably designates a bacteriophage which can infect one or several *S. aureus* strains and which essentially does not infect non-*S. aureus* bacteria under physiological conditions.

As used herein, the term "polypeptide" refers to polypeptides of any size, including small peptides of e.g., from 5 to 20 amino acids, longer polypeptides, proteins or fragments thereof.

In the context of the present specification, the term "isolated bacteriophage" should be considered to mean a bacteriophage that is removed from its natural environment and/or separated from a component of its natural environment and or is issued from directed evolution. The term designates, particularly, a phage that is e.g., cultivated in vitro, purified, and/or formulated with any suitable product for formulation, such as diluent(s) or excipient(s). In relation to a nucleic acid or polypeptide, the term "isolated" designates e.g., a nucleic acid molecule or polypeptide which is separated from at least one component of its natural environment such as, e.g., a protein, lipid, carbohydrate and/or nucleic acid.

The terms "pharmaceutically or veterinary acceptable" as used herein refers to any material (e.g., carrier, excipient or diluent) that is compatible for use in a human or animal subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations, and aerosolized formulations such as liquids or powders.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

As used herein, "CFU" means colony forming unit, as it is well defined in the art for estimating the number of viable bacteria in a sample.

The term "treatment" or "therapy" designates a curative or a prophylactic treatment of a disease. A curative treatment is defined as a treatment that results in a cure of a disease, or a treatment that alleviates, reduces, stabilizes, or eliminates the symptoms of a disease or the suffering that it causes, directly or indirectly, or that improves a subject condition or reduces progression of a disease. A prophylactic treatment comprises a treatment resulting in the prevention of a disease, and/or a treatment reducing and/or delaying the incidence of a disease or the risk of its occurrence.

The term "biofilm" as used herein designates a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial bio film, it is understood a denaturation and/or a penetration of the bio film by bacteriophage, an infection of bio film-associated bacteria and/or a lysis thereof and/or a partial or an entire clearing of the biofilm (i.e., by stopping colonization and/or disrupting bio films).

The term "sample", as used herein, means any sample, such as biological samples, particularly samples containing cells. Examples of samples include body fluids such as blood, plasma, saliva, faeces or urine, as well as biopsies, organs, tissues or cell samples. The sample may be treated.

As used herein, the term "subject" or "patient" refers to an animal, preferably a human, including adult and child. The term "subject" also encompasses animals, such as and not limited to pets (e.g., dogs, cats), farm species, such as horses, cows, goats, pigs, sheep, poultry, non-human primates, and fishes, shells, shrimps etc . . . .

The term "efficacy" of treatment or "response" to a bacteriophage therapy as used herein refers to a treatment which results in a decrease in the number of *S. aureus* strains in a subject after bacteriophage treatment when compared to the number of *S. aureus* strains before treatment. A "good responder" subject refers to a subject who shows or will show a clinically significant recovery when treated with a bacteriophage therapy.

The term "cocktail" of bacteriophages designates a combination of different bacteriophages. The bacteriophages in a cocktail are preferably formulated together in a same vessel or packaging, although they may be used as kits of parts wherein some of the bacteriophages are formulated or packaged separately and combined when used or administered.

The term "sequence identity" as used herein is determined by comparing two optimally aligned sequences over a comparison window, where the fragment of the polynucleotide in the comparison window may comprise additions or deletions (e.g., gaps or overhangs) as compared to the reference sequence, which does not comprise additions or deletions, for optimal alignment of the two sequences. The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection.

DESCRIPTION OF EMBODIMENTS

The present invention is related to novel bacteriophage therapies of *S. aureus* infections. More particularly, the present invention relates to novel bacteriophages having high lytic activity against *S. aureus* strains, their manufacture, components thereof, compositions comprising the same and the uses thereof in phage therapy.

Bacteriophages

In a first aspect, the invention discloses the isolation and characterization of novel bacteriophages having lytic activity against *S. aureus* strains and which exhibit, either alone or in combination(s), remarkable host range spectrum of lytic activity. These bacteriophages have been isolated, sequenced, and characterized. They are, individually and in combination(s), active against *S. aureus* strains. They are remarkably effective against pathogenic *S. aureus* strains, including antibiotic-resistant *S. aureus* strains such as a Methicillin-Resistant *Staphylococcus aureus* (MRSA) strain. These bacteriophages can be combined and formulated in conditions suitable for use as pharmaceutical or veterinary agents to exhibit very potent antibacterial effect against a controlled spectrum of *S. aureus* strains.

More specifically, the following bacteriophages have been isolated. Their corresponding nucleic acid sequence is also indicated.

TABLE 1

| Bacteriophage | SEQ ID |
|---|---|
| PN1137 | SEQ ID NO: 1 |
| PN1493 | SEQ ID NO: 2 |
| PN1815 | SEQ ID NO: 3 |
| PN1957 | SEQ ID NO: 4 |

The lytic profile of these bacteriophages has been determined on a wide range of *S. aureus* strains. The results show a broad spectrum of activity (specific and total) for the four bacteriophages of the invention. These four bacteriophages are members of the Caudovirales order.

The bacteriophage PN1137 is a member of the Podoviridae family and has the nucleic acid sequence of SEQ ID NO: 1 which comprises 17,213 nucleotides. It exhibits a specific lytic activity on 46 out of the 109 *S. aureus* strains tested, which represents 42.2% of the strains. Further, bacteriophage PN1137 exhibits a total lytic activity on 81 of the 109 strains tested, which represents 74.31% of the strains.

The bacteriophage PN1493 is a member of the Myoviridae family and has the nucleic acid sequence of SEQ ID NO: 2 which comprises 134,876 nucleotides. It exhibits a specific lytic activity on 86 out of the 109 *S. aureus* strains tested, which represents 78.9% of the strains. Further, bacteriophage PN1493 exhibits a total lytic activity on 108 of the 109 strains tested, which represents 99.08% of the strains.

The bacteriophage PN1815 is a member of the Myoviridae family and has the nucleic acid sequence of SEQ ID NO: 3 which comprises 136,156 nucleotides. It exhibits a specific lytic activity on 59 out of the 109 *S. aureus* strains tested, which represents 54.13% of the strains. Further, bacteriophage PN1815 exhibits a total lytic activity on 108 of the 109 strains tested, which represents 99.08% of the strains.

The bacteriophage PN1957 is a member of the Podoviridae family and has the nucleic acid sequence of SEQ ID NO: 4 which comprises 17,629 nucleotides. It exhibits a specific lytic activity on 71 out of the 109 *S. aureus* strains tested, which represents 65.14% of the strains. Further, bacteriophage PN1957 exhibits a total lytic activity on 95 of the 109 strains tested, which represents 87.16% of the strains.

Combinations of those bacteriophages have a specific lytic activity which covers at least 74 of the strains (67%). Particularly, together bacteriophages PN1493 and PN1957 have a specific lytic activity which covers 98 of the *S. aureus* strains (89.9%) and a total lytic activity which covers 100% of the *S. aureus* strains.

A particular object of the invention thus resides in a bacteriophage having lytic activity to a *S. aureus* strain and having a genome comprising a nucleotide sequence selected from anyone of SEQ ID NOs: 1 to 4 or a sequence having at least 95% identity thereto, preferably at least 96%, 97%, 98% or 99% identity thereto.

The bacteriophages of the invention can be prepared by standard culture, isolation and purification methods. For example, *S. aureus* producing bacteria are cultured, infected by a sample of a bacteriophage, and then treated to remove bacterial cells and debris. The enriched bacteriophage solution can be plated in a medium, for example agar medium, with embedded susceptible host strains of *S. aureus* to obtain plaques. Then, single plaque can be picked out for subsequent bacteriophage purification and amplification. One or more cycles of selective amplification of bacteriophages of the invention may be performed, for example by mixing bacteriophages with the competent *S. aureus*, followed by addition of a growth medium and incubation at selected test growing conditions. Following centrifugation, the cleared amplified supernatant is filtered through filter and subjected to another cycle of selective amplification or tested for presence of lytic activity.

The titration of bacteriophages in a suspension and the visualization of plaque morphology of bacteriophages of the invention may then be assessed by known methods, for example by plaque counting. Additionally, processing bacteriophages of the invention in various forms (liquid, lyophilized, etc.) for short-, long-, freeze- or any other kind of storage can be carried out by any suitable method as it is well-known in the art (see e.g., Clark, 1962).

The lytic activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *S. aureus* strains after a period of incubation in soft agar medium, resulting in zones of clearing on the plate known as plaques.

The bacteriophages of the invention may be cultured, expanded, isolated, purified, and used in e.g., phage therapy of *S. aureus*-mediated disorders, as will be disclosed in more details below. Furthermore, variants of these bacteriophages retaining a phenotypic character (e.g., lytic activity) of the bacteriophages can be produced and/or isolated by techniques known per se in the art.

Nucleic Acids and Polypeptides

The invention relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from anyone of SEQ ID NOs: 1-4, or a sequence having at least 95%, 96%, 97%, 98%, 99% or more sequence identity to anyone of SEQ ID NOs: 1-4.

The nucleic acid of the invention can be in free form, or cloned in a vector, such as a plasmid, viral vector, expression cassette, cosmid, etc.

In a further aspect, the invention also relates to an isolated polypeptide encoded by a nucleic acid sequence as defined above, preferably a nucleic acid sequence selected from SEQ ID NO: 1, SEQ ID NO: 2, SEQ ID NO: 3, or SEQ ID NO: 4. The polypeptide(s) may be produced by techniques known per se in the art such as synthesis, recombinant technology, or combinations thereof. The polypeptides may be isolated or purified, and used as antibacterial agents or as reagents for in vitro analyses.

Compositions of the Invention

One aspect of the invention relates to compositions comprising at least one bacteriophage as described above, more preferably at least two or more and, optionally, a pharmaceutically or veterinary acceptable excipient. As described, the bacteriophages of the invention have very potent lytic activity against *S. aureus* strains. Combinations of these bacteriophages may be produced to expand the host spectrum and produce highly effective antibacterial compositions.

More particularly, the invention relates to an antibacterial composition comprising at least one bacteriophage having lytic activity against a *S. aureus* strain, said at least one bacteriophage being selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

In one aspect, a bacteriophage having a genome comprising a nucleotide sequence having at least 90% identity to anyone of SEQ ID NOs: 1-4, for example at least 91%, 92%, 93%, 94%, 95%, 96%, 97%, 98% or 99% identity to anyone of SEQ ID NOs: 1 to 4 may have the same phenotypic characteristics than the reference bacteriophage having the sequence of anyone of SEQ ID NOs: 1-4. Typically, said bacteriophage has the same bacteria host range. Such a bacteriophage typically comprises e.g., silent mutations, conservative mutations, minor deletions, and/or minor replications of genetic material.

In another aspect, a bacteriophage having a genome comprising a nucleotide sequence having at least 90% identity to anyone of SEQ ID NOs: 1 to 4, for example at least 91%, 92%, 93%, 94%, 95%, 96%, 97%, 98% or 99% identity to anyone of SEQ ID NOs: 1-4 may result from directed evolution (phage training) and may have a different bacteria host range. Typically, said bacteriophage has an activity on more bacteria strains compared to the reference bacteriophage having the sequence of anyone of SEQ ID NOs: 1-4.

Even more particularly, the invention relates to an antibacterial composition comprising at least two bacteriophages having lytic activity against a *S. aureus* strain, said at least two bacteriophages being selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

In another particular embodiment, the compositions of the invention comprise at least three, even more preferably at least four distinct bacteriophages selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

Specific examples of compositions of the invention comprise:

- a bacteriophage having a genome comprising a nucleotide sequence of SEQ ID NO: 1 or a sequence having at least 90% identity thereto, and a bacteriophage having a genome comprising a nucleotide sequence of SEQ ID NO: 2 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 2 or a sequence having at least 90% identity thereto, and a bacteriophage having a genome comprising a nucleotide sequence of SEQ ID NO: 3 or a sequence having at least 90% identity thereto;
- a bacteriophage having a genome comprising a nucleotide sequence of SEQ ID NO: 2 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 1 or a sequence having at least 90% identity thereto, a bacteriophage having a genome comprising a nucleotide sequence of SEQ ID NO: 2 or a sequence having at least 90% identity thereto, and a bacteriophage having a genome comprising a nucleotide sequence of SEQ ID NO: 3 or a sequence having at least 90% identity thereto;
- a bacteriophage having a genome comprising a nucleotide sequence of SEQ ID NO: 1 or a sequence having at least 90% identity thereto, a bacteriophage having a genome comprising a nucleotide sequence of SEQ ID NO: 2 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 1 or a sequence having at least 90% identity thereto, a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto; or a bacteriophage having a genome comprising a nucleotide sequence of SEQ ID NO: 2 or a sequence having at least 90% identity thereto, a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto.

In a specific embodiment, the compositions of the invention comprise at least:

a bacteriophage having a genome comprising a nucleotide sequence of SEQ ID NO: 1 or a sequence having at least 90% identity thereto;

a bacteriophage having a genome comprising a nucleotide sequence of SEQ ID NO: 2 or a sequence having at least 90% identity thereto;

a bacteriophage having a genome comprising a nucleotide sequence of SEQ ID NO: 3 or a sequence having at least 90% identity thereto; and a bacteriophage having a genome comprising a nucleotide sequence of SEQ ID NO: 4 or a sequence having at least 90% identity thereto.

The compositions of the invention may comprise the cocktails of bacteriophages as presented in Table 2:

TABLE 2

Cocktails of bacteriophages of the invention

| Cocktail | Bacteriophages |
|---|---|
| 1 | PN1137 + PN1493 |
| 2 | PN1137 + PN1815 |
| 3 | PN1137 + PN1957 |
| 4 | PN1493 + PN1815 |
| 5 | PN1493 + PN1957 |
| 6 | PN1815 + PN1957 |
| 7 | PN1137 + PN1493 + PN1815 |
| 8 | PN1137 + PN1493 + PN1957 |
| 9 | PN1137 + PN1815 + PN1957 |
| 10 | PN1493 + PN1815 + PN1957 |
| 11 | PN1137 + PN1493 + PN1815 + PN1957 |

The compositions of the invention may further comprise additional antibacterial agents, particularly other bacteriophages having distinct host specificity.

Most preferred compositions of the invention are lytic against more that 70% of all of the 109 bacterial strains of the panel determined by the Centre National de Référence des Staphylocoques de Lyon. This collection contains a vast number and variety of *S. aureus* strains which are those with the highest incidence in Europe and the United States of America.

The compositions of the invention may comprise any effective amount of the selected bacteriophage(s). Preferably, they comprise between $10^{e1}$ and $10^{e12}$ PFU/ml of each of said bacteriophages, preferably between $10^{e4}$ and $10^{e11}$ PFU/ml. The relative amounts of each type of bacteriophage in a composition of the invention may be adjusted by a skilled artisan. Typically, when the antibacterial composition comprises several (n) distinct bacteriophages as defined above, the total relative amount % A of each bacteriophage in the composition is more preferably % $A=(100/n_i)\times V$, wherein $n_i$ represents the number of distinct bacteriophages and V is a variability factor comprised between 0.2 and 5. Most preferably, V is comprised between 0.3 and 3, even more preferably between 0.5 and 2, generally between 0.8 and 1.5. In a preferred typical embodiment, each type of bacteriophage is present in a composition of the invention in approximately equal relative amounts.

The antibacterial compositions of the invention may be in various forms, such as liquid, semi-liquid, solid or lyophilized formulations. The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, powdered formulations with dry or/and extruded powders, aerosolized formulations with liquid or dry aerosols. Formulations for topical administration may include, bandage, dressings, patches, films, ointments, lotions, creams, gels, drops, suppositories, sprays, tampons, sanitary towels, liquids and powders. Formulations for decontamination or for medical use may also include aerosols or sprays.

The compositions of the invention may be used in the medical field, including the human or veterinary medical areas, for e.g. the treatment of a subject infection or for improving a subject's condition. The compositions may be used to reduce or kill *S. aureus* bacteria in an organism for treating an infection. The composition may also be used for improving the condition of a subject by modifying the microbial flora in said subject. In particular, the compositions of the invention can specifically remove *S. aureus* strains on the skin or mucous membranes of a subject, thus modifying its microbial flora and restoring a proper balance.

In a particular embodiment, the invention also relates to a method for treating an infection in a subject comprising the administration to said subject of a composition or bacteriophages or nucleic acids or polypeptides as defined above.

The invention also relates to the use of a composition of bacteriophages, nucleic acids or polypeptides as described for manufacturing a medicament for treating an infection in a subject, or for restoring microbial flora in said subject.

The compositions of the invention may be used to treat various *S. aureus*-mediated infections, particularly diabetic or non-diabetic foot ulcer infections, or bone such as and not limited to osteomyelitis, or septic arthritis, or joint infections, or prosthetic joint infections, or skin infections such as and not limited to atopic dermatitis, acnea, impetigo, Staphylococcal scalded skin syndrome, or soft tissue infections, or pleuropulmonary infections, or other clinical syndromes such as and not limited to meningitis or urinary tract infections or septicemia or endocarditis or otitis.

The compositions of the invention may be administered by any convenient route, including intravenous, oral, transdermal, subcutaneous, mucosal, intramuscular, intrapulmonary, intranasal, parenteral, rectal, vaginal and topical. The bacteriophages or compositions may be administered by intrapulmonary or intranasal instillation or nebulisation, as well. The compositions may be administered directly or indirectly, e.g., via a support or a device (e.g. a nebulizer, a bandage . . . ). In this regard, the compositions may, for example, be applied or sprayed to the afflicted area. Compositions of the invention can also be administered by oral or parenteral routes. The dosage suitable for applying, spraying, or administrating the compositions of the present invention can be adjusted by the skilled person depending on a variety of factors including formulation, mode of administration, age, weight, sex, condition, diet of the subject being treated at the time of administration, route of administration, and reaction sensitivity. A physician or veterinarian having ordinary skills in the art can readily determine and prescribe the effective amount of the composition required.

The dosing can also be adjusted by the skilled person so that a lytic activity against antibiotic-resistant *S. aureus* strains is obtained. An efficient dose to obtain a lytic activity in vivo typically includes a concentration of at least $10^{e4}$ PFU/ml, preferably from about $10^{e2}$ to $10^{e12}$ PFU/ml, depending on the administration route.

In a particular embodiment, the bacteriophages, compositions, and cocktails of the invention are used for treating diabetic or non-diabetic foot ulcer infections, bone and joint infections, prosthetic joint infections or respiratory tract infections.

In the case of diabetic foot ulcers infected, for example, by methicillin-resistant or susceptible *S. aureus* (MRSA or MSSA), patients may receive dressings impregnated with a phage(s) solution at $10^4$ to $10^{10}$ PFU/ml with a frequency of application comprised between every day and every ten days, for example between every two days and every nine days, preferably between every three days and every eight days, more preferably every seven days, with or without antibiotic(s), until wound closure. The efficacy of the treatment may be measured by the relative reduction in bacterial load.

In the case of relapsing *S. aureus* (MRSA or MSSA) prosthetic joint infections of, for example, hip or knee, patients may receive phage therapy associated to standard surgery, with and without antibiotics. The content of a phage(s) solution at $10^4$ to $10^{10}$ PFU/ml may be scattered in the operative field in the osseous barrels, the articular space and/or the muscular tissues, at the end of explantation. A second identical preparation may be used for a second dispersal just after the reimplantation and before surgical site closure. Additional applications when the wound is still open may be done, for example at the time of wound dressing. Complementary oral phage administration at $10^4$ to $10^{10}$ PFU/ml may be used to support the local treatment.

In the case of plastic surgery with *S. aureus* (MRSA or MSSA) infected bone, a bone curettage may be followed by the placement of a compress imbibed with $10^4$ to $10^{10}$ PFU/ml of bacteriophage(s) at the bottom of the surgical site, in contact with the infected curetted bone. The rest of the cavity may be filled with other sterile compresses and the surgical site occluded by waterproof dressing. In addition, a Vacuum-Assisted Closure (VAC) system may be used, following a cycle of drainage to remove blood or serous fluid from the wound or operation site, followed by phage instillation ($10^4$ to $10^{10}$ PFU/ml) with or without antibiotics. The phages remain during several hours before drainage is reinitiated. The cycle may be repeated several times during the days following operation.

In the case of respiratory tract infection, a $10^4$ to $10^{10}$ PFU/ml phage solution may be applied using a nebulizing device. Nebulization may be carried out with a portable inhaler or with an add-on nebulizer to a medical mechanical ventilator. A phage solution volume ranging for instance from 1 to 20 ml may be nebulized at various time intervals and during the treatment period. Before starting the first nebulization and according to the pathology, lung washing may be performed with the same phage solution.

As shown in the experimental section, the bacteriophages and compositions of the invention are able to effectively kill a broad range of *S. aureus* bacteria. Compositions can destroy mixtures of different *S. aureus* bacteria, even at low dosage. Also, the compositions and bacteriophages of the invention are strictly unable to affect eukaryotic cells, and are therefore specific and devoid of side effects when applied to humans and animals.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, clothing, footwear, housing, military equipment, etc.

The invention also relates to a method for preparing a composition of the invention, wherein the composition comprises at least two bacteriophages, said method comprising separately producing said at least two bacteriophages, and combining said bacteriophages with a suitable carrier or excipient.

The composition of the invention may be used in combination with at least one antibiotic. Such a co-administration allows to reduce the amount of antibiotic used, to restore the efficacy of an antibiotic or to make a bacterium embedded in a biofilm susceptible to an antibiotic.

Diagnostic/Predictive Tests of the Invention-Companion Diagnostic:

The invention also concerns a method for predicting or determining the efficacy of a bacteriophage therapy in a subject, wherein the method comprises a step of determining a lytic activity of one or more bacteriophages of the invention to a *S. aureus* strain from a sample from said subject, such a lytic activity being indicative of an efficient treatment. In a preferred aspect, the method further optionally comprises a step of treating said subject by one or more bacteriophages having a lytic activity to a *S. aureus* strain from a sample of said subject.

In another aspect, the invention provides a method for selecting a subject or determining whether a subject is susceptible to benefit from a bacteriophage therapy, wherein the method comprises the step of determining a lytic activity of one or more bacteriophages of the invention to a *S. aureus* strain from a sample of said subject, a lytic activity of one or more bacteriophages of the invention to at least one *S. aureus* strain indicating a responder subject.

Another object of the invention relates to a method for predicting the response of a subject to a bacteriophage therapy, wherein the method comprises the step of determining a lytic activity of one or more bacteriophage of the invention to a *S. aureus* strain from a sample of said subject, a lytic activity of one or more bacteriophage of the invention to at least one *S. aureus* strain being indicative of a good response to said therapy.

In another aspect, the invention provides a method for assessing the sensitivity of a *S. aureus* strain to a bacteriophage selected from the bacteriophages having a genome comprising a nucleotide sequence of anyone of SEQ ID NO: 1 to 4 or a sequence having at least 90% identity thereto and/or at least one cocktail of bacteriophages of Table 2, comprising:

a) contacting the *S. aureus* strain with said at least one bacteriophage and/or said at least one cocktail of bacteriophages, and b) determining the lytic activity of the bacteriophage and/or of the cocktail on the strain, thereby assessing the sensitivity of the strain to the bacteriophage and/or to the cocktail. Step a) may be carried out in vitro by bringing into contact, exposing or mixing a *S. aureus* strain with the at least one bacteriophage and/or at least one cocktail of bacteriophage in any medium adapted for such step (e.g. a solid or a liquid medium).

In a preferred embodiment, the determination of the lytic activity of the bacteriophage and/or of the cocktail comprises measuring the amplification of the bacteriophage in the *S. aureus* strain, wherein an augmentation of the bacteriophage concentration is indicative of the lytic activity of the bacteriophage and/or of the cocktail on the strain.

The bacteriophage concentration may be measured by any technical well-known from the person skilled in the art, such as plaque forming, Polymorphism Chain reaction (PCR), bioluminescence, etc.

Additionally or alternatively, the determination of the lytic activity of the bacteriophage and/or the cocktail comprises a determination of the apparition of a plaque in a plaque assay.

However, a bacteria strain may also be considered as sensitive to a bacteriophage when in a solid medium culture of the bacteria in presence of the bacteriophage, complete or partial lysis of a bacterial mat is observed.

Other techniques well-known from the person skilled in the art may be used to assess the lytic activity of the bacteriophage and/or of the cocktail.

Another object of the invention relates to a method for determining a cocktail of bacteriophages effective against a target *S. aureus* strain, comprising:

a) separately contacting the target *S. aureus* strain, or a sample containing said strain, with (i) a bacteriophage having a genome comprising a nucleotide sequence of SEQ ID NO: 1 or a sequence having at least 90% identity thereto, and/or (ii) a bacteriophage having a genome comprising a nucleotide sequence of SEQ ID NO: 2 or a sequence having at least 90% identity thereto, and/or (iii) a bacteriophage having a genome comprising a nucleotide sequence of SEQ ID NO: 3 or a sequence having at least 90% identity thereto, and/or (iv) a bacteriophage having a genome comprising a nucleotide sequence of SEQ ID NO: 4 or a sequence having at least 90% identity thereto, and/or (v) one or more combinations thereof;

b) selecting bacteriophages which exhibit lytic activity on the strain, c) optionally further selecting active bacteriophages which, when combined together, exhibit synergistic activity on the strain; and/or d) optionally further selecting active bacteriophages which, when combined together, exhibit no antagonism; and/or e) optionally selecting active bacteriophages which belong to different genus; and f) combining said selected bacteriophages.

This method may be used as a phagogramme in order to determine which cocktail has the best lytic activity on a particular *S. aureus* strain.

Further aspects and advantages of the invention will be disclosed in the following experimental section, which is illustrative only.

EXAMPLES

Methods

Taxonomic Identification of the Phage Families.

Four phages of the invention (PN1137, PN1493, PN1815 and PN1957) were studied using electron microscopy. The results show that the bacteriophages belong to the Caudovirales order and to the Podovirae and Myoviridae families, as described hereinafter:

PN1137: Podovirae,

PN1483: Myoviridae,

PN1815: Myoviridae,

PN1957: Podovirae.

Sequencing and Analysis of Phage Genomes.

Phage DNA was isolated by extraction with phenol: chloroform:isoamyl alcohol (25:24:1, V/V), ethanol precipitation and resolution in water. Whole genome sequencing was done and the BLAST algorithm was used to determine the similarity to described genes in the National Center for Biotechnology Information (NCBI) database. The genomes were scanned for potential open reading frames (ORFs). The nucleic acid sequences are shown as SEQ ID NOs: 1-4. Sequences alignments using databases lead to the same taxonomic identifications than those using electron microscopy.

Example 1: In Vitro Characterization: Host Range

Two different kinds of bacterial lysis are possible. Bacterial lysis resulting from bacteria cell wall hydrolysis by bacteriophage's enzymes (termed "aspecific" lysis) and bacterial lysis resulting of phage amplification (termed "specific" lysis). Both types of lysis are relevant to the utility of the phages. Both the specific and aspecific lysis were determined for each of the bacteriophages using two methods.

Phage Amplification in a Solid Medium

This method allows to assess the capacity of a bacteriophage to lyse bacteria by amplification.

The method consists in depositing a range of dilution (ratio 10) of a bacteriophage suspension at the surface of a bacteria-containing agar. This agar is then incubated at 37° C. for 18 h for allowing the development of a bacterial mat. Deposition areas are analyzed. The following situations are possible:

Case 1: absence of lysis of the bacterial mat at the deposition area,

Case 2: complete lysis of the bacterial mat at the deposition area,

Case 3: partial lysis of the bacterial mat at the deposition area, and

Case 4: observation of a plaque (plaque-forming unit (PFU)) at the deposition area.

It is only the formation of a plaque (Case 4) that attests the capacity of a phage to amplify in the bacteria strain and to effectively lyse the bacteria.

If cases 1, 2 and/or 3 is observed in absence of case 4, the strain is tested in liquid medium.

Phage Amplification in a Liquid Medium

This method allows to assess the capacity of a bacteria to produce a bacteriophage.

The method consists in culturing a bacterial strain and a bacteriophage at 37° C. for 18 h. Bacteriophage concentration in the supernatant is then determined. If the bacteriophage concentration after culturing is superior to the initial bacteriophage concentration, this indicates that the bacteriophage has been amplified by the bacterium.

The capacity of a bacterium to produce a bacteriophage depends on, inter alia, the multiplicity of infection (MOI), i.e., the bacteriophage/bacteria ratio. Several MOI have been tested.

Phage titration after culturing is determined using a method analog to the spot test. A range of dilution (ratio 10) of the culture supernatant is deposited on one hand on an agar surface containing the production strain of the bacteriophage and on the other hand on an agar surface containing the strain of a patient. This agar is then incubated at 37° C. for 18 h. The number of plaques on a depositing area correlated to the dilution factor allows the determination of bacteriophage concentration.

Specific Activity

The spectrum of specific activity, i.e., the capacity of each bacteriophage to lyse by amplification the strains of a panel, has been assessed. A bacteriophage is considered to be amplified by a bacterial strain when:

- in solid medium test, observation of case 4 was made, and
- in liquid medium test, the concentration of the bacteriophage after culturing was 50-fold increased with respect to the initial concentration.

The panel of *S. aureus* was determined by the Centre National de Reference des Staphylocoques de Lyon. It comprises the 109 *S. aureus* strains having the highest incidence in Europe and in the United States of America.

In the following Table 3, the capacity of the bacteriophages of the invention to be amplified by a bacterial strain is represented by a "+" and the incapacity of a bacteriophage to be amplified by a bacterial strain is represented by a "–".

TABLE 3

Spectrum of specific activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 1 | HOCIL001 | + | + | + | + |
| 2 | HOCIL002 | – | + | + | – |
| 3 | HOCIL003 | + | + | + | + |
| 4 | HOCIL004 | + | + | + | + |
| 5 | HOCIL005 | + | + | + | + |
| 6 | HOCIL006 | – | + | + | + |
| 7 | HOCIL007 | – | + | – | + |
| 8 | HOCIL008 | + | + | + | + |
| 9 | HOCIL009 | + | – | – | + |
| 10 | HOCIL010 | – | – | – | + |
| 11 | HOCIL011 | – | + | + | – |
| 12 | HOCIL012 | + | + | + | + |
| 13 | HOCIL013 | – | + | + | + |
| 14 | HOCIL014 | + | + | + | + |
| 15 | HOCIL015 | + | + | + | + |
| 16 | HOCIL016 | + | + | – | + |
| 17 | HOCIL017 | + | + | + | + |
| 18 | HOCIL018 | + | + | + | + |
| 19 | HOCIL020 | – | + | + | – |
| 20 | HOCIL022 | + | + | + | + |
| 21 | HOCIL093 | – | + | – | + |
| 22 | HOCIL095 | + | + | + | – |
| 23 | HOCIL099 | + | + | + | + |
| 24 | HOCIL106 | – | + | – | – |
| 25 | HOCIL117 | – | – | – | + |

TABLE 3-continued

Spectrum of specific activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 26 | HOCIL118 | – | – | – | – |
| 27 | HOCIL124 | – | – | – | + |
| 28 | HOCIL129 | – | – | – | + |
| 29 | HOCIL137 | – | – | – | – |
| 30 | HOCIL139 | – | + | + | + |
| 31 | HOCIL140 | – | – | – | + |
| 32 | HOCIL145 | + | + | + | + |
| 33 | HOCIL148 | – | + | – | – |
| 34 | HOCIL155 | + | + | – | + |
| 35 | HOCIL156 | + | + | – | + |
| 36 | HOCIL161 | – | + | + | – |
| 37 | HOCIL163 | – | – | – | – |
| 38 | HOCIL165 | + | + | + | + |
| 39 | HOCIL167 | + | – | – | + |
| 40 | HOCIL172 | + | + | – | + |
| 41 | HOCIL174 | + | + | – | + |
| 42 | HOCIL175 | – | – | + | + |
| 43 | HOCIL176 | – | – | – | – |
| 44 | HOCIL183 | + | + | – | + |
| 45 | HOCIL184 | + | + | – | + |
| 46 | HOCIL185 | + | + | + | + |
| 47 | HOCIL186 | – | + | – | + |
| 48 | HOCIL187 | – | + | – | – |
| 49 | HOCIL188 | + | + | + | + |
| 50 | HOCIL189 | – | + | – | – |
| 51 | HOCIL190 | – | + | + | + |
| 52 | HOCIL191 | + | + | + | + |
| 53 | HOCIL192 | – | – | – | + |
| 54 | HOCIL193 | + | + | + | + |
| 55 | HOCIL194 | + | + | + | + |
| 56 | HOCIL195 | – | – | – | – |
| 57 | HOCIL196 | – | – | – | – |
| 58 | HOCIL197 | + | + | + | + |
| 59 | HOCIL198 | + | + | + | + |
| 60 | HOCIL199 | – | + | – | + |
| 61 | HOCIL200 | – | + | + | + |
| 62 | HOCIL201 | + | + | – | – |
| 63 | HOCIL202 | – | – | – | – |
| 64 | HOCIL203 | + | + | + | + |
| 65 | HOCIL204 | + | + | + | + |
| 66 | HOCIL205 | + | + | + | + |
| 67 | HOCIL206 | + | + | + | – |
| 68 | HOCIL207 | + | + | + | + |
| 69 | HOCIL210 | – | + | – | – |
| 70 | HOCIL211 | – | + | + | + |
| 71 | HOCIL212 | + | + | + | + |
| 72 | HOCIL213 | – | + | + | + |
| 73 | HOCIL214 | – | + | – | + |
| 74 | HOCIL215 | – | – | – | + |
| 75 | HOCIL216 | – | + | + | + |
| 76 | HOCIL217 | – | – | – | – |
| 77 | HOCIL218 | – | + | – | + |
| 78 | HOCIL219 | + | + | + | + |
| 79 | HOCIL220 | – | – | – | + |
| 80 | HOCIL221 | – | + | + | – |
| 81 | HOCIL222 | – | + | + | – |
| 82 | HOCIL223 | – | + | + | – |
| 83 | HOCIL224 | – | + | – | – |
| 84 | HOCIL225 | – | + | + | – |
| 85 | HOCIL226 | + | + | + | + |
| 86 | HOCIL227 | – | + | + | + |
| 87 | HOCIL228 | – | + | + | + |
| 88 | HOCIL229 | + | + | + | + |
| 89 | HOCIL230 | – | + | + | + |
| 90 | HOCIL231 | – | + | – | – |
| 91 | HOCIL232 | – | + | + | – |
| 92 | HOCIL233 | – | + | – | + |
| 93 | HOCIL234 | – | + | – | – |
| 94 | HOCIL235 | – | + | – | + |
| 95 | HOCIL236 | – | + | + | + |
| 96 | HOCIL237 | + | + | – | + |
| 97 | HOCIL238 | + | + | + | + |
| 98 | HOCIL239 | – | – | – | – |
| 99 | HOCIL240 | + | – | – | + |
| 100 | HOCIL241 | – | + | + | – |

TABLE 3-continued

Spectrum of specific activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 101 | HOCIL242 | − | + | + | − |
| 102 | HOCIL243 | − | + | − | − |
| 103 | HOCIL244 | − | + | − | − |
| 104 | HOCIL245 | − | − | − | − |
| 105 | HOCIL246 | − | + | + | − |
| 106 | HOCIL248 | − | − | − | − |
| 107 | HOCIL249 | + | + | − | + |
| 108 | HOCIL250 | + | + | + | − |
| 109 | HOCIL251 | − | + | + | − |

PN1493 and PN1957 exhibit a specific activity respectively on 86 and 71 of the 109 *S. aureus* strains, which represent 78.9% and 65.14% respectively.

PN1137 and PN1815 also present a broad range of specific activity. They exhibit a specific activity respectively on 46 and 59 of the strains, which represent 42.2% and 54.13% respectively.

Total Lytic Activity

The spectrum of total lytic activity, i.e., the capacity of each bacteriophage to lyse strains either with or without bacteriophage production, has been evaluated. The bacteriophage is considered active on the *S. aureus* strain either when:

- in solid medium test, observations of cases 2, 3 or 4 were made, or
- in liquid medium test, the concentration of the bacteriophage after culturing was 50-fold increase with respect to the initial concentration.

In the following Table 5, the positive lytic activity of a bacteriophage on a bacterial strain is represented by a "+" and the absence of lytic activity of a bacteriophage on a bacterial strain is represented by a "−".

TABLE 5

Spectrum of total activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 1 | HOCIL001 | + | + | + | + |
| 2 | HOCIL002 | + | + | + | + |
| 3 | HOCIL003 | + | + | + | + |
| 4 | HOCIL004 | + | + | + | + |
| 5 | HOCIL005 | + | + | + | + |
| 6 | HOCIL006 | + | + | + | + |
| 7 | HOCIL007 | + | + | + | + |
| 8 | HOCIL008 | + | + | + | + |
| 9 | HOCIL009 | + | + | + | + |
| 10 | HOCIL010 | + | + | + | + |
| 11 | HOCIL011 | + | + | + | + |
| 12 | HOCIL012 | + | + | + | + |
| 13 | HOCIL013 | + | + | + | + |
| 14 | HOCIL014 | + | + | + | + |
| 15 | HOCIL015 | + | + | + | + |
| 16 | HOCIL016 | + | + | + | + |
| 17 | HOCIL017 | + | + | + | + |
| 18 | HOCIL018 | + | + | + | + |
| 19 | HOCIL020 | + | + | + | − |
| 20 | HOCIL022 | + | + | + | + |
| 21 | HOCIL093 | + | + | + | + |
| 22 | HOCIL095 | + | + | + | + |
| 23 | HOCIL099 | + | + | + | + |
| 24 | HOCIL106 | + | + | + | + |
| 25 | HOCIL117 | + | + | + | + |
| 26 | HOCIL118 | + | + | + | + |
| 27 | HOCIL124 | + | + | + | + |
| 28 | HOCIL129 | + | + | + | + |

TABLE 5-continued

Spectrum of total activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 29 | HOCIL137 | + | + | + | + |
| 30 | HOCIL139 | + | + | + | + |
| 31 | HOCIL140 | + | + | + | + |
| 32 | HOCIL145 | + | + | + | + |
| 33 | HOCIL148 | + | + | + | + |
| 34 | HOCIL155 | + | + | + | + |
| 35 | HOCIL156 | + | + | + | + |
| 36 | HOCIL161 | + | + | + | + |
| 37 | HOCIL163 | + | + | + | + |
| 38 | HOCIL165 | + | + | + | + |
| 39 | HOCIL167 | + | + | + | + |
| 40 | HOCIL172 | + | + | + | + |
| 41 | HOCIL174 | + | + | + | + |
| 42 | HOCIL175 | + | + | + | + |
| 43 | HOCIL176 | + | + | + | + |
| 44 | HOCIL183 | + | + | + | + |
| 45 | HOCIL184 | + | + | + | + |
| 46 | HOCIL185 | + | + | + | + |
| 47 | HOCIL186 | + | + | + | + |
| 48 | HOCIL187 | + | + | + | + |
| 49 | HOCIL188 | + | + | + | + |
| 50 | HOCIL189 | + | + | + | + |
| 51 | HOCIL190 | + | + | + | + |
| 52 | HOCIL191 | + | + | + | + |
| 53 | HOCIL192 | − | − | − | + |
| 54 | HOCIL193 | + | + | + | + |
| 55 | HOCIL194 | + | + | + | + |
| 56 | HOCIL195 | + | + | + | + |
| 57 | HOCIL196 | − | + | + | + |
| 58 | HOCIL197 | + | + | + | + |
| 59 | HOCIL198 | + | + | + | + |
| 60 | HOCIL199 | + | + | + | + |
| 61 | HOCIL200 | + | + | + | + |
| 62 | HOCIL201 | + | + | + | + |
| 63 | HOCIL202 | + | + | + | + |
| 64 | HOCIL203 | + | + | + | + |
| 65 | HOCIL204 | + | + | + | + |
| 66 | HOCIL205 | + | + | + | + |
| 67 | HOCIL206 | + | + | + | + |
| 68 | HOCIL207 | + | + | + | + |
| 69 | HOCIL210 | − | + | + | − |
| 70 | HOCIL211 | − | + | + | + |
| 71 | HOCIL212 | + | + | + | + |
| 72 | HOCIL213 | + | + | + | + |
| 73 | HOCIL214 | + | + | + | + |
| 74 | HOCIL215 | − | + | + | + |
| 75 | HOCIL216 | + | + | + | + |
| 76 | HOCIL217 | − | + | + | + |
| 77 | HOCIL218 | − | + | + | + |
| 78 | HOCIL219 | + | + | + | + |
| 79 | HOCIL220 | + | + | + | + |
| 80 | HOCIL221 | − | + | + | − |
| 81 | HOCIL222 | − | + | + | − |
| 82 | HOCIL223 | − | + | + | − |
| 83 | HOCIL224 | + | + | + | + |
| 84 | HOCIL225 | − | + | + | − |
| 85 | HOCIL226 | + | + | + | + |
| 86 | HOCIL227 | − | + | + | + |
| 87 | HOCIL228 | − | + | + | + |
| 88 | HOCIL229 | + | + | + | + |
| 89 | HOCIL230 | − | + | + | + |
| 90 | HOCIL231 | − | + | + | + |
| 91 | HOCIL232 | + | + | + | + |
| 92 | HOCIL233 | − | + | + | + |
| 93 | HOCIL234 | − | + | + | + |
| 94 | HOCIL235 | − | + | + | + |
| 95 | HOCIL236 | − | + | + | + |
| 96 | HOCIL237 | + | + | + | + |
| 97 | HOCIL238 | + | + | + | + |
| 98 | HOCIL239 | − | + | + | − |
| 99 | HOCIL240 | + | + | + | + |
| 100 | HOCIL241 | − | + | + | − |
| 101 | HOCIL242 | − | + | + | − |
| 102 | HOCIL243 | − | + | + | + |
| 103 | HOCIL244 | − | + | + | + |

TABLE 5-continued

Spectrum of total activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 104 | HOCIL245 | − | + | + | − |
| 105 | HOCIL246 | − | + | + | − |
| 106 | HOCIL248 | − | + | + | − |
| 107 | HOCIL249 | + | + | + | + |
| 108 | HOCIL250 | + | + | + | − |
| 109 | HOCIL251 | − | + | + | − |

Those results show a very broad spectrum of activity for the four bacteriophages tested which all present a lytic activity on more than 70% of the 109 *S. aureus* strains. Particularly, bacteriophages PN1493 and PN1815 show very good results with an activity on 108 of the 109 *S. aureus* strains, which represents more than 99% of the strains of the panel. PN1137 and PN1957 also exhibit a broad range of lytic activity. They are effective respectively on 81 and 95 of the strains from the panel (74.31% and 87.16% respectively). Every *S. aureus* strain from the panel is lysed by at least one of the bacteriophages. Further, 79 of the strains are lysed by the four bacteriophages.

Example II: Production of Cocktails

Cocktail 5: PN1493 and PN1957

Those two bacteriophages have a complementary range of lytic activity. Indeed, together they exhibit a specific activity on 98 of the tested *S. aureus* strains which represents 89.9% of the strains. Moreover, their total lytic activity covers all of the tested *S. aureus* strains. A preferred cocktail comprises these two bacteriophages in a 1:1 ratio.

Cocktail 6: PN1815 and PN1957

As for cocktail 5, those two bacteriophages have a complementary range of lytic activity. Together they exhibit a specific activity on 87 of the tested *S. aureus* strains (79.8%). Moreover, their total lytic activity covers all of the tested *S. aureus* strains. A preferred cocktail comprises these two bacteriophages in a 1:1 ratio.

Cocktail 1 (PN1137 and PN1493) and cocktail 4 (PN1493 and PN1815)

Those two cocktail also present a broad range of lytic activity on the tested bacterial strains. Cocktail 1 and 4 have a specific lytic activity respectively on 89 and 87 of the strains (respectively 81.6% and 79.8%). Moreover, they both exhibit a total lytic activity on 108 of the strains, which represents a lytic activity on more than 99% of the tested *S. aureus* strains. Preferred cocktails comprise the two bacteriophages in a 1:1 ratio.

Cocktails 3, 5, 6, 8, 9, 10 and 11

Those cocktails exhibit a total lytic activity on 100% of the strains.

Example II: In Vivo Efficacy

Two mice models are used to assess the efficacy of cocktail of bacteriophages of the invention.

The first model reproduces *S. aureus* infections of a diabetic or non-diabetic foot ulcer. It is based on *S. aureus* hind paw infection of naive mice or diabetic mice.

The second model reproduces *S. aureus* bone and joint infections (BJI) as well as prosthetic joint infection (PJI).

Diabetic Foot Ulcer Model (DFU)

Diabetes are induced using Streptozotocin. The diabetes status of the mice is based on blood glucose around 5 g/l seven days after the induction and on an impaired *S. aureus* blood killing assay.

*S. aureus* Strain

A clinical strain isolated from prosthetic infection is chosen based on the ability of the strain to persist and multiply in situ. The best inoculum is chosen based on a sustained bacterial load 14 days p.i. in diabetic mice with the highest survival rate.

Experimental Design

Diabetes is induced by two injections of Streptozotocin at 48 h interval. One hind paw is infected 14 days after the first Streptozotocin injection. Four groups are compared:

- bacteriophage cocktail-treated. The cocktail is administered locally (SC injection) 30 min p.i. at multiplicity of infection of 1 (MOI 1).
- bacteriophage cocktail-treated. The cocktail is administered locally (SC injection) 30 min p.i. at MOI 10.
- antibiotic-treated. Linezolid is administered systemically (IP injection) 30 min p.i. at 25 mg/kg.
- Untreated control. PBS is administered locally (SC injection) 30 min p.i., Thirty mice per group are studied.

At six time points p.i., mice are euthanized, the number of colony-forming unit (CFU) and plaque-forming unit (PFU) is numerated in the soft tissue and bone of the infected hind paw. Macroscopic observation of the oedema and lesion is scored as mentioned in Chhibber et al. The myeloperoxidase (MPO) level is determined to follow the inflammatory reaction and histology of the hind paw is performed at day 5 to assess the inflammatory reaction differences between the 4 groups.

This model allows to assess the efficacy of a bacteriophage or a cocktail of bacteriophages of the invention on a *S. aureus* infections of a diabetic foot ulcer.

Non-Diabetic Foot Ulcer Model

*S. aureus* Strain

The strain used in the diabetic foot ulcer model is also used in the non-diabetic foot ulcer model. The same inoculum is used.

Experimental Design

One hind paw is infected in naïve mice. The groups compared in the diabetic foot ulcer model are also studied in the non-diabetic foot ulcer model. The same criteria were studied.

This model allows to assess the efficacy of a bacteriophage or a cocktail of bacteriophages of the invention on a *S. aureus* infection of a non-diabetic foot ulcer.

Bone and Joint Infection Model

*S. aureus* Strain

A clinical strain isolated from prosthetic infection is chosen based on the ability of the strain to persist and multiply in situ. The best inoculum is chosen based on a sustained bacterial load 7 days p.i. with the highest survival rate.

Experimental Design

Naive mice are infected through the knee. Seven groups are compared:

- bacteriophage cocktail-treated. The cocktail is administered systemically 30 min p.i. at a high dose.
- bacteriophage cocktail-treated. The cocktail is administered systemically 30 min p.i. at a low dose.
- bacteriophage cocktail-treated. The cocktail is administered locally 30 min p.i. at a high dose.
- bacteriophage cocktail-treated. The cocktail is administered locally 30 min p.i. at a low dose.

antibiotic-treated.

antibiotic+bacteriophage-treated.

untreated control.

Thirty mice per group are studied.

The bacterial load and phage load, the clinical status of the mice, such as the weight, food and water consumption are followed along the course of the infection.

This model allows to assess the efficacy of a bacteriophage or a cocktail of bacteriophages of the invention on a *S. aureus* bone and joint infection.

Prosthetic Joint Infection Model

*S. aureus* Strain

The strain is similar to the BJI model as well as the inoculum.

Experimental Design

A K-wire is inserted into the femoral cavity of a naive mice. The mice are then infected through the knee next to the K-wire. The groups comparison and readouts are similar to the bone and joint infection model.

This model allows to assess the efficacy of a bacteriophage or a cocktail of bacteriophages of the invention on a *S. aureus* prosthetic joint infection.

REFERENCES

Capparelli R, et al. Antimicrob Agents Chemother. Experimental Phage Therapy against *Staphylococcus aureus* in Mice. 2007 August; 51(8): 2765-2773.

Clark W A, 1962, Appl Microbiol. Comparison of several methods for preserving bacteriophages. 1962 September; 10:466-71.

Drulis-Kawa Z, Majkowska-Skrobek G, Maciejewska B, Delattre A S, Lavigne R, 2012, Learning from bacteriophages—advantages and limitations of phage and phage-encoded protein applications; 13(8):699-722.

Weinbauer M G. Ecology of prokaryotic viruses. FEMS Microbiol Rev 2004; 28:127-81.

The invention claimed is:

1. An antibacterial composition comprising at least two distinct bacteriophages having lytic activity against at least one *Staphylococcus aureus* (*S. aureus*) strain and a pharmaceutically acceptable excipient or carrier, said at least two bacteriophages being selected from the bacteriophages having a genome comprising a nucleotide sequence of any one of SEQ ID NOs: 1 to 4 or a sequence having at least 95% identity thereto, and said pharmaceutically acceptable excipient or carrier comprising a preservative in an amount effective to preserve the activity of the bacteriophages.

2. The composition of claim 1, comprising at least three distinct bacteriophages selected from the bacteriophages having a genome comprising a nucleotide sequence of any one of SEQ ID NOs: 1 to 4 or a sequence having 95% identity thereto.

3. The composition of claim 1, comprising at least four distinct bacteriophages selected from the bacteriophages having a genome comprising a nucleotide sequence of any one of SEQ ID NOs: 1 to 4 or a sequence having 95% identity thereto.

4. The composition of claim 1, comprising:

a bacteriophage having a genome comprising the nucleotide sequence of SEQ ID NO: 1 or a sequence having at least 95% identity thereto;

a bacteriophage having a genome comprising the nucleotide sequence of SEQ ID NO: 2 or a sequence having at least 95% identity thereto;

a bacteriophage having a genome comprising the nucleotide sequence of SEQ ID NO: 3 or a sequence having at least 95% identity thereto; and a bacteriophage having a genome comprising the nucleotide sequence of SEQ ID NO: 4 or a sequence having at least 95% identity thereto.

5. The composition of claim 1, which is a liquid, semi-liquid, solid or lyophilized formulation.

6. The composition of claim 1, comprising between $10^1$ and $10^{12}$ PFU/ml of each bacteriophage.

7. A method of treating a *Staphylococcus aureus* (*S. aureus*) infection in a human or animal in need thereof, said method comprising administering to said human or animal an antibacterial composition in an amount effective to treat said infection, wherein said antibacterial composition comprises at least one bacteriophage having lytic activity against at least said *S. aureus* strain, said at least one bacteriophage being selected from the bacteriophages having a genome comprising a nucleotide sequence of any one of SEQ ID NOs: 1 to 4 or a sequence having at least 95% identity thereto.

8. A method of modifying the microbial flora in a human or animal to improve the condition of said human or animal, said method comprising administering to said human or animal an antibacterial composition in an amount effective to modify the microbial flora or to improve the condition, wherein said antibacterial composition comprises at least one bacteriophage having lytic activity against at least one *Staphylococcus aureus* (*S. aureus*) strain, said at least one bacteriophage being selected from bacteriophages having a genome comprising a nucleotide sequence of any one of SEQ ID NOs: 1 to 4 or a sequence having at least 95% identity thereto, and wherein said microbial flora comprises said *S. aureus* strain.

9. A method for decontaminating a material, said method comprising contacting said material with an antibacterial composition in an amount effective to decontaminate said material, wherein said antibacterial composition comprises at least one bacteriophage having lytic activity against at least one *Staphylococcus aureus* (*S. aureus*) strain, said at least one bacteriophage being selected from bacteriophages having a genome comprising a nucleotide sequence of any one of SEQ ID NOs: 1 to 4 or a sequence having at least 95% identity thereto, and wherein said material is contaminated with said *S. aureus* strain.

10. A method for preparing an antibacterial composition, said method comprising separately producing at least two bacteriophages having lytic activity against at least one *Staphylococcus aureus* (*S. aureus*) strain, said at least two bacteriophages being selected from bacteriophages having a genome comprising a nucleotide sequence of any one of SEQ ID NOs: 1 to 4 or a sequence having at least 95% identity thereto, and combining said bacteriophages with a suitable carrier or excipient.

11. A method for determining a cocktail of bacteriophages effective against a target *Staphylococcus aureus* (*S. aureus*) strain, comprising:

a) separately contacting the target *S. aureus* strain, or a sample containing said strain, with (i) a bacteriophage having a genome comprising the nucleotide sequence of SEQ ID NO: 1 or a sequence having at least 95% identity thereto, and/or (ii) a bacteriophage having a genome comprising the nucleotide sequence of SEQ ID NO: 2 or a sequence having at least 95% identity thereto, and/or (iii) a bacteriophage having a genome comprising the nucleotide sequence of SEQ ID NO: 3 or a sequence having at least 95% identity thereto, and/or (iv) a bacteriophage having a genome comprising the nucleotide sequence of SEQ ID NO: 4 or a sequence having at least 95% identity thereto, and (v) one or more combinations thereof;

b) selecting bacteriophages which exhibit lytic activity on the strain, c) optionally further selecting active bacteriophages which, when combined together, exhibit synergistic activity on the strain; and/or d) optionally further selecting active bacteriophages which, when combined together, exhibit no antagonism; and/or e) optionally selecting active bacteriophages which belong to different genus; and f) combining said selected bacteriophages.

12. The composition of claim 1, wherein the pharmaceutically acceptable excipient or carrier is buffered physiological saline.

13. The composition of claim 1, wherein the at least two bacteriophages are selected from the group consisting of PN1137, PN1493, PN1815 and PN1957, said bacteriophages having a genome comprising the nucleotide sequence of any one of SEQ ID NOs: 1 to 4, respectively.

14. The method of claim 7, wherein the at least one bacteriophage is selected from the group consisting of PN1137, PN1493, PN1815 and PN1957, said bacteriophage having a genome comprising the nucleotide sequence of any one of SEQ ID NOs: 1 to 4, respectively.

15. The method of claim 8, wherein the at least one bacteriophage is selected from the group consisting of PN1137, PN1493, PN1815 and PN1957, said bacteriophage having a genome comprising the nucleotide sequence of any one of SEQ ID NOs: 1 to 4, respectively.

16. The method of claim 9, wherein the at least one bacteriophage is selected from the group consisting of PN1137, PN1493, PN1815 and PN1957, said bacteriophage having a genome comprising the nucleotide sequence of any one of SEQ ID NOs: 1 to 4, respectively.

17. The method of claim 11, comprising in the step:

a) separately contacting the target *S. aureus* strain, or a sample containing said strain, with (i) the bacteriophage PN1137 having a genome comprising the nucleotide sequence of SEQ ID NO: 1, and/or (ii) the bacteriophage PN1493 having a genome comprising the nucleotide sequence of SEQ ID NO: 2, and/or (iii) the bacteriophage PN1815 having a genome comprising the nucleotide sequence of SEQ ID NO: 3, and/or (iv) the bacteriophage PN1957 having a genome comprising the nucleotide sequence of SEQ ID NO: 4 or a sequence having at least 95% identity thereto, and (v) one or more combinations thereof.

* * * * *

UNITED STATES PATENT AND TRADEMARK OFFICE
CERTIFICATE OF CORRECTION

PATENT NO. : 11,690,885 B2
APPLICATION NO. : 16/491176
DATED : July 4, 2023
INVENTOR(S) : Cindy Fevre, Hélène Blois and Mathieu Medina Page 1 of 1

It is certified that error appears in the above-identified patent and that said Letters Patent is hereby corrected as shown below:

In the Specification

Column 3,
Line 25, "bio film" should read --biofilm--.

Signed and Sealed this
Twenty-sixth Day of December, 2023

Katherine Kelly Vidal
*Director of the United States Patent and Trademark Office*